US009909129B2

(12) United States Patent
Zhang et al.

(10) Patent No.: US 9,909,129 B2
(45) Date of Patent: Mar. 6, 2018

(54) BIOSYNTHETIC PATHWAYS AND METHODS

(71) Applicant: REGENTS OF THE UNIVERSITY OF MINNESOTA, Minneapolis, MN (US)

(72) Inventors: Kechun Zhang, Roseville, MN (US); Mingyong Xiong, Manitowoc, WI (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 14/653,118

(22) PCT Filed: Dec. 18, 2013

(86) PCT No.: PCT/US2013/076118
§ 371 (c)(1),
(2) Date: Jun. 17, 2015

(87) PCT Pub. No.: WO2014/100173
PCT Pub. Date: Jun. 26, 2014

(65) Prior Publication Data

US 2015/0337342 A1 Nov. 26, 2015

Related U.S. Application Data

(60) Provisional application No. 61/738,752, filed on Dec. 18, 2012, provisional application No. 61/821,490, filed on May 9, 2013.

(51) Int. Cl.

| | |
|---|---|
| ***C12P 7/18*** | (2006.01) |
| ***C12N 9/02*** | (2006.01) |
| ***C12N 9/88*** | (2006.01) |
| ***C12N 9/04*** | (2006.01) |
| ***C12N 15/52*** | (2006.01) |
| ***C12N 9/18*** | (2006.01) |

(52) U.S. Cl.
CPC ........... *C12N 15/52* (2013.01); *C12N 9/0006* (2013.01); *C12N 9/0008* (2013.01); *C12N 9/18* (2013.01); *C12N 9/88* (2013.01); *C12P 7/18* (2013.01); *C12Y 101/01* (2013.01); *C12Y 101/01001* (2013.01); *C12Y 102/01026* (2013.01); *C12Y 301/01* (2013.01); *C12Y 301/01068* (2013.01); *C12Y 401/01007* (2013.01); *C12Y 402/00* (2013.01); *C12Y 402/01082* (2013.01)

(58) Field of Classification Search
None
See application file for complete search history.

(56) References Cited

FOREIGN PATENT DOCUMENTS

WO WO 2011/137192 A1 11/2011

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Prather et al. Curr Opin Biotechnol. Oct. 2008;19(5):468-74.*
Kizer et al. Appl Environ Microbiol. May 2008;74(10):3229-41.*
Brouns et al. J Biol Chem. Sep. 15, 2006;281(37):27378-88. Epub Jul. 17, 2006.*
International Search Report and Written Opinion for PCT/US2013/076118, issued by the European Patent Office dated Mar. 31, 2014; 12 pgs.
International Preliminary Report on Patentability for PCT/US20138/076118, issued by the International Bureau of WIPO on Jul. 2, 2015; 7 pgs.
Baba et al., "Construction of *Escherichia coli* K-12 in-frame, single-gene knockout mutants: the Keio collection," *Mol Syst Biol,* Jan. 1, 2006;2(1):1-11.
Datsenko et al., "One-step inactivation of chromosomal genes in *Escherichia coli* K-12 using PCR products," *Proc Natl Acad Sci USA,* Jun. 6, 2000;97(12):6640-6645.
Gibson et al., "Enzymatic assembly of DNA molecules up to several hundred kilobases," *Nat Meth,* May 2009;6(5):343-345.
Sambrook et al., *Molecular Cloning: A Laboratory Manual,* $2^{nd}$ Edition; Cold Spring Harbor Laboratory Press, 1989, Cover page, title page and table of contents: 31 pgs.
Yim et al., "Metabolic engineering of *Escherichia coli* for direct production of 1,4-butanediol," *Nature Chem Biol,* Jul. 1, 2011;7(7):445-452.
Zhang et al., "A Synthetic Metabolic Pathway for Production of the Platform Chemical Isobutyric Acid," *ChemSusChem,* Aug. 22, 2011;4(8):1068-1070.

* cited by examiner

*Primary Examiner* — Christian Fronda
(74) *Attorney, Agent, or Firm* — Mueting, Raasch & Gebhardt, P.A.

(57) ABSTRACT

This disclosure describes a recombinant microbial cells and methods of making and using such recombinant microbial cells. Generally, the recombinant cells may be modified to exhibit increased biosynthesis of a TCA derivative compared to a wild-type control. In some embodiments, the TCA derivative can include 1,4-butanediol. In various embodiments, the microbial cell is a fungal cell or a bacterial cell. In some embodiments, the increased biosynthesis of the TCA derivative can include an increase in xylose dehydrogenase activity, xylonolactonase activity, xylonate dehydratase activity, or 2-keto-3-deoxyaldonic acid dehydratase activity.

11 Claims, 10 Drawing Sheets

A.

B.

2,5-dioxopentanoic acid succinaldehyde 1,4-butanediol 2,5-dioxopentanoic acid 2-keto-5-hydroxy-pentanoic acid 1,4-butanediol 4-hydroxy-1-butyraldehyde D-arabinose D-arabino-nolactone D-arabinonic acid 2-oxo-4(S),5-dihydroxy-pentanoic acid 2,5-dioxopentanoic acid D-xylose D-xylono-lactone D-xylonic acid 2-oxo-4(*S*),5-dihydroxy-pentanoic acid 2,5-dioxopentanoic acid L-arabinose L-arabino-nolactone L-arabinonic acid 2-oxo-4(*R*),5-dihydroxy-pentanoic acid 2,5-dioxopentanoic acid D-glucaric acid 4-deoxy-5-keto D-glucaric acid 2,5-dioxopentanoic acid D-glucaric acid 4-deoxy-5-keto D-glucaric acid 2,5-dioxopentanoic acid 4(R)-hydroxy-L-proline 4(R)-hydroxy-D-proline 2-carboxy-4(R)-hydroxy-pyrroline 2-oxo-4(*R*),5-hydroxy-5-aminopentanoic acid 2,5-dioxopentanoic acid

BIOSYNTHETIC PATHWAYS AND METHODS

CROSS-REFERENCE TO RELATED APPLICATION

This application is the § 371 U.S. National Stage of International Application No. PCT/US2013/076118, filed 18 Dec. 2013, which claims priority to U.S. Provisional Patent Application Ser. No. 61/738,752, filed Dec. 18, 2012 and U.S. Provisional Patent Application Ser. No. 61/821,490, filed May 9, 2013, each of which is incorporated herein by reference.

SUMMARY

This disclosure describes, in one aspect, a recombinant microbial cell modified to exhibit increased biosynthesis of a TCA derivative compared to a wild-type control. In some embodiments, the TCA derivative can include 1,4-butanediol. In various embodiments, the microbial cell is a fungal cell or a bacterial cell. In some embodiments, the increased biosynthesis of the TCA derivative can include an increase in xylose dehydrogenase activity, xylonolactonase activity, xylonate dehydratase activity, or 2-keto-3-deoxyaldonic acid dehydratase activity.

In another aspect, this disclosure describes a method that generally includes incubating any embodiments of the recombinant cell summarized above in medium that includes a carbon source under conditions effective for the recombinant cell to produce a TCA derivative. In some embodiments, the TCA derivative can include 1,4-butanediol. In some embodiments, the carbon source can include xylose, arabinose, glucaric acid, galactaric acid, or hydroxyproline. In some embodiments, the increased biosynthesis of the TCA derivative can include an increase in pentose dehydrogenase activity, pentonolactonase activity, aldonic acid dehydratase activity, or 2-keto-3-deoxyaldonic acid dehydratase activity. In other embodiments, the increased biosynthesis of the TCA derivative can include an increase in hexic acid dehydratase activity or 5-dehydro-4-deoxyglucarate dehydratase activity.

In another aspect, this disclosure describes a method that generally includes introducing into a host cell a heterologous polynucleotide encoding at least one polypeptide that catalyzes conversion of a carbon source to a TCA derivative, wherein the at least one polypeptide is operably linked to a promoter so that the modified host cell catalyzes conversion of the carbon source to TCA derivative. In some embodiments, the TCA derivative can include 1,4-butanediol. In some embodiments, the carbon source can include xylose.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

This disclosure describes a novel full biosynthetic pathway to biosynthesize high-volume TCA derivatives such as succinate, amino acids, and 1,4-butanediol from xylose by an engineered microbe. The TCA cycle can lead to many commercially important biobased chemicals such as, for example, amino acids (e.g., glutamate, threonine and lysine) and organic acids (e.g., succinate, maleate and fumarate). Here we report the engineering of a shortcut metabolic pathway to TCA cycle. The process from xylose to TCA only involves five steps as compared to conventional published pathways that include more than 20 steps. Because our pathway includes fewer steps from xylose to the TCA cycle, our pathway can produce TCA derivatives with the production of less by-product and, therefore, achieve higher yields than conventional biosynthetic pathways.

We have selected the TCA derivative 1,4-butanediol as a model product to demonstrate the generality of our novel biosynthetic pathway. 1,4-butanediol is a major commodity chemical; 2.5 million tons of 1,4-butanediol are used per year to make, for example, plastics, polyesters, and spandex fibers. 1,4-butanediol also can react, for example, with dicarboxylic acids to yield polyesters, with diisocyanates to yield polyurethanes, and with phosgene to yield chloroformates. Because our pathway permits the biosynthesis of 1,4-butanediol from, for example, xylose in only six steps from xylose to 1,4-butanediol, 1,4-butanediol may be biosynthesized with less by-product being formed and, therefore, a higher yield. For example, our pathway can produce 1.0 g/L 1,4-butanediol from 20 g/L xylose.

1,4-butanediol currently is manufactured from petroleum-based feedstocks such as acetylene, butane, propylene, and butadiene. Given the industrial importance of 1,4-butanediol as a chemical intermediate and the issues associated with petroleum feedstocks, alternative low-cost renewable biosynthetic routes from sugars have been sought. However, the highly reduced nature of 1,4-butanediol relative to carbohydrates has thwarted attempts thus far to develop effective pathways and organisms for direct production.

Figure 1:
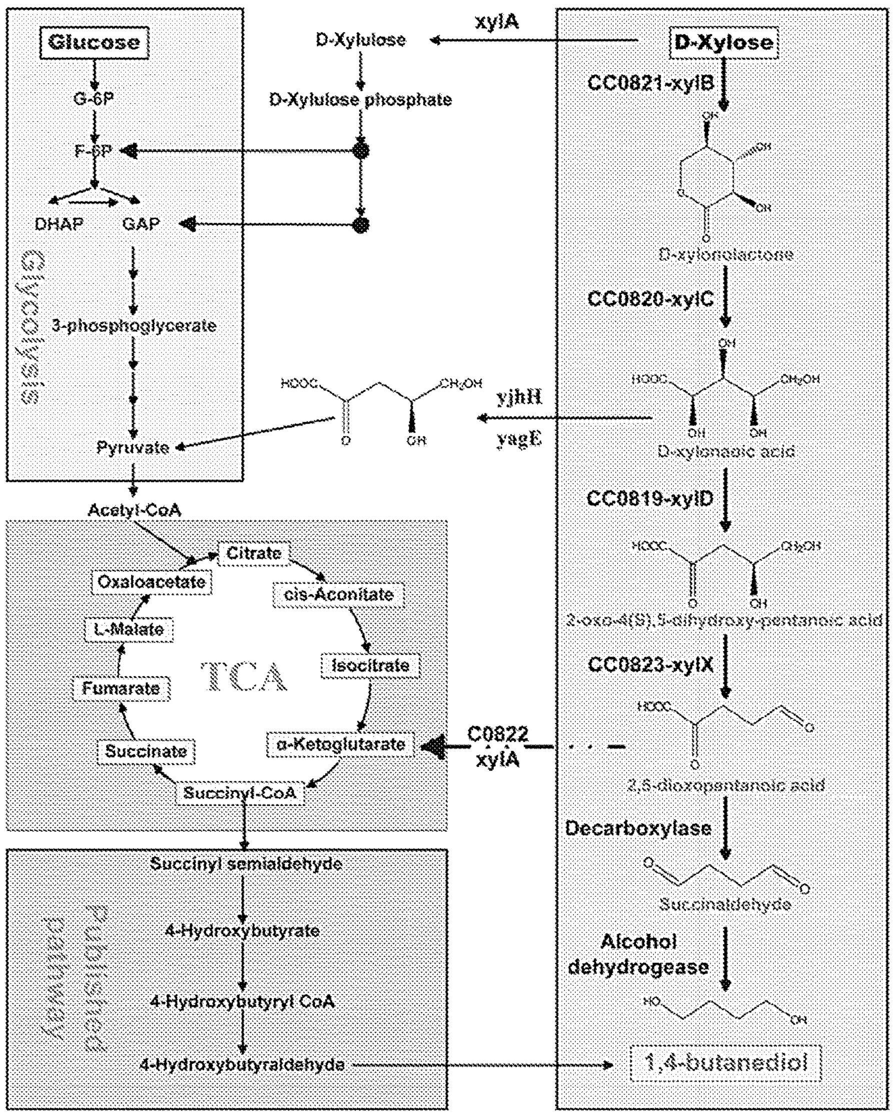
FIG. 1. The 1,4-butanediol synthetic pathway in *E. coli*. (A) The synthetic pathway for 1,4-butanediol from glucose and xylose. Abbreviations: G-6P, glucose-6-phosphate; F-6P, fructose-6-phosphate; DHAP, dihydroxyacetone phosphate; GAP, glyceraldehyde-3-phosphate. (B) Synthetic operon for protein overexpression to drive the xylose towards 2,5-dioxopentanoic acid (left), and then drive 2,5-dioxopentanoic acid towards to 1,4-butanediol (right).
Figure 1:
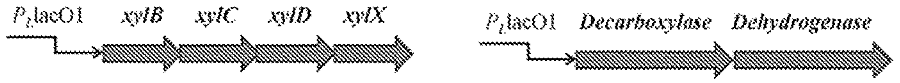

1,4-butanediol has been reported to be synthesized from glucose and xylose by engineered *E. coli* in which the succinyl-CoA intermediate was converted into succinate semialdehyde, 4-hydroxybutyrate, 4-hydroxybutyryl-CoA, 4-hydroxybutyraldehyde, and 1,4-butanediol by multiple enzymes from various organisms. This process involves around 20 chemical steps that include the pentose phosphate pathway, glycolysis, the TCA cycle, and designed artificial downstream metabolic steps. In contrast, this disclosure describes a shortcut pathway that requires only six steps (FIG. 1A).

D-xylose is converted by *Caulobacter crescentus* sequentially to D-xylonolactone, D-xylonate (D-xylonoic acid), 2-keto-3-deoxy-xylonate (2-oxo-4(S),5-dihydroxy-pentanoic acid), then α-ketoglutaric semialdehyde (2,5-dioxo-pentanoic acid) by, respectively, xylose dehydrogenase (xylB), xylonolactonase (xylC), xylonate dehydrogenase (xylD), Kda dehydratase (xylX). We cloned the coding regions of these enzymes into a single plasmid (pBDO-1), which was then transformed into an *E. coli* host cell. The host cell was then further modified to include a second plasmid that included a decarboxylase and an alcohol dehydrogenase. The decarboxylase converts the α-ketoglutaric semialdehyde to succinaldehyde; the alcohol dehydrogenase reduces the succinaldehyde to 1,4-butanediol (FIG. 1A). In some embodiments, the second plasmid was identified as pBDO-3 and included the coding regions of benzoylformate decarboxylase BFD (*Pseudomonas putida*) and an alcohol dehydrogenase of yqhD (*E. coli*). In other embodiments, the second plasmid was identified as pBDO-4 and included the decarboxylase of KIVD (*Lactococcus lactis*) and alcohol dehydrogenase of yqhD (*E. coli*).

The *E. coli* host cell possesses an endogenous xylose metabolism pathway that includes xylA, yjhH and yagE. To improve the product yield from xylose to 1,4-butanediol, expression of these three coding regions were inhibited. The host cell strain SBDO-1 is based on *E. coli* BW25113 in which xylA, yjhH, and yagE are knocked out so that SBDO-1 cannot metabolize xylose. Strain SBDO-2, carrying plasmid pBDO-1, also cannot metabolize xylose.

The strain SBDO-3, which is based on SBDO-2 but carries plasmid pBDO-2 that expresses α-ketoglutaric semialdehyde dehydrogenase xylA, can consume xylose quickly. These results indicate that the endogenous xylose utilization pathway in *E. coli* was blocked fully by the ΔxylA, ΔyjhH, and ΔyagE deletions in SBDO-1. Moreover, these results demonstrate that the *C. crescentus* enzymes function in *E. coli*. Consequently, xylose metabolism observed in SBDO-4 and SBDO-5 is attributable to the xylose pathway from *C. crescentus* that we engineered into the host cell. To produce 1,4-butanediol, plasmids pBDO-3 or pBDO-4, each of which expresses the same alcohol dehydrogenase but a different decarboxylase, were introduced into strain SBDO-2 strain. After two days of fermentation, strain SBDO-4 (carrying pBDO-3) produced 0.25 g/L 1,4-butanediol with 0.1 g/L 1,2,4-butanetriol (a by-product); strain SBDO-5 (carrying pBDP-4) produced 1.0 g/L 1,4-butanediol with 4.0 g/L 1,2,4-butanetriol. Thus, the kivD encoded on pBDO-4 and carried by strain SBDO-5 provides better yield of 1,4-butanediol than BFD. Other than 1,2,4-butanetriol, no other byproducts were detected in significant amounts in the fermentation broth, suggesting that our new 1,4-butanediol producing pathway has higher 1,4-butanediol yield as compared with the published pathway (Yim et al., 2011. *Nat. Chem. Biol.* 7:445-452).

Thus, in one aspect, the invention provides recombinant microbial cell modified to exhibit increased biosynthesis of a TCA derivative compared to a wild-type control.

While described above in the context of an exemplary embodiment in which the TCA derivative is a 1,4-butanediol, the recombinant cells and methods described herein can provide TCA derivatives other than 1,4-butanediol. Exemplary alternative TCA derivatives include, for example, succinate, fumarate, malate, glutamate, lysine, threonine, 4-hydroxybutyrate, and products synthesizable from a product of the TCA cycle in one, two, three, four, or five enzymatic steps. In some of these embodiments, one or more enzymes involved in the synthesis of the TCA derivative may be heterologous to the host cell and, therefore, provided recombinantly. Exemplary TCA derivative products and exemplary enzymes involved in the synthesis of the exemplary TCA derivative products are listed in Table 1. For any embodiment in which the identified enzyme is not endogenous to a host cell, the enzyme may be introduced into the host cell to produce a recombinant cell as described herein.

TABLE 1

Exemplary enzymes, enzyme sources, native substrates, and TCA derivative products

| Common Name | Organism | Encoding gene | Accession No.; GI No. | Native Substrate | TCA derivative product | SEQ ID NO |
|---|---|---|---|---|---|---|
| D-arabinose dehydrogenase | | | | | | |
| alcohol dehydrogenase (AraDH) | *Sulfolobus solfataricus* | SSO1300 | NP_342747.1; GI:15898142 | D-arabinose | D-arabinonic acid from D-arabinose | 1 |

TABLE 1-continued

Exemplary enzymes, enzyme sources, native substrates, and TCA derivative products

| Common Name | Organism | Encoding gene | Accession No.; GI No. | Native Substrate | TCA derivative product | SEQ ID NO |
|---|---|---|---|---|---|---|
| D-arabinonate dehydratase | | | | | | |
| arabinonate dehydratase (AraD) | *Sulfolobus solfataricus* | SSO3124 | NP_344435.1; GI:15899830 | D-arabinonic acid | 2-oxo-4(S),5-dihydroxy-pentanoic acid | 6 |
| 2-Keto-3-deoxy-D-arabinonate Dehydratase | | | | | | |
| 2-keto-4-pentenoate hydratase (KdaD) | *Sulfolobus solfataricus* | SSO3118 | NP_344431.1; GI:15899826 | 2-oxo-4(S),5-dihydroxy-pentanoic acid | 2,5-dioxopentanoic acid | 11 |
| 2,5-dioxopentanoate dehydrogenase | | | | | | |
| aldehyde dehydrogenase (DopDH) | *Sulfolobus solfataricus* | SSO3117 | NP_344430.1; GI:15899825 | 2,5-dioxopentanoic acid | 2-oxoglutaric acid | 16 |
| 2,5-dioxovalerate dehydrogenase | | | | | | |
| 2,5-dioxovalerate dehydrogenase (YcbD) | *Bacillus subtilis* | YcbD | NP_388129.1; GI:16077316 | 2,5-dioxopentanoic acid | 2-oxoglutaric acid | 21 |
| D-xylose dehydrogenase | | | | | | |
| D-Xylose dehydrogenase (XylB) | *Caulobacter crescentus* | CC0821 | YP_002516237.1; GI:221233801 | D-xylose | D-xylonolactone | 26 |
| D-xylonolactonase | | | | | | |
| D-xylonolactonase (XylC) | *Caulobacter crescentus* | CC0820 | YP_002516236.1; GI:221233800 | D-xylonolactone | D-xylonic acid | 31 |
| D-xylonate dehydratase | | | | | | |
| D-xylonate dehydratase (XylD) | *Caulobacter crescentus* | CC0819 | NP_419636.1 GI:16125072 | D-xylonic acid | 2-oxo-4(S),5-dihydroxy-pentanoic acid | 36 |
| 2-Keto-3-deoxy-D-arabinonate dehydratase | | | | | | |
| 2-keto-4-pentenoate hydratase (XylX) | *Caulobacter crescentus* | CC0823 | NP_419640.1; GI:16125076 | 2-oxo-4(S),5-dihydroxy-pentanoic acid | 2,5-dioxopentanoic acid | 41 |
| L-arabinose dehydrogenase | | | | | | |
| dehydrogenase (AraE) | *Burkholderia thailandensis* E264 | BTH_II1629 | YP_439823.1; GI:83716868 | L-arabinose | L-arabinonolactone from L-arabinose | 46 |
| L-arabinonolactonase | | | | | | |
| L-arabinonolactonase (AraI) | *Burkholderia thailandensis* E264 | BTH_II1625 | YP_439819.1; GI:83717359 | L-arabinonolactone | L-arabinonic acid | 51 |
| L-arabinonate dehydratase | | | | | | |
| L-arabinonatedehydratase (AraB) | *Burkholderia thailandensis* E264 | BTH_II1632 | YP_439826.1; GI:83718062 | L-arabinonic acid | 2-oxo-4(R),5-dihydroxy-pentanoic acid | 56 |
| 2-Keto-3-deoxy-L-arabinonate Dehydratase | | | | | | |
| dihydrodipicolinate synthase (AraD) | *Burkholderia thailandensis* E264 | BTH_II1630 | YP_439824.1; GI:83717217 | 2-oxo-4(R),5-dihydroxy-pentanoic acid | 2,5-dioxopentanoic acid | 61 |
| D-glucarate dehydratase | | | | | | |
| D-glucarate dehydratase (YcbF) | *Bacillus subtilis* | YcbF | NP_388131.2; GI:255767063 | D-glucaric acid | 4-deoxy-5-keto-D-glucaric acid | 66 |
| D-galactarate dehydratase | | | | | | |
| D-galactarate dehydratase (YcbH) | *Bacillus subtilis* | YcbH | NP_388133.2; GI:255767065 | D-galactaric acid | 4-deoxy-5-keto-D-glucaric acid | 71 |
| 5-dehydro-4-deoxyglucarate dehydratase | | | | | | |
| 5-dehydro-4-deoxyglucarate dehydratase (YcbC) | *Bacillus subtilis* | YcbC | NP_388128.2; GI:255767061 | 4-deoxy-5-keto-D-glucaric acid | 2,5-dioxopentanoic acid | 76 |

TABLE 1-continued

Exemplary enzymes, enzyme sources, native substrates, and TCA derivative products

| Common Name | Organism | Encoding gene | Accession No.; GI No. | Native Substrate | TCA derivative product | SEQ ID NO |
|---|---|---|---|---|---|---|
| Amino acid transporter LysE | | | | | | |
| Amino acid transporter LysE (HypE) | *Pseudomonas putida* | PP_1248 | NP_743408.1; GI:26987983 | 4(R)-hydroxy-L-proline | 4(R)-hydroxy-D-proline | 81 |
| PP_1245 | | | | | | |
| Hypothetical protein of PP_1245 | *Pseudomonas putida* | PP_1245 | NP_743405.1; GI:26987980 | 4(R)-hydroxy-D-proline | 2-carboxy-4(R)-hydroxy-pyrroline | 86 |
| PP_1247 | | | | | | |
| Hypothetical protein of PP_1247 | *Pseudomonas putida* | PP_1247 | NP_743407.1; GI:26987982 | 2-carboxy-4(R)-hydroxy-pyrroline | 2,5-dioxopentanoic acid | 91 |
| PP_1246 | | | | | | |
| Hypothetical protein of PP_1246 | *Pseudomonas putida* | PP_1246 | NP_743406.1; GI:26987981 | 2,5-dioxopentanoic acid | 2-oxoglutaric acid | 93 |
| Alpha-ketoisovalerate decarboxylase | | | | | | |
| alpha-ketoisovalerate decarboxylase | *Lactococcus lactis* | KivD | YP_003353820.1; GI:281491840 | 2,5-dioxopentanoic acid | Succinaldehyde | 98 |
| Alcohol dehydrogenase (YqhD) | | | | | | |
| alcohol dehydrogenase | *E. coli* | yqhD | YP_001459806.1; GI:157162488 | Succinaldehyde | 1,4-butanediol | 103 |

In addition to the enzymes listed in Table 1, homologs of the listed enzymes may be used. Thus, as an alternative to AraDH (SEQ ID NO:1), one may use, for example, any of the polypeptides depicted in SEQ ID NO:2-5; as an alternative to AraD (SEQ ID NO:6), one may use, for example, any of the polypeptides depicted in SEQ ID NO: 7-10; as an alternative to Kda (SEQ ID NO:11), one may use, for example, any of the polypeptides depicted in SEQ ID NO: 12-15; as an alternative to DopDH (SEQ ID NO:16), one may use, for example, any of the polypeptides depicted in SEQ ID NO:17-20; as an alternative to YcbD (SEQ ID NO:21), one may use, for example, any of the polypeptides depicted in SEQ ID NO:22-25; as an alternative to XylB (SEQ ID NO:26), one may use, for example, any of the polypeptides depicted in SEQ ID NO:27-30; as an alternative to XylC (SEQ ID NO:31), one may use, for example, any of the polypeptides depicted in SEQ ID NO:32-35; as an alternative to XylD (SEQ ID NO:36), one may use, for example, any of the polypeptides depicted in SEQ ID NO:37-40; as an alternative to XylX (SEQ ID NO:41), one may use, for example, any of the polypeptides depicted in SEQ ID NO:42-45; as an alternative to AraE (SEQ ID NO:46), one may use, for example, any of the polypeptides depicted in SEQ ID NO:47-50; as an alternative to AraI (SEQ ID NO:51), one may use, for example, any of the polypeptides depicted in SEQ ID NO:52-55; as an alternative to AraB (SEQ ID NO:56), one may use, for example, any of the polypeptides depicted in SEQ ID NO:57-60; as an alternative to AraD (SEQ ID NO:61), one may use, for example, any of the polypeptides depicted in SEQ ID NO:62-65; as an alternative to YcbF (SEQ ID NO:66), one may use, for example, any of the polypeptides depicted in SEQ ID NO:67-70; as an alternative to YcbH (SEQ ID NO:71), one may use, for example, any of the polypeptides depicted in SEQ ID NO:72-75; as an alternative to YcbC (SEQ ID NO:76), one may use, for example, any of the polypeptides depicted in SEQ ID NO:77-80; as an alternative to HypE (SEQ ID NO:81), one may use, for example, any of the polypeptides depicted in SEQ ID NO:82-85; as an alternative to PP_1245 (SEQ ID NO:86), one may use, for example, any of the polypeptides depicted in SEQ ID NO:87-90; as an alternative to PP_1247 (SEQ ID NO:91), one may use, for example, the polypeptide depicted in SEQ ID NO:92; as an alternative to PP_1246 (SEQ ID NO:93), one may use, for example, any of the polypeptides depicted in SEQ ID NO:94-97; as an alternative to alpha-ketoisovalerate decarboxylase (SEQ ID NO:98), one may use, for example, any of the polypeptides depicted in SEQ ID NO:99-102; as an alternative to YqhD (SEQ ID NO:103), one may use, for example, any of the polypeptides depicted in SEQ ID NO:104-107.

In some cases, the wild-type control may be unable to produce the TCA derivative and, therefore, an increase in the biosynthesis of a particular product may reflect any measurable biosynthesis of that product. In certain embodiments, an increase in the biosynthesis of a TCA derivative can include biosynthesis sufficient for a culture of the microbial cell to accumulate the TCA derivative to a predetermine concentration.

The predetermined concentration may be any predetermined concentration of the product suitable for a given application. Thus, a predetermined concentration may be, for example, a concentration of at least 0.1 g/L such as, for example, at least 0.25 g/L, at least 0.5 g/L, at least 1.0 g/L, at least 2.0 g/L, at least 3.0 g/L, at least 4.0 g/L, at least 5.0 g/L, at least 6.0 g/L, at least 7.0 g/L, at least 8.0 g/L, at least 9.0 g/L, at least 10 g/L, at least 20 g/L, at least 50 g/L, at least 100 g/L, or at least 200 g/L.

While described above in the context of an exemplary embodiment in which the host cell is *E. coli*, the recombinant cells described herein can be constructed, and the methods of making and using the recombinant cells can be performed, using any suitable host cell.

Thus, the recombinant cell can be, or be derived from, any suitable microbe including, for example, a prokaryotic microbe or a eukaryotic microbe. As used herein, the term "or derived from" in connection with a microbe simply allows for the "host cell" to possess one or more genetic modifications before being modified to exhibit the indicated increased biosynthetic activity. Thus, the term "recombinant cell" encompasses a "host cell" that may contain nucleic acid material from more than one species before being modified to exhibit the indicated biosynthetic activity.

In some embodiments, the host cell may be selected to possess one or more natural physiological activities. For example, the host cell may be photosynthetic (e.g., cyanobacteria) or may be cellulolytic (e.g., *Clostridium cellulolyticum*).

In some embodiments, the recombinant cell may be, or be derived from, a eukaryotic microbe such as, for example, a fungal cell. In some of these embodiments, the fungal cell may be, or be derived from, a member of the Saccharomycetaceae family such as, for example, *Saccharomyces cerevisiae, Candida rugosa*, or *Candida albicans*.

In other embodiments, the recombinant cell may be, or be derived from, a prokaryotic microbe such as, for example, a bacterium. In some of these embodiments, the bacterium may be a member of the phylum Protobacteria. Exemplary members of the phylum Protobacteria include, for example, members of the Enterobacteriaceae family (e.g., *Escherichia coli*) and, for example, members of the Pseudomonaceae family (e.g., *Pseudomonas putida*). In other cases, the bacterium may be a member of the phylum Firmicutes. Exemplary members of the phylum Firmicutes include, for example, members of the Bacillaceae family (e.g., *Bacillus subtilis*), members of the Clostridiaceae family (e.g., *Clostridium cellulolyticum*) and, for example, members of the Streptococcaceae family (e.g., *Lactococcus lactis*). In other cases, the bacterium may be a member of the phylum Cyanobacteria.

Figure 2:
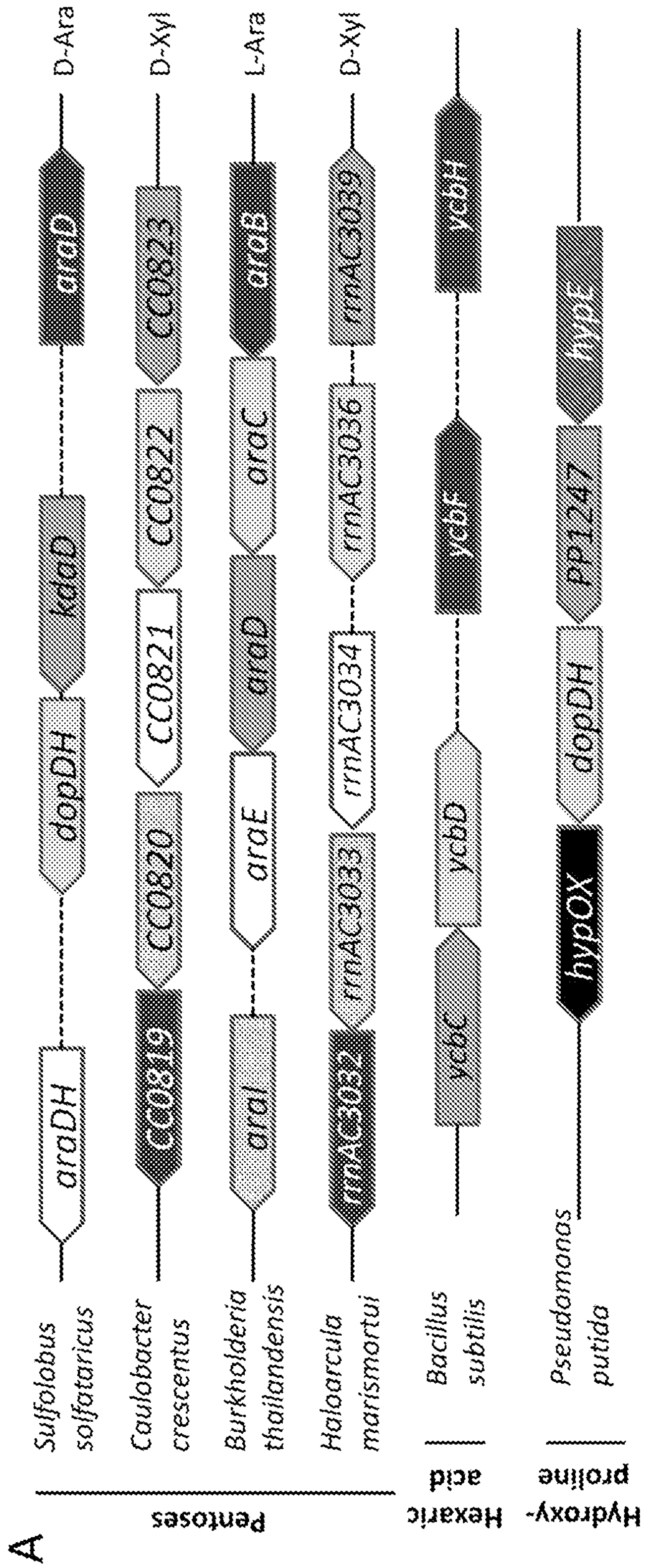
FIG. 2. A, scheme of the organization of conserved genetic clusters involved in the pentose, hexaric acid, and hydroxyproline degradation. Analogous functions are indicated in the same degree of shading. Coding region sizes and distances are not to scale. Protein family numbers are displayed below each coding region according to Clusters of Orthologous Groups of proteins classification system. The coding regions indicated in white or gray encode the following proteins: araA, transcriptional regulator; araF-araH, 1-Ara ABC transporter (periplasmic 1-Ara binding protein, ATP-binding protein, permease); rrnAC3038, heat shock protein X; ycbE, glucarate/galactarate permease; ycbG, transcriptional regulator; PP1249, hydroxyproline permease. B, schematic representation of the convergence of catabolic pathways for pentoses, hexaric acids, and hydroxyproline at the level of 2,5-dioxopentanoate. Enzymatic activities are indicated by their EC number. Dashed lines indicate proposed spontaneous reactions.
Figure 2:
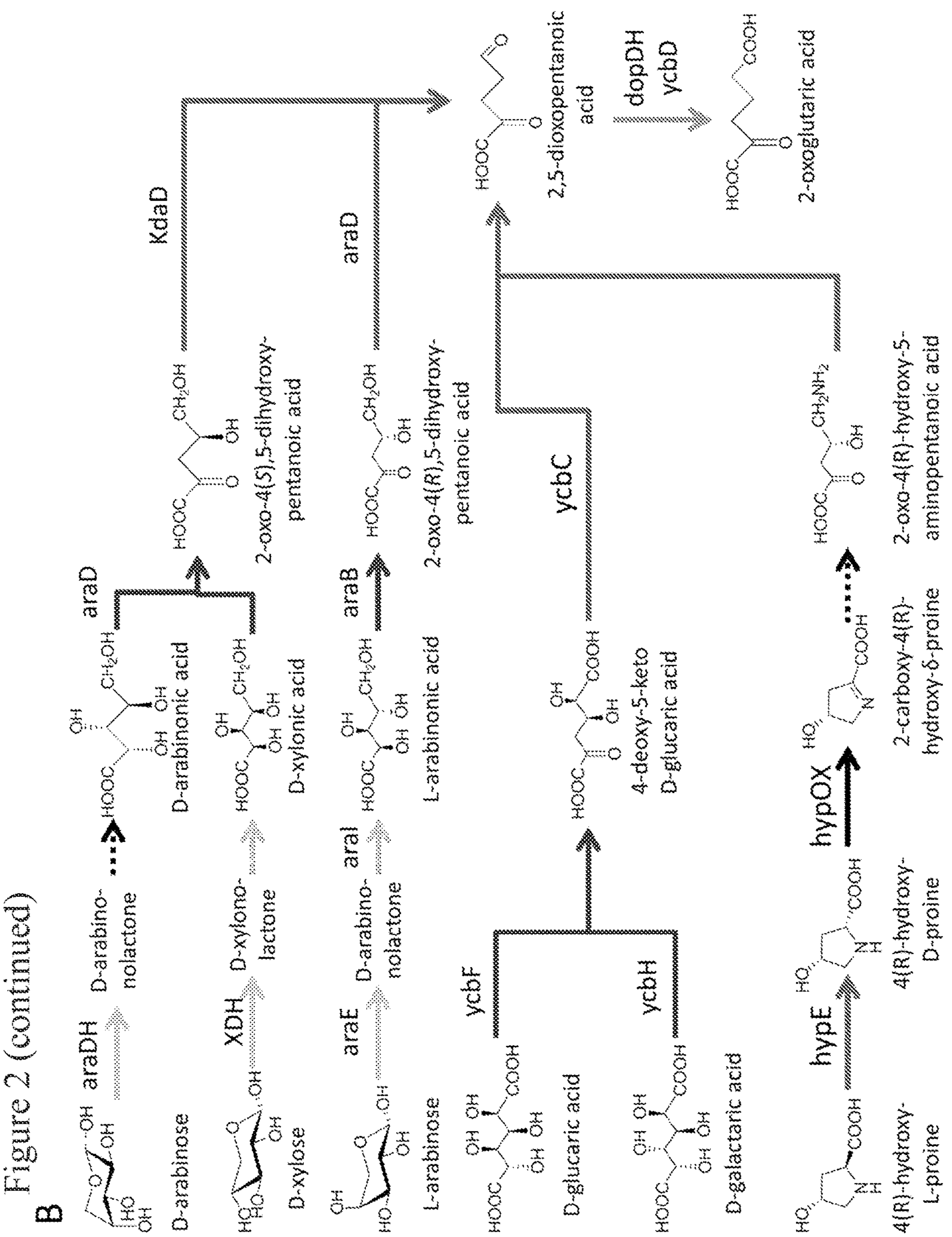
Figure 3:
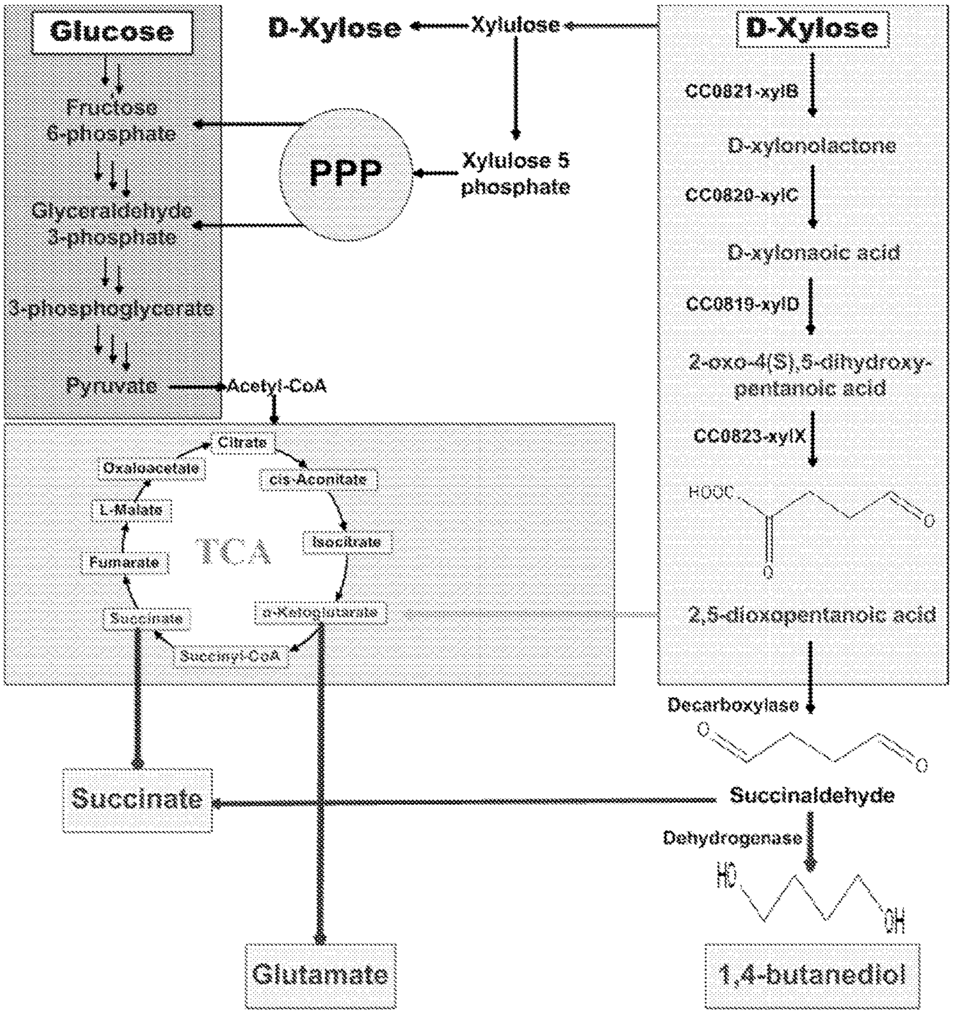
FIG. 3. An engineered 1,4-butanediol synthetic pathway in *E. coli*.

In some embodiments, the increased biosynthesis of the TCA derivative compared to a wild-type control can include an increase in activity of one or more enzymes involved in the metabolism of the carbon source (e.g., xylose or arabinose). Such enzymes may be found in the proteome of microbes such as, for example, *Sulfolobus solfataricus, Caulobacter crescentus, Burkholderia thailandensis, Haloarcula marismortui, Bacillus subtilis*, and *Pseudomonas putida*. Exemplary enzymes, shown in the context of their native metabolic pathways, are shown in FIG. 2. So, for example, increased biosynthesis of the TCA derivative can include an increase in activity of one or more enzymes involved in the metabolism of D-xylose in *Caulobacter crescentus* such as, for example, xylose dehydrogenase (FIG. 2, CC0821) activity, xylonolactonase (FIG. 2, CC0819) activity, xylonate dehydrogenase (FIG. 2, CC0822) activity, and 2-keto-3-deoxyaldonic acid dehydratase (FIG. 2, CC0823) activity compared to the wild-type control.

In some embodiments, the increased biosynthesis of the TCA derivative compared to a wild-type control can further include an increase in benzoylformate decarboxylase activity and an increase in alcohol dehydrogenase activity. In some of these embodiments, the benzoylformate decarboxylase can include BFD of *Pseudomonas putida*. In some of these embodiments, the alcohol dehydrogenase can include yqhD of *E. coli.*

In some embodiments, the increased biosynthesis of the TCA derivative compared to a wild-type control can further include an increase in decarboxylase activity and an increase in alcohol dehydrogenase activity. In some of these embodiments, the decarboxylase can include KIVD of *Lactococcus lactis*. In some of these embodiments, the alcohol dehydrogenase can include yqhD of *E. coli*. See, e.g., Example 2 and FIGS. 12-14.

In some embodiments, the recombinant cell can include an engineered metabolic pathway designed to permit the recombinant cell to increase its consumption of a particular carbon source compared to a wild-type control. Exemplary metabolic pathways are illustrated in, for example, FIG. 6 through FIG. 11. Accordingly, exemplary carbon sources include, for example, arabinose, xylose, arabinose, glucaric acid, galactaric acid, or hydroxyproline. In other embodiments, the recombinant cell may be designed to consume a uronic acid such as, for example, galacturonic acid and/or glucuronic acid as a carbon source. In such embodiments, a heterologous polynucleotide that encodes a uronate dehydrogenase enzyme may be introduced into the recombinant cell to confer to the recombinant cell the ability to convert uronic acid to aldonic acid. In still other embodiments, the recombinant cell can utilize a carbon source that includes, for example, glucose, cellulose, galacturonic acid, glucuronic acid, $CO_2$, or glycerol. In some of these embodiments, the recombinant cell may be further modified to convert the carbon source (e.g., glucose) to one or more of the carbon sources (e.g., xylose and/or a hexaric acid such as, e.g., glucaric acid) that is an entry point to one or more of the engineered pathways described herein.

Figure 6:
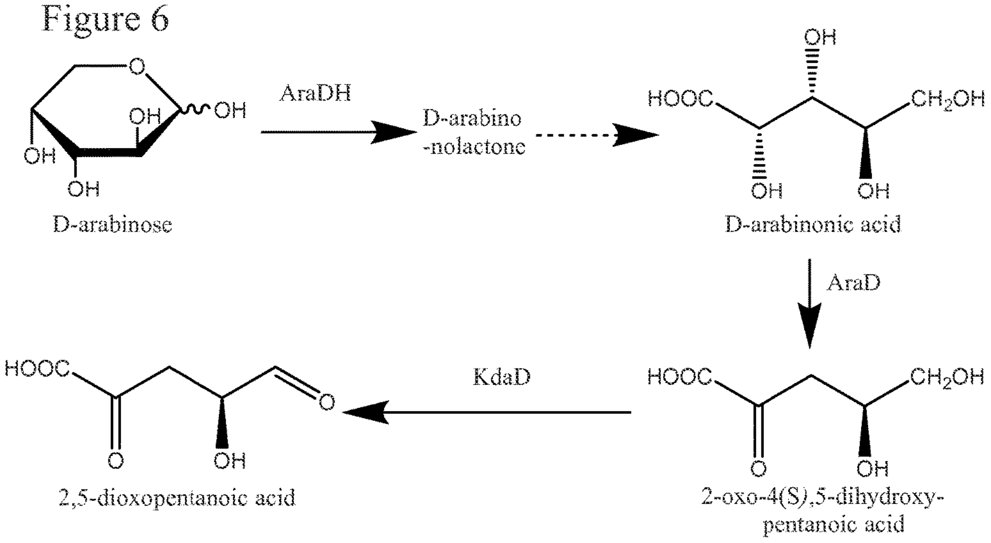
FIG. 6. An exemplary engineered metabolic pathway from D-arabinose to 2,5-dioxopentanoic acid.

FIG. 6 shows an exemplary metabolic pathway that permits a recombinant cell to use D-arabinose as a carbon source for the production of 2,5-dioxopentanoic acid. In this example, the recombinant cell can include an enzyme that can convert D-arabinose into D-arabinolactone such as, for example, a pentose dehydrogenase. One example of a suitable pentose dehydrogenase includes AraDH from *Sulfolobus solfataricus*. The pentose dehydrogenase can provide catalytic conversion of D-arabinose into D-arabinolactone that is, for example, at least 110% greater than that exhibited by a wild-type control.

The exemplary metabolic pathway illustrated in FIG. 6 also includes an enzyme that can convert D-arabinonic acid to 2-oxo-4(S),5-dihydroxy-pentanoic acid such as, for example, an aldonic acid dehydratase. One example of a suitable aldonic acid dehydratase includes AraD from *Sulfolobus solfataricus*. The aldonic acid dehydratase can provide catalytic conversion of D-arabinonic acid into 2-oxo-4(S),5-dihydroxy-pentanoic acid that is, for example, at least 110% greater than that exhibited by a wild-type control.

The exemplary metabolic pathway illustrated in FIG. 6 also includes an enzyme that can convert 2-oxo-4(S),5-dihydroxy-pentanoic acid to 2,5-dioxopentanoic acid such as, for example, a 2-keto-3-deoxyaldonic acid dehydratase. On example of a suitable 2-keto-3-deoxyaldonic acid dehydratase includes KdaD from *Sulfolobus solfataricus*. The 2-keto-3-deoxyaldonic acid dehydratase can provide catalytic conversion of 2-oxo-4(S),5-dihydroxy-pentanoic acid to 2,5-dioxopentanoic acid that is, for example, at least 110% greater than that exhibited by a wild-type control.

Figure 7:
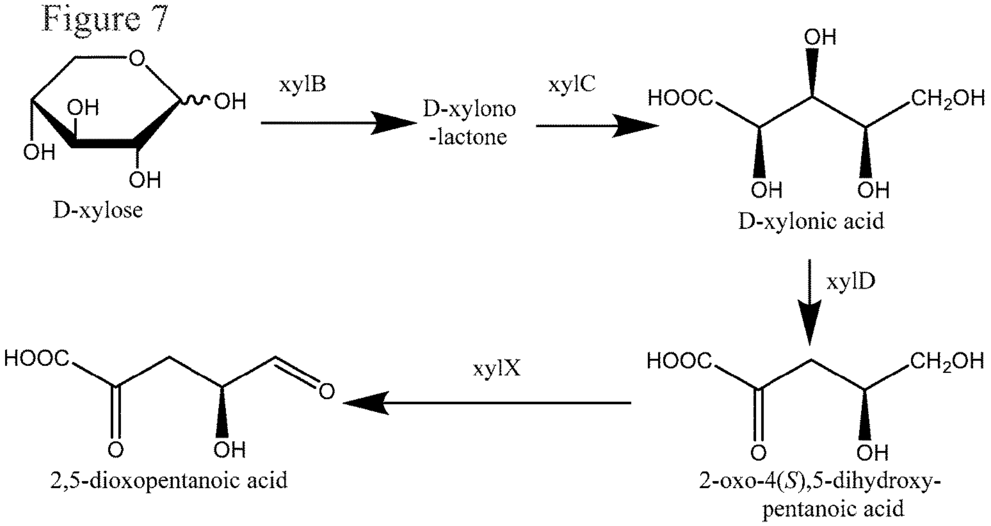
FIG. 7. An exemplary engineered metabolic pathway from D-xylose to 2,5-dioxopentanoic acid.

FIG. 7 shows an exemplary metabolic pathway that permits a recombinant cell to use D-xylose as a carbon source for the production of 2,5-dioxopentanoic acid. In this example, the recombinant cell can include an enzyme that can convert D-xylose to D-xylonolactone such as, for example, a pentose dehydrogenase. Exemplary suitable pentose dehydrogenases include XylB from *Caulobacter crescentus* or rrnAC3034 from *Haloarcula marismortui*. The pentose dehydrogenase can provide catalytic conversion of D-xylose to D-xylonolactone that is, for example, at least 110% greater than that exhibited by a wild-type control.

The exemplary metabolic pathway illustrated in FIG. 7 also includes an enzyme that can convert D-xylonolactone to D-xylonic acid such as, for example, a pentonolactonase. Exemplary suitable pentonolactonases include XylC from *Caulobacter crescentus* or rrnAC3033 from *Haloarcula marismortui*. The pentonolactonase can provide catalytic conversion of D-xylonolactone to D-xylonic acid that is, for example, at least 110% greater than that exhibited by a wild-type control.

The exemplary metabolic pathway illustrated in FIG. 7 also includes an enzyme that can convert D-xylonic acid to 2-oxo-4(S),5-dihydroxy-pentanoic acid such as, for example, an aldonic acid dehydratase. Exemplary suitable aldonic acid dehydratases include XylD front *Caulobacter crescentus* or rrnAC3032 from *Haloarcula marismortui*. The aldonic acid dehydratase can provide catalytic conversion of D-xylonic acid into 2-oxo-4(S),5-dihydroxy-pentanoic acid that is, for example, at least 110% greater than that exhibited by a wild-type control.

The exemplary metabolic pathway illustrated in FIG. 7 also includes an enzyme that can convert 2-oxo-4(S),5-dihydroxy-pentanoic acid to 2,5-dioxopentanoic acid such as, for example, a 2-keto-3-deoxyaldonic acid dehydratase. Exemplary suitable 2-keto-3-deoxyaldonic acid dehydratases include XylX from *Caulobacter crescentus* or rrnAC3039 from *Haloarcula marismortui*. The 2-keto-3-deoxyaldonic acid dehydratase can provide catalytic conversion of 2-oxo-4(S),5-dihydroxy-pentanoic acid to 2,5-dioxopentanoic acid that is, for example, at least 110% greater than that exhibited by a wild-type control.

Figure 8:
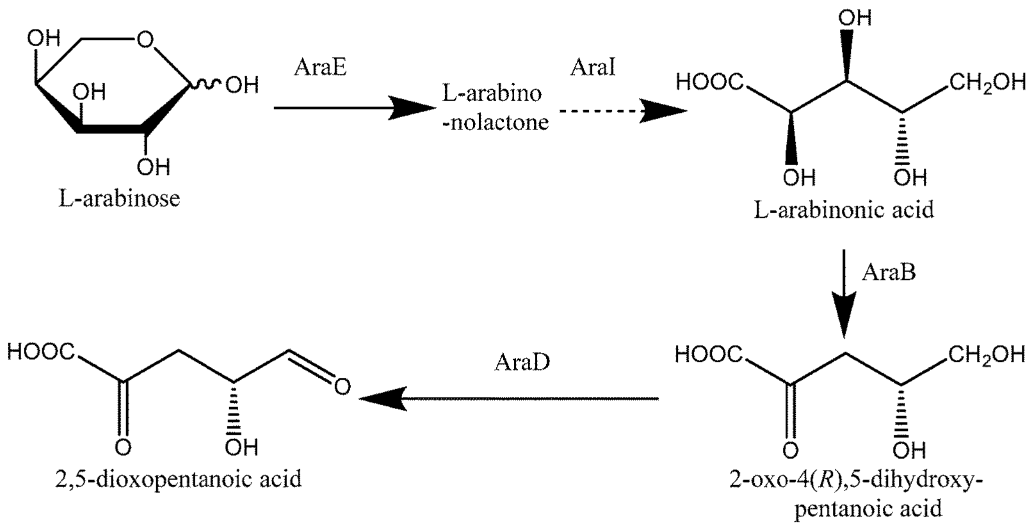
FIG. 8. An exemplary engineered metabolic pathway from L-arabinose to 2,5-dioxopentanoic acid.

FIG. 8 shows an exemplary metabolic pathway that permits a recombinant cell to use L-arabinose as a carbon source for the production of 2,5-dioxopentanoic acid. In this example, the recombinant cell can include an enzyme that can convert L-arabinose to L-arabinolactone such as, for example, a pentose dehydrogenase. One example of a suitable pentose dehydrogenase includes AraE from *Burkholderia thailandensis*. The pentose dehydrogenase can provide catalytic conversion of L-arabinose to L-arabinolactone that is, for example, at least 110% greater than that exhibited by a wild-type control.

The exemplary metabolic pathway illustrated in FIG. 8 also includes an enzyme that can convert L-arabinolactone to L-arabinonic acid such as, for example, a pentonolactonase. One example of a suitable pentonolactonase includes AraI from *Burkholderia thailandensis*. The pentonolactonase can provide catalytic conversion of L-arabinolactone to L-arabinonic acid that is, for example, at least 110% greater than that exhibited by a wild-type control.

The exemplary metabolic pathway illustrated in FIG. 8 also includes an enzyme that can convert L-arabinonic acid to 2-oxo-4(R),5-dihydroxy-pentanoic acid such as, for example, an aldonic acid dehydratase. One example of a suitable aldonic acid dehydratase includes AraB from *Burkholderia thailandensis*. The aldonic acid dehydratase can provide catalytic conversion of L-arabinonic acid to 2-oxo-4(R),5-dihydroxy-pentanoic acid that is, for example, at least 110% greater than that exhibited by a wild-type control.

The exemplary metabolic pathway illustrated in FIG. 8 also includes an enzyme that can convert 2-oxo-4(R),5-dihydroxy-pentanoic acid to 2,5-dioxopentanoic acid such as, for example, a 2-keto-3-deoxyaldonic acid dehydratase. One example of a suitable 2-keto-3-deoxyaldonic acid dehydratase includes AraD from *Burkholderia thailandensis*. The 2-keto-3-deoxyaldonic acid dehydratase can provide catalytic conversion of 2-oxo-4(R),5-dihydroxy-pentanoic acid to 2,5-dioxopentanoic acid that is, for example, at least 110% greater than that exhibited by a wild-type control.

Figure 9:
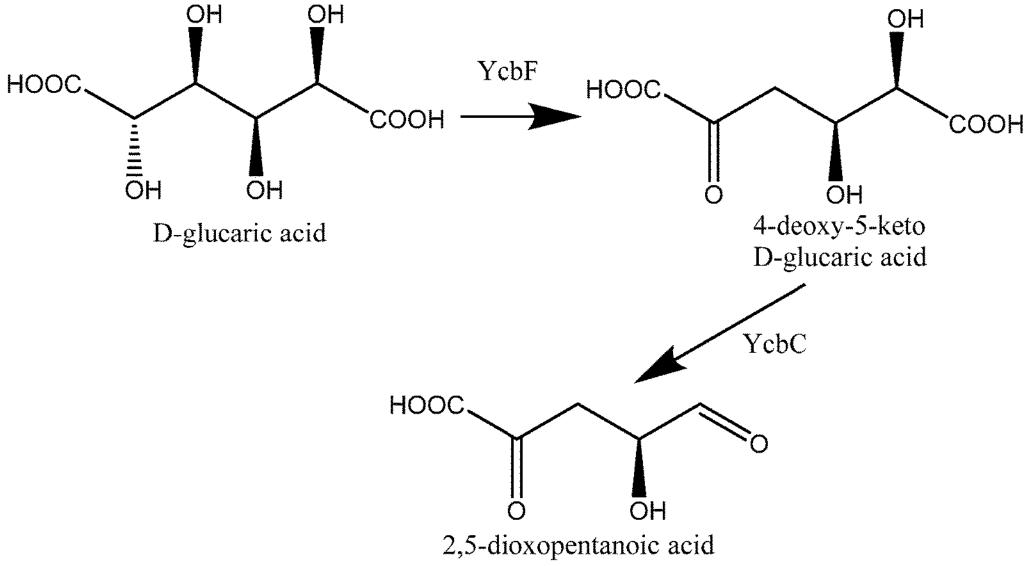
FIG. 9. An exemplary engineered metabolic pathway from D-glucaric acid to 2,5-dioxopentanoic acid.

FIG. 9 shows an exemplary metabolic pathway that permits a recombinant cell to use D-glucaric acid as a carbon source for the production of 2,5-dioxopentanoic acid. In this example, the recombinant cell can include an enzyme that can convert D-glucaric acid to 4-deoxy-5-keto-D-glucaric acid such as, for example, an aldonic acid dehydratase. Suitable exemplary aldonic acid dehydratases include YcbF from *Bacillus subtilis*. The aldonic acid dehydratase can provide catalytic conversion of D-glucaric acid to 4-deoxy-5-keto-D-glucaric acid that is, for example, at least 110% greater than that exhibited by a wild-type control.

The exemplary metabolic pathway illustrated in FIG. 9 also includes an enzyme that can convert 4-deoxy-5-keto-D-glucaric acid to 2,5-dioxopentanoic acid such as, for example, a 2-keto-3-deoxyaldonic acid dehydratase. One example of a suitable 2-keto-3-deoxyaldonic acid dehydratase includes YcbC from *Bacillus subtilis*. The 2-keto-3-deoxyaldonic acid dehydratase can provide catalytic conversion of 4-deoxy-5-keto-D-glucaric acid to 2,5-dioxopentanoic acid that is, for example, at least 110% greater than that exhibited by a wild-type control.

Figure 10:
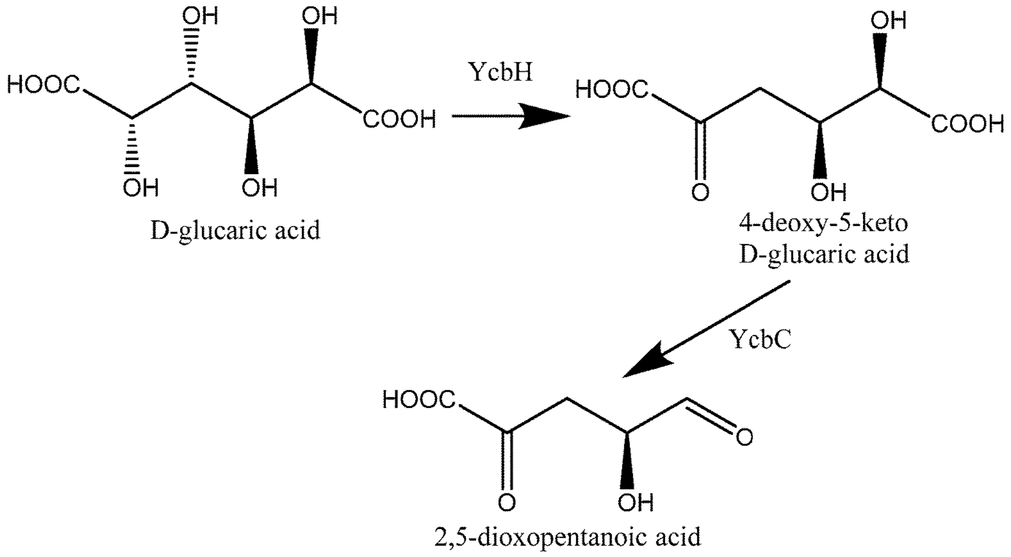
FIG. 10. An exemplary engineered metabolic pathway from D-galactaric acid to 2,5-dioxopentanoic acid.

FIG. 10 shows an exemplary metabolic pathway that permits a recombinant cell to use D-galactaric acid as a carbon source for the production of 2,5-dioxopentanoic acid. In this example, the recombinant cell can include an enzyme that can convert D-galactaric acid to 4-deoxy-5-keto-D-glucaric acid such as, for example, an aldonic acid dehydratase. Suitable exemplary aldonic acid dehydratases include YcbH from *Bacillus subtilis*. The aldonic acid dehydratase can provide catalytic conversion of D-galactaric acid to 4-deoxy-5-keto-D-glucaric acid that is, for example, at least 110% greater than that exhibited by a wild-type control.

The exemplary metabolic pathway illustrated in FIG. 9 also includes an enzyme that can convert 4-deoxy-5-keto-D-glucaric acid to 2,5-dioxopentanoic acid such as, for example, a 2-keto-3-deoxyaldonic acid dehydratase. One example of a suitable 2-keto-3-deoxyaldonic acid dehydratase includes YcbC from *Bacillus subtilis*. The 2-keto-3-deoxyaldonic acid dehydratase can provide catalytic conversion of 4-deoxy-5-keto-D-glucaric acid to 2,5-dioxopentanoic acid that is, for example, at least 110% greater than that exhibited by a wild-type control.

Figure 11:
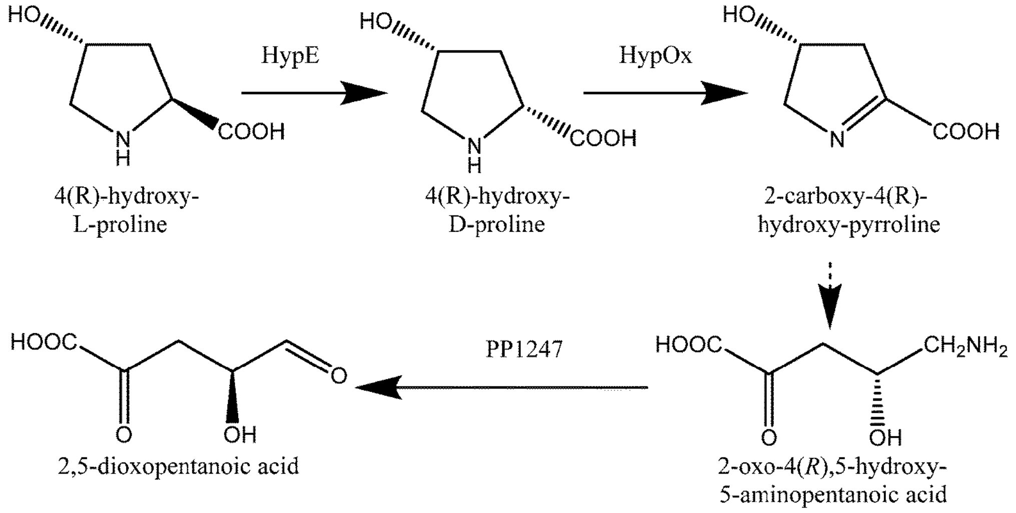
FIG. 11. An exemplary engineered metabolic pathway from 4(R)-hydroxy-L-proline to 2,5-dioxopentanoic acid.

FIG. 11 shows an exemplary metabolic pathway that permits a recombinant cell to use 4(R)-hydroxy-D-proline as a carbon source for the production of 2,5-dioxopentanoic acid. In this example, the recombinant cell can include an enzyme that can convert 4(R)-hydroxy-D-proline to 4(R)-hydroxy-D-proline. One suitable exemplary enzyme for this embodiment includes, amino acid transporter LysE (HypE) from *Pseudomonas*. The enzyme can provide catalytic conversion of 4(R)-hydroxy-D-proline to 4(R)-hydroxy-D-proline that is, for example, at least 110% greater than that exhibited by a wild-type control.

The exemplary metabolic pathway illustrated in FIG. 11 also includes an enzyme that can convert 4(R)-hydroxy-D-proline to 2-carboxy-4(R)-hydroxy-δ-pyrroline. One suitable exemplary enzyme for this embodiment includes, for example, HypOX from *Pseudomonas*. The enzyme can provide catalytic conversion of 4(R)-hydroxy-D-proline to 2-carboxy-4(R)-hydroxy-δ-pyrroline that is, for example, at least 110% greater than that exhibited by a wild-type control.

The exemplary metabolic pathway illustrated in FIG. 11 also includes an enzyme that can convert 2-oxo-4(R)-5-aminopentanoic acid to 2,5-dioxopentanoic acid such as, for example, a 2-keto-3-deoxyaldonic acid dehydratase. One exemplary 2-keto-3-deoxyaldonic acid dehydratase includes PP1247 from *Pseudomonas*. The 2-keto-3-deoxyaldonic acid dehydratase can provide catalytic conversion of 2-oxo-4(R)-5-aminopentanoic acid to 2,5-dioxopentanoic acid that is, for example, at least 110% greater than that exhibited by a wild-type control.

The recombinant cell can be engineered to convert the 2,5-dioxopentanoic acid to any desirable TCA derivative. In some embodiments, the recombinant cell can include an α-ketoglutaric semialdehyde dehydrogenase to shunt the 2,5-dioxopentanoic acid into the TCA cycle. In this manner, TCA cycle derivatives such as, for example, succinate, fumarate, malate, glutamate, lysine, threonine, 4-hydroxybutyrate may be produced.

Figure 4:
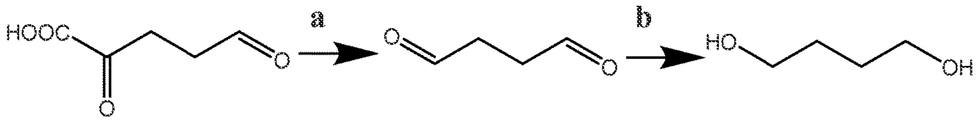
FIG. 4. An exemplary engineered metabolic pathway from 2,5-dioxopentanoic acid to 1,4-butanediol.

In some embodiments, however, the recombinant cell may be further modified to possess a metabolic pathway for the conversion of 2,5-dioxopentanoic acid to 1,4-butanediol. Exemplary metabolic pathways are illustrated, for example, in FIG. 4 and FIG. 5. The exemplary pathway illustrated in FIG. 4 includes an enzyme that can convert 2,5-dioxopentonoic acid to succinaldehyde such as, for example, a 2-ketoacid decarboxylase or a 2-oxoglutarate decarboxylase. Suitable exemplary enzymes include, for example, Kivd, BFD, and IPDC. The exemplary pathway illustrated in FIG. 4 also includes an enzyme that can convert succinaldehyde to 1,4-butanediol such as, for example, an alcohol dehydrogenase. Suitable exemplary alcohol dehydrogenases include YqhD, ADH6, YjgB, and YahK.

Figure 5:
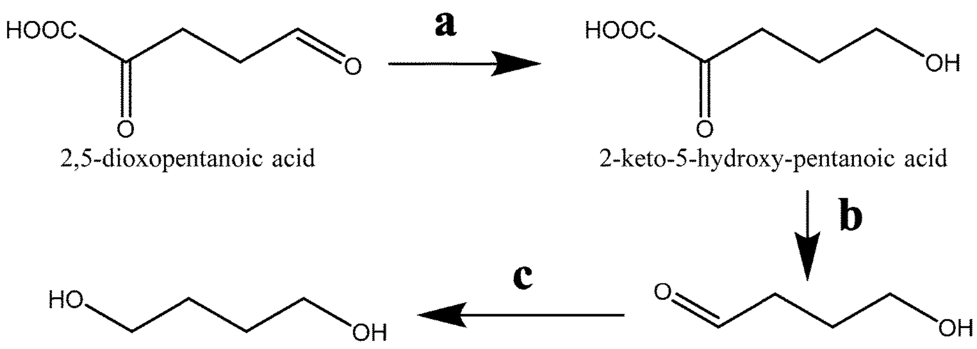
FIG. 5. An exemplary engineered metabolic pathway from 2,5-dioxopentanoic acid to 1,4-butanediol.

The exemplary pathway illustrated in FIG. 5 includes an enzyme that can convert 2,5-dioxopentonoic acid to 2-keto-5-hydroxy-pentonate such as, for example, an alcohol dehydrogenase. Here again, suitable exemplary alcohol dehydrogenases include, for example, YqhD, ADH6, YjgB, and YahK. The exemplary pathway illustrated in FIG. 5 includes an enzyme that can convert 2-keto-5-hydroxy-pentonate to 4-hydroxy-1-butyraldehyde such as, for example, a 2-ketoacid decarboxylase or a 2-oxoglutarate decarboxylase. Suitable exemplary enzymes include, for example, Kivd, BFD, and IPDC. The exemplary pathway illustrated in FIG. 5 includes conversion of 4-hydroxy-1-butyraldehyde into 1,4-butanediol. This conversion may be catalyzed by an alcohol dehydrogenase such as, for example, YqhD, ADH6, YjgB, and YahK. For the metabolic pathway illustrated in FIG. 5, therefore, the recombinant cell can include one or more alcohol dehydrogenases.

In some embodiments, the host cell can include one or more genetic modifications to reduce endogenous metabolism of the carbon source so that metabolism of the carbon source is directed toward the production of the TCA derivative. For example, in embodiments in which the carbon source is xylose and the host cell is *E. coli*, the host cell can include one or more modifications to decrease endogenous metabolism of xylose. In the case of *E. coli*, such modifications can include for example, a decrease in α-ketoglutaric semialdehyde dehydrogenase activity, aldolase activity, and/or 2-keto-3-deoxy gluconate aldolase activity. Such modifications can include modifications to coding regions of, or regulatory regions that control expression of, xylA, yjhH, and/or yagE. Such modifications can include, for example, a deletion of a sufficient amount of one or more coding regions that the enzymatic activity is reduced.

As used herein, the terms "activity" with regard to particular enzyme refers to the ability of a polypeptide, regardless of its common name or native function, to catalyze the conversion of the enzyme's substrate to a product, regardless of whether the "activity" as less than, equal to, or greater than the native activity of the identified enzyme. Methods for measuring the biosynthetic activities of cells are routine and well known to those of ordinary skill in the art.

As used herein, an increase in catalytic activity can be quantitatively measured and described as a percentage of the catalytic activity of an appropriate wild-type control. The catalytic activity exhibited by a genetically-modified polypeptide can be, for example, at least 110%, at least 125%, at least 150%, at least 175%, at least 200% (two-fold), at least 250%, at least 300% (three-fold), at least 400% (four-fold), at least 500% (five-fold), at least 600% (six-fold), at least 700% (seven-fold), at least 800% (eight-fold), at least 900% (nine-fold), at least 1000% (10-fold), at least 2000% (20-fold), at least 3000% (30-fold), at least 4000% (40-fold), at least 5000% (50-fold), at least 6000% (60-fold), at least 7000% (70-fold), at least 8000% (80-fold), at least 9000% (90-fold), at least 10,000% (100-fold), or at least 100,000% (1000-fold) of the activity of an appropriate wild-type control.

Alternatively, an increase in catalytic activity may be expressed as at an increase in $k_{cat}$ such as, for example, at least a two-fold increase, at least a three-fold increase, at least a four-fold increase, at least a five-fold increase, at least a six-fold increase, at least a seven-fold increase, at least an eight-fold increase, at least a nine-fold increase, at least a 10-fold increase, at least a 15-fold increase, or at least a 20-fold increase in the $k_{cat}$ value of the enzymatic conversion.

An increase in catalytic activity also may be expressed in terms of a decrease in $K_m$ such as, for example, at least a two-fold decrease, at least a three-fold decrease, at least a four-fold decrease, at least a five-fold decrease, at least a six-fold decrease, at least a seven-fold decrease, at least an eight-fold decrease, at least a nine-fold decrease, at least a 10-fold decrease, at least a 15-fold decrease, or at least a 20-fold decrease in the $K_m$ value of the enzymatic conversion.

A decrease in catalytic activity can be quantitatively measured and described as a percentage of the catalytic activity of an appropriate wild-type control. The catalytic activity exhibited by a genetically-modified polypeptide can be, for example, no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, no more than 5%, no more than 4%, no more than 3%, no more than 2%, no more than 1% of the activity, or 0% of the activity of a suitable wild-type control.

Alternatively, a decrease in catalytic activity can be expressed as an appropriate change in a catalytic constant. For example, a decrease in catalytic activity may be expressed as at a decrease in $k_{cat}$ such as, for example, at least a two-fold decrease, at least a three-fold decrease, at least a four-fold decrease, at least a five-fold decrease, at least a six-fold decrease, at least a seven-fold decrease, at least an eight-fold decrease, at least a nine-fold decrease, at least a 10-fold decrease, at least a 15-fold decrease, or at least a 20-fold decrease in the $k_{cat}$ value of the enzymatic conversion.

A decrease in catalytic activity also may be expressed in terms of an increase in $K_m$ such as, for example, an increase in $K_m$ of at least two-fold, at least three-fold, at least four-fold, at least five-fold, at least six-fold, at least seven-fold, at least an eight-fold, at least nine-fold, at least 10-fold, at least 15-fold, at least 20-fold, at least 25-fold, at least 30-fold, at least 35-fold, at least 40-fold, at least 45-fold, at least 50-fold, at least 75-fold, at least 100-fold, at least 150-fold, at least 200-fold, at least 230-fold, at least 250-fold, at least 300-fold, at least 350-fold, or at least 400-fold.

Thus, in another aspect, we describe herein methods for biosynthesis of a TCA derivative. Generally, the methods includes incubating a recombinant cell as described herein in medium that includes a carbon source under conditions effective for the recombinant cell to produce the TCA derivative. The carbon source can include, for example, saccharides (e.g., xylose, arabinose, glucose, cellulose), a uronic acid (e.g., galacturonic acid or glucuronic acid), $CO_2$, glycerol, or a native substrate of an enzyme that is part of the engineered metabolic pathway. Exemplary native substrates of exemplary enzymes are shown in Table 1 and include, for example, glucaric acid, galactaric acid, hydroxyproline, arabinonic acid, 2-oxo-4(S),5-dihydroxy-pentanoic acid, 2-oxo-4(R),5-dihydroxy-pentanoic acid, 2,5-dioxopentanoic acid, xylonolactone, xylonic acid, arabinonolactone, 4-deoxy-5-keto-D-glucaric acid, 4(R)-hydroxy-L-proline, 4(R)-hydroxy-D-proline, 2-carboxy-4(R)-hydroxy-pyrroline, 2,5-dioxopentanoic acid, succinaldehyde.

In yet another aspect, we describe herein methods for introducing a heterologous polynucleotide into cell so that the host cell exhibits an increased ability to convert a carbon source to a TCA derivative. The heterologous polynucleotide can encode a polypeptide operably linked to a promoter so that modified cell catalyzes conversion of the carbon source to the TCA derivative. In some of these embodiments, the carbon source can include xylose. The host cells for such methods can include, for example, any of the microbial species identified above with regard to the recombinant cells described herein.

In some embodiments, the heterologous polynucleotide may be inserted into a vector. A vector is a replicating polynucleotide such as, for example, a plasmid, phage, or cosmid, to which another polynucleotide may be inserted so as to bring about the replication of the inserted polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989). A vector can permit, for example, further cloning—i.e., a cloning vector—or expression of the polypeptide encoded by the coding region—i.e., an expression vector. The term vector includes, but is not limited to, plasmid vectors, viral vectors, cosmid vectors, or artificial chromosome vectors. In one embodiment, the vector is a plasmid. Selection of a vector can depend upon a variety of desired characteristics in the resulting construct, such as a selection marker, vector replication rate, and the like.

An expression vector optionally includes regulatory sequences operably linked to the coding region. The polynucleotides described herein are not limited by the use of any particular promoter, and a wide variety of promoters are known. Promoters act as regulatory signals that bind RNA polymerase in a cell to initiate transcription of a downstream (3' direction) coding region. The promoter used can be a constitutive or an inducible promoter. It can be, but need not be, heterologous with respect to the host cell. Exemplary promoters include, for example, trp, tac, and T7.

"Coding sequence" or "coding region" refers to a nucleotide sequence that encodes a polypeptide and, when placed under the control of appropriate regulatory sequences, expresses the encoded polypeptide. The boundaries of a coding region are generally determined by a translation start codon at its 5' end and a translation stop codon at its 3' end. As used herein, the term "polypeptide" refers broadly to a polymer of two or more amino acids joined together by peptide bonds. The term "polypeptide" also includes molecules that contain more than one polypeptide joined by disulfide bonds, ionic bonds, or hydrophobic interactions, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. The term "polypeptide" does not connote a specific length of a polymer of amino acids, nor does it imply or distinguish whether the polypeptide is produced using recombinant techniques, chemical or enzymatic synthesis, or is naturally occurring.

"Regulatory sequence" refers to a nucleotide sequence that regulates expression of a coding region to which it is operably linked. Nonlimiting examples of regulatory sequences include, for example, promoters, transcription initiation sites, translation start sites, translation stop sites, and terminators. "Operably linked" refers to a juxtaposition wherein the components are in a relationship permitting them to function in their intended manner. A regulatory sequence is "operably linked" to a coding region when it is joined in such a way that expression of the coding region is achieved under conditions compatible with the regulatory sequence.

As used in the preceding description, the term "and/or" means one or all of the listed elements or a combination of any two or more of the listed elements; the term "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Bacterial Strains and Plasmids

All the primers were ordered from Eurofins MWG Operon and are listed in Table 1. The *E. coli* strains used in this study are listed in Table 2, which were all derived from *E. coli* K-12 strain BW25113.

TABLE 2

Strains, plasmids and primers used in this study

| Name | Relevant genotype | Reference |
|---|---|---|
| Strains | | |
| BW25113 | rrnB$^{T14}$ ΔlacZ$_{WJ16}$ hsdR514 ΔaraBAD$_{AH33}$ ΔrhaBAD$_{LD78}$ | A |
| SBDO-1 | BW25113 ΔxylA ΔyjhH ΔyagE | This work |
| SBDO-2 | SBDO-1 + pBDO-1 | This work |
| SBDO-3 | SBDO-1 + pBDO-1 and pBDO-2 | This work |
| SBDO-4 | SBDO-1 + pBDO-1 and pBDO-3 | This work |
| SBDO-5 | SBDO-1 + pBDO-1 and pBDO-4 | This work |
| Plasmids | | |
| pIBA7 | ColE1 ori, Amp$^R$, $P_L$lacO$_1$::kivD padA | B |
| pBDO-1 | p15A ori, Kan$^R$, $P_L$lacO$_1$::xylBCDX | This work |
| pBDO-2 | ColE1 ori, Amp$^R$, $P_L$lacO$_1$::xylA | This work |
| pBDO-3 | ColE1 ori, Amp$^R$, $P_L$lacO$_1$::BFD- yqhD | This work |
| pBDO-4 | ColE1 ori, Amp$^R$, $P_L$lacO$_1$::kivD- yqhD | This work |
| Primers | | SEQ ID NO: |
| xylBAcc-F | GGGCCCggtaccatgtcctcagccatctatcccagcct | 108 |
| xylBHinNheBa-R | GGGCCCGCTCAGCAAGCTTGCTAGCggatcctTaacgccagccggcgtcgatccagt | 109 |
| xylCBamHI-F | GGGCCCggatccAGGAGAAATTAACTatgaccgctcaagtcacttgcgtatg | 110 |
| xylCHindNhe-R | GGGCCCAAGCTTgctagcttagacaaggcggacctcatgctggg | 111 |
| xylDNheI-F | GGGCCCgctagcAGGAGAAATTAACTatgaggtccgccttgtctaaccgcac | 112 |
| xylDHind-R | GGGCCCaagctttTagtggttgtggcggggcagcttgg | 113 |
| xylXHind-F | GGGCCCaagcttAGGAGAAATTAACTAtggtttgtcggcggcttctagcatg | 114 |
| xylXBIpRem-R | gcgcagctggcgttgttgtccttggcctttTctgagcagcagggccgaacgaccttcgaa | 115 |
| XylXBIpI-R | GGGCCCGCTCAGCttagaggaggccgcggccggccaggt | 116 |
| pZEkivD-F | actgaccgaattcattaaagaggagaaaggtaccatgtatacagtaggagattacctatt | 117 |
| kivD-R | ttatgatttattttgttcagcaaata | 118 |
| YqhDkivD-F | ctgaacaaaataaatcataaAGGAGAAATTAACTATGAACAACTTTAATCTGCACACCCC | 119 |
| BFDpZE-F | actgaccgaattcattaaagaggagaaaggtaccatggcttcggtacacggcaccacata | 120 |
| BFD-R | tTacttcaccgggcttacggtgctta | 121 |
| CC0822Acc-F | GGGCCCggtaccatgaccgacaccctgcgccattacat | 122 |
| CC0822Xba-R | GGGCCCtctagattacgaccacgagtaggaggttttgg | 123 |

A. Datsenko et al., 2000 Proc. Natl. Acad. Sci. U.S.A. 97: 6640-5.
B. Zhang et al., 2011 ChemSusChem 4: 1068-1070.

All cloning procedures were carried out in the *E. coli* strain XL10-gold (Stratagene, Agilent Technologies, Santa Clara, Calif.). To build the plasmid pBDO-1, the coding regions of xylB, xylC, xylD, and xylX were amplified by PCR with oligos of xylBAcc-F and xylBHinNheBa-R, xylCBamHI-F and xylCHindNhe-R, xylDNheI-F and xylDHind-R, xylXHind-F and xylXBlpRem-R, using genomic DNA of *Caulobacter crescentus* strain as template, and then these four coding regions of xylB, xylC, xylD, and xylX were inserted into the corresponding restriction sites of pZA vector after digestion.

To make the plasmid pBDO-2, the coding region of xylA was PCR amplified by oligos of CC0822Acc-F and CC0822Xba-R using genomic DNA of *C. crescentus* strain as template, and then this coding region was inserted into the site between Acc65I and XbaI of vector pZE after digestion.

To construct the plasmids pBDO-3 and pBDO-4, four coding regions of BFD (using *Pseudomonas putida* genomic DNA as template), yqhD-1 (using *E. coli* genomic DNA as template), KIVD (from *Lactococcus lactis*, using plasmid pIBA7 as template) and yqhD-2 (using *E. coli* genomic DNA as template), were PCR amplified with oligos of BFDpZE-F and BFD-R, yqhDBFD-F and yqhDpZE-R, pZEkivD-F and kivD-R, yqhDkivD-F and yqhDpZE-R, and then pBDO-3 and pBDO-4 were completed by Gibson cloning method (Gibson et al., 2009. *Nat. Meth.* 6:343-345). P1 phages of xylA, yjhH and yagE and were obtained from the Keio collection (Baba et al., 2006 *Mol. Syst. Biol.* 2:10.1038). The phages were used to transfect the BW25113 strain to construct triple knockout strains. All the knockout strains were then transformed with pCP20 plasmid to remove the kanamycin marker. The correct knockouts were verified by PCR.

Cell Cultivation and Shake Flask Fermentation

Unless otherwise stated, cells were grown in test tubes at 37° C. in 2× YT rich medium (16 g/L Bacto-tryptone, 10 g/L yeast extract, and 5 g/L NaCl) supplemented with 100 mg/L ampicillin and 50 mg/L kanamycin. 200 μL of overnight cultures incubated in 2× YT medium were transferred into 5 mL M9 minimal medium supplemented with 5 g/L yeast extract, 5 g/L glucose, 40 g/L xylose, 100 mg/L ampicillin, and 50 mg/L kanamycin in 125 mL conical flasks. Isopropyl-β-D-thiogalactoside (IPTG) was added at a concentration of 0.1 mM to induce protein expression. The fermentation broth was buffered by the presence of 0.5 g $CaCO_3$.

Metabolite Analysis and Dry Cell Weight Determination

Fermentation products were analyzed using an Agilent 1260 Infinity HPLC equipped with an Aminex HPX 87H column (Bio-Rad Laboratories, Inc., Hercules, Calif.) and a refractive-index detector. The mobile phase was 5 mM $H_2SO_4$ with a flow rate 0.6 mL/min. The column temperature and detection temperature were 35° C. and 50° C., respectively. Cell dry weight was determined by filtering 5 mL culture through a 0.45 μm glass fiber filter (Pall Life Sciences, Ann Arbor, Mich.). After removal of medium, the filter was washed with 15 mL of MilliQ water (EMD Millipore Corp., Billerica, Mass.), dried in an oven and then weighed. Cell dry weight was determined in triplicate.

Example 2

To produce 1,4-butanediol from xylose in yeast, one artificial synthetic pathway was introduced into the wild type *Saccharomyces cerevisiae* strain W303. To generate the artificial pathway we cloned a polynucleotide that encodes enzymes that convert xylose into 2,5-dioxopentanoic acid into the host yeast cell. We also cloned a polynucleotide that encoded enzymes that convert 2,5-dioxopentanoic acid into 1,4-butanediol. These enzymes were cloned into plasmids YEplac195-xylBCDX and YEplac112-KivdDyqhD as described in more detail below.

Figure 14:
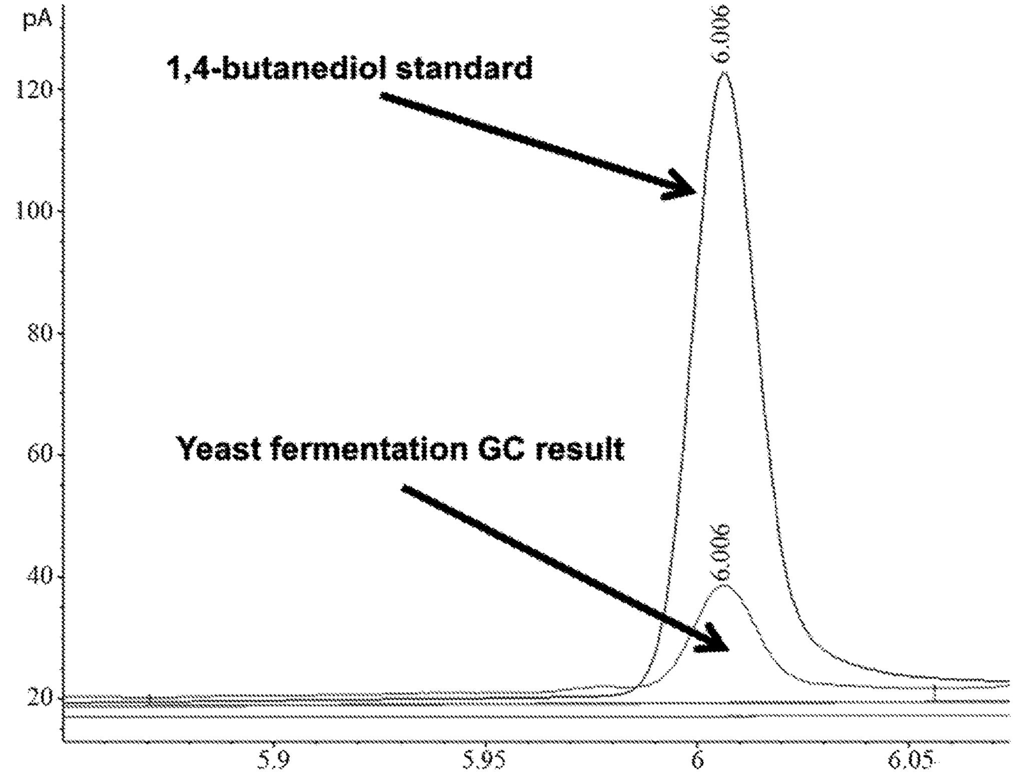
FIG. 14. Gas chromatography data showing production of 1,4-butanediol by genetically engineered *S. cerevisiae*.

The transformed yeast were grown under fermentation conditions as described in more detail below for two day. After the fermentation, 1,4-butanediol was accumulated to a concentration of 20 mg/L. (FIG. 14).

Plasmid Construction in the Yeast 1,4-Butanediol Synthetic Pathway

The construction of plasmid YEplac195-xylBCDX was finished by Gibson assembly. All of the primers are listed in Table 3.

The coding region for HXT7p was PCR amplified with the primer pair Hxt7p195-1F and Hxt7pXylB-R, using *S. cerevisiae* W303 genomic DNA as a template. Similarly, the PGK1p coding region was PCR amplified with the primer pair PGK1Phxt7t-F and PGK1PxylC-R; the ADH1p coding region was PCR amplified with the primer pair ADH1Ppgk1t-F and ADH1PxylD-R; the PDC1p coding region was PCR amplified with the primer pair PDC1PADH1T-F and PDC1PxylX-R; the HXT7t coding region was PCR amplified with the primer pair Hxt7tXylB-F and Hxt7tPGK1P-R; the PGK1t coding region was PCR amplified with the primer pair PGK1tXylC-F and PGK1tADH1p-R; the ADH1t coding region was PCR amplified with the primer pair ADH1TxylD-F and ADH1TPDC1P-R; and the PDC1t coding region was PCR amplified with primer pairs PDC1TxylX-F and PDC1T195-R, each by using *S. cerevisiae* W303 genomic DNA as template.

*Caulobacter crescentus* xylB coding region was PCR amplified with primer pair xylBhxt7p-F and xylBhxt7t-R using *C. crescentus* genomic DNA as template. Similarly, the xylC coding region was PCR amplified with primer pair xylCPGK1P-F and xylCPGK1t-R; the xylD coding region was PCR amplified with primer pair xylDADH1P-F/xylDADH1T-R; and the xylX coding region was PCR amplified with primer pair xylXPDC1P-F/xylXPDC1T-R; each using *C. crescentus* genomic DNA as template.

The combined fragment of HXT7p-xylB-HXT7t was amplified by overlapping PCR with the primer pair Hxt7p195-1F and Hxt7tPGK1P-R using the HXT7p/xylB/HXT7t DNA as a PCR template. The combined fragment PGK1p-xylC-PGK1t was amplified by overlapping PCR with the primer pair PGK1Phxt7t-F and PGK1tADH1p-R using the PGK1p/xylC/PGK1t DNA as a PCR template. The combined fragment ADH1p-xylD-ADH1t was amplified by overlapping PCR with the primer pair ADH1Ppgk1t-F and ADH1TPDC1P-R using the fragment ADH1p/xylD/ADH1t DNA as a PCR template. The combined fragment PDC1p-xylX-PDC1t was amplified by overlapping PCR with the primer pair PDC1PADH1T-F and PDC1T195-R using the PDC1p/xylX/PDC1t DNA as a PCR template.

Figure 12:
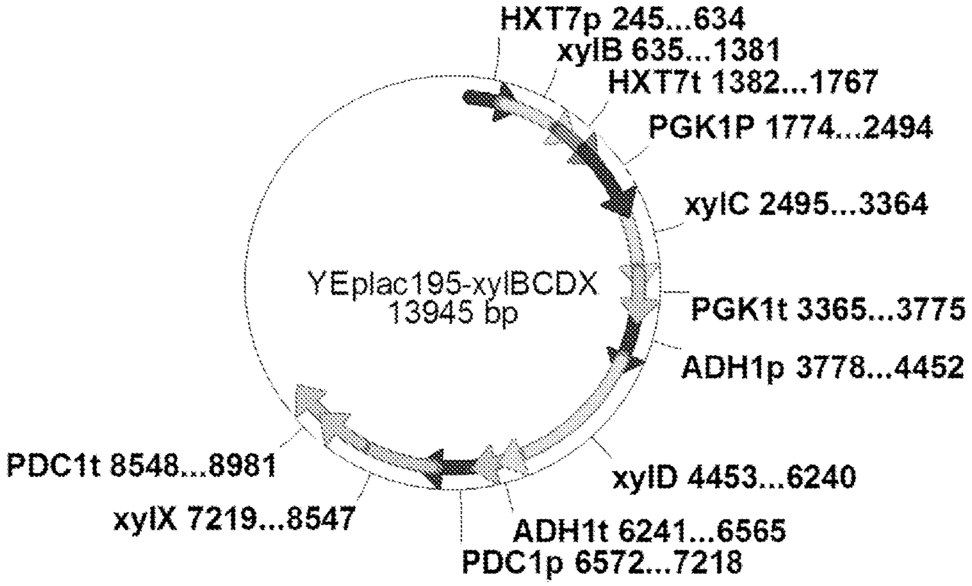
FIG. 12. A plasmid map of YEplac195-xylBCDX (13945 bp).

The vector fragment YEp195v was amplified with primer pair 195HindIII-2F and 195EcoRI-2R by using YEplac195 as template. The fragments of YEp195v, HXT7p-xylB-HXT7t, PGK1p-xylC-PGK1t, ADH1p-xylD-ADH1t, and PDC1p-xylX-PDC1t were assembled by Gibson method to form the plasmid of YEplac195-xylBCDX (FIG. 12).

To build the plasmid of YEplac112-KivD-yqhD, the fragments of HXT7P2, HXT7T2, PGK1P2 and PGK1T2 were PCR amplified using *S. cerevisiae* W303 genmic DNA as a template. The HXT7P2 fragment was PCR amplified using the primer pair Hxt7p195-1F and HXT7PkivD-R; the HXT7T2 fragment was PCR amplified using the primer pair HXT7TKIVD-F and HXT7TPGK1P-R; the PGK1P2 fragment was PCR amplified using the primer pair PGK1PHXT7T-F/PGK1PyqhD-R; and the PGK1T2 fragment was PCR amplified using the primer pair PGK1TyqhD-F and PGK1T112-R.

The KIVD coding region from *Lactococcus lactis* was amplified with the primer pair KIVDHXT7P-F and KIVDHXT7T-R using *L. lactis* genomic DNA as template. The *E. coli* YqhD coding region was amplified with the primer pair yqhDPGK1P-F and yqhDPGK1T-R using *E. coli* genomic DNA as template.

Figure 13:
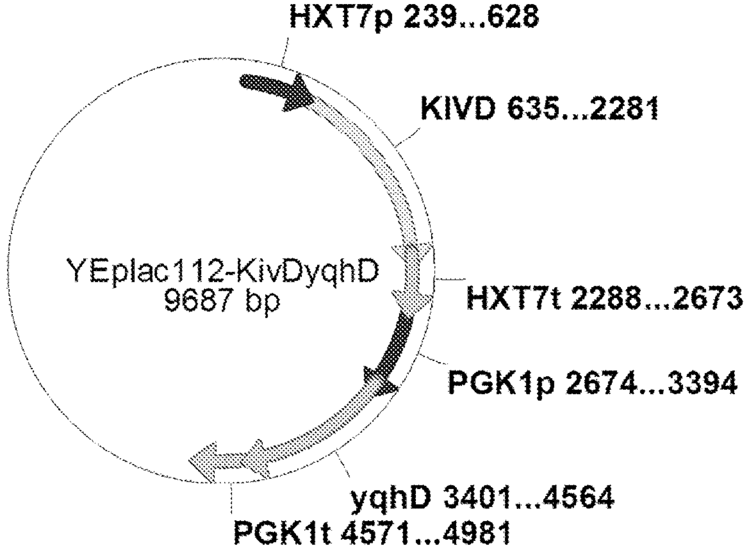
FIG. 13. A plasmid map of YEplac11-KivDyqhD (9687 bp).

The vector fragment YEp112v was amplified with primer pair 195HindIII-2F and 195EcoRI-2R by using YEplac112 as template. The fragments of YEp112v, HXT7P2, KIVD, HXT7T2, PGK1P2, yqhD and PGK1T2 were assembled by Gibson method to generate the plasmid of YEplac112-KivDyqhD. (FIG. 13).

TABLE 3

The used primers in this study

| Primer | | SEQ ID NO: |
|---|---|---|
| 195HindIII-2F | attgtgagcggataacaatttcacacaggaaacagctatgaccatgattacgccaagctt | 124 |
| Hxt7p195-1F | cagctatgaccatgattacgccaagcttGGTACCtcgtaggaacaatttcgggcccctgc | 125 |
| Hxt7pXylB-R | cttcaggctgggatagatggctgaggacatttttttgattaaaattaaaaaaacttttgt | 126 |
| XylBhxt7p-F | acaaaaagtttttttaattttaatcaaaaaatgtcctcagccatctatcccagcctgaag | 127 |
| XylBhxt7t-R | tgatcatgaattaataaaagtgttcgcaaatTaacgccagccggcgtcgatccagtattc | 128 |
| Hxt7tXylB-F | gaatactggatcgacgccggctggcgttAatttgcgaacacttttattaattcatgatca | 129 |
| Hxt7tPGK1P-R | actcacgagtaattcttgcaaatgcctCCTAGGagacacttttttgaagcgggatacagaa | 130 |
| PGK1Phxt7t-F | ttctgtatcccgcttcaaaaagtgtctCCTAGGaggcatttgcaagaattactcgtgagt | 131 |
| PGK1PxylC-R | atcccatacgcaagtgacttgagcggtcattgttttatatttgttgtaaaaagtagataa | 132 |

TABLE 3-continued

The used primers in this study

| Primer | | SEQ ID NO: |
|---|---|---|
| xylCPGK1P-F | ttatctacttttacaacaaatataaaacaatgaccgctcaagtcacttgcgtatgggat | 133 |
| XylCPGK1t-R | attgatctatcgatttcaattcaattcaatttagacaaggcggacctcatgctggggttg | 134 |
| PGK1tXylC-F | caaccccagcatgaggtccgccttgtctaaattgaattgaattgaaatcgatagatcaat | 135 |
| PGK1tADH1p-R | ccgatgtatgggtttggttgccagaaGCtgagcttggagcaggaagaatacactatactg | 136 |
| ADH1Ppgk1t-F | cagtatagtgtattcttcctgctccaagctcaGCttctggcaaccaaacccatacatcgg | 137 |
| ADH1PxylD-R | gggcgtgcggttagacaaggcggacctcattgtatatgagatagttgattgtatgcttgg | 138 |
| xylDADH1P-F | ccaagcatacaatcaactatctcatatacaatgaggtccgccttgtctaaccgcacgccc | 139 |
| xylDADH1T-R | aataaaaatcataaatcataagaaattcgcttTagtggttgtggcggggcagcttggccgc | 140 |
| ADH1Txy1D-F | gcggccaagctgccccgccacaaccactAagcgaatttcttatgatttatgatttttatt | 141 |
| ADH1TPDC1P-R | gaaggtatgggtgcagtgtgcttatctACTAGTtgtggaagaacgattacaacaggtgtt | 142 |
| PDC1PADH1T-F | aacacctgttgtaatcgttcttccacaACTAGTagataagcacactgcacccataccttc | 143 |
| PDC1PxylX-R | ggtccatgctagaagccgccgacaaaccaTtttgattgatttgactgtgttattttgcgt | 144 |
| xylXPDC1P-F | acgcaaaataacacagtcaaatcaatcaaaAtggtttgtcggcggcttctagcatggacc | 145 |
| xylXPDC1T-R | actttaactaataattagagattaaatcgcttagaggaggccgcggccggccaggttgcg | 146 |
| PDC1TxylX-F | cgcaacctggccggccgcggcctcctctaagcgatttaatctctaattattagttaaagt | 147 |
| PDC1T195-R | acgttgtaaaacgacggccagtgaattcTCTAGAgcttgtcttgagcaattgcagagtcg | 148 |
| 195EcoRI-2R | agttgggtaacgccagggttttcccagtcacgacgttgtaaaacgacggccagtgaattc | 149 |
| HXT7PkivD-R | ctaataggtaatctcctactgtatacatGGATCCtttttgattaaaattaaaaaaacttt | 150 |
| KIVDHXT7P-F | aaagtttttttaattttaatcaaaaaGGATCCatgtatacagtaggagattacctattag | 151 |
| KIVDHXT7T-R | tcatgaattaataaaagtgttcgcaaaGGTACCttatgatttattttgttcagcaaatag | 152 |
| HXT7TKIVD-F | ctatttgctgaacaaaataaatcataaGGTACCtttgcgaacacttttattaattcatga | 153 |
| HXT7TPGK1P-R | cttactcacgagtaattcttgcaaatgcctagacacttttttgaagcgggatacagaaaaa | 154 |
| PGK1PHXT7T-F | tttttctgtatcccgcttcaaaaaagtgtctaggcatttgcaagaattactcgtgagtaag | 155 |
| PGK1PyqhD-R | TGGGGTGTGCAGATTAAAGTTGTTCATTCTAGAtgttttatatttgttgtaaaaagtaga | 156 |
| yqhDPGK1P-F | tctacttttacaacaaatataaaacaTCTAGAATGAACAACTTTAATCTGCACACCCCA | 157 |
| yqhDPGK1T-R | gatctatcgatttcaattcaattcaatCTCGAGTTAGCGGGCGGCTTCGTATATACGGCG | 158 |
| PGK1TyqhD-F | CGCCGTATATACGAAGCCGCCCGCTAACTCGAGattgaattgaattgaaatcgatagatc | 159 |
| PGK1T181-R | gtcacgacgttgtaaaacgacggccagtgaattctgagcttggagcaggaagaatacact | 160 |

1,4-Butanediol Fermentation by Yeast in Shake Flask

The W303 yeast strain carrying plasmids of YEplac195-xylBCDX and YEplac112-KivDyqhD was cultured overnight in the Complete Minimal medium without uracil and tryptophan supplements at 30° C. with shaking at 200 rpm. The yeast cells were harvested and washed in the next day, and then inoculated into 10 mL fresh medium identical to the overnight culture medium except that it further contained 20 g/L xylose. The shake flask was then sealed with parafilm, and cultured for two days at 30° C. with shaking at 200 rpm. The fermentation broth was analyzed by gas chromatography to measure the amount of 1,4-butanediol. Results are shown in FIG. 14.

Exemplary Embodiments

Embodiment 1. A recombinant microbial cell modified to exhibit increased biosynthesis of a TCA derivative compared to a wild-type control.

Embodiment 2. The recombinant cell of Embodiment 1 wherein the TCA derivative comprises 1,4-butanediol.

Embodiment 3. The recombinant microbial cell any preceding Embodiment wherein the microbial cell is a fungal cell.

Embodiment 4. The recombinant cell of Embodiment 3 wherein the fungal cell is a member of the Saccharomycetaceae family.

Embodiment 5. The recombinant cell of Embodiment 3 wherein the fungal cell is *Saccharomyces cerevisiae, Candida rugosa*, or *Candida albicans.*

Embodiment 6. The recombinant cell of Embodiment 1 or Embodiment 2 wherein the microbial cell is a bacterial cell.

Embodiment 7. The recombinant cell of Embodiment 6 wherein the bacterial cell is a member of the phylum Protobacteria.

Embodiment 8. The recombinant cell of Embodiment 7 wherein the bacterial cell is a member of the Enterobacteriaceae family.

Embodiment 9. The recombinant cell of Embodiment 8 wherein the bacterial cell is *Escherichia coli.*

Embodiment 10. The recombinant cell of Embodiment 7 wherein the bacterial cell is a member of the Pseudomonaceae family.

Embodiment 11. The recombinant cell of Embodiment 10 wherein the bacterial cell is *Pseudomonas putida.*

Embodiment 12. The recombinant cell of Embodiment 6 wherein the bacterial cell is a member of the phylum Firmicutes.

Embodiment 13. The recombinant cell of Embodiment 12 wherein the bacterial cell is a member of the Bacillaceae family.

Embodiment 14. The recombinant cell of Embodiment 13 wherein the bacterial cell is *Bacillus subtilis.*

Embodiment 15. The recombinant cell of Embodiment 12 wherein the bacterial cell is a member of the Streptococcaceae family.

Embodiment 16. The recombinant cell of Embodiment 15 wherein the bacterial cell is *Lactococcus lactis.*

Embodiment 17. The recombinant cell of Embodiment 12 wherein the bacterial cell is a member of the Clostridiaceae family.

Embodiment 18. The recombinant cell of Embodiment 17 wherein the bacterial cell is *Clostridium cellulolyticum.*

Embodiment 19. The recombinant cell of Embodiment 6 wherein the bacterial cell is a member of the phylum Cyanobacteria.

Embodiment 20. The recombinant cell of any preceding Embodiment wherein the microbial cell is photosynthetic.

Embodiment 21. The recombinant cell of any preceding Embodiment wherein the microbial cell is cellulolytic.

Embodiment 22. The recombinant cell of any preceding Embodiment wherein the increased biosynthesis of the TCA derivative comprises an increase in xylose dehydrogenase activity, xylonolactonase activity, xylonate dehydratase activity, or 2-keto-3-deoxyaldonic acid dehydratase activity.

Embodiment 23. The recombinant cell of Embodiment 22 wherein the increased biosynthesis of the TCA derivative further comprises an increase in benzoylformate decarboxylase activity and an increase in alcohol dehydrogenase activity.

Embodiment 24. The recombinant cell of Embodiment 23 wherein the benzoylformate decarboxylase comprises BFD of *Pseudomonas putida.*

Embodiment 25. The recombinant cell of Embodiment 23 wherein the alcohol dehydrogenase comprises yqhD of *E. coli.*

Embodiment 26. The recombinant cell of Embodiment 22 wherein the increased biosynthesis of the TCA derivative further comprises an increase in decarboxylase activity and an increase in alcohol dehydrogenase activity.

Embodiment 27. The recombinant cell of Embodiment 26 wherein the decarboxylase comprises KIVD of *Lactococcus lactis.*

Embodiment 28. The recombinant cell of Embodiment 26 wherein the alcohol dehydrogenase comprises yqhD of *E. coli.*

Embodiment 29. The recombinant cell of preceding Embodiment wherein the increased biosynthesis of the TCA derivative comprises a decrease in α-ketoglutaric semialdehyde dehydrogenase activity.

Embodiment 30. The recombinant cell of preceding Embodiment wherein the increased biosynthesis of the TCA derivative comprises a decrease in aldolase activity.

Embodiment 31. The recombinant cell of preceding Embodiment wherein the increased biosynthesis of the TCA derivative comprises a decrease in 2-keto-3-deoxy gluconate aldolase activity.

Embodiment 32. The recombinant cell of any preceding Embodiment comprising an engineered metabolic pathway for converting 2,5-dioxopentanoic acid to 1,4-butanediol.

Embodiment 33. The recombinant cell of Embodiment 32 wherein the engineered metabolic pathway for converting 2,5-dioxopentanoic acid to 1,4-butanediol comprises an enzyme that converts 2,5-dioxopentonoic acid into succinaldehyde.

Embodiment 34. The recombinant cell of Embodiment 33 wherein the enzyme that converts 2,5-dioxopentonoic acid into succinaldehyde comprises a 2-ketoacid decarboxylase or a 2-oxoglutarate decarboxylase.

Embodiment 35. The recombinant cell of Embodiment 33 or 34 wherein the enzyme that converts 2,5-dioxopentonoic acid into succinaldehyde comprises KIVD, BFD, or IPDC.

Embodiment 36. The recombinant cell of any one of Embodiments 32-35 wherein the engineered metabolic pathway for converting 2,5-dioxopentanoic acid to 1,4-butanediol comprises an enzyme that converts succinaldehyde to 1,4-butanediol.

Embodiment 37. The recombinant cell of Embodiment 36 wherein the enzyme that converts succinaldehyde to 1,4-butanediol comprises an alcohol dehydrogenase.

Embodiment 38. The recombinant cell of Embodiment 36 or Embodiment 37 wherein the enzyme that converts succinaldehyde to 1,4-butanediol comprises YqhD, ADH6, YjgB, or YahK.

Embodiment 39. The recombinant cell of Embodiment 32 wherein the engineered metabolic pathway for converting 2,5-dioxopentanoic acid to 1,4-butanediol comprises an enzyme that converts 2,5-dioxopentonoic acid into 2-keto-5-hydroxy-pentanoic acid.

Embodiment 40. The recombinant cell of Embodiment 39 wherein the enzyme that converts 2,5-dioxopentonoic acid into 2-keto-5-hydroxy-pentanoic acid comprises an alcohol dehydrogenase.

Embodiment 41. The recombinant cell of Embodiment 39 or Embodiment 40 wherein the enzyme that converts 2,5-dioxopentonoic acid into 2-keto-5-hydroxy-pentanoic acid comprises YqhD, ADH6, YjgB, or YahK.

Embodiment 42. The recombinant cell of any one of Embodiments 39-41 wherein the engineered metabolic pathway for converting 2,5-dioxopentanoic acid to 1,4-butanediol comprises an enzyme that converts 2-keto-5-hydroxy-pentanoic acid to 4-hydroxy-1-butyraldehyde.

Embodiment 43. The recombinant cell of Embodiment 42 wherein the enzyme that converts 2-keto-5-hydroxy-pentanoic acid to 4-hydroxy-1-butyraldehyde comprises a 2-ketoacid decarboxylase or a 2-oxoglutarate decarboxylase.

Embodiment 44. The recombinant cell of Embodiment 42 or Embodiment 43 wherein the enzyme that converts 2-keto-5-hydroxy-pentanoic acid to 4-hydroxy-1-butyraldehyde comprises Kivd, BFD, or IPDC.

Embodiment 45. The recombinant cell of any one of Embodiments 42-44 wherein the engineered metabolic pathway for converting 2,5-dioxopentanoic acid to 1,4-butanediol comprises an enzyme that converts 4-hydroxy-1-butyraldehyde to 1,4-butanediol.

Embodiment 46. The recombinant cell of Embodiment 45 wherein the enzyme that converts 4-hydroxy-1-butyraldehyde to 1,4-butanediol comprises an alcohol dehydrogenase.

Embodiment 47. The recombinant cell of Embodiment 45 or Embodiment 46 wherein the enzyme that converts 4-hydroxy-1-butyraldehyde to 1,4-butanediol comprises YqhD, ADH6, YjgB, or YahK.

Embodiment 48. The recombinant cell of any preceding Embodiment comprising an engineered metabolic pathway for converting a carbon source to 2,5-dioxopentanoic acid.

Embodiment 49. The recombinant cell of Embodiment 48 wherein the engineered metabolic pathway for converting a carbon source to 2,5-dioxopentanoic acid comprises an enzyme that converts D-arabinose into D-arabinolactone.

Embodiment 50. The recombinant cell of Embodiment 49 wherein the enzyme that can convert D-arabinose into D-arabinolactone comprises a pentose dehydrogenase.

Embodiment 51. The recombinant cell of Embodiment 49 or Embodiment 50 wherein the enzyme that can convert D-arabinose into D-arabinonolactone comprises AraDH.

Embodiment 52. The recombinant cell of any one of Embodiments 49-51 wherein the recombinant cell exhibits conversion of D-arabinose into D-arabinonolactone at a level at least 110% of a wild-type control cell.

Embodiment 53. The recombinant cell of any one of Embodiments 49-52 wherein the engineered metabolic pathway for converting a carbon source to 2,5-dioxopentanoic acid comprises an enzyme that converts D-arabinonic acid to 2-oxo-4(s),5-dihydroxy-pentanoic acid.

Embodiment 54. The recombinant cell of Embodiment 53 wherein the enzyme that converts D-arabinonic acid to 2-oxo-4(s),5-dihydroxy-pentanoic acid comprises an aldonic acid dehydratase.

Embodiment 55. The recombinant cell of Embodiment 53 or Embodiment 54 wherein the enzyme that converts D-arabinonic acid to 2-oxo-4(s),5-dihydroxy-pentanoic acid comprises AraD.

Embodiment 56. The recombinant cell of any one of Embodiments 53-55 wherein the recombinant cell exhibits conversion of D-arabinonic acid to 2-oxo-4(s),5-dihydroxy-pentanoic acid at a level at least 110% of a wild-type control cell.

Embodiment 57. The recombinant cell of any one of Embodiments 49-56 wherein the engineered metabolic pathway for converting a carbon source to 2,5-dioxopentanoic acid comprises an enzyme that converts 2-oxo-4(s),5-dihydroxy-pentanoic acid to 2,5-dioxopentanoic acid.

Embodiment 58. The recombinant cell of Embodiment 57 wherein the enzyme that converts 2-oxo-4(s),5-dihydroxy-pentanoic acid to 2,5-dioxopentanoic acid comprises a 2-keto-3-deoxyaldonic acid dehydratase.

Embodiment 59. The recombinant cell of Embodiment 57 or Embodiment 58 wherein the enzyme that converts 2-oxo-4(s),5-dihydroxy-pentanoic acid to 2,5-dioxopentanoic acid comprises KdaD.

Embodiment 60. The recombinant cell of any one of Embodiments 57-59 wherein the recombinant cell exhibits conversion of 2-oxo-4(s),5-dihydroxy-pentanoic acid to 2,5-dioxopentanoic acid at a level at least 110% of a wild-type control cell.

Embodiment 61. The recombinant cell of Embodiment 48 wherein the engineered metabolic pathway for converting a carbon source to 2,5-dioxopentanoic acid comprises an enzyme that converts D-xylose to D-xylonolactone.

Embodiment 62. The recombinant cell of Embodiment 61 wherein the enzyme that converts D-xylose to D-xylonolactone comprises a pentose dehydrogenase.

Embodiment 63. The recombinant cell of Embodiment 61 or Embodiment 62 wherein enzyme that converts D-xylose to D-xylonolactone comprises XylB or rrnAC3034.

Embodiment 64. The recombinant cell of any one of Embodiments 61-63 wherein the recombinant cell exhibits conversion of D-xylose to D-xylonolactone at a level at least 110% of a wild-type control.

Embodiment 65. The recombinant cell of any one of Embodiments 61-64 wherein the engineered metabolic pathway for converting a carbon source to 2,5-dioxopentanoic acid comprises an enzyme that converts D-xylonolactone to D-xylonic acid.

Embodiment 66. The recombinant cell of Embodiment 65 wherein the enzyme that converts D-xylonolactone to D-xylonic acid comprises a pentonolactonase.

Embodiment 67. The recombinant cell of Embodiment 65 or Embodiment 66 wherein the enzyme that converts D-xylonolactone to D-xylonic acid comprises XylC or rrnAC3033.

Embodiment 68. The recombinant cell of any one of Embodiments 65-67 wherein the recombinant cell exhibits conversion of D-xylonolactone to D-xylonic acid at a level at least 110% of a wild-type control.

Embodiment 69. The recombinant cell of any one of Embodiments 61-68 wherein the engineered metabolic pathway for converting a carbon source to 2,5-dioxopentanoic acid comprises an enzyme that converts D-xylonic acid to 2-oxo-4(S),5-dihydroxy-pentanoic acid.

Embodiment 70. The recombinant cell of Embodiment 69 wherein the enzyme that converts D-xylonic acid to 2-oxo-4(S),5-dihydroxy-pentanoic acid comprises an aldonic acid dehydratase.

Embodiment 71. The recombinant cell of Embodiment 69 or Embodiment 70 wherein the enzyme that converts D-xylonic acid to 2-oxo-4(S),5-dihydroxy-pentanoic acid comprises XylD or rrnAC3032.

Embodiment 72. The recombinant cell of any one of Embodiments 69-71 wherein the recombinant cell exhibits conversion of D-xylonic acid to 2-oxo-4(S),5-dihydroxy-pentanoic acid at a level at least 110% of a wild-type control.

Embodiment 73. The recombinant cell of any one of Embodiments 61-72 wherein the engineered metabolic pathway for converting a carbon source to 2,5-dioxopentanoic acid comprises an enzyme that converts 2-oxo-4(S),5-dihydroxy-pentanoic acid to 2,5-dioxopenatnoic acid.

Embodiment 74. The recombinant cell of Embodiment 73 wherein the enzyme that converts 2-oxo-4(S),5-dihydroxy-pentanoic acid to 2,5-dioxopenatnoic acid comprises a 2-keto-3-deoxyaldonic acid dehydratase.

Embodiment 75. The recombinant cell of Embodiment 73 or Embodiment 74 wherein the enzyme that converts 2-oxo-4(S),5-dihydroxy-pentanoic acid to 2,5-dioxopenatnoic acid comprises XylX or rrnAC3039.

Embodiment 76. The recombinant cell of any one of Embodiments 73-75 wherein the recombinant cell exhibits conversion of 2-oxo-4(S),5-dihydroxy-pentanoic acid to 2,5-dioxopenatnoic acid at a level at least 110% of a wild-type control.

Embodiment 77. The recombinant cell of Embodiment 48 wherein the engineered metabolic pathway for converting a carbon source to 2,5-dioxopentanoic acid comprises an enzyme that converts L-arabinose to L-arabinolactone.

Embodiment 78. The recombinant cell of Embodiment 77 wherein the enzyme that converts L-arabinose to L-arabinolactone comprises a pentose dehydrogenase.

Embodiment 79. The recombinant cell of Embodiment 77 or Embodiment 78 wherein the enzyme that converts L-arabinose to L-arabinolactone comprises AraE.

Embodiment 80. The recombinant cell of any one of Embodiments 77-79 wherein the recombinant cell exhibits conversion of L-arabinose to L-arabinolactone at a level at least 110% of a wild-type control.

Embodiment 81. The recombinant cell of any one of Embodiments 77-80 wherein the engineered metabolic pathway for converting a carbon source to 2,5-dioxopentanoic acid comprises an enzyme that converts L-arabinolactone to L-arabinonic acid.

Embodiment 82. The recombinant cell of Embodiment 81 wherein the enzyme that converts L-arabinolactone to L-arabinonic acid comprises a pentonolactonase.

Embodiment 83. The recombinant cell of Embodiment 81 or Embodiment 82 wherein the enzyme that converts L-arabinolactone to L-arabinonic acid comprises AraI.

Embodiment 84. The recombinant cell of any one of Embodiments 81-83 wherein the recombinant cell exhibits conversion of L-arabinolactone to L-arabinonic acid at a level at least 110% of a wild-type control.

Embodiment 85. The recombinant cell of any one of Embodiments 77-84 wherein the engineered metabolic pathway for converting a carbon source to 2,5-dioxopentanoic acid comprises an enzyme that converts L-arabinonic acid to 2-oxo-4(R),5-dihydroxy-pentanoic acid.

Embodiment 86. The recombinant cell of Embodiment 85 wherein the enzyme that converts L-arabinonic acid to 2-oxo-4(R),5-dihydroxy-pentanoic acid comprises an aldonic acid dehydratase.

Embodiment 87. The recombinant cell of Embodiment 85 or Embodiment 86 wherein the enzyme that converts L-arabinonic acid to 2-oxo-4(R),5-dihydroxy-pentanoic acid comprises AraB.

Embodiment 88. The recombinant cell of any one of Embodiments 81-87 wherein the recombinant cell exhibits conversion of L-arabinonic acid to 2-oxo-4(R),5-dihydroxy-pentanoic acid at a level at least 110% of a wild-type control.

Embodiment 89. The recombinant cell of any one of Embodiments 77-88 wherein the engineered metabolic pathway for converting a carbon source to 2,5-dioxopentanoic acid comprises an enzyme that converts 2-oxo-4(R),5-dihydroxy-pentanoic acid to 2,5-dioxopentanoic acid.

Embodiment 90. The recombinant cell of Embodiments 89 wherein the enzyme that converts 2-oxo-4(R),5-dihydroxy-pentanoic acid to 2,5-dioxopentanoic acid comprises a 2-keto-3-deoxyaldonic acid dehydratase.

Embodiment 91. The recombinant cell of Embodiments 89 wherein the enzyme that converts 2-oxo-4(R),5-dihydroxy-pentanoic acid to 2,5-dioxopentanoic acid comprises AraD.

Embodiment 92. The recombinant cell of any one of Embodiments 89-90 wherein the recombinant cell exhibits conversion of 2-oxo-4(R),5-dihydroxy-pentanoic acid to 2,5-dioxopentanoic acid at a level at least 110% of a wild-type control.

Embodiment 93. The recombinant cell of Embodiment 48 wherein the engineered metabolic pathway for converting a carbon source to 2,5-dioxopentanoic acid comprises an enzyme that converts D-glucaric acid to 4-deoxy-5-keto-D-glucaric acid.

Embodiment 94. The recombinant cell of Embodiment 93 wherein the enzyme that converts D-glucaric acid to 4-deoxy-5-keto-D-glucaric acid comprises an aldonic acid dehydratase.

Embodiment 95. The recombinant cell of Embodiment 93 or Embodiment 94 wherein the enzyme that converts D-glucaric acid to 4-deoxy-5-keto-D-glucaric acid comprises YcbF.

Embodiment 96. The recombinant cell of any one of Embodiments 93-95 wherein the recombinant cell exhibits conversion of D-glucaric acid to 4-deoxy-5-keto-D-glucaric acid at a level at least 110% of a wild-type control.

Embodiment 97. The recombinant cell of any one of Embodiments 93-96 wherein the engineered metabolic pathway for converting a carbon source to 2,5-dioxopentanoic acid comprises an enzyme that converts 4-deoxy-5-keto-D-glucaric acid to 2,5-dioxopentanoic acid.

Embodiment 98. The recombinant cell of Embodiment 97 wherein the enzyme that converts 4-deoxy-5-keto-D-glucaric acid to 2,5-dioxopentanoic acid comprises a 2-keto-3-deoxyaldonic acid dehydratase.

Embodiment 99. The recombinant cell of Embodiment 97 or Embodiment 98 wherein the enzyme that converts 4-deoxy-5-keto-D-glucaric acid to 2,5-dioxopentanoic acid comprises YcbC.

Embodiment 100. The recombinant cell of Embodiment 48 wherein the engineered metabolic pathway for converting a carbon source to 2,5-dioxopentanoic acid comprises an enzyme that converts D-galactaric acid to 4-deoxy-5-keto-D-glucaric acid.

Embodiment 101. The recombinant cell of Embodiment 100 wherein the enzyme that converts D-galactaric acid to 4-deoxy-5-keto-D-glucaric acid comprises an aldonic acid dehydratase.

Embodiment 102. The recombinant cell of Embodiment 100 or Embodiment 101 wherein the enzyme that converts D-galactaric acid to 4-deoxy-5-keto-D-glucaric acid comprises YcbH.

Embodiment 103. The recombinant cell of any one of Embodiments 100-102 wherein the recombinant cell exhibits conversion of D-galactaric acid to 4-deoxy-5-keto-D-glucaric acid at a level at least 110% of a wild-type control.

Embodiment 104. The recombinant cell of any one of Embodiments 100-103 wherein the engineered metabolic pathway for converting a carbon source to 2,5-dioxopentanoic acid comprises an enzyme that converts 4-deoxy-5-keto-D-glucaric acid to 2,5-dioxopentanoic acid.

Embodiment 105. The recombinant cell of Embodiment 104 wherein the enzyme that converts 4-deoxy-5-keto-D-glucaric acid to 2,5-dioxopentanoic acid comprises a 2-keto-3-deoxyaldonic acid dehydratase.

Embodiment 106. The recombinant cell of Embodiment 104 or Embodiment 105 wherein the enzyme that converts 4-deoxy-5-keto-D-glucaric acid to 2,5-dioxopentanoic acid comprises YcbC.

Embodiment 107. The recombinant cell of Embodiment 48 wherein the engineered metabolic pathway for converting a carbon source to 2,5-dioxopentanoic acid comprises an enzyme that converts 4(R)-hydroxy-L-proline to 4(R)-hydroxy-D-proline.

Embodiment 108. The recombinant cell of Embodiment 107 wherein the enzyme that converts 4(R)-hydroxy-L-proline to 4(R)-hydroxy-D-proline comprises an amino acid transporter.

Embodiment 109. The recombinant cell of Embodiment 107 or Embodiment 108 wherein the enzyme that converts 4(R)-hydroxy-L-proline to 4(R)-hydroxy-D-proline comprises LysE or HypE.

Embodiment 110. The recombinant cell of any one of Embodiments 107-109 wherein the recombinant cell exhibits conversion of 4(R)-hydroxy-L-proline to 4(R)-hydroxy-D-proline at a level at least 110% of a wild-type control.

Embodiment 111. The recombinant cell of any one of Embodiments 107-110 wherein the engineered metabolic pathway for converting a carbon source to 2,5-dioxopentanoic acid comprises an enzyme that converts 4(R)-hydroxy-D-proline to 2-carboxy-4(R)-hydroxy-δ-pyrroline.

Embodiment 112. The recombinant cell of Embodiment 111 wherein the enzyme that converts 4(R)-hydroxy-D-proline to 2-carboxy-4(R)-hydroxy-δ-pyrroline comprises HypOX.

Embodiment 113. The recombinant cell of Embodiment 111 or Embodiment 112 wherein the recombinant cell exhibits conversion of 4(R)-hydroxy-D-proline to 2-carboxy-4(R)-hydroxy-δ-pyrroline at a level at least 110% of a wild-type control.

Embodiment 114. The recombinant cell of any one of Embodiments 107-113 wherein the engineered metabolic pathway for converting a carbon source to 2,5-dioxopentanoic acid comprises an enzyme that converts 2-oxo-4(R),5-hydroxy-5-aminopentanoic acid to 2,5-dioxopentanoic acid.

Embodiment 115. The recombinant cell of Embodiment 114 wherein the enzyme that converts 2-oxo-4(R),5-hydroxy-5-aminopentanoic acid to 2,5-dioxopentanoic acid comprises a 2-keto-3-deoxyaldonic acid dehydratase.

Embodiment 116. The recombinant cell of Embodiment 114 or Embodiment 115 wherein the enzyme that converts 2-oxo-4(R),5-hydroxy-5-aminopentanoic acid to 2,5-dioxopentanoic acid comprises PP1247.

Embodiment 117. The recombinant cell of any one of Embodiments 114-116 wherein the recombinant cell exhibits conversion of 2-oxo-4(R),5-hydroxy-5-aminopentanoic acid to 2,5-dioxopentanoic acid at a level at least 110% of a wild-type control.

Embodiment 118. The recombinant cell of any one of Embodiments 48-117 modified to exhibit increased α-ketoglutaric semialdehyde dehydrogenase activity compared to a wild-type control.

Embodiment 119. The recombinant cell of Embodiment 118 exhibiting increased conversion of 2,5-dioxopentanoic acid to a TCA derivative compared to a wild-type control.

Embodiment 120. The recombinant cell of Embodiment 119 wherein the TCA derivative comprises succinate, fumarate, malate, glutamate, lysine, threonine, or 4-hydroxybutyrate.

Embodiment 121. The recombinant cell of any preceding Embodiment genetically modified to increase consumption of xylose, arabinose, glucaric acid, galactaric acid, or hydroxyproline compared to a wild-type control.

Embodiment 122. The recombinant cell of any preceding Embodiment genetically modified to in crease consumption of a uronic acid compared to a wild-type control.

Embodiment 123. The recombinant cell of Embodiment 122 wherein the urnic acid comprises galacturonic acid or glucuronic acid.

Embodiment 124. The recombinant cell of Embodiment 122 or Embodiment 123 genetically modified to increase conversion of the uronic acid to an aldonic acid compared to a wild-type control.

Embodiment 125. The recombinant cell of any one of Embodiments 122-124 wherein the recombinant cell comprises an exogenous urinate dehydrogenase.

Embodiment 126. A method comprising:

incubating a recombinant cell of any preceding Embodiment in medium that comprises a carbon source under conditions effective for the recombinant cell to produce a TCA derivative.

Embodiment 127. The method of Embodiment 126 wherein the TCA derivative comprises 1,4-butanediol.

Embodiment 128. The method of Embodiment 126 wherein the carbon source comprises xylose, arabinose, glucaric acid, galactaric acid, or hydroxyproline.

Embodiment 129. The method of any one of Embodiments 126-128 wherein the increased biosynthesis of the TCA derivative comprises an increase in pentose dehydrogenase activity, pentonolactonase activity, aldonic acid dehydratase activity, or 2-keto-3-deoxyaldonic acid dehydratase activity.

Embodiment 130. The method of any one of Embodiments 126-129 wherein the increased biosynthesis of the TCA derivative comprises an increase in hexic acid dehydratase activity or 5-dehydro-4-deoxyglucarate dehydratase activity.

Embodiment 131. A method comprising:

introducing into a host cell a heterologous polynucleotide encoding at least one polypeptide that catalyzes conversion of a carbon source to a TCA derivative, wherein the at least one polypeptide is operably linked to a promoter so that the modified host cell catalyzes conversion of the carbon source to TCA derivative.

Embodiment 132. The method of Embodiment 131 wherein the TCA derivative comprises 1,4-butanediol.

Embodiment 133. The method of Embodiment 131 wherein the carbon source comprises xylose.

Embodiment 134. The method of Embodiment 131 wherein the TCA derivative comprises succinate, fumarate, malate, glutamate, lysine, threonine, 4-hydroxybutyrate.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

D-arabinose dehydrogenase (AraDH)

SEQ ID NO: 1 (NP_342747.1; GI: 15898142; Zinc-containing alcohol dehydrogenase (*Sulfolobus solfataricus* P2))

```
  1 menvnmvksk aallkkfsep lsiedvnipe pqgeevliri ggagvcrtdl
    rvwkgveakq
 61 gfrlpiilgh enagtivevg elakvkkgdn vvvyatwgdl tcrycregkf
    nicknqiipg
121 qttnggfsey mlvkssrwlv klnslspvea apladagtts mgairqalpf
    iskfaepvvi
181 vngigglavy tiqilkalmk nitivgisrs kkhrdfalel gadyvsemkd
    aeslinkltd
241 glgasiaidl vgteettynl gkllaqegai ilvgmegkrv sleafdtavw
    nkkllgsnyg
301 slndledvvr lsesgkikpy iikvplddin kaftnldegr vdgrqvit
```

SEQ ID NO: 2 (Chain A, D-arabinose dehydrogenase (*Sulfolobus solfataricus*))

```
  1 mvkskaallk kfseplsied vnipepqgee vliriggagv crtdlrvwkg
    veakqgfrlp
 61 iilghenagt ivevgelakv kkgdnvvvya twgdltcryc regkfnickn
    qiipgqttng
121 gfseymlvks srwlvklnsl spveaaplad agttsmgair qalpfiskfa
    epvvivngig
181 glavytiqil kalmknitiv gisrskkhrd falelgadyv semkdaesli
    nkltdglgas
241 iaidlvgtee ttynlgklla qegaiilvgm egkrvsleaf dtavwnkkll
    gsnygslndl
301 edvvrlsesg kikpyiikvp lddinkaftn ldegrvdgrq vitp
```

SEQ ID NO: 3 (Alcohol dehydrogenase GroES domain-containing protein (*Sulfolobus islandicus* M.14.25))

```
  1 mfgitfysam rknismvksk aallkkfsep lsiedveipe pkgeevlvri
    ggagvcrtdl
 61 rvwkgveakq gfrlpiilgh enagtvvevg elakakkgdn vvvyatwgdm
    tcrycregkf
121 nicknqvipg qttnggfsey mlvksyrwlv kldslspvda spladagtts
    mgairqalpf
181 mnkfaepvvi vngigglavy tiqilkalmk nivivgisrs kkhrdlalel
    gadyavemke
241 aesliskltd glgasvaidl vgteetsynl gkllaqegai ilvgmegkrv
    sleafdtavw
301 nkkllgsnyg slndledvvr lsesgkikpy vvkipldein kafkdldegr vegrqvitp
```

SEQ ID NO: 4 (Alcohol dehydrogenase GroES domain-containing protein (*Sulfolobus islandicus* M.16.27))

```
  1 mfgitfysam rknismvksk aallkkfsep lsiedveipe pkgeevlvri
    ggagvcrtdl
 61 rvwkgveakq gfrlpiilgh enagtvvevg elakakkgdn vvvyatwgdm
    tcrycregkf
121 nicknqvipg qttnggfsey mlvksyrwlv kldslspvda spladagtts
    mgairqalpf
181 mnkfaepvvi vngigglavy tiqilkalmk nivivgisrs rkhrdlalel
    gadyavemke
241 aesliskltd glgasvaidl vgteetsynl gkllaqegai ilvgmegkrv
    sleafdtavw
301 nkkllgsnyg slndledvvr lsesgkikpy vvkipldein kafkdldegr vegrqvitp
```

SEQ ID NO: 5 (Alcohol dehydrogenase GroES domain-containing protein (*Sulfolobus islandicus* L.S.2.15))

```
  1 mfgitfysam rknismvksk aallkkfsep lsiedveipe pkgeevlvri
    ggagvcrtdl
 61 rvwkgveakq gfrlpiilgh enagtvvevg elakakkgdn vvvyatwgdm
    tcrycregkf
121 nicknqvipg qttnggfsey mlvksyrwlv kldslspvda spladagtts
    mgairqalpf
181 mnkfaepvvi vngigglavy tiqilkalmk nivivgisrs kkhrdlalel
    gadhavemke
241 aesliskltd glgasvaidl vgteetsynl gkllaqegai ilvgmegkrv
    sleafdtavw
301 nkkllgsnyg slndledvvr lsesgkikpy vvkipldein kafkdldegr vegrqvitp
```

-continued

| Sequence Listing Free Text |
|---|

Arabinonate dehydratase (AraD)

SEQ ID NO: 6 (NP_344435.1; GI: 15899830; Mandelate racemase/muconate lactonizing family protein (*Sulfolobus solfataricus* P2))
```
   1 mikdirtykl cyeginderd alaikglaeh pmeivateie tsdgyvgyge
     slaygcsdav
  61 qvtiekilkp lllkedeeli eylwdkmyka tlrfgrrgia iagisgvdta
     lwdimgkkak
 121 kpiykllggs krkvrayitg gyysekkdle klrdeeayyv
     kmgfkgikvk igaksmeedi
 181 erlkairevv gedvkiavda nnvytfeeal emgrrleklg iwffeepiqt
     dyldlsarla
 241 eelevpiagy etaytrwefy eimrkravdi vqtdvmwtgg isemmkignm
     akvmgyplip
 301 hysaggisli gnlhvaaaln spwiemhlrk ndlrdkifke sieidnghlv
     vpdrpglgyt
 361 irdgvfeeyk cks
```

SEQ ID NO: 7 (Mandelate racemase/muconate lactonizing protein (*Sulfolobus islandicus* Y.G.57.14))
```
   1 mikdirtykl cyeginderd alaikglaeh pmeivvteie tsdgyvgyge
     slaygcsdav
  61 qvtiekilkp lllkedeeli eylwdkmyka tlrfgrrgia iagisgvdta
     lwdimgkkak
 121 kpiykllggs krkvrayitg gyysekkdle klrdeeayyv kmgfkgikvk
     igaksmeedi
 181 erlkairevv gedvkiavda nnvytfeeal emgrrleklg iwffeepiqt
     dyldlsarla
 241 eelevpiagy etaytrwefy eimrkravdi vqtdvmwtgg isemmkignm
     akvmgyplip
 301 hysaggisli gnlhvaaaln spwiemhlrk ndlrdkifke sieidnghlv
     vpdrpglgyt
 361 irdgvfeeyk cks
```

SEQ ID NO: 8 (Mandelate racemase/muconate lactonizing domain-containing protein (*Sulfolobus islandicus* L.D.8.5))
```
   1 mikdirtykl cyeginderd alaikglaeh pmeivvteie tsdgyvgyge
     slaygcsdav
  61 qvtiekilkp lllkedeefi eylwdkmyka tlrfgrrgia iagisgvdta
     lwdimgkkak
 121 kpiykllggs krkvrayitg gyysekkdle klrdeeayyv kmgfkgikvk
     igaksmeedi
 181 erlkairevv gedvkiavda nnvytfeeal emgrrleklg iwffeepiqt
     dyldlsarla
 241 eelevpiagy etaytrwefy eimrkravdi vqtdvmwtgg isemmkignm
     akvmgyslip
 301 hysaggisli gnlhvaaaln spwiemhlrk ndlrdkifke sieidnghlv
     vpdrpglgyt
 361 irdgvfeeyk cks
```

SEQ ID NO: 9 (Mandelate racemase/muconate lactonizing protein (*Sulfolobus islandicus* M.14.25))
```
   1 mikdirtykl cyeginderd alaikglaeh pmeivvteie tsdgyvgyge
     slaygcsdav
  61 qvtiekilkp lllkedeeli eylwdkmyka tlrfgrrgia iagisgvdtg
     lwdimgkkak
 121 kpiykllggs krkvrayitg gyysekkdle klrdeeayyv kmgfkgikvk
     igaksmeedi
 181 erlkairevv gedvkiavda nnvytfeeal emgrrleklg iwffeepiqt
     dyldlsarla
 241 eelevpiagy etaytrwefy eimrkravdi vqtdvmwtgg isenmkignm
     akvmgyplip
 301 hysaggisli gnlhvaaaln spwiemhlrk ndlrdkifke sieidnghlv
     vpdrpglgyt
 361 irdgvfeeyk cks
```

SEQ ID NO: 10 (Mandelate racemase/muconate lactonizing protein (*Sulfolobus islandicus* L.S.2.15))
```
   1 mikdirtykl cyeginderd alaikglaeh pmeivvteie tsdgyvgyge
     slaygcsdav
  61 qvtiekilkp lllkedeeli eylwdkmyka tlrfgrrgia iagisgvdta
     lwdimgkkak
 121 kpiykllggs krkvrayitg gyysekkdle klrdeeayyv kmgfkgikik
     igaksmeedi
 181 erlkairevv gedvkiavda nnvytfeeal emgrrleklg iwffeepiqt
     dyldlsarla
```

-continued

| Sequence Listing Free Text |
|---|

```
241 eelevpiagy etaytrwefy eimrkravdi vqtdvmwtgg isemmkignm
    akvmgyplip
301 hysaggisli gnlhvaaaln spwiemhlrk ndlrdkifke sieidnghlv
    vpdrpglgyt
361 irdgvfeeyk cks
```

2-Keto-3-deoxy-D-arabinonate Dehydratase (KdaD)

SEQ ID NO: 11 (NP_344431.1; GI: 15899826; Hypothetical protein SSO3118 (*Sulfolobus solfataricus* P2)

```
  1 mhfimmklfr vvkrgyyisy aildnstiir ldedpikalm rysenkevlg
    drvtgidyqs
 61 llksfqindi ritkpidppe vwgsgisyem areryseenv akilgktiye
    kvydavrpei
121 ffkatpnrcv ghgeaiavrs dsewtlpepe lavvldsngk ilgytimddv
    sardleaenp
181 lylpqskiya gccafgpviv tsdeiknpys lditlkivre grvffegsvn
    tnkmrrkiee
241 qiqylirdnp ipdgtilttg taivpgrdkg lkdediveit isnigtlitp vkkrrkit
```

SEQ ID NO: 12 (Fumarylacetoacetate (FAA) hydro lase (*Sulfolobus islandicus* Y.N.15.51))

```
  1 mltcllptll yakcifimmk lfrvvkrgyy isyaildnst iirldedpik
    almrysenke
 61 vlgdrvtgid yqsllksfqi ndiritkpid ppevwgsgis yemareryse
    envakilgkt
121 iyekvydavr peiffkatpn rcvghgeaia vrsdsewtlp epelavvlds
    ngkilgytim
181 ddvsardlea enplylpqsk iyagccafgp vivtsdeikn pyslditlki
    vregrvffeg
241 svntnkmrrk ieegiqylir dnpipdgtil ttgtaivpgr dkglkdediv
    eitisnigtl
301 itpvkkrrki t
```

SEQ ID NO: 13 (Fumarylacetoacetate (FAA) hydrolase (*Sulfolobus solfataricus* 98/2))

```
  1 mmklfrvvkr gyyisyaild nstiirlded pikalmryse nkevlgdrvt
    gidyqsllks
 61 fqindiritk pidppevwgs gisyemarer yseenvakil gktiyekvyd
    avrpeiffka
121 tpnrcvghge aiavrsdsew tlpepelavv ldsngkilgy timddvsard
    leaenplylp
181 qskiyagcca fgpvivtsde iknpysldit lkivregrvf fegsvntnkm
    rrkieeqiqy
241 lirdnpipdg tilttgtaiv pgrdkglkde diveitisni gtlitpvkkr rkit
```

SEQ ID NO: 14 (Chain in X, 2-keto-3-deoxy-D-arabinonate, dehydratase)

```
  1 mklfrvvkrg yyisyaildn stiirldedp ikalmrysen kevlgdrvtg
    idyqsllksf
 61 qindiritkp idppevwgsg isyemarery seenvakilg ktiyekvyda
    vrpeiffkat
121 pnrcvghgea iavrsdsewt lpepelavvl dsngkilgyt imddvsardl
    eaenplylpq
181 skiyagccaf gpvivtsdei knpyslditl kivregrvff egsvntnkmr
    rkieeqiqyl
241 irdnpipdgt ilttgtaivp grdkglkded iveitisnig tlitpvkkrr kit
```

SEQ ID NO: 15 (Fumarylacetoacetate (FAA) hydrolase (*Sulfolobus islandicus* HVE10/4))

```
  1 mmklfrvvkr gyyisyaild nstiirlded pikalmryse nkevlgdrvt
    gidyqsllks
 61 fqindiritk pidppevwgs gisyemarer yseenvakil gktiyekvyd
    avrpeiffka
121 tpnrcvghge aiavrsdsew tlpepelavv ldsngkilgy timddvsard
    leaenplylp
181 qskiyagcca fgpvivtsde iknpysldit lkivrkdrvf fegsvntnkm
    rrkieeqiqy
241 lirdnpipdg tilttgtaiv pgrdkglkde diveitisni gtlitpvkkr rkit
```

2,5-dioxopentanoate dehydrogenase (DopDH)

SEQ ID NO: 16 (NP_344430.1; GI: 15899825; Aldehyde dehydrogenase (*Sulfolobus solfataricus* P2)

```
  1 mksyqgladk wikgsgeeyl dinpadkdhv lakirlytkd dvkeainkav
    akfdewsrtp
 61 apkrgsillk agelmeqeaq efallmtlee gktlkdsmfe vtrsynllkf
    ygalafkisg
121 ktlpsadpnt riftvkeplg vvalitpwnf plsipvwkla palaagntav
    ikpatktplm
```

Sequence Listing Free Text 181 vaklvevlsk aglpegvvnl vvgkgsevgd tivsddniaa vsftgstevg kriyklvgnk
241 nrmtriqlel ggknalyvdk sadltlaael avrggfgltg qsctatsrli inkdvytqfk
301 qrllervkkw rvgpgtedvd mgpvvdegqf kkdleyieyg knvgakliyg gniipgkgyf
361 leptifegvt sdmrlfkeei fgpvlsvtea kdldeairlv navdyghtag ivasdikain
421 efvsrveagv ikvnkptvgl elqapfggfk nsgattwkem gedalefylk ektvyegw SEQ ID NO: 17 (Aldehyde dehydrogenase (*Sulfolobus islandicus* HVE10/4))
1 mksyqgladk wikgsgeeyl dinpadkdhv lakirlytkd dvkeainkav akfdewsrtp
61 apkrgsillk agelmeqeaq efallmtlee gktlkdsmfe vtrsynllkf ygalgfkisg
121 ktlpsadpnt riftvkeplg vvalitpwnf plsipvwkla palaagntav ikpatktplm
181 vaklvevlsk aglpegvvnl vvgkgsevgd tivsddniaa vsftgstevg kriyklvgnk
241 nrmtriqlel ggknalyvdk sadltlaael avrggfgltg qsctatsrli ihkdvytqfk
301 qrllervkkw rvgpgtedvd mgpvvdegqf kkdleyieyg knagakliyg gniipgkgyf
361 leptifegvt shmrlfkeei fgpvlsvtea kdldeairlv navdyghtag ivasdikain
421 efvsrveagv ikvnkptvgl elqapfggfk nsgattwkem gedalefylk ektvyegw SEQ ID NO: 18 (Aldehyde dehydrogenase (*Sulfolobus islandicus* Y.G.57.14))
1 mksyqgladk wikgsgeeyl dinpadkdhv lakirlytkd dvkeainkav akfdewsrtp
61 apkrgsillk agelmeqeaq efallmtlee gktlkdsmfe vtrsynllkf ygalafkisg
121 ktlpsadpnt riftvkeplg vvalitpwnf plsipvwkla palaagntav ikpatktplm
181 vaklvevlsk aglpegvvnl vvgkgsevgd tivsddniaa vsftgstevg kriyklvgnk
241 nrmtriqlel ggknalyvdk sadltlaael avrggfgltg qsctatsrli inkdvytqfk
301 qrllervkkw rvgpgtedvd mgpvvdegqf kkdleyieyg knvgakliyg gniipgkgyf
361 leptifegvt sdmrlfkeei fgpvlsvtea kdldeairlv navdyghtag ivasdinain
421 efvsrveagv ikvnkptvgl elqapfggfk nsgattwkem gedalefylk ektvyegw SEQ ID NO: 19 (Aldehyde dehydrogenase (*Sulfolobus islandicus* Y.N.15.51))
1 mksyqgladk wikgsgeeyl dinpadkdhv lakirlytkd dvkeainkav akfdewsrtp
61 apkrgsillk agelmeqeaq efallmtlee gktlkdsmfe vtrsynllkf ygalafkisg
121 ktlpsadpnt riftvkeplg vvalitpwnf plsipvwkla palaagntai ikpatktplm
181 vaklvevlsk aglpegvvnl vvgkgsevgd tivsddniaa vsftgstevg kriyklvgnk
241 nrmtriqlel ggknalyvdk sadltlaael avrggfgltg qsctatsrli inkdvytqfk
301 qrllervkkw rvgpgtedvd mgpvvdegqf kkdleyieyg knvgakliyg gniipgkgyf
361 leptifegvt sdmrlfkeei fgpvlsvtea kdldeairlv navdyghtag ivasdikain
421 efvsrveagv ikvnkptvgl elqapfggfk nsgattwkem gedalefylk ektvyegw SEQ ID NO: 20 (Aldehyde dehydrogenase (*Sulfolobus islandicus* L.S.2.15))
1 mksyqgladk wikgsgeeyl dinpadkdhv lakirlytkd dvkeainkav akfdewsrtp
61 apkrgsillk agelmeqeaq efallmtlee gktlkdsmfe vtrsynllkf ygalafkisg
121 ktlpsadpnt riftvkeplg vvalitpwnf plsipvwkla palaagntav ikpatktplm
181 vaklvevlsk aglpegvvnl vvgkgsevgd tivsddniaa vsftgstevg kriyklvgnk
241 nrmtriqlel ggknalyvdk sadltlaael airggfgltg qsctatsrli inkdvytqfk
301 qrllervkkw rvgpgtedvd mgpvvdegqf kkdleyieyg knvgakliyg gniipgkgyf
361 leptifegvt sdmrlfkeei fgpvlsvtea kdldeairlv navdyghtag ivasdikain

Sequence Listing Free Text 421 efvsrveagv ikvnkptvgl elqapfggfk nsgattwkem gedalefylk ektvyegw

2,5-dioxovalerate dehydrogenase (YcbD)

SEQ ID NO: 21 (NP_388129.1; GI: 16077316; 2,5-dioxovalerate dehydrogenase (*Bacillus subtilis* subsp. *subtilis* str. 168))
```
  1 msviteqnty lnfingewvk sqsgdmvkve npadvndivg yvqnstaedv
    eravtaanea
 61 ktawrkltga ergqylykta dimeqrleei aacatremgk tlpeakgeta
    rgiailryya
121 gegmrktgdv ipstdkdalm fttrvplgvv gvispwnfpv aipiwkmapa
    lvygntvvik
181 patetavtca kiiacfeeag lpagvinlvt gpgsvvgqgl aehdgvnavt
    ftgsnqvgki
241 igqaalarga kyqlemggkn pvivaddadl eaaaeavitg afrstgqkqe
    atsrvivqsg
301 iyerfkekll qrtkditigd slkedvwmgp iasknqldnc lsyiekgkqe
    gaslliggek
361 lengkyqngy yvqpaifdnv tsemtiaqee ifgpvialik vdsieealni
    andvkfglsa
421 siftenigrm lsfideidag lvrinaesag velqapfggm kqssshsreq
    geaakdffta
481 iktvfvkp
```

SEQ ID NO: 22 (Aldehyde dehydrogenase, thermostable (*Bacillus subtilis* subsp. *subtilis* str. ISO-NN-1))
```
  1 msviteqnty lnfingewvk sqsgdmvkve npadvndivg yvqnstaedv
    eravaaanea
 61 ktawrkltga ergqylykta dimeqrleei aacatremgk tlpeakgeta
    rgiailryya
121 gegmrktgdv ipstdkdalm fttrvplgvv gvispwnfpv aipiwkmapa
    lvygntvvik
181 patetavtca kiiacfeeag lpagvinlvt gpgsvvgqgl aehegvnavt
    ftgsnqvgki
241 igqaalarga kyqlemggkn pvivaddadl eaaaeavitg afrstgqkct
    atsraivqsg
301 iyerfkekll qrtkditigd slkedvwmgp iasknqldnc lsyiekgkqe
    gaslliggek
361 lengkyqngy yvqpaifdnv tsemtiaqee ifgpvialik vdsmeealni
    andvkfglsa
421 siftenigrm lsfideidag lvrinaesag velqapfggm kgssshsreq
    geaakdffta
481 iktvfvkp
```

SEQ ID NO: 23 (Hypothetical protein BSNT_00439 (*Bacillus subtilis* subsp. natto BEST195))
```
  1 msviteqnty lnfikgewvk sqsgdmvkve npadvndivg yvqnstaedv
    eravaaanea
 61 ktawrkltga ergqylykta dimeqrleei aacatremgk tlpeakgeta
    rgiailryya
121 gegmrktgdv ipstdkaalm fttrvplgvv gvispwnfpv aipiwkmapa
    lvygntvvik
181 patetavtca kiiacfeeag lpagvinlvt gpgsvvgqgl aehdgvnavt
    ftgsnqvgki
241 igqaalarga kyqlemggkn pvivaddadl eaaaeavitg afrstgqkct
    atsrvivqse
301 iyerfkekll qrtkditigd slkedvwmgp iasknqldnc lsyiekgkqe
    gaslliggek
361 lengkyqngy yvqpaifdnv tsemtiaqee ifgpvialik vdsmeealni
    andvkfglsa
421 siftenigrm lsfideidag lvrinaesag velqapfggm kqssshsreq
    geaakdffta
481 iktvfvkp
```

SEQ ID NO: 24 (Aldehyde dehydrogenase (*Bacillus subtilis* subsp. spizizenii TU-B-10))
```
  1 msviteqnty lnfingewvk sqsgdmvkve npadvndivg yvqnstaddv
    eravaaanea
 61 ktawrkltga ergqylykta dimeqrleei aacatremgk tlpeakgeta
    rgiailryya
121 gegmrktgdv ipstdkdalm fttrvplgvv gvispwnfpv aipiwkmapa
    lvygntvvik
181 patetavtca kiiacfeeag lpagvinlvt gpgsvvgqgl aehegvnait
    ftgsnqvgki
241 igqaalarga kyqlemggkn pvivaddadl eaaaeavitg afrstgqkct
    atsrvivqsg
301 iydrfkekll qrtkdikigd slkedvwmgp iasknqldnc lsyiekgkqe
    gaslliggek
```

-continued

Sequence Listing Free Text

```
361 ledgkyqngy yvqpaifdnv tsemtiaqee ifgpvialik vdsmeealdi
    andvkfglsa
421 siftqnigrm lsfvdeidag lvrinaesag velqapfggm kqssshsreq
    geaakdffta
481 iktvfvkp
```

SEQ ID NO: 25 (Aldehyde dehydrogenase (*Bacillus* sp. JS))

```
  1 msviteqnty lnfingewvq sqsgdmvkve npadvndivg yvqnstaedv
    eravaaanka
 61 ktawrkltga ergqylykta dimerrleei aacatremgk tlpeakgeta
    rgiailryya
121 gegmrktgdv ipstdkdalm fttrvplgvv gvispwnfpv aipiwkmapa
    lvygntvvik
181 patetavtca kiiacfeeag lpagvinlvt gpgsvvgqgl aehdsvnavt
    ftgsnqvgki
241 igqaalarga kyqlemggkn pvivaddadl eaaaeavitg afrstgqkct
    atsrvivqsg
301 iyerfkekll qrtkditigd slkedvwmgp iasknqldnc lsyiekgkre
    gasllmggek
361 lenekyqngy yvqpaifdnv tsemtiaqee ifgpvialik vdsmeealdi
    andvkfglsa
421 siftenigkm lsfideidag lvrvnaesag velqapfggm kgssshsreq
    geaakdffta
481 iktvfvkp
```

Xylose dehydrogenase (xylB)
SEQ ID NO: 26 (YP_002516237.1; GI: 221233801; Xylose dehydrogenase xylB (*Caulobacter crescentus* NA1000))

```
  1 mssaiypslk gkrvvitggg sgigagltag farqgaevif ldiadedsra
    leaelagspi
 61 ppvykrcdlm nleaikavfa eigdvdvlvn nagnddrhkl advtgaywde
    rinvnlrhml
121 fctqavapgm kkrgggavin fgsiswhlgl edlvlyetak agiegmtral
    arelgpddir
181 vtcvvpgnvk tkrqekwytp egeaqivaaq clkgrivpen vaalvlflas
    ddaslctghe
241 ywidagwr
```

SEQ ID NO: 27 (Oxidoreductase, short-chain dehydrogenase/reductase (*Phenylobacterium zucineum* HLK1))

```
  1 mgvtsaiyps lkgkrvvvtg ggsgigaglv eafvrqgaev hfldvletes
    rvletslaga
 61 evppvfhrcd ltdagaiegc fakigpvqvl vnnagnddrh tldevtpayf
    ddriavnlrh
121 mvfcakavvp amkaagegai infgsiswhl glpdlvlyet akagiegmtr
    alarelgpfg
181 irvtcvapgn vktlrqmkwy tpegeaeiva qqclksriep advaalvlfl
    asddarmctg
241 heywidagwr
```

SEQ ID NO: 28 (Dehydrogenase of unknown specificity, short-chain alcohol dehydrogenase (*Caulobacter* sp. AP07))

```
  1 mssaiypslq gkrvvvtggg sgigagivaa farqgaevif ldvvdadsea
    laaklsdspi
 61 aptymrcdlt dleamaetfa rigpidvlvn nagnddrhgl aeitpaywdq
    rmavnlrhml
121 fatqavapgm kargggavin fgsiswhlgl pdlvlyetak agiegmtral
    arelgpddir
181 vtcvvpgnvk tkrqekwytp egeaeivaaq alkgrlvpdh vaslvlflas
    ddaalctghe
241 ywidagwr
```

SEQ ID NO: 29 (Short-chain dehydrogenase/reductase SDR (*Caulobacter* sp. K31))

```
  1 mnievkrpqv stssaiypsl kgkrvvvtgg gsgigagiva gfarqgsevi
    fldvadqdsk
 61 alaeqlsgae iapvylrcdl tdldavaktf adigpvdvlv nnagnddrhg
    laqitpaywd
121 ermsvnlrhm lfatqavapg mkargggaii nfgsiswhlg lpdlvlyeta
    kagiegmtra
181 larelgpddi rvtcvvpgni ktkrqekwyt pegeaeivaa galkgrlvpd
    hvaslvmfla
241 sddaslctgh eywidagwr
```

SEQ ID NO: 30 (Short-chain dehydrogenase/reductase SDR (*Caulobacter segnis* ATCC 21756))

```
  1 mssaiypslk gkrvvitggg sgigaglvag fvrqgaevif ldivdadsqa
    lvaelskdav
```

-continued

| Sequence Listing Free Text |
|---|

```
 61 iapvykrcdl mdidalkatf aeigdvdvlv nnagnddrhs ladltpaywd
    nrigvnlrhm
121 vfaaqavagg mkkrgggaii nfgsiswhlg ledlvlyeta kagiegmtra
    larelgpddi
181 rvtcvvpgnv ktkrqekwyt pegeaeivka qclkgrilpd hvaslvlfla
    sddaslctgh
241 eywidagwr
```

Xylonolactonase (xylC)

SEQ ID NO: 31 (YP_002516236.1; GI: 221233800; Xylonolactonase xylC (*Caulobacter crescentus* NA1000))

```
  1 mtaqvtcvwd lkatlgegpi whgdtlwfvd ikqrkihnyh patgerfsfd
    apdqvtflap
 61 ivgatgfvvg lktgihrfhp atgfslllev edaalnnrpn datvdaqgrl
    wfgtmhdgee
121 nnsgslyrmd ltgvarmdrd icitngpcvs pdgktfyhtd tlektiyafd
    laedgllsnk
181 rvfvqfalgd dvypdgsvvd segylwtalw ggfgavrfsp qgdavtriel
    papnvtkpcf
241 ggpdlktlyf ttarkglsde tlaqyplagg vfavpvdvag qpqhevrlv
```

SEQ ID NO: 32 (S MP-30/gluconolaconase/LRE domain-containing protein (*Caulobacter segnis* ATCC 21756))

```
  1 mtaevtcvwd lkatlgegpi whgdalwfvd ikqrkihnyk pttgehfsfd
    apdqvtflap
 61 iadaggfvvg lktgihrfhp itgfrlliev edsaldnrpn datvdangrl
    wfgtmhdgee
121 aksgslyrmd aegvarmdkd icitngpcvs pdgktfyhtd tlektvwayd
    laedgtlsnk
181 rafvhvklgd diypdgtvvd segclwialw ggfgvirvsp ageivgriev
    papnvtkvcf
241 ggpdlktlfl ttarkglsde tlaqyplagg lfaigvniag qpqhevrlv
```

SEQ ID NO: 33 (Gluconolactonase (*Caulobacter* sp. AP07))

```
  1 mpepicvwdl katlgegpiw iaaeqalwfv dikshkvhrf hpesgetksf
    dapdqvtfla
 61 pragggfvag lksglhhfhp etgfaylgei epadlnnrpn datvdaegrl
    wfgtmhdgee
121 tptgalyrlg adgqpvqqdq gvcitngpcv spdgktfyht dtlekviway
    dlgadgelsn
181 krqffrleid dawpdgsvvd aegyvwaalw gghgairisp agelvdrvtl
    painvtkpcf
241 ggpdlktlyf ttarkglgde qlaayplcgg vfalpvavag qpgyevrldl p
```

SEQ ID NO: 34 (SMP-30/gluconolaconase/LRE domain-containing protein (*Caulobacter* sp. K31))

```
  1 mpepicvwdl katlgegpiw saeeqavwfv dikghkvhrf hpasgatasf
    dapdqvtfla
 61 phaggggfva glksglhrfd pttgafvfla qieppelnnr pndatvdaeg
    rlwfgtmhdg
121 emtptgalyr lsadgkpiqq degvcitngp caspdgktfy htdtlekviw
    aydlgadgsl
181 snkreffrle iadawpdgsv vdsegfvwta lwgghgalrl spageivdrv
    ilpainvtkp
241 cfggpdlktv yftsarkgls deqlaaypqc gglfalpvav aggpqyevrl dlr
```

SEQ ID NO: 35 (Gluconolactonase (*Phenylobacteriurn zucineum* HLK1))

```
  1 mkvlsepdcv lradaelgeg pvwradddav wfvdikgrri hryepvtgaa
    wswaapaqpg
 61 fiapvagggw vaglktglhr feprggrfel itavedpsld nrlndgfvda
    kgrlwfgsmh
121 dgetaltgal yrlderglqr cdtgycitng paaspdgrtl yhtdtlqkti
    yafdlspage
181 lsnkrvfari eegggypdgp avdaegcvwt glfagwhvrr yspkgellak
    vgfpvanitk
241 lafggddlts vyattawkgl sadere kqpl agglfrfevd vpglpqnqma ha
```

D-xylonate dehydratase (xylD)

SEQ ID NO: 36 (NP_419636.1; GI: 16125072; Dihydroxy-acid dehydratase)*Caulobacter crescentus* CB15))

```
  1 mrsalsnrtp rrfrsrdwfd npdhidmtal ylerfmnygi tpeelrsgkp
    iigiaqtgsd
 61 ispcnrihld lvqrvrdgir daggipmefp vhpifencrr ptaaldrnls
    ylglvetlhg
```

-continued

Sequence Listing Free Text 121 ypidavvltt gcdkttpagi maattvnipa ivlsggpmld gwhenelvgs
gtviwrsrrk
181 laageiteee fidraassap saghcntmgt astmnavaea lglsltgcaa
ipapyrergq
241 mayktgqriv dlayddvkpl diltkqafen aialvaaagg stnaqphiva
marhagveit
301 addwraaydi plivnmqpag kylgerfhra ggapavlwel lqqgrlhgdv
ltvtgktmse
361 nlqgretsdr evifpyhepl aekagflvlk gnlfdfaimk ssvigeefrk
rylsqpgqeg
421 vfearaivfd gsddyhkrin dpaleiderc ilvirgagpi gwpgsaevvn
mqppdhllkk
481 gimslptlgd grqsgtadsp silnaspesa iggglswlrt gdtiridlnt
grcdalvdea
541 tiaarkqdgi pavpatmtpw qeiyrahasq ldtggvlefa vkyqdlaakl prhnh SEQ ID NO: 37 (Dihydroxy-acid dehydratase (*Caulobacter* sp. K31))
1 mtsantpsgr pprrfrsrdw fdnpdhidmt alylerfmny gitpeelrsg
kpiigiaqtg
61 sdispcnrih ldlvtrirdg irdaggipme fpvhpifenc rrptaaldrn
lsylglvevl
121 hgypidavvl ttgcdkttpa gimaattvni paivlsggpm ldgwhdgelv
gsgtviwrsr
181 rklaageine eefiqrasds apsaghcntm gtastmnava ealglsltgc
aaipapyrer
241 gqmayktgqr ivdlayedvk pldiltkkaf enaialvaaa ggstnaqphi
vamarhagld
301 itaddwraay diplilnmqp agkylgerfh raggapavlw ellqagrlhg
dvmtvtgktm
361 genlegretk drevvfpygq pmseragflv lkgnlfdfai mktsvisqef
rqrylsepgk
421 edsfearavv fdgsddyhar indpslnide rtilvirgag pigwpgsaev
vnmqppdall
481 krgimslptl gdgrqsgtad spsilnaspe saiggglswl rtgdmiridl
ntgrcdalvd
541 eatiaerrke gvppvpatmt pwqeiyraht gqletggvle favkyqdlas klprhnh SEQ ID NO: 38 (Dihydroxyacid dehydratase/phosphogluconate dehydratase (*Caulobacter* sp. AP07))
1 mtspnrtprr frsrdwfdnp dhidmtalyl erfmnygitp eelrsgkpii
giaqtgsdis
61 pcnrihldlv trirdgirda ggipmefpvh pifencrrpt aaldrnlsyl
glvetlhgyp
121 idavvlttgc dkttpagima attvnipaiv lsggpmldgw hdgelvgsgt
viwrsrrkla
181 ageiteeefi qrasdsapsa ghcntmgtas tmnavaealg lsltgcaaip
apyrergqma
241 yrtggrivdl ayedikpkdi ltkqafenai alvaaaggst naqphivama
rhagldvtad
301 dwraaydipl ilnmqpagky lgerfhragg apavlwellq agrlhgdamt
vtgktmaenl
361 egretrdrev vfpyaapmse ragflvlkgn lfdfaimkts visqefrdry
lsepgqegaf
421 earavvfdgs gdyharindp slgidertil virgagpigw pgsaevvnmq
ppdallkkgi
481 mslptlgdgr qsgtadspsi lnaspesavg gglswlrtgd viridlntgr
cdalvdeati
541 aarkleglpp vpetmtpwqe iyrahtgqle tggvlefavk yqdlaaklpr hnh SEQ ID NO: 39 (Dihydroxy-acid dehydratase (*Caulobacter segnis* ATCC 21756))
1 msertprrfr srdwfdnpdh idmtalyler fmnygitpee lrsgkpiigi
aqtgsdispc
61 nrihldlvtr irdgirdagg ipmefpvhpi fencrrptaa ldrnlsylgl
vetlhgypid
121 avvlttgcdk ttpagimaat tvnipaivls ggpmldgwhe gelvgsgtvi
wrsrrklaag
181 eiteeefidr aassapsagh cntmgtastm navaealgls ltgcaaipap
yrergqmayk
241 tgqrivdlay edvkpldilt kkafqnaial vaaaggstna qphivamarh
agveitaddw
301 raaydipliv nmqpagkylg erfhraggap avlwellqqg rlhgdvltvt
gktmgenlqg
361 retsdrevif pyhqplaeka gflvlkgnlf dfaimkssvi geefrkryls
epgkegvfea
421 raivfdgsdd yhkrindpal eidercilvi rgagpigwpg saevvnmqpp
dhllkkgims -continued

| Sequence Listing Free Text |
|---|

481 lptlgdgrqs gtadspsiln aspesaiggg lswlrtgdti ridintgrcd
alvdeatiae
541 rkkegipavp atmtpwqeiy rahtgqlesg gvlefavkyq dlasklprhn h SEQ ID NO: 40 (Dihydroxy-acid dehydratase (*Caulobacter crescentus* NA1000))
1 msnrtprrfr srdwfdnpdh idmtalyler fmnygitpee lrsgkpiigi
aqtgsdispc
61 nrihldlvqr vrdgirdagg ipmefpvhpi fencrrptaa ldrnlsylgl
vetlhgypid
121 avvlttgcdk ttpagimaat tvnipaivls ggpmldgwhe nelvgsgtvi
wrsrrklaag
181 eiteeefidr aassapsagh cntmgtastm navaealgls ltgcaaipap
yrergqmayk
241 tgqrivdlay ddvkpldilt kqafenaial vaaaggstna qphivamarh
agveitaddw
301 raaydipliv nmqpagkylg erfhraggap avlwellqqg rlhgdvltvt
gktmsenlqg
361 retsdrevif pyheplaeka gflvlkgnlf dfaimkssvi geefrkryls
qpgqegvfea
421 raivfdgsdd yhkrindpal eidercilvi rgagpigwpg saevvnmqpp
dhllkkgims
481 lptlgdgrqs gtadspsiln aspesaiggg lswlrtgdti ridlntgrcd
alvdeatiaa
541 rkqdgipavp atmtpwqeiy rahasqldtg gvlefavkyq dlaaklprhn h

| 2-Keto-3-deoxy-D-arabinonate Dehydratase (xylX) |
|---|

SEQ ID NO: 41 (NP_419640.1; GI: 16125076; Hypothetical protein CC_0823 (*Caulobacter crescentus* CB15))
1 mvcrrllawt arareaedfa lvrqptcrph mlalpsader apptvsalqt
lefwgddavg
61 vseflpedwk aatllgridf gegptpvlvr ggrvedvski aptvadlmna
fqpgaviprg
121 edkgpleald irpvwedpdg aapvkllapv dlqclkaagv tfavstlerv
ieerargdag
181 ealkirtlla ermggdlksv epgsqgaqrl kdaliadglw sqylevaigp
daeiftkgpt
241 lssmgwgdqv gvrydshwnn pepevvllcd gsglirgaal gndvnlrdfe
grsalllska
301 kdnnascaig pffrlfdetf glddvrsaev elkitgrdnf vldgksnmsl
isrdpavlag
361 qaygkqhqyp dgfalflgtm fapiqdrdtp gqgfthkvgd rvrvstpklg
vlenevttcd
421 kakpwtfgis alirnlagrg ll SEQ ID NO: 42 (Fumarylacetoacetate hydrolase family protein (*Caulobacter crescentus* NA1000))
1 mgvseflped wkaatllgri dfgegptpvl vrggrvedvs kiaptvadlm
nafqpgavip
61 rgedkgplea ldirpvwedp dgaapvklla pvdlqclkaa gvtfaystle
rvieerargd
121 agealkirtl laermggdlk svepgsqgaq rlkdaliadg lwsqylevai
gpdaeiftkg
181 ptlssmgwgd qvgvrydshw nnpepevvll cdgsglirga algndvnlrd
fegrsallls
241 kakdnnasca igpffrlfde tfglddvrsa evelkitgrd nfvldgksnm
slisrdpavl
301 agqaygkqhq ypdgfalflg tmfapiqdrd tpgqgfthkv gdrvrvstpk
lgvlenevtt
361 cdkakpwtfg isalirnlag rgll SEQ ID NO: 43 (Fumarylacetoacetate (FAA) hydrolase (*Caulobacter segnis* ATCC 21756))
1 mgvseflpdd wknatllgri dfgegptpvl vrggrvedms kvaptvadlm
nafgpgaaip
61 rgedkgples ldirpvwedp dgaapvklla pvdlqclkaa gvtfavstle
rvieerargd
121 aaaalkireq lsasmggdlr svnpgsegae rlkqtlikdg lwsqylevai
gpdaeiftkg
181 ptlssmgwgd hvgvrydshw nnpepevvll cdgagqirga slgndvnlrd
fegrsallls
241 kakdnnasca igpffrlfde tfalddvrsa evelkitgrd nfvldgksnm
slisrdpavl
301 agqaygkqhq ypdgfalflg tmfapiqdrd tpgqgfthkv gdrvrvstpk
lgvlenevtt
361 cdkakpwtfg isalirnlag rgll -continued

| Sequence Listing Free Text |
| --- |

SEQ ID NO: 44 (Hypothetical protein Caul_4000 (*Caulobacter* sp. K31))
1 malsdflpdd wrdatllgri dfgqgptpvl irggriedvs kiapttsdlm nafapgaaip
61 rgedlgplea ldvravwenp qgaaakllap vdlqvlkaag vtfavstler vieerargda
121 aealkiraql adsmggdlrs vnpgsdgaer lkqtlikdgl wsqylevaig pdaeiftkgp
181 tlssmgwgdh vgvrsdshwn npepevvllc dgsgqirgaa lgndvnlrdf egrsalllsk
241 akdnnascai gpffrlfddg fslddvrsae vtlkitgrdn fvldghsnms lisrdpavla
301 gqafgkqhqy pdgfalflgt mfapiqdrda agqgfthkvg drvrvatpkl gvlenevttc
361 dlaapwtfgv salirnlagr gll SEQ ID NO: 45 (Fumarylacetoacetate (FAA) hydrolase family protein (*Caulobacter* sp. AP07))
1 malsdflpdd wrdatllgrv dfgdgptpvl vrggriedvs riapttsdlm nafapgaaip
61 agadlgplea ldvrpvwenp dgaaakllap vdlqvlkaag vtfavstler vieerargda
121 aealkiraql adsmggdlrg vnpgsegaar lketlikggl wsqylevaig pdaeiftkgp
181 tlssmgwgdq vgvrsdshwn npepevvllc dgsgrirgas lgndvnlrdf egrsalllsk
241 akdnnascai gpffrlfddg fglddvrsae vtlkitgrdn fvldghsnms lisrdpavla
301 gqafgkqhqy pdgfvlflgt mfapiqdrdt agqgfthkvg drvrvatpkl gvlenevttc
361 dvappwtfgv salirnlagr gll

| L-arabinose dehydrogenase (AraE) |
| --- |

SEQ ID NO: 46 (YP_439823.1; GI: 83716868; Dehydrogenase (*Burkholderia thailandensis* E264))
1 mnsvytlglv gigkiardqh lpaiaaepgf dllacasrha qvrgvrnypd idallaaepa
61 ldavslaapp qvryaqaraa lgagkhvmle kppgatagei aalralarer grtlfaawhs
121 rhasavepar awlatrtira vqarwkedvr rwhpgqqwiw epgglgvfdp ginalsivtr
181 ilprelvlra atlvvpanah tpiaaeldcv dtagvpvrae fdwrhgpveq wdiavdtdgg
241 vlsigaggar lsiagepval ppereypsly arfraligeg asdvddrplr lvadafmigr
301 riaadpfqr SEQ ID NO: 47 (Dehydrogenase (*Burkholderia thailandensis* TXDOH))
1 mnsvytlglv gigkiardqh lpaiaaepgf dllacasrha qvrgvrnypd idallaaepa
61 ldavslaapp qvryaqaraa lgagkhvmle kppgatagei aalhalarer grtlfaawhs
121 rhasavepar awlatrtira vqvrwkedvr rwhpgqqwiw epgglgvfdp ginalsivtr
181 ilprelvlra atlvvpanah tpiaaeldcv dtagvpvrae fdwrhgpveq wdiavdtdgg
241 vlaigaggar lsiagepval ppereypsly arfraligeg asdvddrplr lvadafmigr
301 riaadpfqr SEQ ID NO: 48 (Galactose 1-dehydrogenase (*Burkholderia ambifaria* IOP40-10))
1 mskvislgvi gigkiardqh lpaiaaepgf altacasrha evngvrnype lgallaaepe
61 leavslcapp qvryaqaraa leagkhvmle kppgatlgev aaldalarer gltlfatwhs
121 rcasavepar awlatrtira vqvrwkedvr rwhpgqqwiw epgglgvfdp ginalsivtr
181 ilprelvlre atlyvpsdvq tpiaaeldca dtdgvpvhae fdwrhgpveq weiavdtsdg
241 vlaisrggaq lsiggepvei gpqreypaly ahfraliarg esdvdvrplr lvadaflfgr
301 rvgtdafgr SEQ ID NO: 49 (Galactose 1-dehydrogenase (*Burkholderia ambifaria* MC40-6))
1 mskvislgvi gigkiardqh lpaiaaepgf altacasrha evngvrnype lgallaaepe -continued Sequence Listing Free Text 61 leavslcapp qvryaqaraa leagkhvmle kppgatlgev aaldalarer
gltlfatwhs
121 rcasavepar awlatrtira vqvrwkedvr rwhpgqqwiw epgglgvfdp
ginalsivtr
181 ilprelvlre atlyvpsdvq tpiaaeldca dtdgvpvhae fdwrhgpveq
weiavdtsdg
241 vlaisrggaq lsiagepvei gpqreypaly ahfraliarg esdvdvrplr
lvadaflfgr
301 rvgtdafgr SEQ ID NO: 50 (Dehydrogenase (*Burkholderia thailandensis* MSMB43))
1 mntvytlglv gigkiardqh lpaiaaepgf dlracasrha evrgvrnhpd
igallaaepa
61 ldavslaapp qvryaqaraa ldagkhvmle kppgatvgei aalralarer
grtlfaswhs
121 rharavepar awlatrtira vqvrwkedvr rwhpgqqwiw epgglgvfdp
ginalsivtr
181 ilprelvlra atlvvpanvh tpiaaefdcv dtagvpvrae fdwrhgpveq
wdiavdtdgg
241 vlaigaggar lsiagepval ppeceypsly arfhaliaar esdvddrplr
lvadafmvgr
301 riaadpfhr L-arabinonolactonase (AraI)

SEQ ID NO: 51 (YP_439819.1; GI: 83717359; Senescence marker protein-30 family protein (*Burkholderia thailandensis* E264))
1 messnrpart gaasaatlrv dcrnalgega twcdatraly wvdiegarlw
rwraagaqgg
61 aatdswempe rigcfaltdd pdvllvglas rlaffdarrr aftpivdvep
dlptrlndgr
121 cdragafvfg mkdegggspr avggyyrlnp dlslqrlalp laaiangitf
spdgsamyfc
181 dsptreiqvc dyrpggdvdr irsfvrladd cgepdgsavd adggvwnaqw
ggarivryda
241 qgveteriav ptpqpscval ddggrlyvts arvglddgal arspgaggvf
vadtrhagla
301 tsrfalarna SEQ ID NO: 52 (Senescence marker protein-30 family protein (*Burkholderia thailandensis* TXDOH))
1 messsrpart gaasaatlrv dcrnalgega twcdatraly wvdiegarlw
rwraagaqgg
61 aatdswempe rigcfaltdd pdvllvglas rlaffdarrr aftpivdvep
dlptrlndgr
121 cdragafvfg mkdegggspr avggyyrlnp dlslqrlalp paaiangiaf
spdgsamyfc
181 dsptreiqvc dyrpggdvdr irpfvrladd cgepdgstvd adggvwsaqw
ggarivryda
241 qgveteriav ptpqpscval ddggrlyvts arvglddgal arspgaggvf
vadtrhagla
301 tsrfalarna SEQ ID NO: 53 (Senescence marker protein-30 family protein (*Burkholderia thailandensis* Bt4)
1 messnrpart gaasaatlrv dcrnalgega twcdatraly wvdiegarlw
rwraagaqgg
61 aatdswempe rigcfaltdd pdvllvglas rlaffdarrr aftpivdvep
dlptrlndgr
121 cdragafvfg mkdegggspr avggyyrlnp dlslqrlalp laaiangiaf
spdgsamyfc
181 dsptreiqvc dyrpggdvdr irsfvrladd cgepdgsavd adggvwnaqw
ggarivryda
241 qgveteriav ptpqpscval ddggrlyvts arvglddgal arspgaggvf
vadtrhagla SEQ ID NO: 54 (Hypothetical protein BPSS0776 (*Burkholderia pseudomallei* K96243))
1 messnrpart heasaatllv dcrnalgega twcdaahaly wvdiegarlw
rwraagahgg
61 ercdswempe riacfaltgd pdvllvglas rlaffdtrrr altpivdvep
drptrlndgr
121 cdragafvfg tkdesggasp raiggyyrln adlslqrlal ppaaiangia
fspdgsamyf
181 cdsptreiqv cdyrpggdvd rvrsfvrlad ahgepdgstv dasggvwnaq
wggarvvryd -continued Sequence Listing Free Text

```
241 aqgvetdria vptpqpscvt ldaagrlyvt sarvglddga lagnpgaggv
    fvahtrhsgs
301 atprfalarh a
```

SEQ ID NO: 55 (Gluconolactonase (*Burkholderia pseudomallei* NCTC 13177))

```
  1 messnrpart heasaatllv dcrnalgega twcdaahaly wvdiegarlw
    rwraagahgg
 61 ercdswempe riacfaltgd pdvllvglas rlaffdtrrr altpivdvep
    drptrlndgr
121 cdragafvfg tkdesggasp raiggyyrln adlslqrlal ppaaiangia
    fspdgsamyf
181 cdsptreiqv cdyrpggdvd rvrsfvrlad ehgepdgstv dasggvwnaq
    wggarvvryd
241 aqgvetdria vptpqpscvt ldaagrlyvt sarvglddga lagnpgaggv
    fvahtrhpgg
301 atprfalarh a
```

L-arabinonate dehydratase (AraB)

SEQ ID NO: 56 (YP_439826.1; GI: 83718062; Dihydroxy- cid dehydratase (*Burkholderia thailandensis* E264))

```
  1 msaskpklrs aqwfgthdkn gfmyrswmkn qgipdhefdg rpivgicntw
    seltpcnahf
 61 rklaehvkrg vyeaggfpve fpvfsngesn lrpsamltrn lasmdveeai
    rgnpidavvl
121 lagcdkttpa llmgaascdv paivvsggpm lngkldgkni gsgtavwqlh
    ealkageidl
181 hrflsaeagm srsagtcntm gtastmacla ealgvalphn aaipavdarr
    yvlahmsgmr
241 ivgmaheglv lskiltraaf enairvnaai ggstnavihl kaiagrlgvp
    leledwlrlg
301 rgtptivdlm psgrflmeef yyagglpavl rrlgeanllp hpgaltvngq
    slwdnvrdap
361 shddevirpl drpliadggi rilrgnlapr gavlkpsaas pellkhrgra
    vvfenfehyk
421 atiddealdv dansvlvlkn cgprgypgma evgnmglppk llrqgvkdmv
    risdarmsgt
481 aygtvvlhva peaaaggpla avrngdwiel dgeagtltld vsddelarrl
    sdhdpasapg
541 vaehaagggy arlyvdhvlq adegcdldfl vgrrgaavpr hsh
```

SEQ ID NO: 57 (Dihydroxy-acid dehydratase (*Burkholderia thailandensis* TXDOH))

```
  1 msaskpklrs aqwfgthdkn gfmyrswmkn qgipdhefdg rpivgicntw
    seltpcnahf
 61 rklaehvkrg vyeaggfpve fpvfsngesn lrpsamltrn lasmdveeai
    rgnpidavvl
121 lagcdkttpa llmgaascdv paivvsggpm lngkldgrni gsgtavwqlh
    ealkageidl
181 hrflsaeagm srsagtcntm gtastmacla ealgvalphn aaipavdarr
    yvlahmsgmr
241 ivgmaheglv lskiltraaf enairvnaai ggstnavihl kaiagrlgvp
    leledwlrlg
301 rgtptivdlm psgrflmeef yyagglpavl rrlgeanllp hpgaltvngq
    slwdnvrdap
361 shddevirpl drpliadggi rilrgnlapr gavlkpsaas pellkhrgra
    vvfenfehyk
421 atiddealev dansvlvlkn cgprgypgma evgnmglppk llrqgvkdmv
    risdarmsgt
481 aygtvvlhva peaaaggpla avrngdwiel dceagtltld vsddelarrl
    sdhdpasapg
541 vaehaagggy arlyvdhvlq adegcdldfl vgrrgaavpr hsh
```

SEQ ID NO: 58 (Dihydroxy-acid dehydratase (*Burkholderia multivorans* ATCC 17616))

```
  1 msatkprlrs aqwfgtndkn gfmyrswmkn qgipdhefdg rpiigicntw
    seltpcnahf
 61 rklaehvkrg ifeaggfpve fpvfsngesn lrpsamltrn lasmdveeai
    rgnpidavvl
121 lagcdkttpa llmgaascdv paivvsggpm lngklegkni gsgtavwqlh
    ealkageidl
181 hhflsaeagm srsagtcntm gtastmacma ealgvalphn aaipavdsrr
    yvlahmsgir
241 ivemaleglv lskvltraaf enairvnaai ggstnavihl kaiagrigvp
    leledwmrig
301 rdtptivdlm psgrflmeef yyagglpavl rrlgeggllp hpdaltvngk
    tlwdnvreap
361 nyddevirpl drpliadggi rilrgnlapr gavlkpsaas pellkhrgra
    vvfenfdhyk
```

-continued

| Sequence Listing Free Text |
|---|

421 atindesldv dansvlvlkn cgprgypgma evgnmglppk llrqgvkdmv
risdarmsgt
481 aygtvvlhva peaaaggpla avrngdwiel dceagtlhld ipddelqrrl
sdvdpaaapg
541 vagqagkggy arlyldhvlq adegcdldfl vgtrgaevps hsh SEQ ID NO: 59 (Dihydroxy-acid dehydratase (*Burkholderia multivorans* CGD2M))
1 msatkprlrs aqwfgtndkn gfmyrswmkn qgipdhefdg rpiigicntw
seltpcnahf
61 rklaehvkrg ifeaggfpve fpvfsngesn lrpsamltrn lasmdveeai
rgnpidavvl
121 lagcdkttpa llmgaascdv paivvsggpm lngklegkni gsgtavwqlh
ealkageidl
181 hhflsaeagm srsagtcntm gtastmacma ealgvalphn aaipavdsrr
yvlahmsgir
241 ivemaleglv lskvltraaf enairvnaai ggstnavihl kaiagrigvp
leledwmrig
301 rdtptivdlm psgrflmeef yyagglpavl rrlgeggllp hpdaltvngk
tlwdnvrdap
361 nyddevirpl drpliadggi rilrgnlapr gavlkpsaas pellkhrgra
vvfenfdhyk
421 atindealdv dansvlvlkn cgprgypgma evgnmglppk llrqgvkdmv
risdarmsgt
481 aygtvvlhva peaaaggpla avrngdwiel dceagtlhld ipddelqrrl
sdvdpaaapg
541 vagqagkggy arlyldhvlq adegcdldfl vgtrgaevps hsh SEQ ID NO: 60 (Dihydroxy-acid dehydratase (*Burkholderia thailandensis* MSMB43))
1 msaskpklrs aqwfgthdkn gfmyrswmkn qgipdhefdg rpivgicntw
seltpcnahf
61 rklaehvkrg vyeaggfpve fpvfsngesn lrpsamltrn lasmdveeai
rgnpidavvl
121 lagcdkttpa llmgaascdv paivvsggpm lngkldgkni gsgtavwqlh
ealkageidl
181 hrflsaeagm srsagtcntm gtastmacla ealgvalphn aaipavdarr
yvlahlsgar
241 ivemahegla lstiltraaf enairanaai ggstnavihl kaiagrlgvp
leledwmrig
301 rdtptivdlm psgrflmeef yyagglpavl rrlgeanllp hpgaltvngk
slwenvrdap
361 nhddevirpl arpliadggi rvlrgnlapr gavlkpsaas pellrhrgra
vvfenfehyk
421 atiddealdv dassvlvlkn cgprgypgma evgnmglppk llrqgvkdmv
risdarmsgt
481 aygtvvlhva peaaaggpla avrngdwial dceagtltld vsddelarrl
sdldpasapg
541 aagqagsggy arlyvdhvlq adegcdldfl vgrrgaavpr hsh 2-Keto-3-deoxy-L-arabinonate Dehydratase (AraD)

SEQ ID NO: 61 (YP_439824.1; GI: 83717217; Dihydrodipicolinate synthase (*Burkholderia thailandensis* E264))
1 mntsrspryr gvfpvvpttf aeageldlps qkravdfmid agseglcila
nfseqfalad
61 derdvltrti lehvagrvpv ivttthystq vcaarsrraq elgaamvmam
ppyhgatfrv
121 pdtqihafya rlsdaldipi miqdapasgt vlsapflarm areieqvsyf
kietpgaank
181 lrelirlggd aiegpwdgee aitlladlna gatgamtgga ypdgirpive
ahregradda
241 falyqrwlpl inhenrqtgl laakalmreg gviacerprh plppihpdsr
aeliaiarrl
301 dplvlrwar SEQ ID NO: 62 (Dihydrodipicolinate synthase, putative (*Burkholderia thailandensis* TXDOH))
1 mntsrspryr gvfpvvpttf teageldlps qkravdfmid agseglcila
nfseqfalad
61 derdvltrti lehvagrvpv ivttthystq vcaarsrraq elgaamvmam
ppyhgatfrv
121 pdtqihafya rlsdaldipi miqdapasgt vlsapflarm areieqvsyf
kietpgaank
181 lrelirlggd aiegpwdgee aitlladlna gatgamtgga ypdgirpive
ahregradda
241 falyqrwlpl inhenrqtgl laakalmreg gviacerprh plppihpdsr
aeliaiarrl
301 dplvlrwar

| Sequence Listing Free Text |
|---|

SEQ ID NO: 63 (Dihydrodipicolinate synthase, putative (*Burkholderia thailandensis* MSMB43))

```
  1 mntsrspryr gvfpvvpttf tetgeldlps qmravdfmid agseglcila
    nfseqfalad
 61 derdvltrti lehvagrvpv ivttthystr vcaarsrraq elgaamvmam
    ppyhgatfry
121 pdtqihafya rlsdaldipi miqdapasgt vlsapflarm areieqvsyf
    kietpgaank
181 lrelirlggd aiegpwdgee aitlladlna gatgamtgga ypdgirpivd
    ahrdgradda
241 falyqrwlpl inhenrqtgl vaakalmreg gviacerprh plppihpdsr
    aelieiarrl
301 dplvlrwar
```

SEQ ID NO: 64 (Dihydrodipicolinate synthase/N-acetylneuraminate lyase (*Burkholderia dolosa* AUO158))

```
  1 mtssrtpryr gifpvvpttf tdtgeldlas qkravdfmid agsdglcila
    nfseqfaitd
 61 derdvltrti lehvagrvpv ivttthystq vcaarslraq qlgaamvmam
    ppyhgatfrv
121 peaqiydfya rvsdaidipi miqdapasgt vlsapllarm areieqvsyf
    kietpgaank
181 lrelirlggd avegpwdgee aitlladlna gatgamtgga ypdgirpile
    ahregrhdda
241 fahygrwlpl inhenrqsgi lsakalmreg gviacerprh pmpelhpdtr
    aeliaiarrl
301 dplvlrwar
```

SEQ ID NO: 65 (Dihydrodipicolinate synthetase family protein (*Burkhoideria multivorans* ATCC BAA-247))

```
  1 mtssrtpryr gifpvvpttf tetgeldlas qkravdfmid agsdglcila
    nfseqfalad
 61 derdvltrti lehvagrvpv ivttshystq tciarsvraq qlgaamvmvm
    ppyhgatfrv
121 peaqihafya rlsdalsipi miqdapasgt vlsapflaql areiehvayf
    kietpgaank
181 lrelirlggd aiegpwdgee aitlladlha gatgamtgga ypdgirpile
    ahregrhdda
241 faryqtwlpl inhenrqsgi ltakalmreg gviaceaprh pmpalhpdtr
    aeliaiarrl
301 dplvlrwar
```

| D-glucarate dehydratase (YcbF) |
|---|

SEQ ID NO: 66 (NP_388131.2; GI: 255767063; Glucarate dehydratase (*Bacillus subtilis* subsp. *subtilis* str.168))

```
  1 msspiqeqvq kekrsnipsi semkvipvag hdsmllnlsg ahspfftrni
    viltdssgnq
 61 gvgevpggeh irrtlelsep lvvgksigay qailqtvrkq fgdqdrggrg
    nqtfdlrttv
121 havtaleaal ldllgkflqe pvaallgegk qrdevkmlgy lfyigdrnrt
    tlpyqsdeqs
181 dcawfrlrhe ealtpeaivr laesaqeryg fqdfklkggv lrgeeeieav
    talskrfpea
241 ritldpngaw sleeaialck gkqdvlayae dpcgdengys arevmaefrr
    atglptatnm
301 iatdwremgh aiqlhavdip ladphfwtmq gsvrvaqmch dwgltwgshs
    nnhfdislam
361 fthvaaaapg ritaidthwi wqdgqrltkq pfeissgcvk vpdkpglgvd
    idmeqvekah
421 eiyrkmnlga rndaipmqfl isnwefdrkr pclvr
```

SEQ ID NO: 67 (Glucarate dehydratase (*Bacillus subtilis*))

```
  1 msspiqeqvq kekrsnipsi semkvipvag hdsmllnlsg ahspfftrni
    viltdssgnq
 61 gvgevpggeh irrtlelsep lvvgksigay qailqtvrkq fgdqdrggrg
    nqtfdlrttv
121 havtaleaal ldflgkflqe pvaallgegk qrdevkmlgy lfyigdrnrt
    tlpyqsdeqs
181 dcawfrlrhe ealtpeaivr laesaqeryg fqdfklkggv lrgeeeieav
    talskrfpea
241 ritldpngaw sleeaialck gkqdvlayae dpcgdengys arevmaefrr
    atglptatnm
301 iatdwremgh aiqlhavdip ladphfwtmq gsvrvaqmch dwgltwgshs
    nnhfdislam
```

-continued

| Sequence Listing Free Text |
| --- |

361 fthvaaaapg ritaidthwi wqdgqrltkq pfeissgcvk vpdkpglgvd
idmeqvekah
421 eiyrkmnlga rndaipmqfl isnwefdrkr pclvr SEQ ID NO: 68 (Hypothetical protein BSNT_00441 (*Bacillus subtilis* subsp. *natto* BEST195))
1 msspiqeqvq kekrsnipsi temkvipvag hdsmllnlsg ahspfftrni
viltdssgnq
61 gvgevpggeh irrtlelsep lvvgksigay qailqtvrkq fgdqdrggrg
nqtfdlrttv
121 havtaleaal ldllgkflqe pvaallgegk qrdevkmlgy lfyigdrkrt
tlpyqsdeqs
181 dcawfrlrhe ealtpeaivr laesaqeryg fqdfklkggv lqgeeeieav
talskrfpea
241 ritldpngaw sleeaialck gkqdvlayae dpcgdengys arevmaefrr
atglptatnm
301 iatdwremgh aiqlhavdip ladphfwtmq gsvrvaqmch dwgltwgshs
nnhfdislam
361 fthvaaaapg ritaidthwi wqdgqrltkq pfeissgcvk vpdkpglgid
idmegvekah
421 eiyrkmnlga rndaipmqfl isnwefdrkr pclvr SEQ ID NO: 69 (Glucarate dehydratase (*Bacillus subtilis* subsp. *spizizenii* TU-B-10))
1 msspiqeqvq kekrsnipsi cemkvipvag hdsmllnlsg ahspfftrni
viltdssgnq
61 gvgevpggeq irrtlelaep lvvgksigay qsilqtvrkg fadqdrggrg
iqtfdlrttv
121 havtaleaal ldllgkflqe pvaallgegk qrdevkmlgy lfyigdrkqt
tlpyqsdeqs
181 dcgwfrlrhe ealtpeaivr laesaqeryg fqdfklkggv lrgedeieav
talakrfpea
241 ritldpngaw sleeaialck gkhdvlayae dpcgdengys arevmaefrr
atglptatnm
301 iatdwremgh aiqlhavdip ladphfwtmq gsvrvaqmch dwgltwgshs
nnhfdislam
361 fthvaaaapg ritaidthwi wqdgqrltkq pfeisegcvk vpnkpglgid
idmeqvekah
421 elyrkmnlga rndavpmqfl isnwefdrkr pclvr SEQ ID NO: 70 (Glucarate dehydratase (*Bacillus subtilis* subsp. *subtilis* str. RO-NN-1))
1 msspmqeqiq kekrsnvpsi semkvipvag hdsmllnlsg ahspfftrni
viltdssgnq
61 gvgevpggeh irrtlelsep lvvgksigay qailqtvrkq fgdqdrggrg
nqtfdlrttv
121 havtaleaal ldllgkflqe pvaallgegk qrdevkmlgy lfyigdrkrt
tlpyqsdeqs
181 ycawfrlrhe ealtpeaivr laesaqeryg fqdfklkggv lrgeeeieav
talskrfpea
241 ritldpngaw sleeaialck gkqdvlayae dpcgdengys arevmaefrr
atglptatnm
301 iatdwremgh aiqlhavdip ladphfwtmq gsvrvaqmcn dwgltwgshs
nnhfdislam
361 fthvaaaapg ritaidthwi wqdgqrltkq pfeissgcvk vpdkpglgvd
idmeqvekah
421 eiyrkmnlga rndaipmqsl isnwefdrkr pclvr

| D-galactarate dehydratase (YcbH) |
| --- |

SEQ ID NO: 71 (NP_388133.2; GI: 255767065; D-galactarate dehydratase (*Bacillus subtilis* subsp. *subtilis* str.168))
1 mamnlrknqa plyikvheid ntaiivndgg lpkgtvfscg lvleedvpqg
hkvaltdlnq
61 gdeivrygev igfadetikr gswirealvr mpappalddl planrvpqpr
pplegytfeg
121 yrnadgsagt knilgittsv qcvvgvldya vkrikeellp kypnvddvvp
lhhqygcgva
181 inapdavipi rtiqnlakhp nfggevmvig lgcekllper iasendddil
slqdhrgfaa
241 miqsilemae erlirinsrt rvscpvsdlv iglqcggsda fsgvtanpav
gyaadllvra
301 gatvlfsevt evrdaihllt prayseevgq slikemkwyd sylrrgdadr
sanpspgnkk
361 gglsnvveka lgsvaksgts pisgvlgpge rakqkgllfa atpasdfvcg
tlqlaagmnl
421 qvfttgrgtp yglaaapvlk vstrhslseh wadlidinag riatgeasie
dvgweifrti
481 ldvasgrkqt wadrwglhnd lclfnpapvt -continued

| Sequence Listing Free Text |
| --- |

SEQ ID NO: 72 (Hypothetical protein BSNT 00443 (*Bacillus subtilis* subsp. *natto* BEST195))
```
  1 mamnlrknqa plyikvheid ntaiivndgg lpkgtvfscg lvleedvpqg
    hkvaltdlnq
 61 gdeivrygev igfadetikr gswirealvr mpappalddl planrvpqpr
    pplegytfeg
121 yrnadgsagt knilgittsv qcvvgvldya vkrikeellp kypnvddvvp
    lhhqygcgva
181 inapdavipi rtiqnlakhp nfggevmvig lgcekllper iasendddil
    slqdhrgfaa
241 miqsilemae erlirinsrt rvscpvsdlv iglqcggsda fsgvtanpav
    gyaadllvra
301 gatvlfsevt evrdaihllt prayseevgq slikemkwyd sylrrgdadr
    sanpspgnkk
361 gglsnvveka lgsvaksgts pisgvlgpge raeqkgllfa atpasdfvcg
    tlqlaagmnl
421 qvfttgrgtp yglaaapvlk vstrhslseh wadlidinag riatgeasie
    dvgweifrti
481 ldvasgrkqt wadrwglhnd lclfnpapvt
```

SEQ ID NO: 73 (D-galactarate dehydratase (*Bacillus subtilis* subsp. *subtilis* str. RO-NN-1))
```
  1 mamnlrknqa plyikvheid ntaiivndgg lpkgtvfscg lvleedvpqg
    hkvaltdlnq
 61 gdeivrygev igfadetikr gswirealvr mpappalddl planrvpqpr
    pplegytfeg
121 yrnadgsagt knilgittsv qcvvgvldya vkrikeellp kypnvddvvp
    lhhqygcgva
181 inapdavipi rtiqnlakhp nfggevmvig lgcekllper iasendddil
    slqdhrgfaa
241 miqsilemae erlirinsrt rvscpvsdlv iglqcggsda fsgvtanpav
    gyaadllvra
301 gatvlfsevt evrdaihllt prayseevgq slieemkwyd sylrrgdadr
    sanpspgnkk
361 gglsnvveka lgsvaksgts pisgvlgpge raeqkgllfa atpasdfvcg
    tlqlaagmnl
421 qvfttgrgtp yglaaapvlk vstrhslseh wadlidinag riatgeasie
    dvgweifrti
481 ldvasgrkqt wadrwglhnd lclfnpapvt
```

SEQ ID NO: 74 (Hypothetical protein BSSC8_40810 (*Bacillus subtilis* subsp. *subtilis* SC-8))
```
  1 mamnlrknqa plyikvheid ntaiivnegg lpkgtvfscg lvleedvpqg
    hkvaltdlnq
 61 gdeivrygev igfadetikr gswirealvr mpappalddl plenrvpqpr
    pplegytfeg
121 yrnadgsagt knilgittsv qcvvgvldya vkrikeellp kypnvddvvp
    lhhqygcgva
181 inapdavipi rtiqnlakhp nfggevmvig lgcekllper iasendddil
    slqdhrgfaa
241 miqsilemae erlirinsrt rvscpvsdlv iglqcggsda fsgvtanpav
    gyaadllvra
301 gatvlfsevt evrdaihllt prayseevgq slikemkwyd sylrrgdadr
    sanpspgnkk
361 gglsnvveka lgsvaksgts pisgvlgpge raeqkgllfa atpasdfvcg
    tlqlaagmnl
421 qvfttgrgtp yglaaapvlk vstrhslseh wadlidinag qiatgeasie
    dvgweifrti
481 ldvasgrkqt wadrwglhnd lclfnpapvt
```

SEQ ID NO: 75 (Galactarate dehydratase (*Bacillus subtilis* BSn15))
```
  1 mamnlrknqa plyikvheid ntaiivndgg lpkgtvfscg lvleedvpqg
    hkvaltdlnq
 61 gdeivrygev igfadetikr gswiredlvr mpappalddl planrvpqpr
    pslegytfeg
121 yrnadgstgt knilgittsv qcvvgvldya vkrikeellp kypnvddvvp
    lhhqygcgva
181 inapdavipi rtiqnlakhp nfggevmvig lgcekllper iasengddil
    slqdhrgfaa
241 miqsilemae erlirinsrt rvscpvsdlv iglqcggsda fsgvtanpav
    gyaadllvra
301 gatvlfsevt evrdaihllt prayseevgq slikemkwyd sylrrgdadr
    sanpspgnkk
361 gglsnvveka lgsvaksgts pisgvlgpge rakqkgllfa atpasdfvcg
    tlqlaagmnl
421 qvfttgrgtp yglaaapvlk vstrhslseh wadlidinag riatgeasie
    dvgweifrti
481 ldvasgrkqt wadrwglhnd lclfnpapvt
```

Sequence Listing Free Text

5-dehydro-4-deoxyglucarate dehydratase (YcbC)

SEQ ID NO: 76 (NP_388128.2; GI: 255767061; 5-dehydro-4-deoxyglucarate dehydratase (*Bacillus subtilis* subsp. *subtilis* str.168))
```
  1 msrirkapag ilgfpvapfn tqgkleeeal fqniefllne gleaifiacg
    sgefqslsqk
 61 eyeqmvevav saaggkvpvy tgvggnlsta ldwaqlsekk gadgylilpp
    ylvhgeqegl
121 yqyaktiies tdlnailyqr dnavlsveqi krlteceqlv gvkdgvgnmd
    lninlvytig
181 drlgwlngmp maevtmpayl pigfhsyssa isnyiphisr mfydalkngn
    delvkelyrh
241 vilpindirk qrkgyavsli kagmeimgln vrntarppvg pvekdhyqql
    eailkqaadr
301 fpkkaatv
```

SEQ ID NO: 77 (Putative 5-dehydro-4-deoxyglucarate dehydratase (*Bacillus subtilis* subsp. *subtilis* str. RO-NN-1))
```
  1 msrirkapag ilgfpvapfn tqgkleeeal fqniefllne gleaifiacg
    sgefqslsqk
 61 eyeqmvevav saaggkvpvy tgvggnlsta lewaqlsekk gadgylilpp
    ylvhgeqegl
121 yqyaktiies tdlnailyqr dnavlsveqi krlteceqlv gvkdgvgnmd
    lninlvytig
181 drlgwlngmp maevtmpayl pigfhsyssa isnyiphisr mfydalkngn
    delvkelyrh
241 vilpindirk qrkgyavsli kagmeimgln vrntarppvg pvekdhyqql
    eailkqaadr
301 fpkkaatv
```

SEQ ID NO: 78 (5-dehydro-4-deoxyglucarate dehydratase (*Bacillus vallismortis* DV1-F-3))
```
  1 mnrirkaptg ilgfpvapfn tqgqleeeal fqniefllee gleaifiacg
    sgefqslsqk
 61 eyeqmvevav saaegkvpvy tgvggnlsta lewarlsekk gadgylilpp
    ylvhgeqegl
121 yqyaktiies tdlnailyqr dnavlsleqi krlteceqlv gvkdgvgnmd
    lninlvytlg
181 drlgwlngmp maevtmpayl pigfhsyssa isnyiphisr mfydalkngn
    delvkelyqh
241 vilpindirk qrkgyavsli kagmeimgln vrntarppvg pvekehyrql
    eailkqaadr
301 fpkkaatv
```

SEQ ID NO: 79 (5-dehydro-4-deoxyglucarate dehydratase (*Bacillus subtilis* subsp. *spizizenii* TU-B-10))
```
  1 msrirkapag ilgfpvapfn tqgkleeeal fqniefllee gleaifiacg
    sgefqslsqk
 61 eyeqmvevai saaggkvpvy tgvggnlsta lewaqlsekk gadgylilpp
    ylvhgeqegl
121 yqyaktiies tdlnailyqr dnavlsveqi krltefeqlv gvkdgvgnmd
    lninlvytlg
181 drlgwlngmp maevtmpayl pigfhsyssa isnyiphisr mfydalkngd
    delvkelyqh
241 vilpindirk qrkgyavsli kagmeimgln vrntarppvg pvekdhyqql
    eailkqaadr
301 fpkkaatv
```

SEQ ID NO: 80 (ycbC (*Bacillus subtilis*))
```
  1 msrirkapag ilgfpvapfn tqgtleeeal fqniefllne gleaifiacg
    sgefqslsqk
 61 eyeqmvevav saaggkvpvy tgvggnlsta ldwaqlsekk gadgylilpp
    ylvhgeqegl
121 yqyaktiies tdlnailyqr dnavlsveqi krlteceqlv gvkdgvgnmd
    lninlvytig
181 drlgwlngmp maevtmpayl pigfhsyssa isnyiphisr mfydalkngn
    delvkelyrh
241 vilpindirk qrkgyavsli kagmeimgln vrntarppvg pvekdhyqql
    eailkqpadr
301 fpkkaatv
```

Amino acid transporter LysE (HypE)

SEQ ID NO: 81 (NP_743408.1; GI: 26987983; Amino acid transporter LysE (*Pseudomonas putida* KT2440))
```
  1 maaesyrlqa ldpsrawhrf fatvqqqvek rafgddsseh clrnaqqelt
    mlgvtdygaf
```

-continued

| Sequence Listing Free Text |
|---|

61 viaflillai pgpgnfalit atgkggikag laatcgvivg dqvllwlava
gvatllatyp
121 aafhmvqwag aaylaylglr mllskpggaa htcrmdngqy lrqtmmitll
npkaimfyma
181 ffplfvdpvk hqglvtfgfm aatvavvtfl ygliavvlth qlaermrasp
rianmferla
241 gaclvgfgik laamr SEQ ID NO: 82 (Amino acid transporter LysE (*Pseudomonas putida* BIRD-1))
1 mqqqvekraf gddssahclr naqqeltmlg vtdygafvia flillaipgp
gnfalitatg
61 kggikaglaa tcgvivgdqv llwlavagva tllatypaaf hvvqwagaay
laylglrmll
121 skpggaahtc rmdngqylrq tmmitllnpk aimfymaffp lfvdpvkhqg
lvtfgfmaat
181 vavvtflygl iavvlthqla ermraspria nmferlagac lvgfgiklaa mr SEQ ID NO: 83 (Amino acid transporter LysE (*Pseudomonas putida* ND6))
1 mqqqvekrav gddssahclr naqqeltmlg vtdygafvia flillaipgp
gnfalitatg
61 kggikaglaa tcgvivgdqv llwlavagva tllatypaaf hmvqwagaay
laylglrmll
121 skpggaahtc rmdngqylrq tmmitllnpk aimfymaffp lfvdpvkhqg
lvtfgfmaat
181 vavvtflygl iavvlthgla ermranpria nmferlagac lvgfgiklaa mr SEQ ID NO: 84 (Lysine exporter protein LysE/YggA (*Pseudomonas putida* F1))
1 mlgvtdygaf viaflillai pgpgnfalit atgkggikag laatcgvivg
dqvllwlava
61 gvatllatyp aafhmvqwag aaylaylglr mllskpggaa htcrmdngqy
lrqtmmitll
121 npkaimfyma ffplfvdpvk hqglvtfgfm aatvavvtfl ygliavvlth
qlaermranp
181 rianmferla gaclvgfgik laamr SEQ ID NO: 85 (Unknown (*Pseudomonas putida*))
1 mlgvtdygaf viafiillai pgpgnfalit atgkggikag laatcgvivg
dqvllwlava
61 gvatllatyp aafhivqwag aaylaylglr mllskpgdap rtsrmdngqy
lrqtmlitll
121 npkaimfyma ffplfidpvk hqglvtfgfm aatvavitfl ygliavvlth
rlaermranp
181 ritnmferla gaclvgfgik laamr

| PP_1245 |
|---|

SEQ ID NO: 86 (NP_743405.1; GI: 26987980; Hypothetical protein PP_1245 (*Pseudomonas putida* KT2440))
1 mrptengvlh lrkkfvasll avaiasttac aqlgiskeqa gtvigglagv
aigstmgsgn
61 gkiaaaliag gigayvgnri ghmldekdqq alalrtqevl sqqqttasaq
pvtwksdhsg
121 ataqivpgke ytktkqvevk rapkiqavps mklinepyvt isdnlnvraa
pngagekvgs
181 lknhteftav gstgdwilvg rkgvtvgyvh knyvepkaqa vakrvtpavn
ldeldvaask
241 etqgfdldsv qslptqtvaa eaacrpvtvs lksgsgqteq eqntfckqan gtweli SEQ ID NO: 87 (SH3 type 3 domain-containing protein (*Pseudomonas putida* W619))
1 mrkkfvasll avaiatttac aqlgiskeqa gtvigglagv aigstmgsgn
gkiaaaliag
61 gigayvgnri ghmldekdqq alalrtqevl sqsatasaqp vtwksdhsga
taqitpgkey
121 tqtkkvevkr apkiqavpsm klinepyvti sdnlnvraap nttgekvgsl
kshteftavg
181 stgdwilvgr kgvtvgyvhk nyvepkaqai akraapavnl ddldvaanke
tqgfdldsiq
241 slptetvaae aacrpvtvsl ksqsgqteqe qntfckqang tweli SEQ ID NO: 88 (Hypothetical protein G1E_03180 (*Pseudomonas* sp. TJI-51))
1 mrkkfvasll avaiasttac aqlgiskeqa gtvigglagv aigstlgsgn
gkiaaaliag
61 gigayvgnri gnmldekdqq alalrtqevl sqqqatasaq pvtwksdhsg
asaqivpgke
121 ytktkqvevk rapkiqavps mklinepyvt tsdnlnvraa pnasgekvgs
lknhteftav -continued

| Sequence Listing Free Text |
|---|

```
 181 gatgdwilvg rkgvtvgyvh kdyvepkaqa vakrvtpavn ldeldvaask
     etqafdldsl
 241 qslptqtvaa eaacrpvtvs lkaqngkteq eqntfckqan gtweli
```

SEQ ID NO: 89 (SH3 type 3 domain-containing protein (*Pseudomonas putida* GB-1))

```
   1 mrkkfvasll avaiasttac aqlgiskeqa gtvigglagv aigstmgsgn
     gkiaaaliag
  61 gigayvgnri ghmldekdqq alalrtqevl sqqqatasaq pvtwksdhsg
     ataqivpgke
 121 ytqtkkvevk rapkiqavps mklinepyvt vsdnlnvraa pnqsgekvgs
     lknhteftav
 181 gstgdwilvg rkgvtvgyvh knyvepkaqa vakrvtpavn ldeldvaask
     etqgfdldsv
 241 qslptetvaa eaacrpvtvs lksqsgqteq eqntfckqan gtweli
```

SEQ ID NO: 90 (SH3 type 3 domain-containing protein (*Pseudomonas putida* F1))

```
   1 mrkkfvasll avaiasttac aqlgiskeqa gtvigglagv aigstmgsgn
     gkiaaaliag
  61 gigayvgnri ghmldekdqq alalrtqevl sqqqttasaq pvtwksdhsg
     ataqivpgke
 121 ytktkqvevk rapkiqavps mklinepyvt isdnlnvraa pnqagekvgs
     lknhteftav
 181 gstgdwilvg rkgvtvgyvh knyvepkaqa vakrvtpavn ldeldvaask
     etqgfdldsv
 241 qslptqtvaa eaacrpvtvs lksqsgqteq eqntfckqan gtweli
```

| PP_1247 |
|---|

SEQ ID NO: 91 (NP_743407.1; GI: 26987982; Hypothetical protein PP_1247 (*Pseudomonas putida* KT2440))

```
   1 mpicssgwrg lawwdsasnw rrcadpkpds vrarltatlk kppathgsrg
     lvhsaitqsi
  61 gfqliglahe qrrkqalafl egvllferav fdqllpdgaf rvavvlglga
     kvtaprrqpn
 121 llaegcelcl gdlllvfaes lfqrfeaava hrvvldlgla gkaahrfsqh
     rlagvravra
 181 nqhraqgtle lgfdivqfrq rlevglandf phlgavvavg dherhrafai
     agaldgevqv
 241 drgtkvtgaa dqkragywla hrhvgapgev rrggptiggq lgtwldfvad
     irhqhdfgpl
 301 ggnvrvahlh aqqldmnaai laysvmgqlq rislqvhpgh iaadielvlg
     parqaffsrt
 361 tlyglhqarq aahellgaig lrrrhadlrv gyrqvagkrr vgnvplrqhi
     lkeiallevv
 421 vvgqrsllar agdhriatte hqhrcghtan qqlllvhlfd hgvcltgpwr
     krcssrsrtv
 481 grprgss
```

SEQ ID NO: 92 (Uncharacterized protein LOC100789425 (Glycine max))

```
   1 msniafrsti vfllfsavls tppedpikca tsenttctit nsygafpdrs
     ickaaqvlyp
  61 tteqelvsvv asatrnktkm kvatrfshsi pklvcpegen gllistkyln
     kilkvdvetr
 121 tmtvesgvtl qqlineaakv glalpyapyw wgltigglmg tgahgstlrg
     kgsavhdyvv
 181 elrivrpagp edgyamvenl neqhedlnaa kvslgvlgvi sqitlklepl
     fkrsityvak
 241 ddsdlggqvv afgdahefad itwypsqhka iyrvddrvpi ntsgnglydf
     ipfrptpsla
 301 svfirtteei qestndangk civastasnt litaaygltn ngiifagypi
     igfqnrlqss
 361 gscldslqda littcawdpr mkglffhqtt fsirlsfvks fiedvqklve
     lepkglcvlg
 421 lyngmlmryv tassaylghq enaldidity yrskdpmtpr lyedileeve
     qlgifkyggl
 481 phwgknrnla fegaikkyks aeyflkvkek ydldglfsst wtdqvlglkd
     gvtilkdgca
 541 leglciclqd shcnpskgyy crpgkvykea rvctnlk
```

| PP_1246 |
|---|

SEQ ID NO: 93 (NP_743406.1; GI: 26987981; Hypothetical protein PP_1246 (*Pseudomonas putida* KT2440))

```
   1 mkkhalalav igacglvpqa fahelafskk dnikvevpgd atswckpqvd
     ltitrpawdn
  61 qellaglltk lpfvfakdcs takvswkavd akgnlyasgs gnasnlglvt
     laaapataap
```

Sequence Listing Free Text

```
121 apaaaptptp apapapapap aaaaapavve aapaqakpap apapapapav
    aaepapapea
181 paaapvvppa papatavaaa ptsdfgrsvv lenrnlmqvt dgtgckwvls
    tsiigdgdtl
241 sfgttpampc pasgfgegsf dkiswkavgt yrgdnwtrvy ahpsglifnk
    nlepavkdka
301 vsyltpqadq aaflvgeipg rqmkvyltft rssygvlrpf ssdpyyvavt
    pdesfaldat
361 kykeaaleif dlikttsptt tdvanlfivk dlsaisnniw gndaqkitrn
    riginrqglf
421 fdvrdganwa vqreqqrvre qrqrqqelar vhtrvleryq qlqdgmsdfk
    greteal aqm
481 agikvrfasp leqqnpatsa svvpmmvhvt gkkgdfysid fpsngrlvad
    eeysegwyvt
541 qvanatpyyp lddgravpty raysagepea ckqdhcadrv sfgavlakef
    pnagidfswt
601 pevsqqyvnd wnnasamvq
```

SEQ ID NO: 94 (Hypothetical protein T1E_4663 (*Pseudomonas putida* DOT-T1E))

```
  1 mvlenrnlmq vtdgtgckwv lstsiigdgd tlsfgttpam pcpasgfgeg
    sfdkiswkav
 61 gtyrgdnwtr vyahpsglif nkhlepavkd kaysyltpqa dqaaflvgei
    pgrqmkvylt
121 ftrssygvlr pfgsdpyyva vtpdesfald atkykeaale ifdlikttsp
    tttdvanlfi
181 vkdlsaisnn iwgndaqkit rnriginrqg lffdvrdgan wavqreqqrv
    reqrqrqqel
241 arvhtrvler yqqlqdgmsd fkgreteala qmagikvrfa spleqqnpat
    sasvvpmmvh
301 vtgkkgdfys idfpsngrlv adeeysegwy vtqvanatpy yplddgravp
    tyraysagep
361 eackqdhcad rvsfgavlak efpnagidfs wtpevsqqyv ndwnnasamv q
```

SEQ ID NO: 95 (Hypothetical protein YSA_07676 (*Pseudomonas putida* ND6))

```
  1 mkkhalalav igacglvpqa fahelafskk dnikvevpgd attwckpqvd
    ltitrpawdn
 61 qellsglltk lpfvfakdcs takvswkavd akgnlyasgs gnasnlglvt
    laaapataap
121 apaaavapap apaqpeapaa aaptpapapa papapaaaaa pavveaapaq
    akpapapapa
181 pavaaepapt peapaaapvv ppapapatav aaaptsdfgr svvlenrnlm
    qvtdgtgckw
241 vlstsiigdg dtlsfgttpa mpcpasgfge gsfdkiswka vgtyrgdnwt
    rvyahpsgli
301 fnkhlepavk dkaysyltpq adqaaflvge ipgrqmkvyl tftrssygvl
    rpfgsdpyyv
361 avtpdesfal datkykeaal eifdliktts ptttdvanlf ivkdlsaisn
    niwgndaqki
421 trnriginrq glffdvrdga nwavqreqqr vreqrqrqqe larvhtrvle
    ryqqlqdgms
481 dfkgreteal aqmagikvrf aspleqqnpa tsasvvpmmv hvtgkkgdfy
    sidfpsngrl
541 vadeeysegw yvtqvanatp yyplddgrav ptyraysage peackqdhca
    drvsfgavla
601 kefpnagidf swtpevsqqy vndwnnasam vq
```

SEQ ID NO: 96 (Hypothetical protein Pput_1275 (*Pseudomonas putida* F1))

```
  1 mkkhalalav igacglvpqa fahelafskk dnikvevpgd attwckpqvd
    ltitrpawdn
 61 qellsglltk lpfvfakdcs takvswkavd akgnlyasgs gnasnlglvt
    laaapapapa
121 papapapaaa apapaaavap apapaqpeap aaaaptpapa papapaaaaa
    pavveaaaaq
181 akpapapapa pavaaepapt peapaaapvv ppapapatav aaaptsdfgr
    svvlenrnlm
241 qvtdgtgckw vlstsiigdg dtlsfgttpa mpcpasgfge gsfdkiswka
    vgtyrgdnwt
301 rvyahpsgli fnknlepavk dkavsyltpq adqaaflvge ipgrqmkvyl
    tftrssygvl
361 rpfgsdpyyv avtpdesfal datkykeaal eifdliktts ptttdvanlf
    ivkdlsaisn
421 niwgndaqki trnriginrq glffdvrdga nwavqreqqr vreqrqrqqe
    larvhtrvle
481 ryqqlqdgms dfkgreteal aqmagikvrf aspleqqnpa tsasvvpmmv
    hvtgkkgdfy
541 sidfpsngrl vadeeysegw yvtqvanatp yyplddgrav ptyraysage
    peackqdhca
601 drvsfgavla kefpnagidf swtpevsqqy vndwnnasam vq
```

-continued

| Sequence Listing Free Text |
| --- |

SEQ ID NO: 97 (Hypothetical protein PputGB1_4145 (*Pseudomonas putida* GB-1))
1 mkkhalalav vgacglvpqa fahelafskk enikvevpgd aatwckpeve ltitrpawdk
61 qellsglltk lpfvfakdca takvswkavd akgnlyasgs gnatnlglvt lavapaaasa
121 apapapapap apapapapap avaalapaap avpapaeapa avaaapapav vepapakaev
181 apapvvaaep apapvaetpv aapvappvpa padavaaapt sdfgravvlq nrnlmqvtdg
241 tgckwvlsts iisdgdtlsf gttpvmpcpa sgfgegsfek iswkavgtyr gdnwtrvyah
301 psglifnknl esavkdkavs yltadadqaa flvgeipsrq mkvyltftrs sygvlrpfss
361 dpyyvavtpd esfaldaaky keaaleifdl ikatsptttd vanlfivkdi saitnsmwgn
421 daqkitrnri gitrqglffd vreganwavq reqqrvreer grqqelarvh trvleryqql
481 qdgmsdfkgr etealaqmag ikvrfaspla qqdpatsarv apmmvhvtgk kgdfytldfp
541 skgrlvadee ysegwyvtqv anatpyypld dgravptyra ysagepeacq qdhcadrvsf
601 gavlakefpn agidfswtpe vsqkyvndwn nasamvq

| Alpha-ketoisovalerate decarboxylase |
| --- |

SEQ ID NO: 98 (YP_003353820.1; GI: 281491840; Alpha-ketoisovalerate decarboxylase (*Lactococcus lactis* subsp. *lactis* KF147))
1 mytvgdylld rlhelgieei fgvpgdynlq fldqiisrkd mkwvgnanel nasymadgya
61 rtkkaaaflt tfgvgelsav nglagsyaen lpvveivgsp tskvqnegkf vhhtladgdf
121 khfmkmhepv taartlltae natveidrvl sallkerkpv yinlpvdvaa akaekpslpl
181 kkenptsnts dqeilnkiqe slknakkpiv itgheiisfg lentvtqfis ktklpittln
241 fgkssvdetl psflgiyngk lsepnlkefv esadfilmlg vkltdsstga fthhlnenkm
301 islnidegki fnesiqnfdf eslisslldl sgieykgkyi dkkqedfvps nallsqdrlw
361 qavenltqsn etivaeqgts ffgassiflk pkshfigqpl wgsigytfpa algsqiadke
421 srhllfigdg slqltvqelg lairekinpi cfiinndgyt vereihgpnq syndipmwny
481 sklpesfgat eervvskivr tenefvsvmk eaqadpnrmy wielvlaked apkvlkkmgk
541 lfaeqnks SEQ ID NO: 99 (Indole-3-pyruvate decarboxylase (*Lactococcus lactis* subsp. *lactis* IO-1))
1 mytvgdylld rlhelgieei fgvpgdynlq fldqiisrkd mkwvgnanel nasymadgya
61 rtkkaaaflt tfgvgelsav nglagsyaen lpvveivgsp tskvqnegkf vhhtladgdf
121 khfvkmhepv taartlltae natveidrvl svllkerkpv yinlpvdvaa akaekpslpl
181 kkenpnsnts dqeilnkiqe slknakkpiv itgheiisfg lektvtqfis ktklpittln
241 fgkssvdeal psflgiyngk lsepnlkefv esadfilmlg vkltdsstga fthhlnenkm
301 islninegki fsesiqnfdf eslisslldl sgieykgkyi dkkqenfvps nallsqdrlw
361 qavenitqsn etivaeqgts ffgassiflk pkshfigqpl wgsigftfpa algsqiadke
421 srhllfigdg slqltvqelg lairekinpi cfiinndgyt vereihgpnq syndipmwny
481 sklpesfgat edrvvskivr tenefvsvmk eaqadpnrmy wielvlaked apkvlkkmgk
541 lfaeqnks SEQ ID NO: 100 (Branched-chain alpha-ketoacid decarboxylase (*Lactococcus lactis*))
1 mytvgdylld rlhelgieei fgvpgdynlq fldqiisred mkwignanel nasymadgya
61 rtkkaaaflt tfgvgelsai nglagsyaen lpvveivgsp tskvqndgkf vhhtladgdf
121 khfmkmhepv taartlltae natyeidrvl sqllkerkpv yinlpvdvaa akaekpalsl -continued Sequence Listing Free Text

```
181 ekessttntt eqvilskiee slknaqkpvv iaghevisfg lektvtqfvs
    etklpittln
241 fgksavdesl psflgiyngk lseislknfv esadfilmlg vkltdsstga
    fthhldenkm
301 islnidegii fnkvvedfdf ravvsslsel kgieyegqyi dkqyeefips
    saplsqdrlw
361 qavesltqsn etivaeqgts ffgastiflk snsrfigqpl wgsigytfpa
    algsqiadke
421 srhllfigdg slqltvqelg lsireklnpi cfiinndgyt vereihgptq
    syndipmwny
481 sklpetfgat edrvvskivr tenefvsvmk eaqadvnrmy wielvleked
    apkllkkmgk
541 lfaeqnk
```

SEQ ID NO: 101 (Chain A, branched-chain ketoacid decarboxylase (Kdca)(*Lactococcus Lactis*))

```
  1 mgsshhhhhh ssglvprgsh masmytvgdy lldrlhelgi eeifgvpgdy
    nlqfldqiis
 61 redmkwigna nelnasymad gyartkkaaa flttfgvgel sainglagsy
    aenlpvveiv
121 gsptskvqnd gkfvhhtlad gdfkhfmkmh epvtaartll taenatyeid
    rvlsqllker
181 kpvyinlpvd vaaakaekpa lslekesstt ntteqvilsk ieeslknaqk
    pvviaghevi
241 sfglektvtq fvsetklpit tlnfgksavd eslpsflgiy ngklseislk
    nfvesadfil
301 mlgvkltdss tgafthhlde nkmislnide giifnkvved fdfravvssl
    selkgieyeg
361 qyidkqyeef ipssaplsqd rlwqaveslt qsnetivaeq gtsffgasti
    flksnsrfig
421 qplwgsigyt fpaalgsqia dkesrhllfi gdgslqltvq elglsirekl
    npicfiinnd
481 gytvereihg ptqsyndipm wnysklpetf gatedrvvsk ivrtenefvs
    vmkeaqadvn
541 rmywielvle kedapkllkk mgklfaeqnk
```

SEQ ID NO: 102 (Indole-3-pyruvate decarboxylase (*Lactococcus lactis* subsp. *lactis* II1403))

```
  1 mytvgdylld rlhelgieei fgvpgdynlq fldqiisrkd mkwvgnanel
    nasymadgya
 61 rtkkaaaflt tfgvgelsav nglagsyaen lpvveivgsp tskvqnegkf
    vhhtladgdf
121 khfmkmhepv taartlltae natveidrvl sallkerkpv yinlpvdvaa
    akaekpslpl
181 kkenptsnts dqeilnkiqe slknakkpiv itgheiisfg lektvtqfis
    ktklpittln
241 fgkssvdetl psflgiyngk lsepnlkefv esadfilmlg vkltdsstga
    fthhlnenkm
301 islninegki fneriqnfdf eslisslldl sgieykgkyi dkkqedfvps
    nallsqdrlw
361 qavenltqsn etivaeqgts ffgassiflk pkshfigqpl wgsigytfpa
    algsqiadke
421 srhllfigdg slqltvqerk lqvqvsqpss shmnsys
```

Alcohol dehydrogenase yqhD

SEQ ID NO: 103 (YP_001459806.1; GI: 157162488; Alcohol dehydrogenase yqhD (*Escherichia coli* HS))

```
  1 mnnfnlhtpt rilfgkgaia glreqiphda rvlitygggs vkktgvldqv
    ldalkgmdvl
 61 efggiepnpa yetlmnavkl vreqkvtfll avgggsvldg tkfiaaaany
    penidpwhil
121 qtggkeiksa ipmgcvltlp atgsesnaga visrkttgdk qafhsahvqp
    vfavldpvyt
181 ytlpprqvan gvvdafvhtv eqyvtkpvda kiqdrfaegi lltliedgpk
    alkepenydv
241 ranvmwaatq alngligagv pqdwathmlg heltamhgld haqtlaivlp
    alwnekrdtk
301 rakllqyaer vwnitegsdd eridaaiaat rnffeqlgvp thlsdygldg
    ssipallkkl
361 eehgmtqlge nhditldvsr riyeaar
```

SEQ ID NO: 104 (Alcohol dehydrogenase, iron-dependent (*Escherichia coli* 97.0259))

```
  1 mnnfnlhtpt rilfgkgaia glreqiphda rvlitygggs vkktgvldqv
    ldalkgmdvl
 61 efggiepnpa yetlmnavkl vreqkvtfll avgggsvldg tkfiaaaany
    penidpwhil
```

-continued

| Sequence Listing Free Text |
|---|

```
 121 qtggkeiksa ipmgcvltlp atgsesnaga visrkttgdk qafhsahvqp
     vfavldpvyt
 181 ytlpprqvan gvvdafvhtv eqyvtkpvda kiqdrfaegi lltliedgpk
     alkepenydv
 241 ranvmwaatq alngligagv pqdwathmlg heltamhgld haqtlaivlp
     alwnekrdtk
 301 rakllqyaer iwnitegsdd eridaaiaat rnffeqlgvp thlsdygldg
     ssipallkkl
 361 eehgmtqlge nhditldvsr riyeaar
```

SEQ ID NO: 105 (Alcohol dehydrogenase (*Escherichia coli* MS 200-1))

```
   1 mnnfnlhtpt rilfgkgaia glreqiphda rvlityggs vkktgvldqv
     lnalkgmdvl
  61 efggiepnpa yetlmnavkl vreqkvtfll avgggsvldg tkfiaaaany
     penidpwhil
 121 qtggkeiksa ipmgcvltlp atgsesnaga visrkttgdk qafhsahvqp
     vfavldpvyt
 181 ytlpprqvan gvvdafvhtv eqyvtkpvda kiqdrfaegi lltliedgpk
     alkepenydv
 241 ranvmwaatq alngligagv pqdwathmlg heltamhgld haqtlaivlp
     alwnekrdtk
 301 rakllqyaer vwnitegsdd eridaaiaat rnffeqlgvp thlsdygldg
     ssipallkkl
 361 eehgmtqlge nhditldvsr riyeaar
```

SEQ ID NO: 106 (Alcohol dehydrogenase yqhD (*Escherichia coli* B7A))

```
   1 mnnfnlhtpt rilfgkgaia glreqiphda rvlitygggs vkktgvldqv
     ldalkgmdvl
  61 efggiepnpa yetlmnavkl vreqkvtfll avgggsvldg tkfiaaaany
     penidpwhil
 121 qtggkeiksa ipmgcvltlp atgsesnaga visrkttgdk qafhsahvqp
     vfavldpvyt
 181 ytlpprqvan gvvdafvhtv eqyvtkpvda kiqdrfaegi lltliedgpk
     alkepenydv
 241 ranvmwaatq alngligagv pqdwathmlg heltamhgld haqtlaivlp
     alwnekretk
 301 rakllqyaer vwnitegsdd eridaaiaat rnffeqlgvp thlsdygldg
     ssipallkkl
 361 eehgmtqlge nhditldvsr riyeaar
```

SEQ ID NO: 107 (Alcohol dehydrogenase (*Escherichia coli* MS 196-1))

```
   1 mnnfnlhtpt rilfgkgaia glreqiphda rvlitygggs vkktgvldqv
     ldalkgmdvl
  61 efggiepnpa yetlmnavkl vreqkvtfll avgggsvldg tkfiaaaany
     penidpwhil
 121 qtggkeiksa ipmgcvltlp atgsesnaga visrkttgdk qafhsahvqp
     vfavldpvyt
 181 ytlpprqvan gvvdafvhtv eqyvtkpvda kiqdrfaegi lltliedgpk
     alkepenydv
 241 ranvmwaatq alngligagv pqdwathmlg hkltamhgld haqtlaivlp
     alwnekrdtk
 301 rakllqyaer vwnitegsdd eridaaiaat rnffeqlgvp thlsdygldg
     ssipallkkl
 361 eehgmtqlge nhditldvsr riyeaar
```

What is claimed is:

1. A recombinant microbial cell modified to exhibit increased biosynthesis of 1,4-butanediol from D-arabinose compared to a wild-type control, the cell comprising an engineered metabolic pathway comprising:

an enzyme that converts D-arabinose to D-arabinolactone comprising the amino acid sequence of SEQ ID NO:1;

an enzyme that converts D-arabinonic acid to 2-oxo-4(s), 5-dihydroxy-pentanoic acid comprising the amino acid sequence of SEQ ID NO:6;

an enzyme that converts 2-oxo-4(s),5-dihydroxy-pentanoic acid to 2,5-dioxopentanoic acid comprising the amino acid sequence of SEQ ID NO:11;

an enzymatic pathway that converts 2,5-dioxopentanoic acid to 1,4-butanediol.

2. The recombinant cell of claim 1 wherein the recombinant cell exhibits conversion of D-arabinose into D-arabinonolactone at a level at least 110% of a wild-type control cell.

3. The recombinant cell of claim 1 wherein the recombinant cell exhibits conversion of D-arabinonic acid to 2-oxo-4(s),5-dihydroxy-pentanoic acid at a level at least 110% of a wild-type control cell.

4. The recombinant cell of claim 1 wherein the recombinant cell exhibits conversion of 2-oxo-4(s), 5-dihydroxy-pentanoic acid to 2,5-dioxopentanoic acid at a level at least 110% of a wild-type control cell.

5. The recombinant cell of claim 1 wherein the enzymatic pathway that converts 2,5-dioxopentanoic acid to 1,4-butanediol comprises:

an enzyme that converts 2,5-dioxopentanoic acid to succinaldehyde; and an enzyme that converts succinaldehyde to 1,4-butanediol.

6. The recombinant cell of claim 5 wherein the enzyme that converts 2,5-dioxopentanoic acid to succinaldehyde is 2-ketoacid decarboxylase or 2-oxoglutarate decarboxylase.

7. The recombinant cell of claim 5 wherein the enzyme that converts succinaldehyde to 1,4-butanediol is an alcohol dehydrogenase.

8. The recombinant cell of claim 1 wherein the enzymatic pathway that converts 2,5-dioxopentanoic acid to 1,4-butanediol comprises:

an enzyme that converts 2,5-dioxopentanoic acid to 2-keto-5-hydroxy-pentonate;

an enzyme that converts 2-keto-5-hydroxy-pentonate to 4-hydroxy-1-butyraldehyde; and an enzyme that converts 4-hydroxy-1-butyraldehyde to 1,4-butanediol.

9. The recombinant cell of claim 8 wherein the enzyme that converts 2,5-dioxopentanoic acid to 2-keto-5-hydroxy-pentonate is an alcohol dehydrogenase.

10. The recombinant cell of claim 8 wherein the enzyme that converts 2-keto-5-hydroxy-pentonate to 4-hydroxy-1-butyraldehyde is a 2-ketoacid decarboxylase or a 2-oxoglutarate decarboxylase.

11. The recombinant cell of claim 8 wherein the enzyme that converts 4-hydroxy-1-butyraldehyde to 1,4-butanediol is an alcohol dehydrogenase.

* * * * *

SEQUENCE LISTING

<160> NUMBER OF SEQ ID NOS: 160

<210> SEQ ID NO 1
<211> LENGTH: 348
<212> TYPE: PRT
<213> ORGANISM: Sulfolobus solfataricus

<400> SEQUENCE: 1

```
Met Glu Asn Val Asn Met Val Lys Ser Lys Ala Ala Leu Leu Lys Lys
1               5                   10                  15

Phe Ser Glu Pro Leu Ser Ile Glu Asp Val Asn Ile Pro Glu Pro Gln
            20                  25                  30

Gly Glu Glu Val Leu Ile Arg Ile Gly Gly Ala Gly Val Cys Arg Thr
```

```
        35                  40                  45

Asp Leu Arg Val Trp Lys Gly Val Glu Ala Lys Gln Gly Phe Arg Leu
    50                  55                  60

Pro Ile Ile Leu Gly His Glu Asn Ala Gly Thr Ile Val Glu Val Gly
65                  70                  75                  80

Glu Leu Ala Lys Val Lys Lys Gly Asp Asn Val Val Val Tyr Ala Thr
                85                  90                  95

Trp Gly Asp Leu Thr Cys Arg Tyr Cys Arg Glu Gly Lys Phe Asn Ile
            100                 105                 110

Cys Lys Asn Gln Ile Ile Pro Gly Gln Thr Thr Asn Gly Gly Phe Ser
        115                 120                 125

Glu Tyr Met Leu Val Lys Ser Ser Arg Trp Leu Val Lys Leu Asn Ser
    130                 135                 140

Leu Ser Pro Val Glu Ala Ala Pro Leu Ala Asp Ala Gly Thr Thr Ser
145                 150                 155                 160

Met Gly Ala Ile Arg Gln Ala Leu Pro Phe Ile Ser Lys Phe Ala Glu
                165                 170                 175

Pro Val Val Ile Val Asn Gly Ile Gly Gly Leu Ala Val Tyr Thr Ile
            180                 185                 190

Gln Ile Leu Lys Ala Leu Met Lys Asn Ile Thr Ile Val Gly Ile Ser
        195                 200                 205

Arg Ser Lys Lys His Arg Asp Phe Ala Leu Glu Leu Gly Ala Asp Tyr
    210                 215                 220

Val Ser Glu Met Lys Asp Ala Glu Ser Leu Ile Asn Lys Leu Thr Asp
225                 230                 235                 240

Gly Leu Gly Ala Ser Ile Ala Ile Asp Leu Val Gly Thr Glu Glu Thr
                245                 250                 255

Thr Tyr Asn Leu Gly Lys Leu Leu Ala Gln Glu Gly Ala Ile Ile Leu
            260                 265                 270

Val Gly Met Glu Gly Lys Arg Val Ser Leu Glu Ala Phe Asp Thr Ala
        275                 280                 285

Val Trp Asn Lys Lys Leu Leu Gly Ser Asn Tyr Gly Ser Leu Asn Asp
    290                 295                 300

Leu Glu Asp Val Val Arg Leu Ser Glu Ser Gly Lys Ile Lys Pro Tyr
305                 310                 315                 320

Ile Ile Lys Val Pro Leu Asp Asp Ile Asn Lys Ala Phe Thr Asn Leu
                325                 330                 335

Asp Glu Gly Arg Val Asp Gly Arg Gln Val Ile Thr
            340                 345
```

<210> SEQ ID NO 2
<211> LENGTH: 344
<212> TYPE: PRT
<213> ORGANISM: Sulfolobus solfataricus

<400> SEQUENCE: 2

```
Met Val Lys Ser Lys Ala Ala Leu Leu Lys Lys Phe Ser Glu Pro Leu
1               5                   10                  15

Ser Ile Glu Asp Val Asn Ile Pro Glu Pro Gln Gly Glu Glu Val Leu
            20                  25                  30

Ile Arg Ile Gly Gly Ala Gly Val Cys Arg Thr Asp Leu Arg Val Trp
        35                  40                  45

Lys Gly Val Glu Ala Lys Gln Gly Phe Arg Leu Pro Ile Ile Leu Gly
    50                  55                  60
```

-continued

```
His Glu Asn Ala Gly Thr Ile Val Glu Val Gly Glu Leu Ala Lys Val
65                  70                  75                  80

Lys Lys Gly Asp Asn Val Val Val Tyr Ala Thr Trp Gly Asp Leu Thr
                85                  90                  95

Cys Arg Tyr Cys Arg Glu Gly Lys Phe Asn Ile Cys Lys Asn Gln Ile
            100                 105                 110

Ile Pro Gly Gln Thr Thr Asn Gly Gly Phe Ser Glu Tyr Met Leu Val
        115                 120                 125

Lys Ser Ser Arg Trp Leu Val Lys Leu Asn Ser Leu Ser Pro Val Glu
    130                 135                 140

Ala Ala Pro Leu Ala Asp Ala Gly Thr Thr Ser Met Gly Ala Ile Arg
145                 150                 155                 160

Gln Ala Leu Pro Phe Ile Ser Lys Phe Ala Glu Pro Val Val Ile Val
                165                 170                 175

Asn Gly Ile Gly Gly Leu Ala Val Tyr Thr Ile Gln Ile Leu Lys Ala
            180                 185                 190

Leu Met Lys Asn Ile Thr Ile Val Gly Ile Ser Arg Ser Lys Lys His
        195                 200                 205

Arg Asp Phe Ala Leu Glu Leu Gly Ala Asp Tyr Val Ser Glu Met Lys
    210                 215                 220

Asp Ala Glu Ser Leu Ile Asn Lys Leu Thr Asp Gly Leu Gly Ala Ser
225                 230                 235                 240

Ile Ala Ile Asp Leu Val Gly Thr Glu Glu Thr Thr Tyr Asn Leu Gly
                245                 250                 255

Lys Leu Leu Ala Gln Glu Gly Ala Ile Ile Leu Val Gly Met Glu Gly
            260                 265                 270

Lys Arg Val Ser Leu Glu Ala Phe Asp Thr Ala Val Trp Asn Lys Lys
        275                 280                 285

Leu Leu Gly Ser Asn Tyr Gly Ser Leu Asn Asp Leu Glu Asp Val Val
    290                 295                 300

Arg Leu Ser Glu Ser Gly Lys Ile Lys Pro Tyr Ile Ile Lys Val Pro
305                 310                 315                 320

Leu Asp Asp Ile Asn Lys Ala Phe Thr Asn Leu Asp Glu Gly Arg Val
                325                 330                 335

Asp Gly Arg Gln Val Ile Thr Pro
            340


<210> SEQ ID NO 3
<211> LENGTH: 359
<212> TYPE: PRT
<213> ORGANISM: Sulfolobus islandicus

<400> SEQUENCE: 3

Met Phe Gly Ile Thr Phe Tyr Ser Ala Met Arg Lys Asn Ile Ser Met
1               5                   10                  15

Val Lys Ser Lys Ala Ala Leu Leu Lys Lys Phe Ser Glu Pro Leu Ser
            20                  25                  30

Ile Glu Asp Val Glu Ile Pro Glu Pro Lys Gly Glu Glu Val Leu Val
        35                  40                  45

Arg Ile Gly Gly Ala Gly Val Cys Arg Thr Asp Leu Arg Val Trp Lys
    50                  55                  60

Gly Val Glu Ala Lys Gln Gly Phe Arg Leu Pro Ile Ile Leu Gly His
65                  70                  75                  80

Glu Asn Ala Gly Thr Val Val Glu Val Gly Glu Leu Ala Lys Ala Lys
                85                  90                  95
```

Lys Gly Asp Asn Val Val Val Tyr Ala Thr Trp Gly Asp Met Thr Cys
100 105 110

Arg Tyr Cys Arg Glu Gly Lys Phe Asn Ile Cys Lys Asn Gln Val Ile
115 120 125

Pro Gly Gln Thr Thr Asn Gly Gly Phe Ser Glu Tyr Met Leu Val Lys
130 135 140

Ser Tyr Arg Trp Leu Val Lys Leu Asp Ser Leu Ser Pro Val Asp Ala
145 150 155 160

Ser Pro Leu Ala Asp Ala Gly Thr Thr Ser Met Gly Ala Ile Arg Gln
165 170 175

Ala Leu Pro Phe Met Asn Lys Phe Ala Glu Pro Val Val Ile Val Asn
180 185 190

Gly Ile Gly Gly Leu Ala Val Tyr Thr Ile Gln Ile Leu Lys Ala Leu
195 200 205

Met Lys Asn Ile Val Ile Val Gly Ile Ser Arg Ser Lys Lys His Arg
210 215 220

Asp Leu Ala Leu Glu Leu Gly Ala Asp Tyr Ala Val Glu Met Lys Glu
225 230 235 240

Ala Glu Ser Leu Ile Ser Lys Leu Thr Asp Gly Leu Gly Ala Ser Val
245 250 255

Ala Ile Asp Leu Val Gly Thr Glu Glu Thr Ser Tyr Asn Leu Gly Lys
260 265 270

Leu Leu Ala Gln Glu Gly Ala Ile Ile Leu Val Gly Met Glu Gly Lys
275 280 285

Arg Val Ser Leu Glu Ala Phe Asp Thr Ala Val Trp Asn Lys Lys Leu
290 295 300

Leu Gly Ser Asn Tyr Gly Ser Leu Asn Asp Leu Glu Asp Val Val Arg
305 310 315 320

Leu Ser Glu Ser Gly Lys Ile Lys Pro Tyr Val Val Lys Ile Pro Leu
325 330 335

Asp Glu Ile Asn Lys Ala Phe Lys Asp Leu Asp Glu Gly Arg Val Glu
340 345 350

Gly Arg Gln Val Ile Thr Pro
355

<210> SEQ ID NO 4
<211> LENGTH: 359
<212> TYPE: PRT
<213> ORGANISM: Sulfolobus islandicus

<400> SEQUENCE: 4

Met Phe Gly Ile Thr Phe Tyr Ser Ala Met Arg Lys Asn Ile Ser Met
1 5 10 15

Val Lys Ser Lys Ala Ala Leu Leu Lys Lys Phe Ser Glu Pro Leu Ser
20 25 30

Ile Glu Asp Val Glu Ile Pro Glu Pro Lys Gly Glu Glu Val Leu Val
35 40 45

Arg Ile Gly Gly Ala Gly Val Cys Arg Thr Asp Leu Arg Val Trp Lys
50 55 60

Gly Val Glu Ala Lys Gln Gly Phe Arg Leu Pro Ile Ile Leu Gly His
65 70 75 80

Glu Asn Ala Gly Thr Val Val Glu Val Gly Glu Leu Ala Lys Ala Lys
85 90 95

Lys Gly Asp Asn Val Val Val Tyr Ala Thr Trp Gly Asp Met Thr Cys

```
            100                 105                 110

Arg Tyr Cys Arg Glu Gly Lys Phe Asn Ile Cys Lys Asn Gln Val Ile
        115                 120                 125

Pro Gly Gln Thr Thr Asn Gly Gly Phe Ser Glu Tyr Met Leu Val Lys
    130                 135                 140

Ser Tyr Arg Trp Leu Val Lys Leu Asp Ser Leu Ser Pro Val Asp Ala
145                 150                 155                 160

Ser Pro Leu Ala Asp Ala Gly Thr Thr Ser Met Gly Ala Ile Arg Gln
                165                 170                 175

Ala Leu Pro Phe Met Asn Lys Phe Ala Glu Pro Val Val Ile Val Asn
            180                 185                 190

Gly Ile Gly Gly Leu Ala Val Tyr Thr Ile Gln Ile Leu Lys Ala Leu
        195                 200                 205

Met Lys Asn Ile Val Ile Val Gly Ile Ser Arg Ser Arg Lys His Arg
    210                 215                 220

Asp Leu Ala Leu Glu Leu Gly Ala Asp Tyr Ala Val Glu Met Lys Glu
225                 230                 235                 240

Ala Glu Ser Leu Ile Ser Lys Leu Thr Asp Gly Leu Gly Ala Ser Val
                245                 250                 255

Ala Ile Asp Leu Val Gly Thr Glu Glu Thr Ser Tyr Asn Leu Gly Lys
            260                 265                 270

Leu Leu Ala Gln Glu Gly Ala Ile Ile Leu Val Gly Met Glu Gly Lys
        275                 280                 285

Arg Val Ser Leu Glu Ala Phe Asp Thr Ala Val Trp Asn Lys Lys Leu
    290                 295                 300

Leu Gly Ser Asn Tyr Gly Ser Leu Asn Asp Leu Glu Asp Val Val Arg
305                 310                 315                 320

Leu Ser Glu Ser Gly Lys Ile Lys Pro Tyr Val Val Lys Ile Pro Leu
                325                 330                 335

Asp Glu Ile Asn Lys Ala Phe Lys Asp Leu Asp Glu Gly Arg Val Glu
            340                 345                 350

Gly Arg Gln Val Ile Thr Pro
        355


<210> SEQ ID NO 5
<211> LENGTH: 359
<212> TYPE: PRT
<213> ORGANISM: Sulfolobus islandicus

<400> SEQUENCE: 5

Met Phe Gly Ile Thr Phe Tyr Ser Ala Met Arg Lys Asn Ile Ser Met
1               5                   10                  15

Val Lys Ser Lys Ala Ala Leu Leu Lys Lys Phe Ser Glu Pro Leu Ser
            20                  25                  30

Ile Glu Asp Val Glu Ile Pro Glu Pro Lys Gly Glu Glu Val Leu Val
        35                  40                  45

Arg Ile Gly Gly Ala Gly Val Cys Arg Thr Asp Leu Arg Val Trp Lys
    50                  55                  60

Gly Val Glu Ala Lys Gln Gly Phe Arg Leu Pro Ile Ile Leu Gly His
65                  70                  75                  80

Glu Asn Ala Gly Thr Val Val Glu Val Gly Glu Leu Ala Lys Ala Lys
                85                  90                  95

Lys Gly Asp Asn Val Val Val Tyr Ala Thr Trp Gly Asp Met Thr Cys
            100                 105                 110
```

```
Arg Tyr Cys Arg Glu Gly Lys Phe Asn Ile Cys Lys Asn Gln Val Ile
        115                 120                 125

Pro Gly Gln Thr Thr Asn Gly Gly Phe Ser Glu Tyr Met Leu Val Lys
    130                 135                 140

Ser Tyr Arg Trp Leu Val Lys Leu Asp Ser Leu Ser Pro Val Asp Ala
145                 150                 155                 160

Ser Pro Leu Ala Asp Ala Gly Thr Thr Ser Met Gly Ala Ile Arg Gln
                165                 170                 175

Ala Leu Pro Phe Met Asn Lys Phe Ala Glu Pro Val Val Ile Val Asn
            180                 185                 190

Gly Ile Gly Gly Leu Ala Val Tyr Thr Ile Gln Ile Leu Lys Ala Leu
        195                 200                 205

Met Lys Asn Ile Val Ile Val Gly Ile Ser Arg Ser Lys Lys His Arg
    210                 215                 220

Asp Leu Ala Leu Glu Leu Gly Ala Asp His Ala Val Glu Met Lys Glu
225                 230                 235                 240

Ala Glu Ser Leu Ile Ser Lys Leu Thr Asp Gly Leu Gly Ala Ser Val
                245                 250                 255

Ala Ile Asp Leu Val Gly Thr Glu Glu Thr Ser Tyr Asn Leu Gly Lys
            260                 265                 270

Leu Leu Ala Gln Glu Gly Ala Ile Ile Leu Val Gly Met Glu Gly Lys
        275                 280                 285

Arg Val Ser Leu Glu Ala Phe Asp Thr Ala Val Trp Asn Lys Lys Leu
    290                 295                 300

Leu Gly Ser Asn Tyr Gly Ser Leu Asn Asp Leu Glu Asp Val Val Arg
305                 310                 315                 320

Leu Ser Glu Ser Gly Lys Ile Lys Pro Tyr Val Val Lys Ile Pro Leu
                325                 330                 335

Asp Glu Ile Asn Lys Ala Phe Lys Asp Leu Asp Glu Gly Arg Val Glu
            340                 345                 350

Gly Arg Gln Val Ile Thr Pro
        355


<210> SEQ ID NO 6
<211> LENGTH: 373
<212> TYPE: PRT
<213> ORGANISM: Sulfolobus solfataricus

<400> SEQUENCE: 6

Met Ile Lys Asp Ile Arg Thr Tyr Lys Leu Cys Tyr Glu Gly Ile Asn
1               5                   10                  15

Asp Glu Arg Asp Ala Leu Ala Ile Lys Gly Leu Ala Glu His Pro Met
            20                  25                  30

Glu Ile Val Ala Thr Glu Ile Glu Thr Ser Asp Gly Tyr Val Gly Tyr
        35                  40                  45

Gly Glu Ser Leu Ala Tyr Gly Cys Ser Asp Ala Val Gln Val Thr Ile
    50                  55                  60

Glu Lys Ile Leu Lys Pro Leu Leu Leu Lys Glu Asp Glu Glu Leu Ile
65                  70                  75                  80

Glu Tyr Leu Trp Asp Lys Met Tyr Lys Ala Thr Leu Arg Phe Gly Arg
                85                  90                  95

Arg Gly Ile Ala Ile Ala Gly Ile Ser Gly Val Asp Thr Ala Leu Trp
            100                 105                 110

Asp Ile Met Gly Lys Lys Ala Lys Lys Pro Ile Tyr Lys Leu Leu Gly
        115                 120                 125
```

```
Gly Ser Lys Arg Lys Val Arg Ala Tyr Ile Thr Gly Gly Tyr Tyr Ser
    130                 135                 140

Glu Lys Lys Asp Leu Glu Lys Leu Arg Asp Glu Glu Ala Tyr Tyr Val
145                 150                 155                 160

Lys Met Gly Phe Lys Gly Ile Lys Val Lys Ile Gly Ala Lys Ser Met
                165                 170                 175

Glu Glu Asp Ile Glu Arg Leu Lys Ala Ile Arg Glu Val Val Gly Glu
            180                 185                 190

Asp Val Lys Ile Ala Val Asp Ala Asn Asn Val Tyr Thr Phe Glu Glu
        195                 200                 205

Ala Leu Glu Met Gly Arg Arg Leu Glu Lys Leu Gly Ile Trp Phe Phe
    210                 215                 220

Glu Glu Pro Ile Gln Thr Asp Tyr Leu Asp Leu Ser Ala Arg Leu Ala
225                 230                 235                 240

Glu Glu Leu Glu Val Pro Ile Ala Gly Tyr Glu Thr Ala Tyr Thr Arg
                245                 250                 255

Trp Glu Phe Tyr Glu Ile Met Arg Lys Arg Ala Val Asp Ile Val Gln
            260                 265                 270

Thr Asp Val Met Trp Thr Gly Gly Ile Ser Glu Met Met Lys Ile Gly
        275                 280                 285

Asn Met Ala Lys Val Met Gly Tyr Pro Leu Ile Pro His Tyr Ser Ala
    290                 295                 300

Gly Gly Ile Ser Leu Ile Gly Asn Leu His Val Ala Ala Ala Leu Asn
305                 310                 315                 320

Ser Pro Trp Ile Glu Met His Leu Arg Lys Asn Asp Leu Arg Asp Lys
                325                 330                 335

Ile Phe Lys Glu Ser Ile Glu Ile Asp Asn Gly His Leu Val Val Pro
            340                 345                 350

Asp Arg Pro Gly Leu Gly Tyr Thr Ile Arg Asp Gly Val Phe Glu Glu
        355                 360                 365

Tyr Lys Cys Lys Ser
    370


<210> SEQ ID NO 7
<211> LENGTH: 373
<212> TYPE: PRT
<213> ORGANISM: Sulfolobus islandicus

<400> SEQUENCE: 7

Met Ile Lys Asp Ile Arg Thr Tyr Lys Leu Cys Tyr Glu Gly Ile Asn
1               5                   10                  15

Asp Glu Arg Asp Ala Leu Ala Ile Lys Gly Leu Ala Glu His Pro Met
            20                  25                  30

Glu Ile Val Val Thr Glu Ile Glu Thr Ser Asp Gly Tyr Val Gly Tyr
        35                  40                  45

Gly Glu Ser Leu Ala Tyr Gly Cys Ser Asp Ala Val Gln Val Thr Ile
    50                  55                  60

Glu Lys Ile Leu Lys Pro Leu Leu Leu Lys Glu Asp Glu Glu Leu Ile
65                  70                  75                  80

Glu Tyr Leu Trp Asp Lys Met Tyr Lys Ala Thr Leu Arg Phe Gly Arg
                85                  90                  95

Arg Gly Ile Ala Ile Ala Gly Ile Ser Gly Val Asp Thr Ala Leu Trp
            100                 105                 110

Asp Ile Met Gly Lys Lys Ala Lys Lys Pro Ile Tyr Lys Leu Leu Gly
```

-continued

```
        115                 120                 125

Gly Ser Lys Arg Lys Val Arg Ala Tyr Ile Thr Gly Gly Tyr Tyr Ser
    130                 135                 140

Glu Lys Lys Asp Leu Glu Lys Leu Arg Asp Glu Glu Ala Tyr Tyr Val
145                 150                 155                 160

Lys Met Gly Phe Lys Gly Ile Lys Val Lys Ile Gly Ala Lys Ser Met
                165                 170                 175

Glu Glu Asp Ile Glu Arg Leu Lys Ala Ile Arg Glu Val Val Gly Glu
            180                 185                 190

Asp Val Lys Ile Ala Val Asp Ala Asn Asn Val Tyr Thr Phe Glu Glu
        195                 200                 205

Ala Leu Glu Met Gly Arg Arg Leu Glu Lys Leu Gly Ile Trp Phe Phe
    210                 215                 220

Glu Glu Pro Ile Gln Thr Asp Tyr Leu Asp Leu Ser Ala Arg Leu Ala
225                 230                 235                 240

Glu Glu Leu Glu Val Pro Ile Ala Gly Tyr Glu Thr Ala Tyr Thr Arg
                245                 250                 255

Trp Glu Phe Tyr Glu Ile Met Arg Lys Arg Ala Val Asp Ile Val Gln
            260                 265                 270

Thr Asp Val Met Trp Thr Gly Gly Ile Ser Glu Met Met Lys Ile Gly
        275                 280                 285

Asn Met Ala Lys Val Met Gly Tyr Pro Leu Ile Pro His Tyr Ser Ala
    290                 295                 300

Gly Gly Ile Ser Leu Ile Gly Asn Leu His Val Ala Ala Ala Leu Asn
305                 310                 315                 320

Ser Pro Trp Ile Glu Met His Leu Arg Lys Asn Asp Leu Arg Asp Lys
                325                 330                 335

Ile Phe Lys Glu Ser Ile Glu Ile Asp Asn Gly His Leu Val Val Pro
            340                 345                 350

Asp Arg Pro Gly Leu Gly Tyr Thr Ile Arg Asp Gly Val Phe Glu Glu
        355                 360                 365

Tyr Lys Cys Lys Ser
    370


<210> SEQ ID NO 8
<211> LENGTH: 373
<212> TYPE: PRT
<213> ORGANISM: Sulfolobus islandicus

<400> SEQUENCE: 8

Met Ile Lys Asp Ile Arg Thr Tyr Lys Leu Cys Tyr Glu Gly Ile Asn
1               5                   10                  15

Asp Glu Arg Asp Ala Leu Ala Ile Lys Gly Leu Ala Glu His Pro Met
            20                  25                  30

Glu Ile Val Val Thr Glu Ile Glu Thr Ser Asp Gly Tyr Val Gly Tyr
        35                  40                  45

Gly Glu Ser Leu Ala Tyr Gly Cys Ser Asp Ala Val Gln Val Thr Ile
    50                  55                  60

Glu Lys Ile Leu Lys Pro Leu Leu Leu Lys Glu Asp Glu Glu Phe Ile
65                  70                  75                  80

Glu Tyr Leu Trp Asp Lys Met Tyr Lys Ala Thr Leu Arg Phe Gly Arg
                85                  90                  95

Arg Gly Ile Ala Ile Ala Gly Ile Ser Gly Val Asp Thr Ala Leu Trp
            100                 105                 110
```

-continued

```
Asp Ile Met Gly Lys Lys Ala Lys Lys Pro Ile Tyr Lys Leu Leu Gly
        115                 120                 125

Gly Ser Lys Arg Lys Val Arg Ala Tyr Ile Thr Gly Gly Tyr Tyr Ser
    130                 135                 140

Glu Lys Lys Asp Leu Glu Lys Leu Arg Asp Glu Glu Ala Tyr Tyr Val
145                 150                 155                 160

Lys Met Gly Phe Lys Gly Ile Lys Val Lys Ile Gly Ala Lys Ser Met
                165                 170                 175

Glu Glu Asp Ile Glu Arg Leu Lys Ala Ile Arg Glu Val Val Gly Glu
            180                 185                 190

Asp Val Lys Ile Ala Val Asp Ala Asn Asn Val Tyr Thr Phe Glu Glu
        195                 200                 205

Ala Leu Glu Met Gly Arg Arg Leu Glu Lys Leu Gly Ile Trp Phe Phe
    210                 215                 220

Glu Glu Pro Ile Gln Thr Asp Tyr Leu Asp Leu Ser Ala Arg Leu Ala
225                 230                 235                 240

Glu Glu Leu Glu Val Pro Ile Ala Gly Tyr Glu Thr Ala Tyr Thr Arg
                245                 250                 255

Trp Glu Phe Tyr Glu Ile Met Arg Lys Arg Ala Val Asp Ile Val Gln
            260                 265                 270

Thr Asp Val Met Trp Thr Gly Gly Ile Ser Glu Met Met Lys Ile Gly
        275                 280                 285

Asn Met Ala Lys Val Met Gly Tyr Ser Leu Ile Pro His Tyr Ser Ala
    290                 295                 300

Gly Gly Ile Ser Leu Ile Gly Asn Leu His Val Ala Ala Ala Leu Asn
305                 310                 315                 320

Ser Pro Trp Ile Glu Met His Leu Arg Lys Asn Asp Leu Arg Asp Lys
                325                 330                 335

Ile Phe Lys Glu Ser Ile Glu Ile Asp Asn Gly His Leu Val Val Pro
            340                 345                 350

Asp Arg Pro Gly Leu Gly Tyr Thr Ile Arg Asp Gly Val Phe Glu Glu
        355                 360                 365

Tyr Lys Cys Lys Ser
    370


<210> SEQ ID NO 9
<211> LENGTH: 373
<212> TYPE: PRT
<213> ORGANISM: Sulfolobus islandicus

<400> SEQUENCE: 9

Met Ile Lys Asp Ile Arg Thr Tyr Lys Leu Cys Tyr Glu Gly Ile Asn
1               5                   10                  15

Asp Glu Arg Asp Ala Leu Ala Ile Lys Gly Leu Ala Glu His Pro Met
            20                  25                  30

Glu Ile Val Val Thr Glu Ile Glu Thr Ser Asp Gly Tyr Val Gly Tyr
        35                  40                  45

Gly Glu Ser Leu Ala Tyr Gly Cys Ser Asp Ala Val Gln Val Thr Ile
    50                  55                  60

Glu Lys Ile Leu Lys Pro Leu Leu Leu Lys Glu Asp Glu Glu Leu Ile
65                  70                  75                  80

Glu Tyr Leu Trp Asp Lys Met Tyr Lys Ala Thr Leu Arg Phe Gly Arg
                85                  90                  95

Arg Gly Ile Ala Ile Ala Gly Ile Ser Gly Val Asp Thr Gly Leu Trp
            100                 105                 110
```

-continued

```
Asp Ile Met Gly Lys Lys Ala Lys Lys Pro Ile Tyr Lys Leu Leu Gly
        115                 120                 125

Gly Ser Lys Arg Lys Val Arg Ala Tyr Ile Thr Gly Gly Tyr Tyr Ser
    130                 135                 140

Glu Lys Lys Asp Leu Glu Lys Leu Arg Asp Glu Glu Ala Tyr Tyr Val
145                 150                 155                 160

Lys Met Gly Phe Lys Gly Ile Lys Val Lys Ile Gly Ala Lys Ser Met
                165                 170                 175

Glu Glu Asp Ile Glu Arg Leu Lys Ala Ile Arg Glu Val Val Gly Glu
            180                 185                 190

Asp Val Lys Ile Ala Val Asp Ala Asn Asn Val Tyr Thr Phe Glu Glu
        195                 200                 205

Ala Leu Glu Met Gly Arg Arg Leu Glu Lys Leu Gly Ile Trp Phe Phe
    210                 215                 220

Glu Glu Pro Ile Gln Thr Asp Tyr Leu Asp Leu Ser Ala Arg Leu Ala
225                 230                 235                 240

Glu Glu Leu Glu Val Pro Ile Ala Gly Tyr Glu Thr Ala Tyr Thr Arg
                245                 250                 255

Trp Glu Phe Tyr Glu Ile Met Arg Lys Arg Ala Val Asp Ile Val Gln
            260                 265                 270

Thr Asp Val Met Trp Thr Gly Gly Ile Ser Glu Met Met Lys Ile Gly
        275                 280                 285

Asn Met Ala Lys Val Met Gly Tyr Pro Leu Ile Pro His Tyr Ser Ala
    290                 295                 300

Gly Gly Ile Ser Leu Ile Gly Asn Leu His Val Ala Ala Ala Leu Asn
305                 310                 315                 320

Ser Pro Trp Ile Glu Met His Leu Arg Lys Asn Asp Leu Arg Asp Lys
                325                 330                 335

Ile Phe Lys Glu Ser Ile Glu Ile Asp Asn Gly His Leu Val Val Pro
            340                 345                 350

Asp Arg Pro Gly Leu Gly Tyr Thr Ile Arg Asp Gly Val Phe Glu Glu
        355                 360                 365

Tyr Lys Cys Lys Ser
    370


<210> SEQ ID NO 10
<211> LENGTH: 373
<212> TYPE: PRT
<213> ORGANISM: Sulfolobus islandicus

<400> SEQUENCE: 10

Met Ile Lys Asp Ile Arg Thr Tyr Lys Leu Cys Tyr Glu Gly Ile Asn
1               5                   10                  15

Asp Glu Arg Asp Ala Leu Ala Ile Lys Gly Leu Ala Glu His Pro Met
            20                  25                  30

Glu Ile Val Val Thr Glu Ile Glu Thr Ser Asp Gly Tyr Val Gly Tyr
        35                  40                  45

Gly Glu Ser Leu Ala Tyr Gly Cys Ser Asp Ala Val Gln Val Thr Ile
    50                  55                  60

Glu Lys Ile Leu Lys Pro Leu Leu Leu Lys Glu Asp Glu Glu Leu Ile
65                  70                  75                  80

Glu Tyr Leu Trp Asp Lys Met Tyr Lys Ala Thr Leu Arg Phe Gly Arg
                85                  90                  95

Arg Gly Ile Ala Ile Ala Gly Ile Ser Gly Val Asp Thr Ala Leu Trp
```

-continued

```
            100                 105                 110

Asp Ile Met Gly Lys Lys Ala Lys Lys Pro Ile Tyr Lys Leu Leu Gly
        115                 120                 125

Gly Ser Lys Arg Lys Val Arg Ala Tyr Ile Thr Gly Gly Tyr Tyr Ser
    130                 135                 140

Glu Lys Lys Asp Leu Glu Lys Leu Arg Asp Glu Glu Ala Tyr Tyr Val
145                 150                 155                 160

Lys Met Gly Phe Lys Gly Ile Lys Ile Lys Ile Gly Ala Lys Ser Met
                165                 170                 175

Glu Glu Asp Ile Glu Arg Leu Lys Ala Ile Arg Glu Val Val Gly Glu
            180                 185                 190

Asp Val Lys Ile Ala Val Asp Ala Asn Asn Val Tyr Thr Phe Glu Glu
        195                 200                 205

Ala Leu Glu Met Gly Arg Arg Leu Glu Lys Leu Gly Ile Trp Phe Phe
    210                 215                 220

Glu Glu Pro Ile Gln Thr Asp Tyr Leu Asp Leu Ser Ala Arg Leu Ala
225                 230                 235                 240

Glu Glu Leu Glu Val Pro Ile Ala Gly Tyr Glu Thr Ala Tyr Thr Arg
                245                 250                 255

Trp Glu Phe Tyr Glu Ile Met Arg Lys Arg Ala Val Asp Ile Val Gln
            260                 265                 270

Thr Asp Val Met Trp Thr Gly Gly Ile Ser Glu Met Met Lys Ile Gly
        275                 280                 285

Asn Met Ala Lys Val Met Gly Tyr Pro Leu Ile Pro His Tyr Ser Ala
    290                 295                 300

Gly Gly Ile Ser Leu Ile Gly Asn Leu His Val Ala Ala Ala Leu Asn
305                 310                 315                 320

Ser Pro Trp Ile Glu Met His Leu Arg Lys Asn Asp Leu Arg Asp Lys
                325                 330                 335

Ile Phe Lys Glu Ser Ile Glu Ile Asp Asn Gly His Leu Val Val Pro
            340                 345                 350

Asp Arg Pro Gly Leu Gly Tyr Thr Ile Arg Asp Gly Val Phe Glu Glu
        355                 360                 365

Tyr Lys Cys Lys Ser
    370


<210> SEQ ID NO 11
<211> LENGTH: 298
<212> TYPE: PRT
<213> ORGANISM: Sulfolobus solfataricus

<400> SEQUENCE: 11

Met His Phe Ile Met Met Lys Leu Phe Arg Val Val Lys Arg Gly Tyr
1               5                   10                  15

Tyr Ile Ser Tyr Ala Ile Leu Asp Asn Ser Thr Ile Ile Arg Leu Asp
            20                  25                  30

Glu Asp Pro Ile Lys Ala Leu Met Arg Tyr Ser Glu Asn Lys Glu Val
        35                  40                  45

Leu Gly Asp Arg Val Thr Gly Ile Asp Tyr Gln Ser Leu Leu Lys Ser
    50                  55                  60

Phe Gln Ile Asn Asp Ile Arg Ile Thr Lys Pro Ile Asp Pro Pro Glu
65                  70                  75                  80

Val Trp Gly Ser Gly Ile Ser Tyr Glu Met Ala Arg Glu Arg Tyr Ser
                85                  90                  95
```

```
Glu Glu Asn Val Ala Lys Ile Leu Gly Lys Thr Ile Tyr Glu Lys Val
            100                 105                 110

Tyr Asp Ala Val Arg Pro Glu Ile Phe Phe Lys Ala Thr Pro Asn Arg
        115                 120                 125

Cys Val Gly His Gly Glu Ala Ile Ala Val Arg Ser Asp Ser Glu Trp
    130                 135                 140

Thr Leu Pro Glu Pro Glu Leu Ala Val Val Leu Asp Ser Asn Gly Lys
145                 150                 155                 160

Ile Leu Gly Tyr Thr Ile Met Asp Asp Val Ser Ala Arg Asp Leu Glu
                165                 170                 175

Ala Glu Asn Pro Leu Tyr Leu Pro Gln Ser Lys Ile Tyr Ala Gly Cys
            180                 185                 190

Cys Ala Phe Gly Pro Val Ile Val Thr Ser Asp Glu Ile Lys Asn Pro
        195                 200                 205

Tyr Ser Leu Asp Ile Thr Leu Lys Ile Val Arg Glu Gly Arg Val Phe
    210                 215                 220

Phe Glu Gly Ser Val Asn Thr Asn Lys Met Arg Arg Lys Ile Glu Glu
225                 230                 235                 240

Gln Ile Gln Tyr Leu Ile Arg Asp Asn Pro Ile Pro Asp Gly Thr Ile
                245                 250                 255

Leu Thr Thr Gly Thr Ala Ile Val Pro Gly Arg Asp Lys Gly Leu Lys
            260                 265                 270

Asp Glu Asp Ile Val Glu Ile Thr Ile Ser Asn Ile Gly Thr Leu Ile
        275                 280                 285

Thr Pro Val Lys Lys Arg Arg Lys Ile Thr
    290                 295
```

<210> SEQ ID NO 12
<211> LENGTH: 311
<212> TYPE: PRT
<213> ORGANISM: Sulfolobus islandicus

<400> SEQUENCE: 12

```
Met Leu Thr Cys Leu Leu Pro Thr Leu Leu Tyr Ala Lys Cys Ile Phe
1               5                   10                  15

Ile Met Met Lys Leu Phe Arg Val Val Lys Arg Gly Tyr Tyr Ile Ser
            20                  25                  30

Tyr Ala Ile Leu Asp Asn Ser Thr Ile Ile Arg Leu Asp Glu Asp Pro
        35                  40                  45

Ile Lys Ala Leu Met Arg Tyr Ser Glu Asn Lys Glu Val Leu Gly Asp
    50                  55                  60

Arg Val Thr Gly Ile Asp Tyr Gln Ser Leu Leu Lys Ser Phe Gln Ile
65                  70                  75                  80

Asn Asp Ile Arg Ile Thr Lys Pro Ile Asp Pro Pro Glu Val Trp Gly
                85                  90                  95

Ser Gly Ile Ser Tyr Glu Met Ala Arg Glu Arg Tyr Ser Glu Glu Asn
            100                 105                 110

Val Ala Lys Ile Leu Gly Lys Thr Ile Tyr Glu Lys Val Tyr Asp Ala
        115                 120                 125

Val Arg Pro Glu Ile Phe Phe Lys Ala Thr Pro Asn Arg Cys Val Gly
    130                 135                 140

His Gly Glu Ala Ile Ala Val Arg Ser Asp Ser Glu Trp Thr Leu Pro
145                 150                 155                 160

Glu Pro Glu Leu Ala Val Val Leu Asp Ser Asn Gly Lys Ile Leu Gly
                165                 170                 175
```

```
Tyr Thr Ile Met Asp Asp Val Ser Ala Arg Asp Leu Glu Ala Glu Asn
            180                 185                 190

Pro Leu Tyr Leu Pro Gln Ser Lys Ile Tyr Ala Gly Cys Cys Ala Phe
        195                 200                 205

Gly Pro Val Ile Val Thr Ser Asp Glu Ile Lys Asn Pro Tyr Ser Leu
    210                 215                 220

Asp Ile Thr Leu Lys Ile Val Arg Glu Gly Arg Val Phe Phe Glu Gly
225                 230                 235                 240

Ser Val Asn Thr Asn Lys Met Arg Arg Lys Ile Glu Glu Gln Ile Gln
                245                 250                 255

Tyr Leu Ile Arg Asp Asn Pro Ile Pro Asp Gly Thr Ile Leu Thr Thr
            260                 265                 270

Gly Thr Ala Ile Val Pro Gly Arg Asp Lys Gly Leu Lys Asp Glu Asp
        275                 280                 285

Ile Val Glu Ile Thr Ile Ser Asn Ile Gly Thr Leu Ile Thr Pro Val
    290                 295                 300

Lys Lys Arg Arg Lys Ile Thr
305                 310
```

<210> SEQ ID NO 13
<211> LENGTH: 294
<212> TYPE: PRT
<213> ORGANISM: Sulfolobus solfataricus

<400> SEQUENCE: 13

```
Met Met Lys Leu Phe Arg Val Val Lys Arg Gly Tyr Tyr Ile Ser Tyr
1               5                   10                  15

Ala Ile Leu Asp Asn Ser Thr Ile Ile Arg Leu Asp Glu Asp Pro Ile
            20                  25                  30

Lys Ala Leu Met Arg Tyr Ser Glu Asn Lys Glu Val Leu Gly Asp Arg
        35                  40                  45

Val Thr Gly Ile Asp Tyr Gln Ser Leu Leu Lys Ser Phe Gln Ile Asn
    50                  55                  60

Asp Ile Arg Ile Thr Lys Pro Ile Asp Pro Pro Glu Val Trp Gly Ser
65                  70                  75                  80

Gly Ile Ser Tyr Glu Met Ala Arg Glu Arg Tyr Ser Glu Glu Asn Val
                85                  90                  95

Ala Lys Ile Leu Gly Lys Thr Ile Tyr Glu Lys Val Tyr Asp Ala Val
            100                 105                 110

Arg Pro Glu Ile Phe Phe Lys Ala Thr Pro Asn Arg Cys Val Gly His
        115                 120                 125

Gly Glu Ala Ile Ala Val Arg Ser Asp Ser Glu Trp Thr Leu Pro Glu
    130                 135                 140

Pro Glu Leu Ala Val Val Leu Asp Ser Asn Gly Lys Ile Leu Gly Tyr
145                 150                 155                 160

Thr Ile Met Asp Asp Val Ser Ala Arg Asp Leu Glu Ala Glu Asn Pro
                165                 170                 175

Leu Tyr Leu Pro Gln Ser Lys Ile Tyr Ala Gly Cys Cys Ala Phe Gly
            180                 185                 190

Pro Val Ile Val Thr Ser Asp Glu Ile Lys Asn Pro Tyr Ser Leu Asp
        195                 200                 205

Ile Thr Leu Lys Ile Val Arg Glu Gly Arg Val Phe Phe Glu Gly Ser
    210                 215                 220

Val Asn Thr Asn Lys Met Arg Arg Lys Ile Glu Glu Gln Ile Gln Tyr
```

```
225                 230                 235                 240

Leu Ile Arg Asp Asn Pro Ile Pro Asp Gly Thr Ile Leu Thr Thr Gly
                245                 250                 255

Thr Ala Ile Val Pro Gly Arg Asp Lys Gly Leu Lys Asp Glu Asp Ile
            260                 265                 270

Val Glu Ile Thr Ile Ser Asn Ile Gly Thr Leu Ile Thr Pro Val Lys
        275                 280                 285

Lys Arg Arg Lys Ile Thr
    290


<210> SEQ ID NO 14
<211> LENGTH: 293
<212> TYPE: PRT
<213> ORGANISM: Sulfolobus solfataricus

<400> SEQUENCE: 14

Met Lys Leu Phe Arg Val Val Lys Arg Gly Tyr Tyr Ile Ser Tyr Ala
1               5                   10                  15

Ile Leu Asp Asn Ser Thr Ile Ile Arg Leu Asp Glu Asp Pro Ile Lys
            20                  25                  30

Ala Leu Met Arg Tyr Ser Glu Asn Lys Glu Val Leu Gly Asp Arg Val
        35                  40                  45

Thr Gly Ile Asp Tyr Gln Ser Leu Leu Lys Ser Phe Gln Ile Asn Asp
    50                  55                  60

Ile Arg Ile Thr Lys Pro Ile Asp Pro Pro Glu Val Trp Gly Ser Gly
65                  70                  75                  80

Ile Ser Tyr Glu Met Ala Arg Glu Arg Tyr Ser Glu Glu Asn Val Ala
                85                  90                  95

Lys Ile Leu Gly Lys Thr Ile Tyr Glu Lys Val Tyr Asp Ala Val Arg
            100                 105                 110

Pro Glu Ile Phe Phe Lys Ala Thr Pro Asn Arg Cys Val Gly His Gly
        115                 120                 125

Glu Ala Ile Ala Val Arg Ser Asp Ser Glu Trp Thr Leu Pro Glu Pro
    130                 135                 140

Glu Leu Ala Val Val Leu Asp Ser Asn Gly Lys Ile Leu Gly Tyr Thr
145                 150                 155                 160

Ile Met Asp Asp Val Ser Ala Arg Asp Leu Glu Ala Glu Asn Pro Leu
                165                 170                 175

Tyr Leu Pro Gln Ser Lys Ile Tyr Ala Gly Cys Cys Ala Phe Gly Pro
            180                 185                 190

Val Ile Val Thr Ser Asp Glu Ile Lys Asn Pro Tyr Ser Leu Asp Ile
        195                 200                 205

Thr Leu Lys Ile Val Arg Glu Gly Arg Val Phe Phe Glu Gly Ser Val
    210                 215                 220

Asn Thr Asn Lys Met Arg Arg Lys Ile Glu Glu Gln Ile Gln Tyr Leu
225                 230                 235                 240

Ile Arg Asp Asn Pro Ile Pro Asp Gly Thr Ile Leu Thr Thr Gly Thr
                245                 250                 255

Ala Ile Val Pro Gly Arg Asp Lys Gly Leu Lys Asp Glu Asp Ile Val
            260                 265                 270

Glu Ile Thr Ile Ser Asn Ile Gly Thr Leu Ile Thr Pro Val Lys Lys
        275                 280                 285

Arg Arg Lys Ile Thr
    290
```

<210> SEQ ID NO 15
<211> LENGTH: 294
<212> TYPE: PRT
<213> ORGANISM: Sulfolobus islandicus

<400> SEQUENCE: 15

```
Met Met Lys Leu Phe Arg Val Val Lys Arg Gly Tyr Tyr Ile Ser Tyr
1               5                   10                  15

Ala Ile Leu Asp Asn Ser Thr Ile Ile Arg Leu Asp Glu Asp Pro Ile
            20                  25                  30

Lys Ala Leu Met Arg Tyr Ser Glu Asn Lys Glu Val Leu Gly Asp Arg
        35                  40                  45

Val Thr Gly Ile Asp Tyr Gln Ser Leu Leu Lys Ser Phe Gln Ile Asn
    50                  55                  60

Asp Ile Arg Ile Thr Lys Pro Ile Asp Pro Pro Glu Val Trp Gly Ser
65                  70                  75                  80

Gly Ile Ser Tyr Glu Met Ala Arg Glu Arg Tyr Ser Glu Glu Asn Val
                85                  90                  95

Ala Lys Ile Leu Gly Lys Thr Ile Tyr Glu Lys Val Tyr Asp Ala Val
            100                 105                 110

Arg Pro Glu Ile Phe Phe Lys Ala Thr Pro Asn Arg Cys Val Gly His
        115                 120                 125

Gly Glu Ala Ile Ala Val Arg Ser Asp Ser Glu Trp Thr Leu Pro Glu
    130                 135                 140

Pro Glu Leu Ala Val Val Leu Asp Ser Asn Gly Lys Ile Leu Gly Tyr
145                 150                 155                 160

Thr Ile Met Asp Asp Val Ser Ala Arg Asp Leu Glu Ala Glu Asn Pro
                165                 170                 175

Leu Tyr Leu Pro Gln Ser Lys Ile Tyr Ala Gly Cys Cys Ala Phe Gly
            180                 185                 190

Pro Val Ile Val Thr Ser Asp Glu Ile Lys Asn Pro Tyr Ser Leu Asp
        195                 200                 205

Ile Thr Leu Lys Ile Val Arg Lys Asp Arg Val Phe Phe Glu Gly Ser
    210                 215                 220

Val Asn Thr Asn Lys Met Arg Arg Lys Ile Glu Glu Gln Ile Gln Tyr
225                 230                 235                 240

Leu Ile Arg Asp Asn Pro Ile Pro Asp Gly Thr Ile Leu Thr Thr Gly
                245                 250                 255

Thr Ala Ile Val Pro Gly Arg Asp Lys Gly Leu Lys Asp Glu Asp Ile
            260                 265                 270

Val Glu Ile Thr Ile Ser Asn Ile Gly Thr Leu Ile Thr Pro Val Lys
        275                 280                 285

Lys Arg Arg Lys Ile Thr
   290
```

<210> SEQ ID NO 16
<211> LENGTH: 478
<212> TYPE: PRT
<213> ORGANISM: Sulfolobus solfataricus

<400> SEQUENCE: 16

```
Met Lys Ser Tyr Gln Gly Leu Ala Asp Lys Trp Ile Lys Gly Ser Gly
1               5                   10                  15

Glu Glu Tyr Leu Asp Ile Asn Pro Ala Asp Lys Asp His Val Leu Ala
            20                  25                  30
```

-continued

```
Lys Ile Arg Leu Tyr Thr Lys Asp Asp Val Lys Glu Ala Ile Asn Lys
        35                  40                  45

Ala Val Ala Lys Phe Asp Glu Trp Ser Arg Thr Pro Ala Pro Lys Arg
    50                  55                  60

Gly Ser Ile Leu Leu Lys Ala Gly Glu Leu Met Glu Gln Glu Ala Gln
65                  70                  75                  80

Glu Phe Ala Leu Leu Met Thr Leu Glu Glu Gly Lys Thr Leu Lys Asp
                85                  90                  95

Ser Met Phe Glu Val Thr Arg Ser Tyr Asn Leu Leu Lys Phe Tyr Gly
            100                 105                 110

Ala Leu Ala Phe Lys Ile Ser Gly Lys Thr Leu Pro Ser Ala Asp Pro
        115                 120                 125

Asn Thr Arg Ile Phe Thr Val Lys Glu Pro Leu Gly Val Val Ala Leu
    130                 135                 140

Ile Thr Pro Trp Asn Phe Pro Leu Ser Ile Pro Val Trp Lys Leu Ala
145                 150                 155                 160

Pro Ala Leu Ala Ala Gly Asn Thr Ala Val Ile Lys Pro Ala Thr Lys
                165                 170                 175

Thr Pro Leu Met Val Ala Lys Leu Val Glu Val Leu Ser Lys Ala Gly
            180                 185                 190

Leu Pro Glu Gly Val Val Asn Leu Val Val Gly Lys Gly Ser Glu Val
        195                 200                 205

Gly Asp Thr Ile Val Ser Asp Asp Asn Ile Ala Ala Val Ser Phe Thr
    210                 215                 220

Gly Ser Thr Glu Val Gly Lys Arg Ile Tyr Lys Leu Val Gly Asn Lys
225                 230                 235                 240

Asn Arg Met Thr Arg Ile Gln Leu Glu Leu Gly Gly Lys Asn Ala Leu
                245                 250                 255

Tyr Val Asp Lys Ser Ala Asp Leu Thr Leu Ala Ala Glu Leu Ala Val
            260                 265                 270

Arg Gly Gly Phe Gly Leu Thr Gly Gln Ser Cys Thr Ala Thr Ser Arg
        275                 280                 285

Leu Ile Ile Asn Lys Asp Val Tyr Thr Gln Phe Lys Gln Arg Leu Leu
    290                 295                 300

Glu Arg Val Lys Lys Trp Arg Val Gly Pro Gly Thr Glu Asp Val Asp
305                 310                 315                 320

Met Gly Pro Val Val Asp Glu Gly Gln Phe Lys Lys Asp Leu Glu Tyr
                325                 330                 335

Ile Glu Tyr Gly Lys Asn Val Gly Ala Lys Leu Ile Tyr Gly Gly Asn
            340                 345                 350

Ile Ile Pro Gly Lys Gly Tyr Phe Leu Glu Pro Thr Ile Phe Glu Gly
        355                 360                 365

Val Thr Ser Asp Met Arg Leu Phe Lys Glu Glu Ile Phe Gly Pro Val
    370                 375                 380

Leu Ser Val Thr Glu Ala Lys Asp Leu Asp Glu Ala Ile Arg Leu Val
385                 390                 395                 400

Asn Ala Val Asp Tyr Gly His Thr Ala Gly Ile Val Ala Ser Asp Ile
                405                 410                 415

Lys Ala Ile Asn Glu Phe Val Ser Arg Val Glu Ala Gly Val Ile Lys
            420                 425                 430

Val Asn Lys Pro Thr Val Gly Leu Glu Leu Gln Ala Pro Phe Gly Gly
        435                 440                 445

Phe Lys Asn Ser Gly Ala Thr Thr Trp Lys Glu Met Gly Glu Asp Ala
```

450 455 460

Leu Glu Phe Tyr Leu Lys Glu Lys Thr Val Tyr Glu Gly Trp
465 470 475

<210> SEQ ID NO 17
<211> LENGTH: 478
<212> TYPE: PRT
<213> ORGANISM: Sulfolobus islandicus

<400> SEQUENCE: 17

Met Lys Ser Tyr Gln Gly Leu Ala Asp Lys Trp Ile Lys Gly Ser Gly
1 5 10 15

Glu Glu Tyr Leu Asp Ile Asn Pro Ala Asp Lys Asp His Val Leu Ala
20 25 30

Lys Ile Arg Leu Tyr Thr Lys Asp Asp Val Lys Glu Ala Ile Asn Lys
35 40 45

Ala Val Ala Lys Phe Asp Glu Trp Ser Arg Thr Pro Ala Pro Lys Arg
50 55 60

Gly Ser Ile Leu Leu Lys Ala Gly Glu Leu Met Glu Gln Glu Ala Gln
65 70 75 80

Glu Phe Ala Leu Leu Met Thr Leu Glu Glu Gly Lys Thr Leu Lys Asp
85 90 95

Ser Met Phe Glu Val Thr Arg Ser Tyr Asn Leu Leu Lys Phe Tyr Gly
100 105 110

Ala Leu Gly Phe Lys Ile Ser Gly Lys Thr Leu Pro Ser Ala Asp Pro
115 120 125

Asn Thr Arg Ile Phe Thr Val Lys Glu Pro Leu Gly Val Val Ala Leu
130 135 140

Ile Thr Pro Trp Asn Phe Pro Leu Ser Ile Pro Val Trp Lys Leu Ala
145 150 155 160

Pro Ala Leu Ala Ala Gly Asn Thr Ala Val Ile Lys Pro Ala Thr Lys
165 170 175

Thr Pro Leu Met Val Ala Lys Leu Val Glu Val Leu Ser Lys Ala Gly
180 185 190

Leu Pro Glu Gly Val Val Asn Leu Val Val Gly Lys Gly Ser Glu Val
195 200 205

Gly Asp Thr Ile Val Ser Asp Asp Asn Ile Ala Ala Val Ser Phe Thr
210 215 220

Gly Ser Thr Glu Val Gly Lys Arg Ile Tyr Lys Leu Val Gly Asn Lys
225 230 235 240

Asn Arg Met Thr Arg Ile Gln Leu Glu Leu Gly Gly Lys Asn Ala Leu
245 250 255

Tyr Val Asp Lys Ser Ala Asp Leu Thr Leu Ala Ala Glu Leu Ala Val
260 265 270

Arg Gly Gly Phe Gly Leu Thr Gly Gln Ser Cys Thr Ala Thr Ser Arg
275 280 285

Leu Ile Ile His Lys Asp Val Tyr Thr Gln Phe Lys Gln Arg Leu Leu
290 295 300

Glu Arg Val Lys Lys Trp Arg Val Gly Pro Gly Thr Glu Asp Val Asp
305 310 315 320

Met Gly Pro Val Val Asp Glu Gly Gln Phe Lys Lys Asp Leu Glu Tyr
325 330 335

Ile Glu Tyr Gly Lys Asn Ala Gly Ala Lys Leu Ile Tyr Gly Gly Asn
340 345 350

-continued

```
Ile Ile Pro Gly Lys Gly Tyr Phe Leu Glu Pro Thr Ile Phe Glu Gly
        355                 360                 365

Val Thr Ser His Met Arg Leu Phe Lys Glu Glu Ile Phe Gly Pro Val
    370                 375                 380

Leu Ser Val Thr Glu Ala Lys Asp Leu Asp Glu Ala Ile Arg Leu Val
385                 390                 395                 400

Asn Ala Val Asp Tyr Gly His Thr Ala Gly Ile Val Ala Ser Asp Ile
                405                 410                 415

Lys Ala Ile Asn Glu Phe Val Ser Arg Val Glu Ala Gly Val Ile Lys
            420                 425                 430

Val Asn Lys Pro Thr Val Gly Leu Glu Leu Gln Ala Pro Phe Gly Gly
        435                 440                 445

Phe Lys Asn Ser Gly Ala Thr Thr Trp Lys Glu Met Gly Glu Asp Ala
    450                 455                 460

Leu Glu Phe Tyr Leu Lys Glu Lys Thr Val Tyr Glu Gly Trp
465                 470                 475


<210> SEQ ID NO 18
<211> LENGTH: 478
<212> TYPE: PRT
<213> ORGANISM: Sulfolobus islandicus

<400> SEQUENCE: 18

Met Lys Ser Tyr Gln Gly Leu Ala Asp Lys Trp Ile Lys Gly Ser Gly
1               5                   10                  15

Glu Glu Tyr Leu Asp Ile Asn Pro Ala Asp Lys Asp His Val Leu Ala
            20                  25                  30

Lys Ile Arg Leu Tyr Thr Lys Asp Asp Val Lys Glu Ala Ile Asn Lys
        35                  40                  45

Ala Val Ala Lys Phe Asp Glu Trp Ser Arg Thr Pro Ala Pro Lys Arg
    50                  55                  60

Gly Ser Ile Leu Leu Lys Ala Gly Glu Leu Met Glu Gln Glu Ala Gln
65                  70                  75                  80

Glu Phe Ala Leu Leu Met Thr Leu Glu Glu Gly Lys Thr Leu Lys Asp
                85                  90                  95

Ser Met Phe Glu Val Thr Arg Ser Tyr Asn Leu Leu Lys Phe Tyr Gly
            100                 105                 110

Ala Leu Ala Phe Lys Ile Ser Gly Lys Thr Leu Pro Ser Ala Asp Pro
        115                 120                 125

Asn Thr Arg Ile Phe Thr Val Lys Glu Pro Leu Gly Val Val Ala Leu
    130                 135                 140

Ile Thr Pro Trp Asn Phe Pro Leu Ser Ile Pro Val Trp Lys Leu Ala
145                 150                 155                 160

Pro Ala Leu Ala Ala Gly Asn Thr Ala Val Ile Lys Pro Ala Thr Lys
                165                 170                 175

Thr Pro Leu Met Val Ala Lys Leu Val Glu Val Leu Ser Lys Ala Gly
            180                 185                 190

Leu Pro Glu Gly Val Val Asn Leu Val Val Gly Lys Gly Ser Glu Val
        195                 200                 205

Gly Asp Thr Ile Val Ser Asp Asp Asn Ile Ala Ala Val Ser Phe Thr
    210                 215                 220

Gly Ser Thr Glu Val Gly Lys Arg Ile Tyr Lys Leu Val Gly Asn Lys
225                 230                 235                 240

Asn Arg Met Thr Arg Ile Gln Leu Glu Leu Gly Gly Lys Asn Ala Leu
                245                 250                 255
```

```
Tyr Val Asp Lys Ser Ala Asp Leu Thr Leu Ala Ala Glu Leu Ala Val
            260                 265                 270

Arg Gly Gly Phe Gly Leu Thr Gly Gln Ser Cys Thr Ala Thr Ser Arg
        275                 280                 285

Leu Ile Ile Asn Lys Asp Val Tyr Thr Gln Phe Lys Gln Arg Leu Leu
    290                 295                 300

Glu Arg Val Lys Lys Trp Arg Val Gly Pro Gly Thr Glu Asp Val Asp
305                 310                 315                 320

Met Gly Pro Val Val Asp Glu Gly Gln Phe Lys Lys Asp Leu Glu Tyr
                325                 330                 335

Ile Glu Tyr Gly Lys Asn Val Gly Ala Lys Leu Ile Tyr Gly Gly Asn
            340                 345                 350

Ile Ile Pro Gly Lys Gly Tyr Phe Leu Glu Pro Thr Ile Phe Glu Gly
        355                 360                 365

Val Thr Ser Asp Met Arg Leu Phe Lys Glu Glu Ile Phe Gly Pro Val
    370                 375                 380

Leu Ser Val Thr Glu Ala Lys Asp Leu Asp Glu Ala Ile Arg Leu Val
385                 390                 395                 400

Asn Ala Val Asp Tyr Gly His Thr Ala Gly Ile Val Ala Ser Asp Ile
                405                 410                 415

Asn Ala Ile Asn Glu Phe Val Ser Arg Val Glu Ala Gly Val Ile Lys
            420                 425                 430

Val Asn Lys Pro Thr Val Gly Leu Glu Leu Gln Ala Pro Phe Gly Gly
        435                 440                 445

Phe Lys Asn Ser Gly Ala Thr Thr Trp Lys Glu Met Gly Glu Asp Ala
    450                 455                 460

Leu Glu Phe Tyr Leu Lys Glu Lys Thr Val Tyr Glu Gly Trp
465                 470                 475
```

<210> SEQ ID NO 19
<211> LENGTH: 478
<212> TYPE: PRT
<213> ORGANISM: Sulfolobus islandicus

<400> SEQUENCE: 19

```
Met Lys Ser Tyr Gln Gly Leu Ala Asp Lys Trp Ile Lys Gly Ser Gly
1               5                   10                  15

Glu Glu Tyr Leu Asp Ile Asn Pro Ala Asp Lys Asp His Val Leu Ala
            20                  25                  30

Lys Ile Arg Leu Tyr Thr Lys Asp Asp Val Lys Glu Ala Ile Asn Lys
        35                  40                  45

Ala Val Ala Lys Phe Asp Glu Trp Ser Arg Thr Pro Ala Pro Lys Arg
    50                  55                  60

Gly Ser Ile Leu Leu Lys Ala Gly Glu Leu Met Glu Gln Glu Ala Gln
65                  70                  75                  80

Glu Phe Ala Leu Leu Met Thr Leu Glu Glu Gly Lys Thr Leu Lys Asp
                85                  90                  95

Ser Met Phe Glu Val Thr Arg Ser Tyr Asn Leu Leu Lys Phe Tyr Gly
            100                 105                 110

Ala Leu Ala Phe Lys Ile Ser Gly Lys Thr Leu Pro Ser Ala Asp Pro
        115                 120                 125

Asn Thr Arg Ile Phe Thr Val Lys Glu Pro Leu Gly Val Val Ala Leu
    130                 135                 140

Ile Thr Pro Trp Asn Phe Pro Leu Ser Ile Pro Val Trp Lys Leu Ala
```

-continued

```
145                 150                 155                 160

Pro Ala Leu Ala Ala Gly Asn Thr Ala Ile Ile Lys Pro Ala Thr Lys
                165                 170                 175

Thr Pro Leu Met Val Ala Lys Leu Val Glu Val Leu Ser Lys Ala Gly
            180                 185                 190

Leu Pro Glu Gly Val Val Asn Leu Val Val Gly Lys Gly Ser Glu Val
        195                 200                 205

Gly Asp Thr Ile Val Ser Asp Asp Asn Ile Ala Ala Val Ser Phe Thr
    210                 215                 220

Gly Ser Thr Glu Val Gly Lys Arg Ile Tyr Lys Leu Val Gly Asn Lys
225                 230                 235                 240

Asn Arg Met Thr Arg Ile Gln Leu Glu Leu Gly Gly Lys Asn Ala Leu
                245                 250                 255

Tyr Val Asp Lys Ser Ala Asp Leu Thr Leu Ala Ala Glu Leu Ala Val
            260                 265                 270

Arg Gly Gly Phe Gly Leu Thr Gly Gln Ser Cys Thr Ala Thr Ser Arg
        275                 280                 285

Leu Ile Ile Asn Lys Asp Val Tyr Thr Gln Phe Lys Gln Arg Leu Leu
    290                 295                 300

Glu Arg Val Lys Lys Trp Arg Val Gly Pro Gly Thr Glu Asp Val Asp
305                 310                 315                 320

Met Gly Pro Val Val Asp Glu Gly Gln Phe Lys Lys Asp Leu Glu Tyr
                325                 330                 335

Ile Glu Tyr Gly Lys Asn Val Gly Ala Lys Leu Ile Tyr Gly Gly Asn
            340                 345                 350

Ile Ile Pro Gly Lys Gly Tyr Phe Leu Glu Pro Thr Ile Phe Glu Gly
        355                 360                 365

Val Thr Ser Asp Met Arg Leu Phe Lys Glu Glu Ile Phe Gly Pro Val
    370                 375                 380

Leu Ser Val Thr Glu Ala Lys Asp Leu Asp Glu Ala Ile Arg Leu Val
385                 390                 395                 400

Asn Ala Val Asp Tyr Gly His Thr Ala Gly Ile Val Ala Ser Asp Ile
                405                 410                 415

Lys Ala Ile Asn Glu Phe Val Ser Arg Val Glu Ala Gly Val Ile Lys
            420                 425                 430

Val Asn Lys Pro Thr Val Gly Leu Glu Leu Gln Ala Pro Phe Gly Gly
        435                 440                 445

Phe Lys Asn Ser Gly Ala Thr Thr Trp Lys Glu Met Gly Glu Asp Ala
    450                 455                 460

Leu Glu Phe Tyr Leu Lys Glu Lys Thr Val Tyr Glu Gly Trp
465                 470                 475
```

<210> SEQ ID NO 20
<211> LENGTH: 478
<212> TYPE: PRT
<213> ORGANISM: Sulfolobus islandicus

<400> SEQUENCE: 20

```
Met Lys Ser Tyr Gln Gly Leu Ala Asp Lys Trp Ile Lys Gly Ser Gly
1               5                   10                  15

Glu Glu Tyr Leu Asp Ile Asn Pro Ala Asp Lys Asp His Val Leu Ala
            20                  25                  30

Lys Ile Arg Leu Tyr Thr Lys Asp Asp Val Lys Glu Ala Ile Asn Lys
        35                  40                  45
```

-continued

```
Ala Val Ala Lys Phe Asp Glu Trp Ser Arg Thr Pro Ala Pro Lys Arg
    50                  55                  60

Gly Ser Ile Leu Leu Lys Ala Gly Glu Leu Met Glu Gln Glu Ala Gln
65                  70                  75                  80

Glu Phe Ala Leu Leu Met Thr Leu Glu Glu Gly Lys Thr Leu Lys Asp
                85                  90                  95

Ser Met Phe Glu Val Thr Arg Ser Tyr Asn Leu Leu Lys Phe Tyr Gly
            100                 105                 110

Ala Leu Ala Phe Lys Ile Ser Gly Lys Thr Leu Pro Ser Ala Asp Pro
        115                 120                 125

Asn Thr Arg Ile Phe Thr Val Lys Glu Pro Leu Gly Val Val Ala Leu
    130                 135                 140

Ile Thr Pro Trp Asn Phe Pro Leu Ser Ile Pro Val Trp Lys Leu Ala
145                 150                 155                 160

Pro Ala Leu Ala Ala Gly Asn Thr Ala Val Ile Lys Pro Ala Thr Lys
                165                 170                 175

Thr Pro Leu Met Val Ala Lys Leu Val Glu Val Leu Ser Lys Ala Gly
            180                 185                 190

Leu Pro Glu Gly Val Val Asn Leu Val Val Gly Lys Gly Ser Glu Val
        195                 200                 205

Gly Asp Thr Ile Val Ser Asp Asp Asn Ile Ala Ala Val Ser Phe Thr
    210                 215                 220

Gly Ser Thr Glu Val Gly Lys Arg Ile Tyr Lys Leu Val Gly Asn Lys
225                 230                 235                 240

Asn Arg Met Thr Arg Ile Gln Leu Glu Leu Gly Gly Lys Asn Ala Leu
                245                 250                 255

Tyr Val Asp Lys Ser Ala Asp Leu Thr Leu Ala Ala Glu Leu Ala Ile
            260                 265                 270

Arg Gly Gly Phe Gly Leu Thr Gly Gln Ser Cys Thr Ala Thr Ser Arg
        275                 280                 285

Leu Ile Ile Asn Lys Asp Val Tyr Thr Gln Phe Lys Gln Arg Leu Leu
    290                 295                 300

Glu Arg Val Lys Lys Trp Arg Val Gly Pro Gly Thr Glu Asp Val Asp
305                 310                 315                 320

Met Gly Pro Val Val Asp Glu Gly Gln Phe Lys Lys Asp Leu Glu Tyr
                325                 330                 335

Ile Glu Tyr Gly Lys Asn Val Gly Ala Lys Leu Ile Tyr Gly Gly Asn
            340                 345                 350

Ile Ile Pro Gly Lys Gly Tyr Phe Leu Glu Pro Thr Ile Phe Glu Gly
        355                 360                 365

Val Thr Ser Asp Met Arg Leu Phe Lys Glu Glu Ile Phe Gly Pro Val
    370                 375                 380

Leu Ser Val Thr Glu Ala Lys Asp Leu Asp Glu Ala Ile Arg Leu Val
385                 390                 395                 400

Asn Ala Val Asp Tyr Gly His Thr Ala Gly Ile Val Ala Ser Asp Ile
                405                 410                 415

Lys Ala Ile Asn Glu Phe Val Ser Arg Val Glu Ala Gly Val Ile Lys
            420                 425                 430

Val Asn Lys Pro Thr Val Gly Leu Glu Leu Gln Ala Pro Phe Gly Gly
        435                 440                 445

Phe Lys Asn Ser Gly Ala Thr Thr Trp Lys Glu Met Gly Glu Asp Ala
    450                 455                 460

Leu Glu Phe Tyr Leu Lys Glu Lys Thr Val Tyr Glu Gly Trp
```

-continued 465 470 475

<210> SEQ ID NO 21
<211> LENGTH: 488
<212> TYPE: PRT
<213> ORGANISM: Bacillus subtilis

<400> SEQUENCE: 21

```
Met Ser Val Ile Thr Glu Gln Asn Thr Tyr Leu Asn Phe Ile Asn Gly
1               5                   10                  15

Glu Trp Val Lys Ser Gln Ser Gly Asp Met Val Lys Val Glu Asn Pro
            20                  25                  30

Ala Asp Val Asn Asp Ile Val Gly Tyr Val Gln Asn Ser Thr Ala Glu
        35                  40                  45

Asp Val Glu Arg Ala Val Thr Ala Ala Asn Glu Ala Lys Thr Ala Trp
    50                  55                  60

Arg Lys Leu Thr Gly Ala Glu Arg Gly Gln Tyr Leu Tyr Lys Thr Ala
65                  70                  75                  80

Asp Ile Met Glu Gln Arg Leu Glu Glu Ile Ala Ala Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Met Arg Lys Thr Gly
        115                 120                 125

Asp Val Ile Pro Ser Thr Asp Lys Asp Ala Leu Met Phe Thr Thr Arg
    130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Val Tyr Gly Asn Thr
                165                 170                 175

Val Val Ile Lys Pro Ala Thr Glu Thr Ala Val Thr Cys Ala Lys Ile
            180                 185                 190

Ile Ala Cys Phe Glu Glu Ala Gly Leu Pro Ala Gly Val Ile Asn Leu
        195                 200                 205

Val Thr Gly Pro Gly Ser Val Val Gly Gln Gly Leu Ala Glu His Asp
    210                 215                 220

Gly Val Asn Ala Val Thr Phe Thr Gly Ser Asn Gln Val Gly Lys Ile
225                 230                 235                 240

Ile Gly Gln Ala Ala Leu Ala Arg Gly Ala Lys Tyr Gln Leu Glu Met
                245                 250                 255

Gly Gly Lys Asn Pro Val Ile Val Ala Asp Asp Ala Asp Leu Glu Ala
            260                 265                 270

Ala Ala Glu Ala Val Ile Thr Gly Ala Phe Arg Ser Thr Gly Gln Lys
        275                 280                 285

Cys Thr Ala Thr Ser Arg Val Ile Val Gln Ser Gly Ile Tyr Glu Arg
    290                 295                 300

Phe Lys Glu Lys Leu Leu Gln Arg Thr Lys Asp Ile Thr Ile Gly Asp
305                 310                 315                 320

Ser Leu Lys Glu Asp Val Trp Met Gly Pro Ile Ala Ser Lys Asn Gln
                325                 330                 335

Leu Asp Asn Cys Leu Ser Tyr Ile Glu Lys Gly Lys Gln Glu Gly Ala
            340                 345                 350

Ser Leu Leu Ile Gly Gly Glu Lys Leu Glu Asn Gly Lys Tyr Gln Asn
        355                 360                 365
```

```
Gly Tyr Tyr Val Gln Pro Ala Ile Phe Asp Asn Val Thr Ser Glu Met
    370                 375                 380

Thr Ile Ala Gln Glu Glu Ile Phe Gly Pro Val Ile Ala Leu Ile Lys
385                 390                 395                 400

Val Asp Ser Ile Glu Glu Ala Leu Asn Ile Ala Asn Asp Val Lys Phe
                405                 410                 415

Gly Leu Ser Ala Ser Ile Phe Thr Glu Asn Ile Gly Arg Met Leu Ser
            420                 425                 430

Phe Ile Asp Glu Ile Asp Ala Gly Leu Val Arg Ile Asn Ala Glu Ser
        435                 440                 445

Ala Gly Val Glu Leu Gln Ala Pro Phe Gly Gly Met Lys Gln Ser Ser
    450                 455                 460

Ser His Ser Arg Glu Gln Gly Glu Ala Ala Lys Asp Phe Phe Thr Ala
465                 470                 475                 480

Ile Lys Thr Val Phe Val Lys Pro
                485


<210> SEQ ID NO 22
<211> LENGTH: 488
<212> TYPE: PRT
<213> ORGANISM: Bacillus subtilis

<400> SEQUENCE: 22

Met Ser Val Ile Thr Glu Gln Asn Thr Tyr Leu Asn Phe Ile Asn Gly
1               5                   10                  15

Glu Trp Val Lys Ser Gln Ser Gly Asp Met Val Lys Val Glu Asn Pro
            20                  25                  30

Ala Asp Val Asn Asp Ile Val Gly Tyr Val Gln Asn Ser Thr Ala Glu
        35                  40                  45

Asp Val Glu Arg Ala Val Ala Ala Ala Asn Glu Ala Lys Thr Ala Trp
    50                  55                  60

Arg Lys Leu Thr Gly Ala Glu Arg Gly Gln Tyr Leu Tyr Lys Thr Ala
65                  70                  75                  80

Asp Ile Met Glu Gln Arg Leu Glu Glu Ile Ala Ala Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Met Arg Lys Thr Gly
        115                 120                 125

Asp Val Ile Pro Ser Thr Asp Lys Asp Ala Leu Met Phe Thr Thr Arg
    130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Val Tyr Gly Asn Thr
                165                 170                 175

Val Val Ile Lys Pro Ala Thr Glu Thr Ala Val Thr Cys Ala Lys Ile
            180                 185                 190

Ile Ala Cys Phe Glu Glu Ala Gly Leu Pro Ala Gly Val Ile Asn Leu
        195                 200                 205

Val Thr Gly Pro Gly Ser Val Val Gly Gln Gly Leu Ala Glu His Glu
    210                 215                 220

Gly Val Asn Ala Val Thr Phe Thr Gly Ser Asn Gln Val Gly Lys Ile
225                 230                 235                 240

Ile Gly Gln Ala Ala Leu Ala Arg Gly Ala Lys Tyr Gln Leu Glu Met
                245                 250                 255
```

```
Gly Gly Lys Asn Pro Val Ile Val Ala Asp Asp Ala Asp Leu Glu Ala
            260                 265                 270

Ala Ala Glu Ala Val Ile Thr Gly Ala Phe Arg Ser Thr Gly Gln Lys
        275                 280                 285

Cys Thr Ala Thr Ser Arg Ala Ile Val Gln Ser Gly Ile Tyr Glu Arg
    290                 295                 300

Phe Lys Glu Lys Leu Leu Gln Arg Thr Lys Asp Ile Thr Ile Gly Asp
305                 310                 315                 320

Ser Leu Lys Glu Asp Val Trp Met Gly Pro Ile Ala Ser Lys Asn Gln
                325                 330                 335

Leu Asp Asn Cys Leu Ser Tyr Ile Glu Lys Gly Lys Gln Glu Gly Ala
            340                 345                 350

Ser Leu Leu Ile Gly Gly Glu Lys Leu Glu Asn Gly Lys Tyr Gln Asn
        355                 360                 365

Gly Tyr Tyr Val Gln Pro Ala Ile Phe Asp Asn Val Thr Ser Glu Met
    370                 375                 380

Thr Ile Ala Gln Glu Glu Ile Phe Gly Pro Val Ile Ala Leu Ile Lys
385                 390                 395                 400

Val Asp Ser Met Glu Glu Ala Leu Asn Ile Ala Asn Asp Val Lys Phe
                405                 410                 415

Gly Leu Ser Ala Ser Ile Phe Thr Glu Asn Ile Gly Arg Met Leu Ser
            420                 425                 430

Phe Ile Asp Glu Ile Asp Ala Gly Leu Val Arg Ile Asn Ala Glu Ser
        435                 440                 445

Ala Gly Val Glu Leu Gln Ala Pro Phe Gly Gly Met Lys Gln Ser Ser
    450                 455                 460

Ser His Ser Arg Glu Gln Gly Glu Ala Ala Lys Asp Phe Phe Thr Ala
465                 470                 475                 480

Ile Lys Thr Val Phe Val Lys Pro
                485


<210> SEQ ID NO 23
<211> LENGTH: 488
<212> TYPE: PRT
<213> ORGANISM: Bacillus subtilis

<400> SEQUENCE: 23

Met Ser Val Ile Thr Glu Gln Asn Thr Tyr Leu Asn Phe Ile Lys Gly
1               5                   10                  15

Glu Trp Val Lys Ser Gln Ser Gly Asp Met Val Lys Val Glu Asn Pro
            20                  25                  30

Ala Asp Val Asn Asp Ile Val Gly Tyr Val Gln Asn Ser Thr Ala Glu
        35                  40                  45

Asp Val Glu Arg Ala Val Ala Ala Ala Asn Glu Ala Lys Thr Ala Trp
    50                  55                  60

Arg Lys Leu Thr Gly Ala Glu Arg Gly Gln Tyr Leu Tyr Lys Thr Ala
65                  70                  75                  80

Asp Ile Met Glu Gln Arg Leu Glu Glu Ile Ala Ala Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Met Arg Lys Thr Gly
        115                 120                 125

Asp Val Ile Pro Ser Thr Asp Lys Ala Ala Leu Met Phe Thr Thr Arg
```

```
    130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Val Tyr Gly Asn Thr
                165                 170                 175

Val Val Ile Lys Pro Ala Thr Glu Thr Ala Val Thr Cys Ala Lys Ile
            180                 185                 190

Ile Ala Cys Phe Glu Glu Ala Gly Leu Pro Ala Gly Val Ile Asn Leu
        195                 200                 205

Val Thr Gly Pro Gly Ser Val Val Gly Gln Gly Leu Ala Glu His Asp
    210                 215                 220

Gly Val Asn Ala Val Thr Phe Thr Gly Ser Asn Gln Val Gly Lys Ile
225                 230                 235                 240

Ile Gly Gln Ala Ala Leu Ala Arg Gly Ala Lys Tyr Gln Leu Glu Met
                245                 250                 255

Gly Gly Lys Asn Pro Val Ile Val Ala Asp Asp Ala Asp Leu Glu Ala
            260                 265                 270

Ala Ala Glu Ala Val Ile Thr Gly Ala Phe Arg Ser Thr Gly Gln Lys
        275                 280                 285

Cys Thr Ala Thr Ser Arg Val Ile Val Gln Ser Glu Ile Tyr Glu Arg
    290                 295                 300

Phe Lys Glu Lys Leu Leu Gln Arg Thr Lys Asp Ile Thr Ile Gly Asp
305                 310                 315                 320

Ser Leu Lys Glu Asp Val Trp Met Gly Pro Ile Ala Ser Lys Asn Gln
                325                 330                 335

Leu Asp Asn Cys Leu Ser Tyr Ile Glu Lys Gly Lys Gln Glu Gly Ala
            340                 345                 350

Ser Leu Leu Ile Gly Gly Glu Lys Leu Glu Asn Gly Lys Tyr Gln Asn
        355                 360                 365

Gly Tyr Tyr Val Gln Pro Ala Ile Phe Asp Asn Val Thr Ser Glu Met
    370                 375                 380

Thr Ile Ala Gln Glu Glu Ile Phe Gly Pro Val Ile Ala Leu Ile Lys
385                 390                 395                 400

Val Asp Ser Met Glu Glu Ala Leu Asn Ile Ala Asn Asp Val Lys Phe
                405                 410                 415

Gly Leu Ser Ala Ser Ile Phe Thr Glu Asn Ile Gly Arg Met Leu Ser
            420                 425                 430

Phe Ile Asp Glu Ile Asp Ala Gly Leu Val Arg Ile Asn Ala Glu Ser
        435                 440                 445

Ala Gly Val Glu Leu Gln Ala Pro Phe Gly Gly Met Lys Gln Ser Ser
    450                 455                 460

Ser His Ser Arg Glu Gln Gly Glu Ala Ala Lys Asp Phe Phe Thr Ala
465                 470                 475                 480

Ile Lys Thr Val Phe Val Lys Pro
                485


<210> SEQ ID NO 24
<211> LENGTH: 488
<212> TYPE: PRT
<213> ORGANISM: Bacillus subtilis

<400> SEQUENCE: 24

Met Ser Val Ile Thr Glu Gln Asn Thr Tyr Leu Asn Phe Ile Asn Gly
1               5                   10                  15
```

-continued

```
Glu Trp Val Lys Ser Gln Ser Gly Asp Met Val Lys Val Glu Asn Pro
            20                  25                  30

Ala Asp Val Asn Asp Ile Val Gly Tyr Val Gln Asn Ser Thr Ala Asp
        35                  40                  45

Asp Val Glu Arg Ala Val Ala Ala Ala Asn Glu Ala Lys Thr Ala Trp
    50                  55                  60

Arg Lys Leu Thr Gly Ala Glu Arg Gly Gln Tyr Leu Tyr Lys Thr Ala
65                  70                  75                  80

Asp Ile Met Glu Gln Arg Leu Glu Glu Ile Ala Ala Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Met Arg Lys Thr Gly
        115                 120                 125

Asp Val Ile Pro Ser Thr Asp Lys Asp Ala Leu Met Phe Thr Thr Arg
    130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Val Tyr Gly Asn Thr
                165                 170                 175

Val Val Ile Lys Pro Ala Thr Glu Thr Ala Val Thr Cys Ala Lys Ile
            180                 185                 190

Ile Ala Cys Phe Glu Glu Ala Gly Leu Pro Ala Gly Val Ile Asn Leu
        195                 200                 205

Val Thr Gly Pro Gly Ser Val Val Gly Gln Gly Leu Ala Glu His Glu
    210                 215                 220

Gly Val Asn Ala Ile Thr Phe Thr Gly Ser Asn Gln Val Gly Lys Ile
225                 230                 235                 240

Ile Gly Gln Ala Ala Leu Ala Arg Gly Ala Lys Tyr Gln Leu Glu Met
                245                 250                 255

Gly Gly Lys Asn Pro Val Ile Val Ala Asp Asp Ala Asp Leu Glu Ala
            260                 265                 270

Ala Ala Glu Ala Val Ile Thr Gly Ala Phe Arg Ser Thr Gly Gln Lys
        275                 280                 285

Cys Thr Ala Thr Ser Arg Val Ile Val Gln Ser Gly Ile Tyr Asp Arg
    290                 295                 300

Phe Lys Glu Lys Leu Leu Gln Arg Thr Lys Asp Ile Lys Ile Gly Asp
305                 310                 315                 320

Ser Leu Lys Glu Asp Val Trp Met Gly Pro Ile Ala Ser Lys Asn Gln
                325                 330                 335

Leu Asp Asn Cys Leu Ser Tyr Ile Glu Lys Gly Lys Gln Glu Gly Ala
            340                 345                 350

Ser Leu Leu Ile Gly Gly Glu Lys Leu Glu Asp Gly Lys Tyr Gln Asn
        355                 360                 365

Gly Tyr Tyr Val Gln Pro Ala Ile Phe Asp Asn Val Thr Ser Glu Met
    370                 375                 380

Thr Ile Ala Gln Glu Glu Ile Phe Gly Pro Val Ile Ala Leu Ile Lys
385                 390                 395                 400

Val Asp Ser Met Glu Glu Ala Leu Asp Ile Ala Asn Asp Val Lys Phe
                405                 410                 415

Gly Leu Ser Ala Ser Ile Phe Thr Gln Asn Ile Gly Arg Met Leu Ser
            420                 425                 430

Phe Val Asp Glu Ile Asp Ala Gly Leu Val Arg Ile Asn Ala Glu Ser
```

```
        435                 440                 445

Ala Gly Val Glu Leu Gln Ala Pro Phe Gly Gly Met Lys Gln Ser Ser
    450                 455                 460

Ser His Ser Arg Glu Gln Gly Glu Ala Ala Lys Asp Phe Phe Thr Ala
465                 470                 475                 480

Ile Lys Thr Val Phe Val Lys Pro
                485


<210> SEQ ID NO 25
<211> LENGTH: 488
<212> TYPE: PRT
<213> ORGANISM: Bacillus sp. JS

<400> SEQUENCE: 25

Met Ser Val Ile Thr Glu Gln Asn Thr Tyr Leu Asn Phe Ile Asn Gly
1               5                   10                  15

Glu Trp Val Gln Ser Gln Ser Gly Asp Met Val Lys Val Glu Asn Pro
            20                  25                  30

Ala Asp Val Asn Asp Ile Val Gly Tyr Val Gln Asn Ser Thr Ala Glu
        35                  40                  45

Asp Val Glu Arg Ala Val Ala Ala Ala Asn Lys Ala Lys Thr Ala Trp
    50                  55                  60

Arg Lys Leu Thr Gly Ala Glu Arg Gly Gln Tyr Leu Tyr Lys Thr Ala
65                  70                  75                  80

Asp Ile Met Glu Arg Arg Leu Glu Glu Ile Ala Ala Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Met Arg Lys Thr Gly
        115                 120                 125

Asp Val Ile Pro Ser Thr Asp Lys Asp Ala Leu Met Phe Thr Thr Arg
    130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Val Tyr Gly Asn Thr
                165                 170                 175

Val Val Ile Lys Pro Ala Thr Glu Thr Ala Val Thr Cys Ala Lys Ile
            180                 185                 190

Ile Ala Cys Phe Glu Glu Ala Gly Leu Pro Ala Gly Val Ile Asn Leu
        195                 200                 205

Val Thr Gly Pro Gly Ser Val Val Gly Gln Gly Leu Ala Glu His Asp
    210                 215                 220

Ser Val Asn Ala Val Thr Phe Thr Gly Ser Asn Gln Val Gly Lys Ile
225                 230                 235                 240

Ile Gly Gln Ala Ala Leu Ala Arg Gly Ala Lys Tyr Gln Leu Glu Met
                245                 250                 255

Gly Gly Lys Asn Pro Val Ile Val Ala Asp Asp Ala Asp Leu Glu Ala
            260                 265                 270

Ala Ala Glu Ala Val Ile Thr Gly Ala Phe Arg Ser Thr Gly Gln Lys
        275                 280                 285

Cys Thr Ala Thr Ser Arg Val Ile Val Gln Ser Gly Ile Tyr Glu Arg
    290                 295                 300

Phe Lys Glu Lys Leu Leu Gln Arg Thr Lys Asp Ile Thr Ile Gly Asp
305                 310                 315                 320
```

```
Ser Leu Lys Glu Asp Val Trp Met Gly Pro Ile Ala Ser Lys Asn Gln
                325                 330                 335

Leu Asp Asn Cys Leu Ser Tyr Ile Glu Lys Gly Lys Arg Glu Gly Ala
            340                 345                 350

Ser Leu Leu Met Gly Gly Glu Lys Leu Glu Asn Glu Lys Tyr Gln Asn
        355                 360                 365

Gly Tyr Tyr Val Gln Pro Ala Ile Phe Asp Asn Val Thr Ser Glu Met
    370                 375                 380

Thr Ile Ala Gln Glu Glu Ile Phe Gly Pro Val Ile Ala Leu Ile Lys
385                 390                 395                 400

Val Asp Ser Met Glu Glu Ala Leu Asp Ile Ala Asn Asp Val Lys Phe
                405                 410                 415

Gly Leu Ser Ala Ser Ile Phe Thr Glu Asn Ile Gly Lys Met Leu Ser
            420                 425                 430

Phe Ile Asp Glu Ile Asp Ala Gly Leu Val Arg Val Asn Ala Glu Ser
        435                 440                 445

Ala Gly Val Glu Leu Gln Ala Pro Phe Gly Gly Met Lys Gln Ser Ser
    450                 455                 460

Ser His Ser Arg Glu Gln Gly Glu Ala Ala Lys Asp Phe Phe Thr Ala
465                 470                 475                 480

Ile Lys Thr Val Phe Val Lys Pro
                485


<210> SEQ ID NO 26
<211> LENGTH: 248
<212> TYPE: PRT
<213> ORGANISM: Caulobacter crescentus

<400> SEQUENCE: 26

Met Ser Ser Ala Ile Tyr Pro Ser Leu Lys Gly Lys Arg Val Val Ile
1               5                   10                  15

Thr Gly Gly Gly Ser Gly Ile Gly Ala Gly Leu Thr Ala Gly Phe Ala
            20                  25                  30

Arg Gln Gly Ala Glu Val Ile Phe Leu Asp Ile Ala Asp Glu Asp Ser
        35                  40                  45

Arg Ala Leu Glu Ala Glu Leu Ala Gly Ser Pro Ile Pro Pro Val Tyr
    50                  55                  60

Lys Arg Cys Asp Leu Met Asn Leu Glu Ala Ile Lys Ala Val Phe Ala
65                  70                  75                  80

Glu Ile Gly Asp Val Asp Val Leu Val Asn Asn Ala Gly Asn Asp Asp
                85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
        115                 120                 125

Gly Met Lys Lys Arg Gly Gly Gly Ala Val Ile Asn Phe Gly Ser Ile
    130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Gln Ile Val Ala
        195                 200                 205
```

Ala Gln Cys Leu Lys Gly Arg Ile Val Pro Glu Asn Val Ala Ala Leu
210 215 220

Val Leu Phe Leu Ala Ser Asp Asp Ala Ser Leu Cys Thr Gly His Glu
225 230 235 240

Tyr Trp Ile Asp Ala Gly Trp Arg
245

<210> SEQ ID NO 27
<211> LENGTH: 250
<212> TYPE: PRT
<213> ORGANISM: Phenylobacterium zucineum

<400> SEQUENCE: 27

Met Gly Val Thr Ser Ala Ile Tyr Pro Ser Leu Lys Gly Lys Arg Val
1 5 10 15

Val Val Thr Gly Gly Gly Ser Gly Ile Gly Ala Gly Leu Val Glu Ala
20 25 30

Phe Val Arg Gln Gly Ala Glu Val His Phe Leu Asp Val Leu Glu Thr
35 40 45

Glu Ser Arg Val Leu Glu Thr Ser Leu Ala Gly Ala Glu Val Pro Pro
50 55 60

Val Phe His Arg Cys Asp Leu Thr Asp Ala Gly Ala Ile Glu Gly Cys
65 70 75 80

Phe Ala Lys Ile Gly Pro Val Gln Val Leu Val Asn Asn Ala Gly Asn
85 90 95

Asp Asp Arg His Thr Leu Asp Glu Val Thr Pro Ala Tyr Phe Asp Asp
100 105 110

Arg Ile Ala Val Asn Leu Arg His Met Val Phe Cys Ala Lys Ala Val
115 120 125

Val Pro Ala Met Lys Ala Ala Gly Glu Gly Ala Ile Ile Asn Phe Gly
130 135 140

Ser Ile Ser Trp His Leu Gly Leu Pro Asp Leu Val Leu Tyr Glu Thr
145 150 155 160

Ala Lys Ala Gly Ile Glu Gly Met Thr Arg Ala Leu Ala Arg Glu Leu
165 170 175

Gly Pro Phe Gly Ile Arg Val Thr Cys Val Ala Pro Gly Asn Val Lys
180 185 190

Thr Leu Arg Gln Met Lys Trp Tyr Thr Pro Glu Gly Glu Ala Glu Ile
195 200 205

Val Ala Gln Gln Cys Leu Lys Ser Arg Ile Glu Pro Ala Asp Val Ala
210 215 220

Ala Leu Val Leu Phe Leu Ala Ser Asp Asp Ala Arg Met Cys Thr Gly
225 230 235 240

His Glu Tyr Trp Ile Asp Ala Gly Trp Arg
245 250

<210> SEQ ID NO 28
<211> LENGTH: 248
<212> TYPE: PRT
<213> ORGANISM: Caulobacter sp. AP07

<400> SEQUENCE: 28

Met Ser Ser Ala Ile Tyr Pro Ser Leu Gln Gly Lys Arg Val Val Val
1 5 10 15

Thr Gly Gly Gly Ser Gly Ile Gly Ala Gly Ile Val Ala Ala Phe Ala
20 25 30

```
Arg Gln Gly Ala Glu Val Ile Phe Leu Asp Val Val Asp Ala Asp Ser
        35                  40                  45

Glu Ala Leu Ala Ala Lys Leu Ser Asp Ser Pro Ile Ala Pro Thr Tyr
    50                  55                  60

Met Arg Cys Asp Leu Thr Asp Leu Glu Ala Met Ala Glu Thr Phe Ala
65                  70                  75                  80

Arg Ile Gly Pro Ile Asp Val Leu Val Asn Asn Ala Gly Asn Asp Asp
                85                  90                  95

Arg His Gly Leu Ala Glu Ile Thr Pro Ala Tyr Trp Asp Gln Arg Met
            100                 105                 110

Ala Val Asn Leu Arg His Met Leu Phe Ala Thr Gln Ala Val Ala Pro
        115                 120                 125

Gly Met Lys Ala Arg Gly Gly Gly Ala Val Ile Asn Phe Gly Ser Ile
    130                 135                 140

Ser Trp His Leu Gly Leu Pro Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Glu Ile Val Ala
        195                 200                 205

Ala Gln Ala Leu Lys Gly Arg Leu Val Pro Asp His Val Ala Ser Leu
    210                 215                 220

Val Leu Phe Leu Ala Ser Asp Asp Ala Ala Leu Cys Thr Gly His Glu
225                 230                 235                 240

Tyr Trp Ile Asp Ala Gly Trp Arg
                245
```

<210> SEQ ID NO 29
<211> LENGTH: 259
<212> TYPE: PRT
<213> ORGANISM: Caulobacter sp. K31

<400> SEQUENCE: 29

```
Met Asn Ile Glu Val Lys Arg Pro Gln Val Ser Thr Ser Ser Ala Ile
1               5                   10                  15

Tyr Pro Ser Leu Lys Gly Lys Arg Val Val Val Thr Gly Gly Gly Ser
            20                  25                  30

Gly Ile Gly Ala Gly Ile Val Ala Gly Phe Ala Arg Gln Gly Ser Glu
        35                  40                  45

Val Ile Phe Leu Asp Val Ala Asp Gln Asp Ser Lys Ala Leu Ala Glu
    50                  55                  60

Gln Leu Ser Gly Ala Glu Ile Ala Pro Val Tyr Leu Arg Cys Asp Leu
65                  70                  75                  80

Thr Asp Leu Asp Ala Val Ala Lys Thr Phe Ala Asp Ile Gly Pro Val
                85                  90                  95

Asp Val Leu Val Asn Asn Ala Gly Asn Asp Asp Arg His Gly Leu Ala
            100                 105                 110

Gln Ile Thr Pro Ala Tyr Trp Asp Glu Arg Met Ser Val Asn Leu Arg
        115                 120                 125

His Met Leu Phe Ala Thr Gln Ala Val Ala Pro Gly Met Lys Ala Arg
    130                 135                 140

Gly Gly Gly Ala Ile Ile Asn Phe Gly Ser Ile Ser Trp His Leu Gly
```

-continued 145 150 155 160

Leu Pro Asp Leu Val Leu Tyr Glu Thr Ala Lys Ala Gly Ile Glu Gly
165 170 175

Met Thr Arg Ala Leu Ala Arg Glu Leu Gly Pro Asp Asp Ile Arg Val
180 185 190

Thr Cys Val Val Pro Gly Asn Ile Lys Thr Lys Arg Gln Glu Lys Trp
195 200 205

Tyr Thr Pro Glu Gly Glu Ala Glu Ile Val Ala Ala Gln Ala Leu Lys
210 215 220

Gly Arg Leu Val Pro Asp His Val Ala Ser Leu Val Met Phe Leu Ala
225 230 235 240

Ser Asp Asp Ala Ser Leu Cys Thr Gly His Glu Tyr Trp Ile Asp Ala
245 250 255

Gly Trp Arg

<210> SEQ ID NO 30
<211> LENGTH: 249
<212> TYPE: PRT
<213> ORGANISM: Caulobacter segnis

<400> SEQUENCE: 30

Met Ser Ser Ala Ile Tyr Pro Ser Leu Lys Gly Lys Arg Val Val Ile
1 5 10 15

Thr Gly Gly Gly Ser Gly Ile Gly Ala Gly Leu Val Ala Gly Phe Val
20 25 30

Arg Gln Gly Ala Glu Val Ile Phe Leu Asp Ile Val Asp Ala Asp Ser
35 40 45

Gln Ala Leu Val Ala Glu Leu Ser Lys Asp Ala Val Ile Ala Pro Val
50 55 60

Tyr Lys Arg Cys Asp Leu Met Asp Ile Asp Ala Leu Lys Ala Thr Phe
65 70 75 80

Ala Glu Ile Gly Asp Val Asp Val Leu Val Asn Asn Ala Gly Asn Asp
85 90 95

Asp Arg His Ser Leu Ala Asp Leu Thr Pro Ala Tyr Trp Asp Asn Arg
100 105 110

Ile Gly Val Asn Leu Arg His Met Val Phe Ala Ala Gln Ala Val Ala
115 120 125

Gly Gly Met Lys Lys Arg Gly Gly Gly Ala Ile Ile Asn Phe Gly Ser
130 135 140

Ile Ser Trp His Leu Gly Leu Glu Asp Leu Val Leu Tyr Glu Thr Ala
145 150 155 160

Lys Ala Gly Ile Glu Gly Met Thr Arg Ala Leu Ala Arg Glu Leu Gly
165 170 175

Pro Asp Asp Ile Arg Val Thr Cys Val Val Pro Gly Asn Val Lys Thr
180 185 190

Lys Arg Gln Glu Lys Trp Tyr Thr Pro Glu Gly Glu Ala Glu Ile Val
195 200 205

Lys Ala Gln Cys Leu Lys Gly Arg Ile Leu Pro Asp His Val Ala Ser
210 215 220

Leu Val Leu Phe Leu Ala Ser Asp Asp Ala Ser Leu Cys Thr Gly His
225 230 235 240

Glu Tyr Trp Ile Asp Ala Gly Trp Arg
245

<210> SEQ ID NO 31
<211> LENGTH: 289
<212> TYPE: PRT
<213> ORGANISM: Caulobacter crescentus

<400> SEQUENCE: 31

Met Thr Ala Gln Val Thr Cys Val Trp Asp Leu Lys Ala Thr Leu Gly
1 5 10 15

Glu Gly Pro Ile Trp His Gly Asp Thr Leu Trp Phe Val Asp Ile Lys
20 25 30

Gln Arg Lys Ile His Asn Tyr His Pro Ala Thr Gly Glu Arg Phe Ser
35 40 45

Phe Asp Ala Pro Asp Gln Val Thr Phe Leu Ala Pro Ile Val Gly Ala
50 55 60

Thr Gly Phe Val Val Gly Leu Lys Thr Gly Ile His Arg Phe His Pro
65 70 75 80

Ala Thr Gly Phe Ser Leu Leu Leu Glu Val Glu Asp Ala Ala Leu Asn
85 90 95

Asn Arg Pro Asn Asp Ala Thr Val Asp Ala Gln Gly Arg Leu Trp Phe
100 105 110

Gly Thr Met His Asp Gly Glu Glu Asn Asn Ser Gly Ser Leu Tyr Arg
115 120 125

Met Asp Leu Thr Gly Val Ala Arg Met Asp Arg Asp Ile Cys Ile Thr
130 135 140

Asn Gly Pro Cys Val Ser Pro Asp Gly Lys Thr Phe Tyr His Thr Asp
145 150 155 160

Thr Leu Glu Lys Thr Ile Tyr Ala Phe Asp Leu Ala Glu Asp Gly Leu
165 170 175

Leu Ser Asn Lys Arg Val Phe Val Gln Phe Ala Leu Gly Asp Asp Val
180 185 190

Tyr Pro Asp Gly Ser Val Val Asp Ser Glu Gly Tyr Leu Trp Thr Ala
195 200 205

Leu Trp Gly Gly Phe Gly Ala Val Arg Phe Ser Pro Gln Gly Asp Ala
210 215 220

Val Thr Arg Ile Glu Leu Pro Ala Pro Asn Val Thr Lys Pro Cys Phe
225 230 235 240

Gly Gly Pro Asp Leu Lys Thr Leu Tyr Phe Thr Thr Ala Arg Lys Gly
245 250 255

Leu Ser Asp Glu Thr Leu Ala Gln Tyr Pro Leu Ala Gly Gly Val Phe
260 265 270

Ala Val Pro Val Asp Val Ala Gly Gln Pro Gln His Glu Val Arg Leu
275 280 285

Val

<210> SEQ ID NO 32
<211> LENGTH: 289
<212> TYPE: PRT
<213> ORGANISM: Caulobacter segnis

<400> SEQUENCE: 32

Met Thr Ala Glu Val Thr Cys Val Trp Asp Leu Lys Ala Thr Leu Gly
1 5 10 15

Glu Gly Pro Ile Trp His Gly Asp Ala Leu Trp Phe Val Asp Ile Lys
20 25 30

Gln Arg Lys Ile His Asn Tyr Lys Pro Thr Thr Gly Glu His Phe Ser
35 40 45

Phe Asp Ala Pro Asp Gln Val Thr Phe Leu Ala Pro Ile Ala Asp Ala
50 55 60

Gly Gly Phe Val Val Gly Leu Lys Thr Gly Ile His Arg Phe His Pro
65 70 75 80

Ile Thr Gly Phe Arg Leu Leu Ile Glu Val Glu Asp Ser Ala Leu Asp
85 90 95

Asn Arg Pro Asn Asp Ala Thr Val Asp Ala Asn Gly Arg Leu Trp Phe
100 105 110

Gly Thr Met His Asp Gly Glu Glu Ala Lys Ser Gly Ser Leu Tyr Arg
115 120 125

Met Asp Ala Glu Gly Val Ala Arg Met Asp Lys Asp Ile Cys Ile Thr
130 135 140

Asn Gly Pro Cys Val Ser Pro Asp Gly Lys Thr Phe Tyr His Thr Asp
145 150 155 160

Thr Leu Glu Lys Thr Val Trp Ala Tyr Asp Leu Ala Glu Asp Gly Thr
165 170 175

Leu Ser Asn Lys Arg Ala Phe Val His Val Lys Leu Gly Asp Asp Ile
180 185 190

Tyr Pro Asp Gly Thr Val Val Asp Ser Glu Gly Cys Leu Trp Ile Ala
195 200 205

Leu Trp Gly Gly Phe Gly Val Ile Arg Val Ser Pro Ala Gly Glu Ile
210 215 220

Val Gly Arg Ile Glu Val Pro Ala Pro Asn Val Thr Lys Val Cys Phe
225 230 235 240

Gly Gly Pro Asp Leu Lys Thr Leu Phe Leu Thr Thr Ala Arg Lys Gly
245 250 255

Leu Ser Asp Glu Thr Leu Ala Gln Tyr Pro Leu Ala Gly Gly Leu Phe
260 265 270

Ala Ile Gly Val Asn Ile Ala Gly Gln Pro Gln His Glu Val Arg Leu
275 280 285

Val

<210> SEQ ID NO 33
<211> LENGTH: 291
<212> TYPE: PRT
<213> ORGANISM: Caulobacter sp. AP07

<400> SEQUENCE: 33

Met Pro Glu Pro Ile Cys Val Trp Asp Leu Lys Ala Thr Leu Gly Glu
1 5 10 15

Gly Pro Ile Trp Ile Ala Ala Glu Gln Ala Leu Trp Phe Val Asp Ile
20 25 30

Lys Ser His Lys Val His Arg Phe His Pro Glu Ser Gly Glu Thr Lys
35 40 45

Ser Phe Asp Ala Pro Asp Gln Val Thr Phe Leu Ala Pro Arg Ala Gly
50 55 60

Gly Gly Phe Val Ala Gly Leu Lys Ser Gly Leu His His Phe His Pro
65 70 75 80

Glu Thr Gly Phe Ala Tyr Leu Gly Glu Ile Glu Pro Ala Asp Leu Asn
85 90 95

Asn Arg Pro Asn Asp Ala Thr Val Asp Ala Glu Gly Arg Leu Trp Phe
100 105 110

Gly Thr Met His Asp Gly Glu Glu Thr Pro Thr Gly Ala Leu Tyr Arg
115 120 125

```
Leu Gly Ala Asp Gly Gln Pro Val Gln Gln Asp Gln Gly Val Cys Ile
    130                 135                 140

Thr Asn Gly Pro Cys Val Ser Pro Asp Gly Lys Thr Phe Tyr His Thr
145                 150                 155                 160

Asp Thr Leu Glu Lys Val Ile Trp Ala Tyr Asp Leu Gly Ala Asp Gly
                165                 170                 175

Glu Leu Ser Asn Lys Arg Gln Phe Phe Arg Leu Glu Ile Asp Asp Ala
            180                 185                 190

Trp Pro Asp Gly Ser Val Val Asp Ala Glu Gly Tyr Val Trp Ala Ala
        195                 200                 205

Leu Trp Gly Gly His Gly Ala Ile Arg Ile Ser Pro Ala Gly Glu Leu
    210                 215                 220

Val Asp Arg Val Thr Leu Pro Ala Ile Asn Val Thr Lys Pro Cys Phe
225                 230                 235                 240

Gly Gly Pro Asp Leu Lys Thr Leu Tyr Phe Thr Thr Ala Arg Lys Gly
                245                 250                 255

Leu Gly Asp Glu Gln Leu Ala Ala Tyr Pro Leu Cys Gly Gly Val Phe
            260                 265                 270

Ala Leu Pro Val Ala Val Ala Gly Gln Pro Gln Tyr Glu Val Arg Leu
        275                 280                 285

Asp Leu Pro
    290


<210> SEQ ID NO 34
<211> LENGTH: 293
<212> TYPE: PRT
<213> ORGANISM: Caulobacter sp. K31

<400> SEQUENCE: 34

Met Pro Glu Pro Ile Cys Val Trp Asp Leu Lys Ala Thr Leu Gly Glu
1               5                   10                  15

Gly Pro Ile Trp Ser Ala Glu Glu Gln Ala Val Trp Phe Val Asp Ile
            20                  25                  30

Lys Gly His Lys Val His Arg Phe His Pro Ala Ser Gly Ala Thr Ala
        35                  40                  45

Ser Phe Asp Ala Pro Asp Gln Val Thr Phe Leu Ala Pro His Ala Gly
    50                  55                  60

Gly Gly Gly Phe Val Ala Gly Leu Lys Ser Gly Leu His Arg Phe Asp
65                  70                  75                  80

Pro Thr Thr Gly Ala Phe Val Phe Leu Ala Gln Ile Glu Pro Pro Glu
                85                  90                  95

Leu Asn Asn Arg Pro Asn Asp Ala Thr Val Asp Ala Glu Gly Arg Leu
            100                 105                 110

Trp Phe Gly Thr Met His Asp Gly Glu Met Thr Pro Thr Gly Ala Leu
        115                 120                 125

Tyr Arg Leu Ser Ala Asp Gly Lys Pro Ile Gln Gln Asp Glu Gly Val
    130                 135                 140

Cys Ile Thr Asn Gly Pro Cys Ala Ser Pro Asp Gly Lys Thr Phe Tyr
145                 150                 155                 160

His Thr Asp Thr Leu Glu Lys Val Ile Trp Ala Tyr Asp Leu Gly Ala
                165                 170                 175

Asp Gly Ser Leu Ser Asn Lys Arg Glu Phe Phe Arg Leu Glu Ile Ala
            180                 185                 190

Asp Ala Trp Pro Asp Gly Ser Val Val Asp Ser Glu Gly Phe Val Trp
```

```
        195                 200                 205

Thr Ala Leu Trp Gly Gly His Gly Ala Leu Arg Leu Ser Pro Ala Gly
    210                 215                 220

Glu Ile Val Asp Arg Val Ile Leu Pro Ala Ile Asn Val Thr Lys Pro
225                 230                 235                 240

Cys Phe Gly Gly Pro Asp Leu Lys Thr Val Tyr Phe Thr Ser Ala Arg
                245                 250                 255

Lys Gly Leu Ser Asp Glu Gln Leu Ala Ala Tyr Pro Gln Cys Gly Gly
            260                 265                 270

Leu Phe Ala Leu Pro Val Ala Val Ala Gly Gln Pro Gln Tyr Glu Val
        275                 280                 285

Arg Leu Asp Leu Arg
    290


<210> SEQ ID NO 35
<211> LENGTH: 292
<212> TYPE: PRT
<213> ORGANISM: Phenylobacterium zucineum

<400> SEQUENCE: 35

Met Lys Val Leu Ser Glu Pro Asp Cys Val Leu Arg Ala Asp Ala Glu
1               5                   10                  15

Leu Gly Glu Gly Pro Val Trp Arg Ala Asp Asp Asp Ala Val Trp Phe
            20                  25                  30

Val Asp Ile Lys Gly Arg Arg Ile His Arg Tyr Glu Pro Val Thr Gly
        35                  40                  45

Ala Ala Trp Ser Trp Ala Ala Pro Ala Gln Pro Gly Phe Ile Ala Pro
    50                  55                  60

Val Ala Gly Gly Gly Trp Val Ala Gly Leu Lys Thr Gly Leu His Arg
65                  70                  75                  80

Phe Glu Pro Arg Gly Gly Arg Phe Glu Leu Ile Thr Ala Val Glu Asp
                85                  90                  95

Pro Ser Leu Asp Asn Arg Leu Asn Asp Gly Phe Val Asp Ala Lys Gly
            100                 105                 110

Arg Leu Trp Phe Gly Ser Met His Asp Gly Glu Thr Ala Leu Thr Gly
        115                 120                 125

Ala Leu Tyr Arg Leu Asp Glu Arg Gly Leu Gln Arg Cys Asp Thr Gly
    130                 135                 140

Tyr Cys Ile Thr Asn Gly Pro Ala Ala Ser Pro Asp Gly Arg Thr Leu
145                 150                 155                 160

Tyr His Thr Asp Thr Leu Gln Lys Thr Ile Tyr Ala Phe Asp Leu Ser
                165                 170                 175

Pro Ala Gly Glu Leu Ser Asn Lys Arg Val Phe Ala Arg Ile Glu Glu
            180                 185                 190

Gly Gly Gly Tyr Pro Asp Gly Pro Ala Val Asp Ala Glu Gly Cys Val
        195                 200                 205

Trp Thr Gly Leu Phe Ala Gly Trp His Val Arg Arg Tyr Ser Pro Lys
    210                 215                 220

Gly Glu Leu Leu Ala Lys Val Gly Phe Pro Val Ala Asn Ile Thr Lys
225                 230                 235                 240

Leu Ala Phe Gly Gly Asp Asp Leu Thr Ser Val Tyr Ala Thr Thr Ala
                245                 250                 255

Trp Lys Gly Leu Ser Ala Asp Glu Arg Glu Lys Gln Pro Leu Ala Gly
            260                 265                 270
```

```
Gly Leu Phe Arg Phe Glu Val Asp Val Pro Gly Leu Pro Gln Asn Gln
        275                 280                 285

Met Ala His Ala
    290


<210> SEQ ID NO 36
<211> LENGTH: 595
<212> TYPE: PRT
<213> ORGANISM: Caulobacter crescentus

<400> SEQUENCE: 36

Met Arg Ser Ala Leu Ser Asn Arg Thr Pro Arg Arg Phe Arg Ser Arg
1               5                   10                  15

Asp Trp Phe Asp Asn Pro Asp His Ile Asp Met Thr Ala Leu Tyr Leu
            20                  25                  30

Glu Arg Phe Met Asn Tyr Gly Ile Thr Pro Glu Glu Leu Arg Ser Gly
        35                  40                  45

Lys Pro Ile Ile Gly Ile Ala Gln Thr Gly Ser Asp Ile Ser Pro Cys
    50                  55                  60

Asn Arg Ile His Leu Asp Leu Val Gln Arg Val Arg Asp Gly Ile Arg
65                  70                  75                  80

Asp Ala Gly Gly Ile Pro Met Glu Phe Pro Val His Pro Ile Phe Glu
                85                  90                  95

Asn Cys Arg Arg Pro Thr Ala Ala Leu Asp Arg Asn Leu Ser Tyr Leu
            100                 105                 110

Gly Leu Val Glu Thr Leu His Gly Tyr Pro Ile Asp Ala Val Val Leu
        115                 120                 125

Thr Thr Gly Cys Asp Lys Thr Thr Pro Ala Gly Ile Met Ala Ala Thr
    130                 135                 140

Thr Val Asn Ile Pro Ala Ile Val Leu Ser Gly Gly Pro Met Leu Asp
145                 150                 155                 160

Gly Trp His Glu Asn Glu Leu Val Gly Ser Gly Thr Val Ile Trp Arg
                165                 170                 175

Ser Arg Arg Lys Leu Ala Ala Gly Glu Ile Thr Glu Glu Glu Phe Ile
            180                 185                 190

Asp Arg Ala Ala Ser Ser Ala Pro Ser Ala Gly His Cys Asn Thr Met
        195                 200                 205

Gly Thr Ala Ser Thr Met Asn Ala Val Ala Glu Ala Leu Gly Leu Ser
    210                 215                 220

Leu Thr Gly Cys Ala Ala Ile Pro Ala Pro Tyr Arg Glu Arg Gly Gln
225                 230                 235                 240

Met Ala Tyr Lys Thr Gly Gln Arg Ile Val Asp Leu Ala Tyr Asp Asp
                245                 250                 255

Val Lys Pro Leu Asp Ile Leu Thr Lys Gln Ala Phe Glu Asn Ala Ile
            260                 265                 270

Ala Leu Val Ala Ala Ala Gly Gly Ser Thr Asn Ala Gln Pro His Ile
        275                 280                 285

Val Ala Met Ala Arg His Ala Gly Val Glu Ile Thr Ala Asp Asp Trp
    290                 295                 300

Arg Ala Ala Tyr Asp Ile Pro Leu Ile Val Asn Met Gln Pro Ala Gly
305                 310                 315                 320

Lys Tyr Leu Gly Glu Arg Phe His Arg Ala Gly Gly Ala Pro Ala Val
                325                 330                 335

Leu Trp Glu Leu Leu Gln Gln Gly Arg Leu His Gly Asp Val Leu Thr
            340                 345                 350
```

Val Thr Gly Lys Thr Met Ser Glu Asn Leu Gln Gly Arg Glu Thr Ser
355 360 365

Asp Arg Glu Val Ile Phe Pro Tyr His Glu Pro Leu Ala Glu Lys Ala
370 375 380

Gly Phe Leu Val Leu Lys Gly Asn Leu Phe Asp Phe Ala Ile Met Lys
385 390 395 400

Ser Ser Val Ile Gly Glu Glu Phe Arg Lys Arg Tyr Leu Ser Gln Pro
405 410 415

Gly Gln Glu Gly Val Phe Glu Ala Arg Ala Ile Val Phe Asp Gly Ser
420 425 430

Asp Asp Tyr His Lys Arg Ile Asn Asp Pro Ala Leu Glu Ile Asp Glu
435 440 445

Arg Cys Ile Leu Val Ile Arg Gly Ala Gly Pro Ile Gly Trp Pro Gly
450 455 460

Ser Ala Glu Val Val Asn Met Gln Pro Pro Asp His Leu Leu Lys Lys
465 470 475 480

Gly Ile Met Ser Leu Pro Thr Leu Gly Asp Gly Arg Gln Ser Gly Thr
485 490 495

Ala Asp Ser Pro Ser Ile Leu Asn Ala Ser Pro Glu Ser Ala Ile Gly
500 505 510

Gly Gly Leu Ser Trp Leu Arg Thr Gly Asp Thr Ile Arg Ile Asp Leu
515 520 525

Asn Thr Gly Arg Cys Asp Ala Leu Val Asp Glu Ala Thr Ile Ala Ala
530 535 540

Arg Lys Gln Asp Gly Ile Pro Ala Val Pro Ala Thr Met Thr Pro Trp
545 550 555 560

Gln Glu Ile Tyr Arg Ala His Ala Ser Gln Leu Asp Thr Gly Gly Val
565 570 575

Leu Glu Phe Ala Val Lys Tyr Gln Asp Leu Ala Ala Lys Leu Pro Arg
580 585 590

His Asn His
595

<210> SEQ ID NO 37
<211> LENGTH: 597
<212> TYPE: PRT
<213> ORGANISM: Caulobacter sp. K31

<400> SEQUENCE: 37

Met Thr Ser Ala Asn Thr Pro Ser Gly Arg Pro Pro Arg Arg Phe Arg
1 5 10 15

Ser Arg Asp Trp Phe Asp Asn Pro Asp His Ile Asp Met Thr Ala Leu
20 25 30

Tyr Leu Glu Arg Phe Met Asn Tyr Gly Ile Thr Pro Glu Glu Leu Arg
35 40 45

Ser Gly Lys Pro Ile Ile Gly Ile Ala Gln Thr Gly Ser Asp Ile Ser
50 55 60

Pro Cys Asn Arg Ile His Leu Asp Leu Val Thr Arg Ile Arg Asp Gly
65 70 75 80

Ile Arg Asp Ala Gly Gly Ile Pro Met Glu Phe Pro Val His Pro Ile
85 90 95

Phe Glu Asn Cys Arg Arg Pro Thr Ala Ala Leu Asp Arg Asn Leu Ser
100 105 110

Tyr Leu Gly Leu Val Glu Val Leu His Gly Tyr Pro Ile Asp Ala Val

-continued

```
        115                 120                 125

Val Leu Thr Thr Gly Cys Asp Lys Thr Thr Pro Ala Gly Ile Met Ala
    130                 135                 140

Ala Thr Thr Val Asn Ile Pro Ala Ile Val Leu Ser Gly Gly Pro Met
145                 150                 155                 160

Leu Asp Gly Trp His Asp Gly Glu Leu Val Gly Ser Gly Thr Val Ile
                165                 170                 175

Trp Arg Ser Arg Arg Lys Leu Ala Ala Gly Glu Ile Asn Glu Glu Glu
            180                 185                 190

Phe Ile Gln Arg Ala Ser Asp Ser Ala Pro Ser Ala Gly His Cys Asn
        195                 200                 205

Thr Met Gly Thr Ala Ser Thr Met Asn Ala Val Ala Glu Ala Leu Gly
    210                 215                 220

Leu Ser Leu Thr Gly Cys Ala Ala Ile Pro Ala Pro Tyr Arg Glu Arg
225                 230                 235                 240

Gly Gln Met Ala Tyr Lys Thr Gly Gln Arg Ile Val Asp Leu Ala Tyr
                245                 250                 255

Glu Asp Val Lys Pro Leu Asp Ile Leu Thr Lys Lys Ala Phe Glu Asn
            260                 265                 270

Ala Ile Ala Leu Val Ala Ala Ala Gly Gly Ser Thr Asn Ala Gln Pro
        275                 280                 285

His Ile Val Ala Met Ala Arg His Ala Gly Leu Asp Ile Thr Ala Asp
    290                 295                 300

Asp Trp Arg Ala Ala Tyr Asp Ile Pro Leu Ile Leu Asn Met Gln Pro
305                 310                 315                 320

Ala Gly Lys Tyr Leu Gly Glu Arg Phe His Arg Ala Gly Gly Ala Pro
                325                 330                 335

Ala Val Leu Trp Glu Leu Leu Gln Ala Gly Arg Leu His Gly Asp Val
            340                 345                 350

Met Thr Val Thr Gly Lys Thr Met Gly Glu Asn Leu Glu Gly Arg Glu
        355                 360                 365

Thr Lys Asp Arg Glu Val Val Phe Pro Tyr Gly Gln Pro Met Ser Glu
    370                 375                 380

Arg Ala Gly Phe Leu Val Leu Lys Gly Asn Leu Phe Asp Phe Ala Ile
385                 390                 395                 400

Met Lys Thr Ser Val Ile Ser Gln Glu Phe Arg Gln Arg Tyr Leu Ser
                405                 410                 415

Glu Pro Gly Lys Glu Asp Ser Phe Glu Ala Arg Ala Val Val Phe Asp
            420                 425                 430

Gly Ser Asp Asp Tyr His Ala Arg Ile Asn Asp Pro Ser Leu Asn Ile
        435                 440                 445

Asp Glu Arg Thr Ile Leu Val Ile Arg Gly Ala Gly Pro Ile Gly Trp
    450                 455                 460

Pro Gly Ser Ala Glu Val Val Asn Met Gln Pro Pro Asp Ala Leu Leu
465                 470                 475                 480

Lys Arg Gly Ile Met Ser Leu Pro Thr Leu Gly Asp Gly Arg Gln Ser
                485                 490                 495

Gly Thr Ala Asp Ser Pro Ser Ile Leu Asn Ala Ser Pro Glu Ser Ala
            500                 505                 510

Ile Gly Gly Gly Leu Ser Trp Leu Arg Thr Gly Asp Met Ile Arg Ile
        515                 520                 525

Asp Leu Asn Thr Gly Arg Cys Asp Ala Leu Val Asp Glu Ala Thr Ile
    530                 535                 540
```

```
Ala Glu Arg Arg Lys Glu Gly Val Pro Pro Val Pro Ala Thr Met Thr
545                 550                 555                 560

Pro Trp Gln Glu Ile Tyr Arg Ala His Thr Gly Gln Leu Glu Thr Gly
                565                 570                 575

Gly Val Leu Glu Phe Ala Val Lys Tyr Gln Asp Leu Ala Ser Lys Leu
            580                 585                 590

Pro Arg His Asn His
        595


<210> SEQ ID NO 38
<211> LENGTH: 593
<212> TYPE: PRT
<213> ORGANISM: Caulobacter sp. AP07

<400> SEQUENCE: 38

Met Thr Ser Pro Asn Arg Thr Pro Arg Arg Phe Arg Ser Arg Asp Trp
1               5                   10                  15

Phe Asp Asn Pro Asp His Ile Asp Met Thr Ala Leu Tyr Leu Glu Arg
            20                  25                  30

Phe Met Asn Tyr Gly Ile Thr Pro Glu Glu Leu Arg Ser Gly Lys Pro
        35                  40                  45

Ile Ile Gly Ile Ala Gln Thr Gly Ser Asp Ile Ser Pro Cys Asn Arg
    50                  55                  60

Ile His Leu Asp Leu Val Thr Arg Ile Arg Asp Gly Ile Arg Asp Ala
65                  70                  75                  80

Gly Gly Ile Pro Met Glu Phe Pro Val His Pro Ile Phe Glu Asn Cys
                85                  90                  95

Arg Arg Pro Thr Ala Ala Leu Asp Arg Asn Leu Ser Tyr Leu Gly Leu
            100                 105                 110

Val Glu Thr Leu His Gly Tyr Pro Ile Asp Ala Val Val Leu Thr Thr
        115                 120                 125

Gly Cys Asp Lys Thr Thr Pro Ala Gly Ile Met Ala Ala Thr Thr Val
    130                 135                 140

Asn Ile Pro Ala Ile Val Leu Ser Gly Gly Pro Met Leu Asp Gly Trp
145                 150                 155                 160

His Asp Gly Glu Leu Val Gly Ser Gly Thr Val Ile Trp Arg Ser Arg
                165                 170                 175

Arg Lys Leu Ala Ala Gly Glu Ile Thr Glu Glu Glu Phe Ile Gln Arg
            180                 185                 190

Ala Ser Asp Ser Ala Pro Ser Ala Gly His Cys Asn Thr Met Gly Thr
        195                 200                 205

Ala Ser Thr Met Asn Ala Val Ala Glu Ala Leu Gly Leu Ser Leu Thr
    210                 215                 220

Gly Cys Ala Ala Ile Pro Ala Pro Tyr Arg Glu Arg Gly Gln Met Ala
225                 230                 235                 240

Tyr Arg Thr Gly Gln Arg Ile Val Asp Leu Ala Tyr Glu Asp Ile Lys
                245                 250                 255

Pro Lys Asp Ile Leu Thr Lys Gln Ala Phe Glu Asn Ala Ile Ala Leu
            260                 265                 270

Val Ala Ala Ala Gly Gly Ser Thr Asn Ala Gln Pro His Ile Val Ala
        275                 280                 285

Met Ala Arg His Ala Gly Leu Asp Val Thr Ala Asp Asp Trp Arg Ala
    290                 295                 300

Ala Tyr Asp Ile Pro Leu Ile Leu Asn Met Gln Pro Ala Gly Lys Tyr
```

-continued

```
305                 310                 315                 320

Leu Gly Glu Arg Phe His Arg Ala Gly Gly Ala Pro Ala Val Leu Trp
                325                 330                 335

Glu Leu Leu Gln Ala Gly Arg Leu His Gly Asp Ala Met Thr Val Thr
            340                 345                 350

Gly Lys Thr Met Ala Glu Asn Leu Glu Gly Arg Glu Thr Arg Asp Arg
        355                 360                 365

Glu Val Val Phe Pro Tyr Ala Ala Pro Met Ser Glu Arg Ala Gly Phe
    370                 375                 380

Leu Val Leu Lys Gly Asn Leu Phe Asp Phe Ala Ile Met Lys Thr Ser
385                 390                 395                 400

Val Ile Ser Gln Glu Phe Arg Asp Arg Tyr Leu Ser Glu Pro Gly Gln
                405                 410                 415

Glu Gly Ala Phe Glu Ala Arg Ala Val Val Phe Asp Gly Ser Gly Asp
            420                 425                 430

Tyr His Ala Arg Ile Asn Asp Pro Ser Leu Gly Ile Asp Glu Arg Thr
        435                 440                 445

Ile Leu Val Ile Arg Gly Ala Gly Pro Ile Gly Trp Pro Gly Ser Ala
    450                 455                 460

Glu Val Val Asn Met Gln Pro Pro Asp Ala Leu Leu Lys Lys Gly Ile
465                 470                 475                 480

Met Ser Leu Pro Thr Leu Gly Asp Gly Arg Gln Ser Gly Thr Ala Asp
                485                 490                 495

Ser Pro Ser Ile Leu Asn Ala Ser Pro Glu Ser Ala Val Gly Gly Gly
            500                 505                 510

Leu Ser Trp Leu Arg Thr Gly Asp Val Ile Arg Ile Asp Leu Asn Thr
        515                 520                 525

Gly Arg Cys Asp Ala Leu Val Asp Glu Ala Thr Ile Ala Ala Arg Lys
    530                 535                 540

Leu Glu Gly Leu Pro Pro Val Pro Glu Thr Met Thr Pro Trp Gln Glu
545                 550                 555                 560

Ile Tyr Arg Ala His Thr Gly Gln Leu Glu Thr Gly Gly Val Leu Glu
                565                 570                 575

Phe Ala Val Lys Tyr Gln Asp Leu Ala Ala Lys Leu Pro Arg His Asn
            580                 585                 590

His


<210> SEQ ID NO 39
<211> LENGTH: 591
<212> TYPE: PRT
<213> ORGANISM: Caulobacter segnis

<400> SEQUENCE: 39

Met Ser Glu Arg Thr Pro Arg Arg Phe Arg Ser Arg Asp Trp Phe Asp
1               5                   10                  15

Asn Pro Asp His Ile Asp Met Thr Ala Leu Tyr Leu Glu Arg Phe Met
            20                  25                  30

Asn Tyr Gly Ile Thr Pro Glu Glu Leu Arg Ser Gly Lys Pro Ile Ile
        35                  40                  45

Gly Ile Ala Gln Thr Gly Ser Asp Ile Ser Pro Cys Asn Arg Ile His
    50                  55                  60

Leu Asp Leu Val Thr Arg Ile Arg Asp Gly Ile Arg Asp Ala Gly Gly
65                  70                  75                  80

Ile Pro Met Glu Phe Pro Val His Pro Ile Phe Glu Asn Cys Arg Arg
```

-continued

```
                85                  90                  95

Pro Thr Ala Ala Leu Asp Arg Asn Leu Ser Tyr Leu Gly Leu Val Glu
            100                 105                 110

Thr Leu His Gly Tyr Pro Ile Asp Ala Val Val Leu Thr Thr Gly Cys
        115                 120                 125

Asp Lys Thr Thr Pro Ala Gly Ile Met Ala Ala Thr Thr Val Asn Ile
    130                 135                 140

Pro Ala Ile Val Leu Ser Gly Gly Pro Met Leu Asp Gly Trp His Glu
145                 150                 155                 160

Gly Glu Leu Val Gly Ser Gly Thr Val Ile Trp Arg Ser Arg Arg Lys
                165                 170                 175

Leu Ala Ala Gly Glu Ile Thr Glu Glu Glu Phe Ile Asp Arg Ala Ala
            180                 185                 190

Ser Ser Ala Pro Ser Ala Gly His Cys Asn Thr Met Gly Thr Ala Ser
        195                 200                 205

Thr Met Asn Ala Val Ala Glu Ala Leu Gly Leu Ser Leu Thr Gly Cys
    210                 215                 220

Ala Ala Ile Pro Ala Pro Tyr Arg Glu Arg Gly Gln Met Ala Tyr Lys
225                 230                 235                 240

Thr Gly Gln Arg Ile Val Asp Leu Ala Tyr Glu Asp Val Lys Pro Leu
                245                 250                 255

Asp Ile Leu Thr Lys Lys Ala Phe Gln Asn Ala Ile Ala Leu Val Ala
            260                 265                 270

Ala Ala Gly Gly Ser Thr Asn Ala Gln Pro His Ile Val Ala Met Ala
        275                 280                 285

Arg His Ala Gly Val Glu Ile Thr Ala Asp Asp Trp Arg Ala Ala Tyr
    290                 295                 300

Asp Ile Pro Leu Ile Val Asn Met Gln Pro Ala Gly Lys Tyr Leu Gly
305                 310                 315                 320

Glu Arg Phe His Arg Ala Gly Gly Ala Pro Ala Val Leu Trp Glu Leu
                325                 330                 335

Leu Gln Gln Gly Arg Leu His Gly Asp Val Leu Thr Val Thr Gly Lys
            340                 345                 350

Thr Met Gly Glu Asn Leu Gln Gly Arg Glu Thr Ser Asp Arg Glu Val
        355                 360                 365

Ile Phe Pro Tyr His Gln Pro Leu Ala Glu Lys Ala Gly Phe Leu Val
    370                 375                 380

Leu Lys Gly Asn Leu Phe Asp Phe Ala Ile Met Lys Ser Ser Val Ile
385                 390                 395                 400

Gly Glu Glu Phe Arg Lys Arg Tyr Leu Ser Glu Pro Gly Lys Glu Gly
                405                 410                 415

Val Phe Glu Ala Arg Ala Ile Val Phe Asp Gly Ser Asp Asp Tyr His
            420                 425                 430

Lys Arg Ile Asn Asp Pro Ala Leu Glu Ile Asp Glu Arg Cys Ile Leu
        435                 440                 445

Val Ile Arg Gly Ala Gly Pro Ile Gly Trp Pro Gly Ser Ala Glu Val
    450                 455                 460

Val Asn Met Gln Pro Pro Asp His Leu Leu Lys Lys Gly Ile Met Ser
465                 470                 475                 480

Leu Pro Thr Leu Gly Asp Gly Arg Gln Ser Gly Thr Ala Asp Ser Pro
                485                 490                 495

Ser Ile Leu Asn Ala Ser Pro Glu Ser Ala Ile Gly Gly Gly Leu Ser
            500                 505                 510
```

```
Trp Leu Arg Thr Gly Asp Thr Ile Arg Ile Asp Ile Asn Thr Gly Arg
        515                 520                 525

Cys Asp Ala Leu Val Asp Glu Ala Thr Ile Ala Glu Arg Lys Lys Glu
    530                 535                 540

Gly Ile Pro Ala Val Pro Ala Thr Met Thr Pro Trp Gln Glu Ile Tyr
545                 550                 555                 560

Arg Ala His Thr Gly Gln Leu Glu Ser Gly Gly Val Leu Glu Phe Ala
                565                 570                 575

Val Lys Tyr Gln Asp Leu Ala Ser Lys Leu Pro Arg His Asn His
            580                 585                 590


<210> SEQ ID NO 40
<211> LENGTH: 591
<212> TYPE: PRT
<213> ORGANISM: Caulobacter crescentus

<400> SEQUENCE: 40

Met Ser Asn Arg Thr Pro Arg Arg Phe Arg Ser Arg Asp Trp Phe Asp
1               5                   10                  15

Asn Pro Asp His Ile Asp Met Thr Ala Leu Tyr Leu Glu Arg Phe Met
            20                  25                  30

Asn Tyr Gly Ile Thr Pro Glu Glu Leu Arg Ser Gly Lys Pro Ile Ile
        35                  40                  45

Gly Ile Ala Gln Thr Gly Ser Asp Ile Ser Pro Cys Asn Arg Ile His
    50                  55                  60

Leu Asp Leu Val Gln Arg Val Arg Asp Gly Ile Arg Asp Ala Gly Gly
65                  70                  75                  80

Ile Pro Met Glu Phe Pro Val His Pro Ile Phe Glu Asn Cys Arg Arg
                85                  90                  95

Pro Thr Ala Ala Leu Asp Arg Asn Leu Ser Tyr Leu Gly Leu Val Glu
            100                 105                 110

Thr Leu His Gly Tyr Pro Ile Asp Ala Val Val Leu Thr Thr Gly Cys
        115                 120                 125

Asp Lys Thr Thr Pro Ala Gly Ile Met Ala Ala Thr Thr Val Asn Ile
    130                 135                 140

Pro Ala Ile Val Leu Ser Gly Gly Pro Met Leu Asp Gly Trp His Glu
145                 150                 155                 160

Asn Glu Leu Val Gly Ser Gly Thr Val Ile Trp Arg Ser Arg Arg Lys
                165                 170                 175

Leu Ala Ala Gly Glu Ile Thr Glu Glu Glu Phe Ile Asp Arg Ala Ala
            180                 185                 190

Ser Ser Ala Pro Ser Ala Gly His Cys Asn Thr Met Gly Thr Ala Ser
        195                 200                 205

Thr Met Asn Ala Val Ala Glu Ala Leu Gly Leu Ser Leu Thr Gly Cys
    210                 215                 220

Ala Ala Ile Pro Ala Pro Tyr Arg Glu Arg Gly Gln Met Ala Tyr Lys
225                 230                 235                 240

Thr Gly Gln Arg Ile Val Asp Leu Ala Tyr Asp Asp Val Lys Pro Leu
                245                 250                 255

Asp Ile Leu Thr Lys Gln Ala Phe Glu Asn Ala Ile Ala Leu Val Ala
            260                 265                 270

Ala Ala Gly Gly Ser Thr Asn Ala Gln Pro His Ile Val Ala Met Ala
        275                 280                 285

Arg His Ala Gly Val Glu Ile Thr Ala Asp Asp Trp Arg Ala Ala Tyr
```

-continued

```
    290                 295                 300

Asp Ile Pro Leu Ile Val Asn Met Gln Pro Ala Gly Lys Tyr Leu Gly
305                 310                 315                 320

Glu Arg Phe His Arg Ala Gly Gly Ala Pro Ala Val Leu Trp Glu Leu
                325                 330                 335

Leu Gln Gln Gly Arg Leu His Gly Asp Val Leu Thr Val Thr Gly Lys
            340                 345                 350

Thr Met Ser Glu Asn Leu Gln Gly Arg Glu Thr Ser Asp Arg Glu Val
        355                 360                 365

Ile Phe Pro Tyr His Glu Pro Leu Ala Glu Lys Ala Gly Phe Leu Val
    370                 375                 380

Leu Lys Gly Asn Leu Phe Asp Phe Ala Ile Met Lys Ser Ser Val Ile
385                 390                 395                 400

Gly Glu Glu Phe Arg Lys Arg Tyr Leu Ser Gln Pro Gly Gln Glu Gly
                405                 410                 415

Val Phe Glu Ala Arg Ala Ile Val Phe Asp Gly Ser Asp Asp Tyr His
            420                 425                 430

Lys Arg Ile Asn Asp Pro Ala Leu Glu Ile Asp Glu Arg Cys Ile Leu
        435                 440                 445

Val Ile Arg Gly Ala Gly Pro Ile Gly Trp Pro Gly Ser Ala Glu Val
    450                 455                 460

Val Asn Met Gln Pro Pro Asp His Leu Leu Lys Lys Gly Ile Met Ser
465                 470                 475                 480

Leu Pro Thr Leu Gly Asp Gly Arg Gln Ser Gly Thr Ala Asp Ser Pro
                485                 490                 495

Ser Ile Leu Asn Ala Ser Pro Glu Ser Ala Ile Gly Gly Gly Leu Ser
            500                 505                 510

Trp Leu Arg Thr Gly Asp Thr Ile Arg Ile Asp Leu Asn Thr Gly Arg
        515                 520                 525

Cys Asp Ala Leu Val Asp Glu Ala Thr Ile Ala Ala Arg Lys Gln Asp
    530                 535                 540

Gly Ile Pro Ala Val Pro Ala Thr Met Thr Pro Trp Gln Glu Ile Tyr
545                 550                 555                 560

Arg Ala His Ala Ser Gln Leu Asp Thr Gly Gly Val Leu Glu Phe Ala
                565                 570                 575

Val Lys Tyr Gln Asp Leu Ala Ala Lys Leu Pro Arg His Asn His
            580                 585                 590


<210> SEQ ID NO 41
<211> LENGTH: 442
<212> TYPE: PRT
<213> ORGANISM: Caulobacter crescentus

<400> SEQUENCE: 41

Met Val Cys Arg Arg Leu Leu Ala Trp Thr Ala Arg Ala Arg Glu Ala
1               5                   10                  15

Glu Asp Phe Ala Leu Val Arg Gln Pro Thr Cys Arg Pro His Met Leu
            20                  25                  30

Ala Leu Pro Ser Ala Asp Glu Arg Ala Pro Pro Thr Val Ser Ala Leu
        35                  40                  45

Gln Thr Leu Glu Phe Trp Gly Asp Asp Ala Val Gly Val Ser Glu Phe
    50                  55                  60

Leu Pro Glu Asp Trp Lys Ala Ala Thr Leu Leu Gly Arg Ile Asp Phe
65                  70                  75                  80
```

-continued

```
Gly Glu Gly Pro Thr Pro Val Leu Val Arg Gly Gly Arg Val Glu Asp
                85                  90                  95

Val Ser Lys Ile Ala Pro Thr Val Ala Asp Leu Met Asn Ala Phe Gln
            100                 105                 110

Pro Gly Ala Val Ile Pro Arg Gly Glu Asp Lys Gly Pro Leu Glu Ala
        115                 120                 125

Leu Asp Ile Arg Pro Val Trp Glu Asp Pro Asp Gly Ala Ala Pro Val
    130                 135                 140

Lys Leu Leu Ala Pro Val Asp Leu Gln Cys Leu Lys Ala Ala Gly Val
145                 150                 155                 160

Thr Phe Ala Val Ser Thr Leu Glu Arg Val Ile Glu Glu Arg Ala Arg
                165                 170                 175

Gly Asp Ala Gly Glu Ala Leu Lys Ile Arg Thr Leu Leu Ala Glu Arg
            180                 185                 190

Met Gly Gly Asp Leu Lys Ser Val Glu Pro Gly Ser Gln Gly Ala Gln
        195                 200                 205

Arg Leu Lys Asp Ala Leu Ile Ala Asp Gly Leu Trp Ser Gln Tyr Leu
    210                 215                 220

Glu Val Ala Ile Gly Pro Asp Ala Glu Ile Phe Thr Lys Gly Pro Thr
225                 230                 235                 240

Leu Ser Ser Met Gly Trp Gly Asp Gln Val Gly Val Arg Tyr Asp Ser
                245                 250                 255

His Trp Asn Asn Pro Glu Pro Glu Val Val Leu Leu Cys Asp Gly Ser
            260                 265                 270

Gly Leu Ile Arg Gly Ala Ala Leu Gly Asn Asp Val Asn Leu Arg Asp
        275                 280                 285

Phe Glu Gly Arg Ser Ala Leu Leu Leu Ser Lys Ala Lys Asp Asn Asn
    290                 295                 300

Ala Ser Cys Ala Ile Gly Pro Phe Phe Arg Leu Phe Asp Glu Thr Phe
305                 310                 315                 320

Gly Leu Asp Asp Val Arg Ser Ala Glu Val Glu Leu Lys Ile Thr Gly
                325                 330                 335

Arg Asp Asn Phe Val Leu Asp Gly Lys Ser Asn Met Ser Leu Ile Ser
            340                 345                 350

Arg Asp Pro Ala Val Leu Ala Gly Gln Ala Tyr Gly Lys Gln His Gln
        355                 360                 365

Tyr Pro Asp Gly Phe Ala Leu Phe Leu Gly Thr Met Phe Ala Pro Ile
    370                 375                 380

Gln Asp Arg Asp Thr Pro Gly Gln Gly Phe Thr His Lys Val Gly Asp
385                 390                 395                 400

Arg Val Arg Val Ser Thr Pro Lys Leu Gly Val Leu Glu Asn Glu Val
                405                 410                 415

Thr Thr Cys Asp Lys Ala Lys Pro Trp Thr Phe Gly Ile Ser Ala Leu
            420                 425                 430

Ile Arg Asn Leu Ala Gly Arg Gly Leu Leu
        435                 440
```

<210> SEQ ID NO 42
<211> LENGTH: 384
<212> TYPE: PRT
<213> ORGANISM: Caulobacter crescentus

<400> SEQUENCE: 42

```
Met Gly Val Ser Glu Phe Leu Pro Glu Asp Trp Lys Ala Ala Thr Leu
1               5                   10                  15
```

```
Leu Gly Arg Ile Asp Phe Gly Glu Gly Pro Thr Pro Val Leu Val Arg
            20                  25                  30

Gly Gly Arg Val Glu Asp Val Ser Lys Ile Ala Pro Thr Val Ala Asp
        35                  40                  45

Leu Met Asn Ala Phe Gln Pro Gly Ala Val Ile Pro Arg Gly Glu Asp
    50                  55                  60

Lys Gly Pro Leu Glu Ala Leu Asp Ile Arg Pro Val Trp Glu Asp Pro
65                  70                  75                  80

Asp Gly Ala Ala Pro Val Lys Leu Leu Ala Pro Val Asp Leu Gln Cys
                85                  90                  95

Leu Lys Ala Ala Gly Val Thr Phe Ala Val Ser Thr Leu Glu Arg Val
            100                 105                 110

Ile Glu Glu Arg Ala Arg Gly Asp Ala Gly Glu Ala Leu Lys Ile Arg
        115                 120                 125

Thr Leu Leu Ala Glu Arg Met Gly Gly Asp Leu Lys Ser Val Glu Pro
    130                 135                 140

Gly Ser Gln Gly Ala Gln Arg Leu Lys Asp Ala Leu Ile Ala Asp Gly
145                 150                 155                 160

Leu Trp Ser Gln Tyr Leu Glu Val Ala Ile Gly Pro Asp Ala Glu Ile
                165                 170                 175

Phe Thr Lys Gly Pro Thr Leu Ser Ser Met Gly Trp Gly Asp Gln Val
            180                 185                 190

Gly Val Arg Tyr Asp Ser His Trp Asn Asn Pro Glu Pro Glu Val Val
        195                 200                 205

Leu Leu Cys Asp Gly Ser Gly Leu Ile Arg Gly Ala Ala Leu Gly Asn
    210                 215                 220

Asp Val Asn Leu Arg Asp Phe Glu Gly Arg Ser Ala Leu Leu Leu Ser
225                 230                 235                 240

Lys Ala Lys Asp Asn Asn Ala Ser Cys Ala Ile Gly Pro Phe Phe Arg
                245                 250                 255

Leu Phe Asp Glu Thr Phe Gly Leu Asp Asp Val Arg Ser Ala Glu Val
            260                 265                 270

Glu Leu Lys Ile Thr Gly Arg Asp Asn Phe Val Leu Asp Gly Lys Ser
        275                 280                 285

Asn Met Ser Leu Ile Ser Arg Asp Pro Ala Val Leu Ala Gly Gln Ala
    290                 295                 300

Tyr Gly Lys Gln His Gln Tyr Pro Asp Gly Phe Ala Leu Phe Leu Gly
305                 310                 315                 320

Thr Met Phe Ala Pro Ile Gln Asp Arg Asp Thr Pro Gly Gln Gly Phe
                325                 330                 335

Thr His Lys Val Gly Asp Arg Val Arg Val Ser Thr Pro Lys Leu Gly
            340                 345                 350

Val Leu Glu Asn Glu Val Thr Thr Cys Asp Lys Ala Lys Pro Trp Thr
        355                 360                 365

Phe Gly Ile Ser Ala Leu Ile Arg Asn Leu Ala Gly Arg Gly Leu Leu
    370                 375                 380
```

<210> SEQ ID NO 43
<211> LENGTH: 384
<212> TYPE: PRT
<213> ORGANISM: Caulobacter segnis

<400> SEQUENCE: 43

```
Met Gly Val Ser Glu Phe Leu Pro Asp Asp Trp Lys Asn Ala Thr Leu
```

-continued

```
1               5                   10                  15

Leu Gly Arg Ile Asp Phe Gly Glu Gly Pro Thr Pro Val Leu Val Arg
            20                  25                  30

Gly Gly Arg Val Glu Asp Met Ser Lys Val Ala Pro Thr Val Ala Asp
        35                  40                  45

Leu Met Asn Ala Phe Gly Pro Gly Ala Ala Ile Pro Arg Gly Glu Asp
    50                  55                  60

Lys Gly Pro Leu Glu Ser Leu Asp Ile Arg Pro Val Trp Glu Asp Pro
65                  70                  75                  80

Asp Gly Ala Ala Pro Val Lys Leu Leu Ala Pro Val Asp Leu Gln Cys
                85                  90                  95

Leu Lys Ala Ala Gly Val Thr Phe Ala Val Ser Thr Leu Glu Arg Val
            100                 105                 110

Ile Glu Glu Arg Ala Arg Gly Asp Ala Ala Ala Ala Leu Lys Ile Arg
        115                 120                 125

Glu Gln Leu Ser Ala Ser Met Gly Gly Asp Leu Arg Ser Val Asn Pro
    130                 135                 140

Gly Ser Glu Gly Ala Glu Arg Leu Lys Gln Thr Leu Ile Lys Asp Gly
145                 150                 155                 160

Leu Trp Ser Gln Tyr Leu Glu Val Ala Ile Gly Pro Asp Ala Glu Ile
                165                 170                 175

Phe Thr Lys Gly Pro Thr Leu Ser Ser Met Gly Trp Gly Asp His Val
            180                 185                 190

Gly Val Arg Tyr Asp Ser His Trp Asn Asn Pro Glu Pro Glu Val Val
        195                 200                 205

Leu Leu Cys Asp Gly Ala Gly Gln Ile Arg Gly Ala Ser Leu Gly Asn
    210                 215                 220

Asp Val Asn Leu Arg Asp Phe Glu Gly Arg Ser Ala Leu Leu Leu Ser
225                 230                 235                 240

Lys Ala Lys Asp Asn Asn Ala Ser Cys Ala Ile Gly Pro Phe Phe Arg
                245                 250                 255

Leu Phe Asp Glu Thr Phe Ala Leu Asp Asp Val Arg Ser Ala Glu Val
            260                 265                 270

Glu Leu Lys Ile Thr Gly Arg Asp Asn Phe Val Leu Asp Gly Lys Ser
        275                 280                 285

Asn Met Ser Leu Ile Ser Arg Asp Pro Ala Val Leu Ala Gly Gln Ala
    290                 295                 300

Tyr Gly Lys Gln His Gln Tyr Pro Asp Gly Phe Ala Leu Phe Leu Gly
305                 310                 315                 320

Thr Met Phe Ala Pro Ile Gln Asp Arg Asp Thr Pro Gly Gln Gly Phe
                325                 330                 335

Thr His Lys Val Gly Asp Arg Val Arg Val Ser Thr Pro Lys Leu Gly
            340                 345                 350

Val Leu Glu Asn Glu Val Thr Thr Cys Asp Lys Ala Lys Pro Trp Thr
        355                 360                 365

Phe Gly Ile Ser Ala Leu Ile Arg Asn Leu Ala Gly Arg Gly Leu Leu
    370                 375                 380
```

<210> SEQ ID NO 44
<211> LENGTH: 383
<212> TYPE: PRT
<213> ORGANISM: Caulobacter sp. K31

<400> SEQUENCE: 44

-continued

```
Met Ala Leu Ser Asp Phe Leu Pro Asp Asp Trp Arg Asp Ala Thr Leu
1               5                   10                  15

Leu Gly Arg Ile Asp Phe Gly Gln Gly Pro Thr Pro Val Leu Ile Arg
            20                  25                  30

Gly Gly Arg Ile Glu Asp Val Ser Lys Ile Ala Pro Thr Thr Ser Asp
        35                  40                  45

Leu Met Asn Ala Phe Ala Pro Gly Ala Ala Ile Pro Arg Gly Glu Asp
    50                  55                  60

Leu Gly Pro Leu Glu Ala Leu Asp Val Arg Ala Val Trp Glu Asn Pro
65                  70                  75                  80

Gln Gly Ala Ala Ala Lys Leu Leu Ala Pro Val Asp Leu Gln Val Leu
                85                  90                  95

Lys Ala Ala Gly Val Thr Phe Ala Val Ser Thr Leu Glu Arg Val Ile
            100                 105                 110

Glu Glu Arg Ala Arg Gly Asp Ala Ala Glu Ala Leu Lys Ile Arg Ala
        115                 120                 125

Gln Leu Ala Asp Ser Met Gly Gly Asp Leu Arg Ser Val Asn Pro Gly
    130                 135                 140

Ser Asp Gly Ala Glu Arg Leu Lys Gln Thr Leu Ile Lys Asp Gly Leu
145                 150                 155                 160

Trp Ser Gln Tyr Leu Glu Val Ala Ile Gly Pro Asp Ala Glu Ile Phe
                165                 170                 175

Thr Lys Gly Pro Thr Leu Ser Ser Met Gly Trp Gly Asp His Val Gly
            180                 185                 190

Val Arg Ser Asp Ser His Trp Asn Asn Pro Glu Pro Glu Val Val Leu
        195                 200                 205

Leu Cys Asp Gly Ser Gly Gln Ile Arg Gly Ala Ala Leu Gly Asn Asp
    210                 215                 220

Val Asn Leu Arg Asp Phe Glu Gly Arg Ser Ala Leu Leu Leu Ser Lys
225                 230                 235                 240

Ala Lys Asp Asn Asn Ala Ser Cys Ala Ile Gly Pro Phe Phe Arg Leu
                245                 250                 255

Phe Asp Asp Gly Phe Ser Leu Asp Asp Val Arg Ser Ala Glu Val Thr
            260                 265                 270

Leu Lys Ile Thr Gly Arg Asp Asn Phe Val Leu Asp Gly His Ser Asn
        275                 280                 285

Met Ser Leu Ile Ser Arg Asp Pro Ala Val Leu Ala Gly Gln Ala Phe
    290                 295                 300

Gly Lys Gln His Gln Tyr Pro Asp Gly Phe Ala Leu Phe Leu Gly Thr
305                 310                 315                 320

Met Phe Ala Pro Ile Gln Asp Arg Asp Ala Ala Gly Gln Gly Phe Thr
                325                 330                 335

His Lys Val Gly Asp Arg Val Arg Val Ala Thr Pro Lys Leu Gly Val
            340                 345                 350

Leu Glu Asn Glu Val Thr Thr Cys Asp Leu Ala Ala Pro Trp Thr Phe
        355                 360                 365

Gly Val Ser Ala Leu Ile Arg Asn Leu Ala Gly Arg Gly Leu Leu
    370                 375                 380
```

<210> SEQ ID NO 45
<211> LENGTH: 383
<212> TYPE: PRT
<213> ORGANISM: Caulobacter sp. AP07

<400> SEQUENCE: 45

```
Met Ala Leu Ser Asp Phe Leu Pro Asp Asp Trp Arg Asp Ala Thr Leu
1               5                   10                  15

Leu Gly Arg Val Asp Phe Gly Asp Gly Pro Thr Pro Val Leu Val Arg
            20                  25                  30

Gly Gly Arg Ile Glu Asp Val Ser Arg Ile Ala Pro Thr Thr Ser Asp
        35                  40                  45

Leu Met Asn Ala Phe Ala Pro Gly Ala Ala Ile Pro Ala Gly Ala Asp
    50                  55                  60

Leu Gly Pro Leu Glu Ala Leu Asp Val Arg Pro Val Trp Glu Asn Pro
65                  70                  75                  80

Asp Gly Ala Ala Ala Lys Leu Leu Ala Pro Val Asp Leu Gln Val Leu
                85                  90                  95

Lys Ala Ala Gly Val Thr Phe Ala Val Ser Thr Leu Glu Arg Val Ile
            100                 105                 110

Glu Glu Arg Ala Arg Gly Asp Ala Ala Glu Ala Leu Lys Ile Arg Ala
        115                 120                 125

Gln Leu Ala Asp Ser Met Gly Gly Asp Leu Arg Gly Val Asn Pro Gly
    130                 135                 140

Ser Glu Gly Ala Ala Arg Leu Lys Glu Thr Leu Ile Lys Gly Gly Leu
145                 150                 155                 160

Trp Ser Gln Tyr Leu Glu Val Ala Ile Gly Pro Asp Ala Glu Ile Phe
                165                 170                 175

Thr Lys Gly Pro Thr Leu Ser Ser Met Gly Trp Gly Asp Gln Val Gly
            180                 185                 190

Val Arg Ser Asp Ser His Trp Asn Asn Pro Glu Pro Glu Val Val Leu
        195                 200                 205

Leu Cys Asp Gly Ser Gly Arg Ile Arg Gly Ala Ser Leu Gly Asn Asp
    210                 215                 220

Val Asn Leu Arg Asp Phe Glu Gly Arg Ser Ala Leu Leu Leu Ser Lys
225                 230                 235                 240

Ala Lys Asp Asn Asn Ala Ser Cys Ala Ile Gly Pro Phe Phe Arg Leu
                245                 250                 255

Phe Asp Asp Gly Phe Gly Leu Asp Asp Val Arg Ser Ala Glu Val Thr
            260                 265                 270

Leu Lys Ile Thr Gly Arg Asp Asn Phe Val Leu Asp Gly His Ser Asn
        275                 280                 285

Met Ser Leu Ile Ser Arg Asp Pro Ala Val Leu Ala Gly Gln Ala Phe
    290                 295                 300

Gly Lys Gln His Gln Tyr Pro Asp Gly Phe Val Leu Phe Leu Gly Thr
305                 310                 315                 320

Met Phe Ala Pro Ile Gln Asp Arg Asp Thr Ala Gly Gln Gly Phe Thr
                325                 330                 335

His Lys Val Gly Asp Arg Val Arg Val Ala Thr Pro Lys Leu Gly Val
            340                 345                 350

Leu Glu Asn Glu Val Thr Thr Cys Asp Val Ala Pro Pro Trp Thr Phe
        355                 360                 365

Gly Val Ser Ala Leu Ile Arg Asn Leu Ala Gly Arg Gly Leu Leu
    370                 375                 380
```

<210> SEQ ID NO 46
<211> LENGTH: 309
<212> TYPE: PRT
<213> ORGANISM: Burkholderia thailandensis -continued

<400> SEQUENCE: 46

```
Met Asn Ser Val Tyr Thr Leu Gly Leu Val Gly Ile Gly Lys Ile Ala
1               5                   10                  15

Arg Asp Gln His Leu Pro Ala Ile Ala Ala Glu Pro Gly Phe Asp Leu
            20                  25                  30

Leu Ala Cys Ala Ser Arg His Ala Gln Val Arg Gly Val Arg Asn Tyr
        35                  40                  45

Pro Asp Ile Asp Ala Leu Leu Ala Ala Glu Pro Ala Leu Asp Ala Val
    50                  55                  60

Ser Leu Ala Ala Pro Pro Gln Val Arg Tyr Ala Gln Ala Arg Ala Ala
65                  70                  75                  80

Leu Gly Ala Gly Lys His Val Met Leu Glu Lys Pro Pro Gly Ala Thr
                85                  90                  95

Ala Gly Glu Ile Ala Ala Leu Arg Ala Leu Ala Arg Glu Arg Gly Arg
            100                 105                 110

Thr Leu Phe Ala Ala Trp His Ser Arg His Ala Ser Ala Val Glu Pro
        115                 120                 125

Ala Arg Ala Trp Leu Ala Thr Arg Thr Ile Arg Ala Val Gln Ala Arg
    130                 135                 140

Trp Lys Glu Asp Val Arg Arg Trp His Pro Gly Gln Gln Trp Ile Trp
145                 150                 155                 160

Glu Pro Gly Gly Leu Gly Val Phe Asp Pro Gly Ile Asn Ala Leu Ser
                165                 170                 175

Ile Val Thr Arg Ile Leu Pro Arg Glu Leu Val Leu Arg Ala Ala Thr
            180                 185                 190

Leu Val Val Pro Ala Asn Ala His Thr Pro Ile Ala Ala Glu Leu Asp
        195                 200                 205

Cys Val Asp Thr Ala Gly Val Pro Val Arg Ala Glu Phe Asp Trp Arg
    210                 215                 220

His Gly Pro Val Glu Gln Trp Asp Ile Ala Val Asp Thr Asp Gly Gly
225                 230                 235                 240

Val Leu Ser Ile Gly Ala Gly Gly Ala Arg Leu Ser Ile Ala Gly Glu
                245                 250                 255

Pro Val Ala Leu Pro Pro Glu Arg Glu Tyr Pro Ser Leu Tyr Ala Arg
            260                 265                 270

Phe Arg Ala Leu Ile Gly Glu Gly Ala Ser Asp Val Asp Asp Arg Pro
        275                 280                 285

Leu Arg Leu Val Ala Asp Ala Phe Met Ile Gly Arg Arg Ile Ala Ala
    290                 295                 300

Asp Pro Phe Gln Arg
305
```

<210> SEQ ID NO 47
<211> LENGTH: 309
<212> TYPE: PRT
<213> ORGANISM: Burkholderia thailandensis

<400> SEQUENCE: 47

```
Met Asn Ser Val Tyr Thr Leu Gly Leu Val Gly Ile Gly Lys Ile Ala
1               5                   10                  15

Arg Asp Gln His Leu Pro Ala Ile Ala Ala Glu Pro Gly Phe Asp Leu
            20                  25                  30

Leu Ala Cys Ala Ser Arg His Ala Gln Val Arg Gly Val Arg Asn Tyr
        35                  40                  45
```

```
Pro Asp Ile Asp Ala Leu Leu Ala Ala Glu Pro Ala Leu Asp Ala Val
    50                  55                  60

Ser Leu Ala Ala Pro Pro Gln Val Arg Tyr Ala Gln Ala Arg Ala Ala
65                  70                  75                  80

Leu Gly Ala Gly Lys His Val Met Leu Glu Lys Pro Pro Gly Ala Thr
                85                  90                  95

Ala Gly Glu Ile Ala Ala Leu His Ala Leu Ala Arg Glu Arg Gly Arg
            100                 105                 110

Thr Leu Phe Ala Ala Trp His Ser Arg His Ala Ser Ala Val Glu Pro
        115                 120                 125

Ala Arg Ala Trp Leu Ala Thr Arg Thr Ile Arg Ala Val Gln Val Arg
    130                 135                 140

Trp Lys Glu Asp Val Arg Arg Trp His Pro Gly Gln Gln Trp Ile Trp
145                 150                 155                 160

Glu Pro Gly Gly Leu Gly Val Phe Asp Pro Gly Ile Asn Ala Leu Ser
                165                 170                 175

Ile Val Thr Arg Ile Leu Pro Arg Glu Leu Val Leu Arg Ala Ala Thr
            180                 185                 190

Leu Val Val Pro Ala Asn Ala His Thr Pro Ile Ala Ala Glu Leu Asp
        195                 200                 205

Cys Val Asp Thr Ala Gly Val Pro Val Arg Ala Glu Phe Asp Trp Arg
    210                 215                 220

His Gly Pro Val Glu Gln Trp Asp Ile Ala Val Asp Thr Asp Gly Gly
225                 230                 235                 240

Val Leu Ser Ile Gly Ala Gly Gly Ala Arg Leu Ser Ile Ala Gly Glu
                245                 250                 255

Pro Val Ala Leu Pro Pro Glu Arg Glu Tyr Pro Ser Leu Tyr Ala Arg
            260                 265                 270

Phe Arg Ala Leu Ile Gly Glu Gly Ala Ser Asp Val Asp Asp Arg Pro
        275                 280                 285

Leu Arg Leu Val Ala Asp Ala Phe Met Ile Gly Arg Arg Ile Ala Ala
    290                 295                 300

Asp Pro Phe Gln Arg
305
```

<210> SEQ ID NO 48
<211> LENGTH: 309
<212> TYPE: PRT
<213> ORGANISM: Burkholderia ambifaria

<400> SEQUENCE: 48

```
Met Ser Lys Val Ile Ser Leu Gly Val Ile Gly Ile Gly Lys Ile Ala
1               5                   10                  15

Arg Asp Gln His Leu Pro Ala Ile Ala Ala Glu Pro Gly Phe Ala Leu
            20                  25                  30

Thr Ala Cys Ala Ser Arg His Ala Glu Val Asn Gly Val Arg Asn Tyr
        35                  40                  45

Pro Glu Leu Gly Ala Leu Leu Ala Ala Glu Pro Glu Leu Glu Ala Val
    50                  55                  60

Ser Leu Cys Ala Pro Pro Gln Val Arg Tyr Ala Gln Ala Arg Ala Ala
65                  70                  75                  80

Leu Glu Ala Gly Lys His Val Met Leu Glu Lys Pro Pro Gly Ala Thr
                85                  90                  95

Leu Gly Glu Val Ala Ala Leu Asp Ala Leu Ala Arg Glu Arg Gly Leu
            100                 105                 110
```

Thr Leu Phe Ala Thr Trp His Ser Arg Cys Ala Ser Ala Val Glu Pro
115 120 125

Ala Arg Ala Trp Leu Ala Thr Arg Thr Ile Arg Ala Val Gln Val Arg
130 135 140

Trp Lys Glu Asp Val Arg Arg Trp His Pro Gly Gln Gln Trp Ile Trp
145 150 155 160

Glu Pro Gly Gly Leu Gly Val Phe Asp Pro Gly Ile Asn Ala Leu Ser
165 170 175

Ile Val Thr Arg Ile Leu Pro Arg Glu Leu Val Leu Arg Glu Ala Thr
180 185 190

Leu Tyr Val Pro Ser Asp Val Gln Thr Pro Ile Ala Ala Glu Leu Asp
195 200 205

Cys Ala Asp Thr Asp Gly Val Pro Val His Ala Glu Phe Asp Trp Arg
210 215 220

His Gly Pro Val Glu Gln Trp Glu Ile Ala Val Asp Thr Ser Asp Gly
225 230 235 240

Val Leu Ala Ile Ser Arg Gly Gly Ala Gln Leu Ser Ile Gly Gly Glu
245 250 255

Pro Val Glu Ile Gly Pro Gln Arg Glu Tyr Pro Ala Leu Tyr Ala His
260 265 270

Phe Arg Ala Leu Ile Ala Arg Gly Glu Ser Asp Val Asp Val Arg Pro
275 280 285

Leu Arg Leu Val Ala Asp Ala Phe Leu Phe Gly Arg Arg Val Gly Thr
290 295 300

Asp Ala Phe Gly Arg
305

<210> SEQ ID NO 49
<211> LENGTH: 309
<212> TYPE: PRT
<213> ORGANISM: Burkholderia ambifaria

<400> SEQUENCE: 49

Met Ser Lys Val Ile Ser Leu Gly Val Ile Gly Ile Gly Lys Ile Ala
1 5 10 15

Arg Asp Gln His Leu Pro Ala Ile Ala Ala Glu Pro Gly Phe Ala Leu
20 25 30

Thr Ala Cys Ala Ser Arg His Ala Glu Val Asn Gly Val Arg Asn Tyr
35 40 45

Pro Glu Leu Gly Ala Leu Leu Ala Ala Glu Pro Glu Leu Glu Ala Val
50 55 60

Ser Leu Cys Ala Pro Pro Gln Val Arg Tyr Ala Gln Ala Arg Ala Ala
65 70 75 80

Leu Glu Ala Gly Lys His Val Met Leu Glu Lys Pro Pro Gly Ala Thr
85 90 95

Leu Gly Glu Val Ala Ala Leu Asp Ala Leu Ala Arg Glu Arg Gly Leu
100 105 110

Thr Leu Phe Ala Thr Trp His Ser Arg Cys Ala Ser Ala Val Glu Pro
115 120 125

Ala Arg Ala Trp Leu Ala Thr Arg Thr Ile Arg Ala Val Gln Val Arg
130 135 140

Trp Lys Glu Asp Val Arg Arg Trp His Pro Gly Gln Gln Trp Ile Trp
145 150 155 160

Glu Pro Gly Gly Leu Gly Val Phe Asp Pro Gly Ile Asn Ala Leu Ser

-continued

```
                165                 170                 175

Ile Val Thr Arg Ile Leu Pro Arg Glu Leu Val Leu Arg Glu Ala Thr
            180                 185                 190

Leu Tyr Val Pro Ser Asp Val Gln Thr Pro Ile Ala Ala Glu Leu Asp
        195                 200                 205

Cys Ala Asp Thr Asp Gly Val Pro Val His Ala Glu Phe Asp Trp Arg
    210                 215                 220

His Gly Pro Val Glu Gln Trp Glu Ile Ala Val Asp Thr Ser Asp Gly
225                 230                 235                 240

Val Leu Ala Ile Ser Arg Gly Gly Ala Gln Leu Ser Ile Ala Gly Glu
                245                 250                 255

Pro Val Glu Ile Gly Pro Gln Arg Glu Tyr Pro Ala Leu Tyr Ala His
            260                 265                 270

Phe Arg Ala Leu Ile Ala Arg Gly Glu Ser Asp Val Asp Val Arg Pro
        275                 280                 285

Leu Arg Leu Val Ala Asp Ala Phe Leu Phe Gly Arg Arg Val Gly Thr
    290                 295                 300

Asp Ala Phe Gly Arg
305


<210> SEQ ID NO 50
<211> LENGTH: 309
<212> TYPE: PRT
<213> ORGANISM: Burkholderia thailandensis

<400> SEQUENCE: 50

Met Asn Thr Val Tyr Thr Leu Gly Leu Val Gly Ile Gly Lys Ile Ala
1               5                   10                  15

Arg Asp Gln His Leu Pro Ala Ile Ala Ala Glu Pro Gly Phe Asp Leu
            20                  25                  30

Arg Ala Cys Ala Ser Arg His Ala Glu Val Arg Gly Val Arg Asn His
        35                  40                  45

Pro Asp Ile Gly Ala Leu Leu Ala Ala Glu Pro Ala Leu Asp Ala Val
    50                  55                  60

Ser Leu Ala Ala Pro Pro Gln Val Arg Tyr Ala Gln Ala Arg Ala Ala
65                  70                  75                  80

Leu Asp Ala Gly Lys His Val Met Leu Glu Lys Pro Pro Gly Ala Thr
                85                  90                  95

Val Gly Glu Ile Ala Ala Leu Arg Ala Leu Ala Arg Glu Arg Gly Arg
            100                 105                 110

Thr Leu Phe Ala Ser Trp His Ser Arg His Ala Arg Ala Val Glu Pro
        115                 120                 125

Ala Arg Ala Trp Leu Ala Thr Arg Thr Ile Arg Ala Val Gln Val Arg
    130                 135                 140

Trp Lys Glu Asp Val Arg Arg Trp His Pro Gly Gln Gln Trp Ile Trp
145                 150                 155                 160

Glu Pro Gly Gly Leu Gly Val Phe Asp Pro Gly Ile Asn Ala Leu Ser
                165                 170                 175

Ile Val Thr Arg Ile Leu Pro Arg Glu Leu Val Leu Arg Ala Ala Thr
            180                 185                 190

Leu Val Val Pro Ala Asn Val His Thr Pro Ile Ala Ala Glu Phe Asp
        195                 200                 205

Cys Val Asp Thr Ala Gly Val Pro Val Arg Ala Glu Phe Asp Trp Arg
    210                 215                 220
```

His Gly Pro Val Glu Gln Trp Asp Ile Ala Val Asp Thr Asp Gly Gly
225 230 235 240

Val Leu Ala Ile Gly Ala Gly Gly Ala Arg Leu Ser Ile Ala Gly Glu
245 250 255

Pro Val Ala Leu Pro Pro Glu Cys Glu Tyr Pro Ser Leu Tyr Ala Arg
260 265 270

Phe His Ala Leu Ile Ala Ala Arg Glu Ser Asp Val Asp Asp Arg Pro
275 280 285

Leu Arg Leu Val Ala Asp Ala Phe Met Val Gly Arg Arg Ile Ala Ala
290 295 300

Asp Pro Phe His Arg
305

<210> SEQ ID NO 51
<211> LENGTH: 310
<212> TYPE: PRT
<213> ORGANISM: Burkholderia thailandensis

<400> SEQUENCE: 51

Met Glu Ser Ser Asn Arg Pro Ala Arg Thr Gly Ala Ala Ser Ala Ala
1 5 10 15

Thr Leu Arg Val Asp Cys Arg Asn Ala Leu Gly Glu Gly Ala Thr Trp
20 25 30

Cys Asp Ala Thr Arg Ala Leu Tyr Trp Val Asp Ile Glu Gly Ala Arg
35 40 45

Leu Trp Arg Trp Arg Ala Ala Gly Ala Gln Gly Gly Ala Ala Thr Asp
50 55 60

Ser Trp Glu Met Pro Glu Arg Ile Gly Cys Phe Ala Leu Thr Asp Asp
65 70 75 80

Pro Asp Val Leu Leu Val Gly Leu Ala Ser Arg Leu Ala Phe Phe Asp
85 90 95

Ala Arg Arg Arg Ala Phe Thr Pro Ile Val Asp Val Glu Pro Asp Leu
100 105 110

Pro Thr Arg Leu Asn Asp Gly Arg Cys Asp Arg Ala Gly Ala Phe Val
115 120 125

Phe Gly Met Lys Asp Glu Gly Gly Gly Ser Pro Arg Ala Val Gly Gly
130 135 140

Tyr Tyr Arg Leu Asn Pro Asp Leu Ser Leu Gln Arg Leu Ala Leu Pro
145 150 155 160

Leu Ala Ala Ile Ala Asn Gly Ile Thr Phe Ser Pro Asp Gly Ser Ala
165 170 175

Met Tyr Phe Cys Asp Ser Pro Thr Arg Glu Ile Gln Val Cys Asp Tyr
180 185 190

Arg Pro Gly Gly Asp Val Asp Arg Ile Arg Ser Phe Val Arg Leu Ala
195 200 205

Asp Asp Cys Gly Glu Pro Asp Gly Ser Ala Val Asp Ala Asp Gly Gly
210 215 220

Val Trp Asn Ala Gln Trp Gly Gly Ala Arg Ile Val Arg Tyr Asp Ala
225 230 235 240

Gln Gly Val Glu Thr Glu Arg Ile Ala Val Pro Thr Pro Gln Pro Ser
245 250 255

Cys Val Ala Leu Asp Asp Gly Gly Arg Leu Tyr Val Thr Ser Ala Arg
260 265 270

Val Gly Leu Asp Asp Gly Ala Leu Ala Arg Ser Pro Gly Ala Gly Gly
275 280 285

```
Val Phe Val Ala Asp Thr Arg His Ala Gly Leu Ala Thr Ser Arg Phe
    290                 295                 300

Ala Leu Ala Arg Asn Ala
305                 310


<210> SEQ ID NO 52
<211> LENGTH: 310
<212> TYPE: PRT
<213> ORGANISM: Burkholderia thailandensis

<400> SEQUENCE: 52

Met Glu Ser Ser Ser Arg Pro Ala Arg Thr Gly Ala Ala Ser Ala Ala
1               5                   10                  15

Thr Leu Arg Val Asp Cys Arg Asn Ala Leu Gly Glu Gly Ala Thr Trp
            20                  25                  30

Cys Asp Ala Thr Arg Ala Leu Tyr Trp Val Asp Ile Glu Gly Ala Arg
        35                  40                  45

Leu Trp Arg Trp Arg Ala Ala Gly Ala Gln Gly Gly Ala Ala Thr Asp
    50                  55                  60

Ser Trp Glu Met Pro Glu Arg Ile Gly Cys Phe Ala Leu Thr Asp Asp
65                  70                  75                  80

Pro Asp Val Leu Leu Val Gly Leu Ala Ser Arg Leu Ala Phe Phe Asp
                85                  90                  95

Ala Arg Arg Arg Ala Phe Thr Pro Ile Val Asp Val Glu Pro Asp Leu
            100                 105                 110

Pro Thr Arg Leu Asn Asp Gly Arg Cys Asp Arg Ala Gly Ala Phe Val
        115                 120                 125

Phe Gly Met Lys Asp Glu Gly Gly Gly Ser Pro Arg Ala Val Gly Gly
    130                 135                 140

Tyr Tyr Arg Leu Asn Pro Asp Leu Ser Leu Gln Arg Leu Ala Leu Pro
145                 150                 155                 160

Pro Ala Ala Ile Ala Asn Gly Ile Ala Phe Ser Pro Asp Gly Ser Ala
                165                 170                 175

Met Tyr Phe Cys Asp Ser Pro Thr Arg Glu Ile Gln Val Cys Asp Tyr
            180                 185                 190

Arg Pro Gly Gly Asp Val Asp Arg Ile Arg Pro Phe Val Arg Leu Ala
        195                 200                 205

Asp Asp Cys Gly Glu Pro Asp Gly Ser Thr Val Asp Ala Asp Gly Gly
    210                 215                 220

Val Trp Ser Ala Gln Trp Gly Gly Ala Arg Ile Val Arg Tyr Asp Ala
225                 230                 235                 240

Gln Gly Val Glu Thr Glu Arg Ile Ala Val Pro Thr Pro Gln Pro Ser
                245                 250                 255

Cys Val Ala Leu Asp Asp Gly Gly Arg Leu Tyr Val Thr Ser Ala Arg
            260                 265                 270

Val Gly Leu Asp Asp Gly Ala Leu Ala Arg Ser Pro Gly Ala Gly Gly
        275                 280                 285

Val Phe Val Ala Asp Thr Arg His Ala Gly Leu Ala Thr Ser Arg Phe
    290                 295                 300

Ala Leu Ala Arg Asn Ala
305                 310


<210> SEQ ID NO 53
<211> LENGTH: 300
<212> TYPE: PRT
```

<213> ORGANISM: Burkholderia thailandensis

<400> SEQUENCE: 53

Met Glu Ser Ser Asn Arg Pro Ala Arg Thr Gly Ala Ala Ser Ala Ala
1 5 10 15

Thr Leu Arg Val Asp Cys Arg Asn Ala Leu Gly Glu Gly Ala Thr Trp
20 25 30

Cys Asp Ala Thr Arg Ala Leu Tyr Trp Val Asp Ile Glu Gly Ala Arg
35 40 45

Leu Trp Arg Trp Arg Ala Ala Gly Ala Gln Gly Gly Ala Ala Thr Asp
50 55 60

Ser Trp Glu Met Pro Glu Arg Ile Gly Cys Phe Ala Leu Thr Asp Asp
65 70 75 80

Pro Asp Val Leu Leu Val Gly Leu Ala Ser Arg Leu Ala Phe Phe Asp
85 90 95

Ala Arg Arg Arg Ala Phe Thr Pro Ile Val Asp Val Glu Pro Asp Leu
100 105 110

Pro Thr Arg Leu Asn Asp Gly Arg Cys Asp Arg Ala Gly Ala Phe Val
115 120 125

Phe Gly Met Lys Asp Glu Gly Gly Gly Ser Pro Arg Ala Val Gly Gly
130 135 140

Tyr Tyr Arg Leu Asn Pro Asp Leu Ser Leu Gln Arg Leu Ala Leu Pro
145 150 155 160

Leu Ala Ala Ile Ala Asn Gly Ile Ala Phe Ser Pro Asp Gly Ser Ala
165 170 175

Met Tyr Phe Cys Asp Ser Pro Thr Arg Glu Ile Gln Val Cys Asp Tyr
180 185 190

Arg Pro Gly Gly Asp Val Asp Arg Ile Arg Ser Phe Val Arg Leu Ala
195 200 205

Asp Asp Cys Gly Glu Pro Asp Gly Ser Ala Val Asp Ala Asp Gly Gly
210 215 220

Val Trp Asn Ala Gln Trp Gly Gly Ala Arg Ile Val Arg Tyr Asp Ala
225 230 235 240

Gln Gly Val Glu Thr Glu Arg Ile Ala Val Pro Thr Pro Gln Pro Ser
245 250 255

Cys Val Ala Leu Asp Asp Gly Gly Arg Leu Tyr Val Thr Ser Ala Arg
260 265 270

Val Gly Leu Asp Asp Gly Ala Leu Ala Arg Ser Pro Gly Ala Gly Gly
275 280 285

Val Phe Val Ala Asp Thr Arg His Ala Gly Leu Ala
290 295 300

<210> SEQ ID NO 54
<211> LENGTH: 311
<212> TYPE: PRT
<213> ORGANISM: Burkholderia pseudomallei

<400> SEQUENCE: 54

Met Glu Ser Ser Asn Arg Pro Ala Arg Thr His Glu Ala Ser Ala Ala
1 5 10 15

Thr Leu Leu Val Asp Cys Arg Asn Ala Leu Gly Glu Gly Ala Thr Trp
20 25 30

Cys Asp Ala Ala His Ala Leu Tyr Trp Val Asp Ile Glu Gly Ala Arg
35 40 45

Leu Trp Arg Trp Arg Ala Ala Gly Ala His Gly Gly Glu Arg Cys Asp

-continued

```
    50                  55                  60

Ser Trp Glu Met Pro Glu Arg Ile Ala Cys Phe Ala Leu Thr Gly Asp
65                  70                  75                  80

Pro Asp Val Leu Leu Val Gly Leu Ala Ser Arg Leu Ala Phe Phe Asp
                85                  90                  95

Thr Arg Arg Arg Ala Leu Thr Pro Ile Val Asp Val Glu Pro Asp Arg
            100                 105                 110

Pro Thr Arg Leu Asn Asp Gly Arg Cys Asp Arg Ala Gly Ala Phe Val
        115                 120                 125

Phe Gly Thr Lys Asp Glu Ser Gly Gly Ala Ser Pro Arg Ala Ile Gly
    130                 135                 140

Gly Tyr Tyr Arg Leu Asn Ala Asp Leu Ser Leu Gln Arg Leu Ala Leu
145                 150                 155                 160

Pro Pro Ala Ala Ile Ala Asn Gly Ile Ala Phe Ser Pro Asp Gly Ser
                165                 170                 175

Ala Met Tyr Phe Cys Asp Ser Pro Thr Arg Glu Ile Gln Val Cys Asp
            180                 185                 190

Tyr Arg Pro Gly Gly Asp Val Asp Arg Val Arg Ser Phe Val Arg Leu
        195                 200                 205

Ala Asp Ala His Gly Glu Pro Asp Gly Ser Thr Val Asp Ala Ser Gly
    210                 215                 220

Gly Val Trp Asn Ala Gln Trp Gly Gly Ala Arg Val Val Arg Tyr Asp
225                 230                 235                 240

Ala Gln Gly Val Glu Thr Asp Arg Ile Ala Val Pro Thr Pro Gln Pro
                245                 250                 255

Ser Cys Val Thr Leu Asp Ala Ala Gly Arg Leu Tyr Val Thr Ser Ala
            260                 265                 270

Arg Val Gly Leu Asp Asp Gly Ala Leu Ala Gly Asn Pro Gly Ala Gly
        275                 280                 285

Gly Val Phe Val Ala His Thr Arg His Ser Gly Ser Ala Thr Pro Arg
    290                 295                 300

Phe Ala Leu Ala Arg His Ala
305                 310


<210> SEQ ID NO 55
<211> LENGTH: 311
<212> TYPE: PRT
<213> ORGANISM: Burkholderia pseudomallei

<400> SEQUENCE: 55

Met Glu Ser Ser Asn Arg Pro Ala Arg Thr His Glu Ala Ser Ala Ala
1               5                   10                  15

Thr Leu Leu Val Asp Cys Arg Asn Ala Leu Gly Glu Gly Ala Thr Trp
            20                  25                  30

Cys Asp Ala Ala His Ala Leu Tyr Trp Val Asp Ile Glu Gly Ala Arg
        35                  40                  45

Leu Trp Arg Trp Arg Ala Ala Gly Ala His Gly Gly Glu Arg Cys Asp
    50                  55                  60

Ser Trp Glu Met Pro Glu Arg Ile Ala Cys Phe Ala Leu Thr Gly Asp
65                  70                  75                  80

Pro Asp Val Leu Leu Val Gly Leu Ala Ser Arg Leu Ala Phe Phe Asp
                85                  90                  95

Thr Arg Arg Arg Ala Leu Thr Pro Ile Val Asp Val Glu Pro Asp Arg
            100                 105                 110
```

-continued

```
Pro Thr Arg Leu Asn Asp Gly Arg Cys Asp Arg Ala Gly Ala Phe Val
        115                 120                 125

Phe Gly Thr Lys Asp Glu Ser Gly Gly Ala Ser Pro Arg Ala Ile Gly
    130                 135                 140

Gly Tyr Tyr Arg Leu Asn Ala Asp Leu Ser Leu Gln Arg Leu Ala Leu
145                 150                 155                 160

Pro Pro Ala Ala Ile Ala Asn Gly Ile Ala Phe Ser Pro Asp Gly Ser
                165                 170                 175

Ala Met Tyr Phe Cys Asp Ser Pro Thr Arg Glu Ile Gln Val Cys Asp
            180                 185                 190

Tyr Arg Pro Gly Gly Asp Val Asp Arg Val Arg Ser Phe Val Arg Leu
        195                 200                 205

Ala Asp Glu His Gly Glu Pro Asp Gly Ser Thr Val Asp Ala Ser Gly
    210                 215                 220

Gly Val Trp Asn Ala Gln Trp Gly Gly Ala Arg Val Val Arg Tyr Asp
225                 230                 235                 240

Ala Gln Gly Val Glu Thr Asp Arg Ile Ala Val Pro Thr Pro Gln Pro
                245                 250                 255

Ser Cys Val Thr Leu Asp Ala Ala Gly Arg Leu Tyr Val Thr Ser Ala
            260                 265                 270

Arg Val Gly Leu Asp Asp Gly Ala Leu Ala Gly Asn Pro Gly Ala Gly
        275                 280                 285

Gly Val Phe Val Ala His Thr Arg His Pro Gly Gly Ala Thr Pro Arg
    290                 295                 300

Phe Ala Leu Ala Arg His Ala
305                 310


<210> SEQ ID NO 56
<211> LENGTH: 583
<212> TYPE: PRT
<213> ORGANISM: Burkholderia thailandensis

<400> SEQUENCE: 56

Met Ser Ala Ser Lys Pro Lys Leu Arg Ser Ala Gln Trp Phe Gly Thr
1               5                   10                  15

His Asp Lys Asn Gly Phe Met Tyr Arg Ser Trp Met Lys Asn Gln Gly
            20                  25                  30

Ile Pro Asp His Glu Phe Asp Gly Arg Pro Ile Val Gly Ile Cys Asn
        35                  40                  45

Thr Trp Ser Glu Leu Thr Pro Cys Asn Ala His Phe Arg Lys Leu Ala
    50                  55                  60

Glu His Val Lys Arg Gly Val Tyr Glu Ala Gly Gly Phe Pro Val Glu
65                  70                  75                  80

Phe Pro Val Phe Ser Asn Gly Glu Ser Asn Leu Arg Pro Ser Ala Met
                85                  90                  95

Leu Thr Arg Asn Leu Ala Ser Met Asp Val Glu Glu Ala Ile Arg Gly
            100                 105                 110

Asn Pro Ile Asp Ala Val Val Leu Leu Ala Gly Cys Asp Lys Thr Thr
        115                 120                 125

Pro Ala Leu Leu Met Gly Ala Ala Ser Cys Asp Val Pro Ala Ile Val
    130                 135                 140

Val Ser Gly Gly Pro Met Leu Asn Gly Lys Leu Asp Gly Lys Asn Ile
145                 150                 155                 160

Gly Ser Gly Thr Ala Val Trp Gln Leu His Glu Ala Leu Lys Ala Gly
                165                 170                 175
```

-continued

```
Glu Ile Asp Leu His Arg Phe Leu Ser Ala Glu Ala Gly Met Ser Arg
            180                 185                 190

Ser Ala Gly Thr Cys Asn Thr Met Gly Thr Ala Ser Thr Met Ala Cys
        195                 200                 205

Leu Ala Glu Ala Leu Gly Val Ala Leu Pro His Asn Ala Ala Ile Pro
    210                 215                 220

Ala Val Asp Ala Arg Arg Tyr Val Leu Ala His Met Ser Gly Met Arg
225                 230                 235                 240

Ile Val Gly Met Ala His Glu Gly Leu Val Leu Ser Lys Ile Leu Thr
                245                 250                 255

Arg Ala Ala Phe Glu Asn Ala Ile Arg Val Asn Ala Ala Ile Gly Gly
            260                 265                 270

Ser Thr Asn Ala Val Ile His Leu Lys Ala Ile Ala Gly Arg Leu Gly
        275                 280                 285

Val Pro Leu Glu Leu Glu Asp Trp Leu Arg Leu Gly Arg Gly Thr Pro
    290                 295                 300

Thr Ile Val Asp Leu Met Pro Ser Gly Arg Phe Leu Met Glu Glu Phe
305                 310                 315                 320

Tyr Tyr Ala Gly Gly Leu Pro Ala Val Leu Arg Arg Leu Gly Glu Ala
                325                 330                 335

Asn Leu Leu Pro His Pro Gly Ala Leu Thr Val Asn Gly Gln Ser Leu
            340                 345                 350

Trp Asp Asn Val Arg Asp Ala Pro Ser His Asp Asp Glu Val Ile Arg
        355                 360                 365

Pro Leu Asp Arg Pro Leu Ile Ala Asp Gly Gly Ile Arg Ile Leu Arg
    370                 375                 380

Gly Asn Leu Ala Pro Arg Gly Ala Val Leu Lys Pro Ser Ala Ala Ser
385                 390                 395                 400

Pro Glu Leu Leu Lys His Arg Gly Arg Ala Val Val Phe Glu Asn Phe
                405                 410                 415

Glu His Tyr Lys Ala Thr Ile Asp Asp Glu Ala Leu Asp Val Asp Ala
            420                 425                 430

Asn Ser Val Leu Val Leu Lys Asn Cys Gly Pro Arg Gly Tyr Pro Gly
        435                 440                 445

Met Ala Glu Val Gly Asn Met Gly Leu Pro Pro Lys Leu Leu Arg Gln
    450                 455                 460

Gly Val Lys Asp Met Val Arg Ile Ser Asp Ala Arg Met Ser Gly Thr
465                 470                 475                 480

Ala Tyr Gly Thr Val Val Leu His Val Ala Pro Glu Ala Ala Ala Gly
                485                 490                 495

Gly Pro Leu Ala Ala Val Arg Asn Gly Asp Trp Ile Glu Leu Asp Gly
            500                 505                 510

Glu Ala Gly Thr Leu Thr Leu Asp Val Ser Asp Asp Glu Leu Ala Arg
        515                 520                 525

Arg Leu Ser Asp His Asp Pro Ala Ser Ala Pro Gly Val Ala Glu His
    530                 535                 540

Ala Ala Gly Gly Gly Tyr Ala Arg Leu Tyr Val Asp His Val Leu Gln
545                 550                 555                 560

Ala Asp Glu Gly Cys Asp Leu Asp Phe Leu Val Gly Arg Arg Gly Ala
                565                 570                 575

Ala Val Pro Arg His Ser His
            580
```

<210> SEQ ID NO 57
<211> LENGTH: 583
<212> TYPE: PRT
<213> ORGANISM: Burkholderia thailandensis

<400> SEQUENCE: 57

```
Met Ser Ala Ser Lys Pro Lys Leu Arg Ser Ala Gln Trp Phe Gly Thr
1               5                   10                  15

His Asp Lys Asn Gly Phe Met Tyr Arg Ser Trp Met Lys Asn Gln Gly
            20                  25                  30

Ile Pro Asp His Glu Phe Asp Gly Arg Pro Ile Val Gly Ile Cys Asn
        35                  40                  45

Thr Trp Ser Glu Leu Thr Pro Cys Asn Ala His Phe Arg Lys Leu Ala
    50                  55                  60

Glu His Val Lys Arg Gly Val Tyr Glu Ala Gly Gly Phe Pro Val Glu
65                  70                  75                  80

Phe Pro Val Phe Ser Asn Gly Glu Ser Asn Leu Arg Pro Ser Ala Met
                85                  90                  95

Leu Thr Arg Asn Leu Ala Ser Met Asp Val Glu Glu Ala Ile Arg Gly
            100                 105                 110

Asn Pro Ile Asp Ala Val Val Leu Leu Ala Gly Cys Asp Lys Thr Thr
        115                 120                 125

Pro Ala Leu Leu Met Gly Ala Ala Ser Cys Asp Val Pro Ala Ile Val
    130                 135                 140

Val Ser Gly Gly Pro Met Leu Asn Gly Lys Leu Asp Gly Arg Asn Ile
145                 150                 155                 160

Gly Ser Gly Thr Ala Val Trp Gln Leu His Glu Ala Leu Lys Ala Gly
                165                 170                 175

Glu Ile Asp Leu His Arg Phe Leu Ser Ala Glu Ala Gly Met Ser Arg
            180                 185                 190

Ser Ala Gly Thr Cys Asn Thr Met Gly Thr Ala Ser Thr Met Ala Cys
        195                 200                 205

Leu Ala Glu Ala Leu Gly Val Ala Leu Pro His Asn Ala Ala Ile Pro
    210                 215                 220

Ala Val Asp Ala Arg Arg Tyr Val Leu Ala His Met Ser Gly Met Arg
225                 230                 235                 240

Ile Val Gly Met Ala His Glu Gly Leu Val Leu Ser Lys Ile Leu Thr
                245                 250                 255

Arg Ala Ala Phe Glu Asn Ala Ile Arg Val Asn Ala Ala Ile Gly Gly
            260                 265                 270

Ser Thr Asn Ala Val Ile His Leu Lys Ala Ile Ala Gly Arg Leu Gly
        275                 280                 285

Val Pro Leu Glu Leu Glu Asp Trp Leu Arg Leu Gly Arg Gly Thr Pro
    290                 295                 300

Thr Ile Val Asp Leu Met Pro Ser Gly Arg Phe Leu Met Glu Glu Phe
305                 310                 315                 320

Tyr Tyr Ala Gly Gly Leu Pro Ala Val Leu Arg Arg Leu Gly Glu Ala
                325                 330                 335

Asn Leu Leu Pro His Pro Gly Ala Leu Thr Val Asn Gly Gln Ser Leu
            340                 345                 350

Trp Asp Asn Val Arg Asp Ala Pro Ser His Asp Asp Glu Val Ile Arg
        355                 360                 365

Pro Leu Asp Arg Pro Leu Ile Ala Asp Gly Gly Ile Arg Ile Leu Arg
    370                 375                 380
```

```
Gly Asn Leu Ala Pro Arg Gly Ala Val Leu Lys Pro Ser Ala Ala Ser
385                 390                 395                 400

Pro Glu Leu Leu Lys His Arg Gly Arg Ala Val Val Phe Glu Asn Phe
                405                 410                 415

Glu His Tyr Lys Ala Thr Ile Asp Asp Glu Ala Leu Glu Val Asp Ala
            420                 425                 430

Asn Ser Val Leu Val Leu Lys Asn Cys Gly Pro Arg Gly Tyr Pro Gly
        435                 440                 445

Met Ala Glu Val Gly Asn Met Gly Leu Pro Pro Lys Leu Leu Arg Gln
    450                 455                 460

Gly Val Lys Asp Met Val Arg Ile Ser Asp Ala Arg Met Ser Gly Thr
465                 470                 475                 480

Ala Tyr Gly Thr Val Val Leu His Val Ala Pro Glu Ala Ala Ala Gly
                485                 490                 495

Gly Pro Leu Ala Ala Val Arg Asn Gly Asp Trp Ile Glu Leu Asp Cys
            500                 505                 510

Glu Ala Gly Thr Leu Thr Leu Asp Val Ser Asp Asp Glu Leu Ala Arg
        515                 520                 525

Arg Leu Ser Asp His Asp Pro Ala Ser Ala Pro Gly Val Ala Glu His
    530                 535                 540

Ala Ala Gly Gly Gly Tyr Ala Arg Leu Tyr Val Asp His Val Leu Gln
545                 550                 555                 560

Ala Asp Glu Gly Cys Asp Leu Asp Phe Leu Val Gly Arg Arg Gly Ala
                565                 570                 575

Ala Val Pro Arg His Ser His
            580


<210> SEQ ID NO 58
<211> LENGTH: 583
<212> TYPE: PRT
<213> ORGANISM: Burkholderia multivorans

<400> SEQUENCE: 58

Met Ser Ala Thr Lys Pro Arg Leu Arg Ser Ala Gln Trp Phe Gly Thr
1               5                   10                  15

Asn Asp Lys Asn Gly Phe Met Tyr Arg Ser Trp Met Lys Asn Gln Gly
            20                  25                  30

Ile Pro Asp His Glu Phe Asp Gly Arg Pro Ile Ile Gly Ile Cys Asn
        35                  40                  45

Thr Trp Ser Glu Leu Thr Pro Cys Asn Ala His Phe Arg Lys Leu Ala
    50                  55                  60

Glu His Val Lys Arg Gly Ile Phe Glu Ala Gly Gly Phe Pro Val Glu
65                  70                  75                  80

Phe Pro Val Phe Ser Asn Gly Glu Ser Asn Leu Arg Pro Ser Ala Met
                85                  90                  95

Leu Thr Arg Asn Leu Ala Ser Met Asp Val Glu Glu Ala Ile Arg Gly
            100                 105                 110

Asn Pro Ile Asp Ala Val Val Leu Leu Ala Gly Cys Asp Lys Thr Thr
        115                 120                 125

Pro Ala Leu Leu Met Gly Ala Ala Ser Cys Asp Val Pro Ala Ile Val
    130                 135                 140

Val Ser Gly Gly Pro Met Leu Asn Gly Lys Leu Glu Gly Lys Asn Ile
145                 150                 155                 160

Gly Ser Gly Thr Ala Val Trp Gln Leu His Glu Ala Leu Lys Ala Gly
```

-continued

```
                165                 170                 175

Glu Ile Asp Leu His His Phe Leu Ser Ala Glu Ala Gly Met Ser Arg
            180                 185                 190

Ser Ala Gly Thr Cys Asn Thr Met Gly Thr Ala Ser Thr Met Ala Cys
        195                 200                 205

Met Ala Glu Ala Leu Gly Val Ala Leu Pro His Asn Ala Ala Ile Pro
    210                 215                 220

Ala Val Asp Ser Arg Arg Tyr Val Leu Ala His Met Ser Gly Ile Arg
225                 230                 235                 240

Ile Val Glu Met Ala Leu Glu Gly Leu Val Leu Ser Lys Val Leu Thr
                245                 250                 255

Arg Ala Ala Phe Glu Asn Ala Ile Arg Val Asn Ala Ala Ile Gly Gly
            260                 265                 270

Ser Thr Asn Ala Val Ile His Leu Lys Ala Ile Ala Gly Arg Ile Gly
        275                 280                 285

Val Pro Leu Glu Leu Glu Asp Trp Met Arg Ile Gly Arg Asp Thr Pro
    290                 295                 300

Thr Ile Val Asp Leu Met Pro Ser Gly Arg Phe Leu Met Glu Glu Phe
305                 310                 315                 320

Tyr Tyr Ala Gly Gly Leu Pro Ala Val Leu Arg Arg Leu Gly Glu Gly
                325                 330                 335

Gly Leu Leu Pro His Pro Asp Ala Leu Thr Val Asn Gly Lys Thr Leu
            340                 345                 350

Trp Asp Asn Val Arg Glu Ala Pro Asn Tyr Asp Asp Glu Val Ile Arg
        355                 360                 365

Pro Leu Asp Arg Pro Leu Ile Ala Asp Gly Gly Ile Arg Ile Leu Arg
    370                 375                 380

Gly Asn Leu Ala Pro Arg Gly Ala Val Leu Lys Pro Ser Ala Ala Ser
385                 390                 395                 400

Pro Glu Leu Leu Lys His Arg Gly Arg Ala Val Val Phe Glu Asn Phe
                405                 410                 415

Asp His Tyr Lys Ala Thr Ile Asn Asp Glu Ser Leu Asp Val Asp Ala
            420                 425                 430

Asn Ser Val Leu Val Leu Lys Asn Cys Gly Pro Arg Gly Tyr Pro Gly
        435                 440                 445

Met Ala Glu Val Gly Asn Met Gly Leu Pro Pro Lys Leu Leu Arg Gln
    450                 455                 460

Gly Val Lys Asp Met Val Arg Ile Ser Asp Ala Arg Met Ser Gly Thr
465                 470                 475                 480

Ala Tyr Gly Thr Val Val Leu His Val Ala Pro Glu Ala Ala Ala Gly
                485                 490                 495

Gly Pro Leu Ala Ala Val Arg Asn Gly Asp Trp Ile Glu Leu Asp Cys
            500                 505                 510

Glu Ala Gly Thr Leu His Leu Asp Ile Pro Asp Asp Glu Leu Gln Arg
        515                 520                 525

Arg Leu Ser Asp Val Asp Pro Ala Ala Ala Pro Gly Val Ala Gly Gln
    530                 535                 540

Ala Gly Lys Gly Gly Tyr Ala Arg Leu Tyr Leu Asp His Val Leu Gln
545                 550                 555                 560

Ala Asp Glu Gly Cys Asp Leu Asp Phe Leu Val Gly Thr Arg Gly Ala
                565                 570                 575

Glu Val Pro Ser His Ser His
            580
```

<210> SEQ ID NO 59
<211> LENGTH: 583
<212> TYPE: PRT
<213> ORGANISM: Burkholderia multivorans

<400> SEQUENCE: 59

```
Met Ser Ala Thr Lys Pro Arg Leu Arg Ser Ala Gln Trp Phe Gly Thr
1               5                   10                  15

Asn Asp Lys Asn Gly Phe Met Tyr Arg Ser Trp Met Lys Asn Gln Gly
            20                  25                  30

Ile Pro Asp His Glu Phe Asp Gly Arg Pro Ile Ile Gly Ile Cys Asn
        35                  40                  45

Thr Trp Ser Glu Leu Thr Pro Cys Asn Ala His Phe Arg Lys Leu Ala
    50                  55                  60

Glu His Val Lys Arg Gly Ile Phe Glu Ala Gly Gly Phe Pro Val Glu
65                  70                  75                  80

Phe Pro Val Phe Ser Asn Gly Glu Ser Asn Leu Arg Pro Ser Ala Met
                85                  90                  95

Leu Thr Arg Asn Leu Ala Ser Met Asp Val Glu Glu Ala Ile Arg Gly
            100                 105                 110

Asn Pro Ile Asp Ala Val Val Leu Leu Ala Gly Cys Asp Lys Thr Thr
        115                 120                 125

Pro Ala Leu Leu Met Gly Ala Ala Ser Cys Asp Val Pro Ala Ile Val
    130                 135                 140

Val Ser Gly Gly Pro Met Leu Asn Gly Lys Leu Glu Gly Lys Asn Ile
145                 150                 155                 160

Gly Ser Gly Thr Ala Val Trp Gln Leu His Glu Ala Leu Lys Ala Gly
                165                 170                 175

Glu Ile Asp Leu His His Phe Leu Ser Ala Glu Ala Gly Met Ser Arg
            180                 185                 190

Ser Ala Gly Thr Cys Asn Thr Met Gly Thr Ala Ser Thr Met Ala Cys
        195                 200                 205

Met Ala Glu Ala Leu Gly Val Ala Leu Pro His Asn Ala Ala Ile Pro
    210                 215                 220

Ala Val Asp Ser Arg Arg Tyr Val Leu Ala His Met Ser Gly Ile Arg
225                 230                 235                 240

Ile Val Glu Met Ala Leu Glu Gly Leu Val Leu Ser Lys Val Leu Thr
                245                 250                 255

Arg Ala Ala Phe Glu Asn Ala Ile Arg Val Asn Ala Ala Ile Gly Gly
            260                 265                 270

Ser Thr Asn Ala Val Ile His Leu Lys Ala Ile Ala Gly Arg Ile Gly
        275                 280                 285

Val Pro Leu Glu Leu Glu Asp Trp Met Arg Ile Gly Arg Asp Thr Pro
    290                 295                 300

Thr Ile Val Asp Leu Met Pro Ser Gly Arg Phe Leu Met Glu Glu Phe
305                 310                 315                 320

Tyr Tyr Ala Gly Gly Leu Pro Ala Val Leu Arg Arg Leu Gly Glu Gly
                325                 330                 335

Gly Leu Leu Pro His Pro Asp Ala Leu Thr Val Asn Gly Lys Thr Leu
            340                 345                 350

Trp Asp Asn Val Arg Asp Ala Pro Asn Tyr Asp Asp Glu Val Ile Arg
        355                 360                 365

Pro Leu Asp Arg Pro Leu Ile Ala Asp Gly Gly Ile Arg Ile Leu Arg
```

```
    370                 375                 380

Gly Asn Leu Ala Pro Arg Gly Ala Val Leu Lys Pro Ser Ala Ala Ser
385                 390                 395                 400

Pro Glu Leu Leu Lys His Arg Gly Arg Ala Val Val Phe Glu Asn Phe
                405                 410                 415

Asp His Tyr Lys Ala Thr Ile Asn Asp Glu Ala Leu Asp Val Asp Ala
            420                 425                 430

Asn Ser Val Leu Val Leu Lys Asn Cys Gly Pro Arg Gly Tyr Pro Gly
        435                 440                 445

Met Ala Glu Val Gly Asn Met Gly Leu Pro Pro Lys Leu Leu Arg Gln
    450                 455                 460

Gly Val Lys Asp Met Val Arg Ile Ser Asp Ala Arg Met Ser Gly Thr
465                 470                 475                 480

Ala Tyr Gly Thr Val Val Leu His Val Ala Pro Glu Ala Ala Ala Gly
                485                 490                 495

Gly Pro Leu Ala Ala Val Arg Asn Gly Asp Trp Ile Glu Leu Asp Cys
            500                 505                 510

Glu Ala Gly Thr Leu His Leu Asp Ile Pro Asp Asp Glu Leu Gln Arg
        515                 520                 525

Arg Leu Ser Asp Val Asp Pro Ala Ala Ala Pro Gly Val Ala Gly Gln
    530                 535                 540

Ala Gly Lys Gly Gly Tyr Ala Arg Leu Tyr Leu Asp His Val Leu Gln
545                 550                 555                 560

Ala Asp Glu Gly Cys Asp Leu Asp Phe Leu Val Gly Thr Arg Gly Ala
                565                 570                 575

Glu Val Pro Ser His Ser His
            580


<210> SEQ ID NO 60
<211> LENGTH: 583
<212> TYPE: PRT
<213> ORGANISM: Burkholderia thailandensis

<400> SEQUENCE: 60

Met Ser Ala Ser Lys Pro Lys Leu Arg Ser Ala Gln Trp Phe Gly Thr
1               5                   10                  15

His Asp Lys Asn Gly Phe Met Tyr Arg Ser Trp Met Lys Asn Gln Gly
            20                  25                  30

Ile Pro Asp His Glu Phe Asp Gly Arg Pro Ile Val Gly Ile Cys Asn
        35                  40                  45

Thr Trp Ser Glu Leu Thr Pro Cys Asn Ala His Phe Arg Lys Leu Ala
    50                  55                  60

Glu His Val Lys Arg Gly Val Tyr Glu Ala Gly Gly Phe Pro Val Glu
65                  70                  75                  80

Phe Pro Val Phe Ser Asn Gly Glu Ser Asn Leu Arg Pro Ser Ala Met
                85                  90                  95

Leu Thr Arg Asn Leu Ala Ser Met Asp Val Glu Glu Ala Ile Arg Gly
            100                 105                 110

Asn Pro Ile Asp Ala Val Val Leu Leu Ala Gly Cys Asp Lys Thr Thr
        115                 120                 125

Pro Ala Leu Leu Met Gly Ala Ala Ser Cys Asp Val Pro Ala Ile Val
    130                 135                 140

Val Ser Gly Gly Pro Met Leu Asn Gly Lys Leu Asp Gly Lys Asn Ile
145                 150                 155                 160
```

-continued

```
Gly Ser Gly Thr Ala Val Trp Gln Leu His Glu Ala Leu Lys Ala Gly
                165                 170                 175

Glu Ile Asp Leu His Arg Phe Leu Ser Ala Glu Ala Gly Met Ser Arg
            180                 185                 190

Ser Ala Gly Thr Cys Asn Thr Met Gly Thr Ala Ser Thr Met Ala Cys
        195                 200                 205

Leu Ala Glu Ala Leu Gly Val Ala Leu Pro His Asn Ala Ala Ile Pro
    210                 215                 220

Ala Val Asp Ala Arg Arg Tyr Val Leu Ala His Leu Ser Gly Ala Arg
225                 230                 235                 240

Ile Val Glu Met Ala His Glu Gly Leu Ala Leu Ser Thr Ile Leu Thr
                245                 250                 255

Arg Ala Ala Phe Glu Asn Ala Ile Arg Ala Asn Ala Ala Ile Gly Gly
            260                 265                 270

Ser Thr Asn Ala Val Ile His Leu Lys Ala Ile Ala Gly Arg Leu Gly
        275                 280                 285

Val Pro Leu Glu Leu Glu Asp Trp Met Arg Ile Gly Arg Asp Thr Pro
    290                 295                 300

Thr Ile Val Asp Leu Met Pro Ser Gly Arg Phe Leu Met Glu Glu Phe
305                 310                 315                 320

Tyr Tyr Ala Gly Gly Leu Pro Ala Val Leu Arg Arg Leu Gly Glu Ala
                325                 330                 335

Asn Leu Leu Pro His Pro Gly Ala Leu Thr Val Asn Gly Lys Ser Leu
            340                 345                 350

Trp Glu Asn Val Arg Asp Ala Pro Asn His Asp Asp Glu Val Ile Arg
        355                 360                 365

Pro Leu Ala Arg Pro Leu Ile Ala Asp Gly Gly Ile Arg Val Leu Arg
    370                 375                 380

Gly Asn Leu Ala Pro Arg Gly Ala Val Leu Lys Pro Ser Ala Ala Ser
385                 390                 395                 400

Pro Glu Leu Leu Arg His Arg Gly Arg Ala Val Val Phe Glu Asn Phe
                405                 410                 415

Glu His Tyr Lys Ala Thr Ile Asp Asp Glu Ala Leu Asp Val Asp Ala
            420                 425                 430

Ser Ser Val Leu Val Leu Lys Asn Cys Gly Pro Arg Gly Tyr Pro Gly
        435                 440                 445

Met Ala Glu Val Gly Asn Met Gly Leu Pro Pro Lys Leu Leu Arg Gln
    450                 455                 460

Gly Val Lys Asp Met Val Arg Ile Ser Asp Ala Arg Met Ser Gly Thr
465                 470                 475                 480

Ala Tyr Gly Thr Val Val Leu His Val Ala Pro Glu Ala Ala Ala Gly
                485                 490                 495

Gly Pro Leu Ala Ala Val Arg Asn Gly Asp Trp Ile Ala Leu Asp Cys
            500                 505                 510

Glu Ala Gly Thr Leu Thr Leu Asp Val Ser Asp Asp Glu Leu Ala Arg
        515                 520                 525

Arg Leu Ser Asp Leu Asp Pro Ala Ser Ala Pro Gly Ala Ala Gly Gln
    530                 535                 540

Ala Gly Ser Gly Gly Tyr Ala Arg Leu Tyr Val Asp His Val Leu Gln
545                 550                 555                 560

Ala Asp Glu Gly Cys Asp Leu Asp Phe Leu Val Gly Arg Arg Gly Ala
                565                 570                 575

Ala Val Pro Arg His Ser His
```

580

<210> SEQ ID NO 61
<211> LENGTH: 309
<212> TYPE: PRT
<213> ORGANISM: Burkholderia thailandensis

<400> SEQUENCE: 61

```
Met Asn Thr Ser Arg Ser Pro Arg Tyr Arg Gly Val Phe Pro Val Val
1               5                   10                  15

Pro Thr Thr Phe Ala Glu Ala Gly Glu Leu Asp Leu Pro Ser Gln Lys
            20                  25                  30

Arg Ala Val Asp Phe Met Ile Asp Ala Gly Ser Glu Gly Leu Cys Ile
        35                  40                  45

Leu Ala Asn Phe Ser Glu Gln Phe Ala Leu Ala Asp Asp Glu Arg Asp
    50                  55                  60

Val Leu Thr Arg Thr Ile Leu Glu His Val Ala Gly Arg Val Pro Val
65                  70                  75                  80

Ile Val Thr Thr Thr His Tyr Ser Thr Gln Val Cys Ala Ala Arg Ser
                85                  90                  95

Arg Arg Ala Gln Glu Leu Gly Ala Ala Met Val Met Ala Met Pro Pro
            100                 105                 110

Tyr His Gly Ala Thr Phe Arg Val Pro Asp Thr Gln Ile His Ala Phe
        115                 120                 125

Tyr Ala Arg Leu Ser Asp Ala Leu Asp Ile Pro Ile Met Ile Gln Asp
    130                 135                 140

Ala Pro Ala Ser Gly Thr Val Leu Ser Ala Pro Phe Leu Ala Arg Met
145                 150                 155                 160

Ala Arg Glu Ile Glu Gln Val Ser Tyr Phe Lys Ile Glu Thr Pro Gly
                165                 170                 175

Ala Ala Asn Lys Leu Arg Glu Leu Ile Arg Leu Gly Gly Asp Ala Ile
            180                 185                 190

Glu Gly Pro Trp Asp Gly Glu Glu Ala Ile Thr Leu Leu Ala Asp Leu
        195                 200                 205

Asn Ala Gly Ala Thr Gly Ala Met Thr Gly Gly Ala Tyr Pro Asp Gly
    210                 215                 220

Ile Arg Pro Ile Val Glu Ala His Arg Glu Gly Arg Ala Asp Asp Ala
225                 230                 235                 240

Phe Ala Leu Tyr Gln Arg Trp Leu Pro Leu Ile Asn His Glu Asn Arg
                245                 250                 255

Gln Thr Gly Leu Leu Ala Ala Lys Ala Leu Met Arg Glu Gly Gly Val
            260                 265                 270

Ile Ala Cys Glu Arg Pro Arg His Pro Leu Pro Pro Ile His Pro Asp
        275                 280                 285

Ser Arg Ala Glu Leu Ile Ala Ile Ala Arg Arg Leu Asp Pro Leu Val
    290                 295                 300

Leu Arg Trp Ala Arg
305
```

<210> SEQ ID NO 62
<211> LENGTH: 309
<212> TYPE: PRT
<213> ORGANISM: Burkholderia thailandensis

<400> SEQUENCE: 62

```
Met Asn Thr Ser Arg Ser Pro Arg Tyr Arg Gly Val Phe Pro Val Val
```

-continued 1 5 10 15

Pro Thr Thr Phe Thr Glu Ala Gly Glu Leu Asp Leu Pro Ser Gln Lys
20 25 30

Arg Ala Val Asp Phe Met Ile Asp Ala Gly Ser Glu Gly Leu Cys Ile
35 40 45

Leu Ala Asn Phe Ser Glu Gln Phe Ala Leu Ala Asp Asp Glu Arg Asp
50 55 60

Val Leu Thr Arg Thr Ile Leu Glu His Val Ala Gly Arg Val Pro Val
65 70 75 80

Ile Val Thr Thr Thr His Tyr Ser Thr Gln Val Cys Ala Ala Arg Ser
85 90 95

Arg Arg Ala Gln Glu Leu Gly Ala Ala Met Val Met Ala Met Pro Pro
100 105 110

Tyr His Gly Ala Thr Phe Arg Val Pro Asp Thr Gln Ile His Ala Phe
115 120 125

Tyr Ala Arg Leu Ser Asp Ala Leu Asp Ile Pro Ile Met Ile Gln Asp
130 135 140

Ala Pro Ala Ser Gly Thr Val Leu Ser Ala Pro Phe Leu Ala Arg Met
145 150 155 160

Ala Arg Glu Ile Glu Gln Val Ser Tyr Phe Lys Ile Glu Thr Pro Gly
165 170 175

Ala Ala Asn Lys Leu Arg Glu Leu Ile Arg Leu Gly Gly Asp Ala Ile
180 185 190

Glu Gly Pro Trp Asp Gly Glu Glu Ala Ile Thr Leu Leu Ala Asp Leu
195 200 205

Asn Ala Gly Ala Thr Gly Ala Met Thr Gly Gly Ala Tyr Pro Asp Gly
210 215 220

Ile Arg Pro Ile Val Glu Ala His Arg Glu Gly Arg Ala Asp Asp Ala
225 230 235 240

Phe Ala Leu Tyr Gln Arg Trp Leu Pro Leu Ile Asn His Glu Asn Arg
245 250 255

Gln Thr Gly Leu Leu Ala Ala Lys Ala Leu Met Arg Glu Gly Gly Val
260 265 270

Ile Ala Cys Glu Arg Pro Arg His Pro Leu Pro Pro Ile His Pro Asp
275 280 285

Ser Arg Ala Glu Leu Ile Ala Ile Ala Arg Arg Leu Asp Pro Leu Val
290 295 300

Leu Arg Trp Ala Arg
305

<210> SEQ ID NO 63
<211> LENGTH: 309
<212> TYPE: PRT
<213> ORGANISM: Burkholderia thailandensis

<400> SEQUENCE: 63

Met Asn Thr Ser Arg Ser Pro Arg Tyr Arg Gly Val Phe Pro Val Val
1 5 10 15

Pro Thr Thr Phe Thr Glu Thr Gly Glu Leu Asp Leu Pro Ser Gln Met
20 25 30

Arg Ala Val Asp Phe Met Ile Asp Ala Gly Ser Glu Gly Leu Cys Ile
35 40 45

Leu Ala Asn Phe Ser Glu Gln Phe Ala Leu Ala Asp Asp Glu Arg Asp
50 55 60

Val Leu Thr Arg Thr Ile Leu Glu His Val Ala Gly Arg Val Pro Val
65 70 75 80

Ile Val Thr Thr Thr His Tyr Ser Thr Arg Val Cys Ala Ala Arg Ser
85 90 95

Arg Arg Ala Gln Glu Leu Gly Ala Ala Met Val Met Ala Met Pro Pro
100 105 110

Tyr His Gly Ala Thr Phe Arg Val Pro Asp Thr Gln Ile His Ala Phe
115 120 125

Tyr Ala Arg Leu Ser Asp Ala Leu Asp Ile Pro Ile Met Ile Gln Asp
130 135 140

Ala Pro Ala Ser Gly Thr Val Leu Ser Ala Pro Phe Leu Ala Arg Met
145 150 155 160

Ala Arg Glu Ile Glu Gln Val Ser Tyr Phe Lys Ile Glu Thr Pro Gly
165 170 175

Ala Ala Asn Lys Leu Arg Glu Leu Ile Arg Leu Gly Gly Asp Ala Ile
180 185 190

Glu Gly Pro Trp Asp Gly Glu Glu Ala Ile Thr Leu Leu Ala Asp Leu
195 200 205

Asn Ala Gly Ala Thr Gly Ala Met Thr Gly Gly Ala Tyr Pro Asp Gly
210 215 220

Ile Arg Pro Ile Val Asp Ala His Arg Asp Gly Arg Ala Asp Asp Ala
225 230 235 240

Phe Ala Leu Tyr Gln Arg Trp Leu Pro Leu Ile Asn His Glu Asn Arg
245 250 255

Gln Thr Gly Leu Val Ala Ala Lys Ala Leu Met Arg Glu Gly Gly Val
260 265 270

Ile Ala Cys Glu Arg Pro Arg His Pro Leu Pro Pro Ile His Pro Asp
275 280 285

Ser Arg Ala Glu Leu Ile Glu Ile Ala Arg Arg Leu Asp Pro Leu Val
290 295 300

Leu Arg Trp Ala Arg
305

<210> SEQ ID NO 64
<211> LENGTH: 309
<212> TYPE: PRT
<213> ORGANISM: Burkholderia dolosa

<400> SEQUENCE: 64

Met Thr Ser Ser Arg Thr Pro Arg Tyr Arg Gly Ile Phe Pro Val Val
1 5 10 15

Pro Thr Thr Phe Thr Asp Thr Gly Glu Leu Asp Leu Ala Ser Gln Lys
20 25 30

Arg Ala Val Asp Phe Met Ile Asp Ala Gly Ser Asp Gly Leu Cys Ile
35 40 45

Leu Ala Asn Phe Ser Glu Gln Phe Ala Ile Thr Asp Asp Glu Arg Asp
50 55 60

Val Leu Thr Arg Thr Ile Leu Glu His Val Ala Gly Arg Val Pro Val
65 70 75 80

Ile Val Thr Thr Thr His Tyr Ser Thr Gln Val Cys Ala Ala Arg Ser
85 90 95

Leu Arg Ala Gln Gln Leu Gly Ala Ala Met Val Met Ala Met Pro Pro
100 105 110

Tyr His Gly Ala Thr Phe Arg Val Pro Glu Ala Gln Ile Tyr Asp Phe
115 120 125

Tyr Ala Arg Val Ser Asp Ala Ile Asp Ile Pro Ile Met Ile Gln Asp
130 135 140

Ala Pro Ala Ser Gly Thr Val Leu Ser Ala Pro Leu Leu Ala Arg Met
145 150 155 160

Ala Arg Glu Ile Glu Gln Val Ser Tyr Phe Lys Ile Glu Thr Pro Gly
165 170 175

Ala Ala Asn Lys Leu Arg Glu Leu Ile Arg Leu Gly Gly Asp Ala Val
180 185 190

Glu Gly Pro Trp Asp Gly Glu Glu Ala Ile Thr Leu Leu Ala Asp Leu
195 200 205

Asn Ala Gly Ala Thr Gly Ala Met Thr Gly Gly Ala Tyr Pro Asp Gly
210 215 220

Ile Arg Pro Ile Leu Glu Ala His Arg Glu Gly Arg His Asp Asp Ala
225 230 235 240

Phe Ala His Tyr Gln Arg Trp Leu Pro Leu Ile Asn His Glu Asn Arg
245 250 255

Gln Ser Gly Ile Leu Ser Ala Lys Ala Leu Met Arg Glu Gly Gly Val
260 265 270

Ile Ala Cys Glu Arg Pro Arg His Pro Met Pro Glu Leu His Pro Asp
275 280 285

Thr Arg Ala Glu Leu Ile Ala Ile Ala Arg Arg Leu Asp Pro Leu Val
290 295 300

Leu Arg Trp Ala Arg
305

<210> SEQ ID NO 65
<211> LENGTH: 309
<212> TYPE: PRT
<213> ORGANISM: Burkholderia multivorans

<400> SEQUENCE: 65

Met Thr Ser Ser Arg Thr Pro Arg Tyr Arg Gly Ile Phe Pro Val Val
1 5 10 15

Pro Thr Thr Phe Thr Glu Thr Gly Glu Leu Asp Leu Ala Ser Gln Lys
20 25 30

Arg Ala Val Asp Phe Met Ile Asp Ala Gly Ser Asp Gly Leu Cys Ile
35 40 45

Leu Ala Asn Phe Ser Glu Gln Phe Ala Leu Ala Asp Asp Glu Arg Asp
50 55 60

Val Leu Thr Arg Thr Ile Leu Glu His Val Ala Gly Arg Val Pro Val
65 70 75 80

Ile Val Thr Thr Ser His Tyr Ser Thr Gln Thr Cys Ile Ala Arg Ser
85 90 95

Val Arg Ala Gln Gln Leu Gly Ala Ala Met Val Met Val Met Pro Pro
100 105 110

Tyr His Gly Ala Thr Phe Arg Val Pro Glu Ala Gln Ile His Ala Phe
115 120 125

Tyr Ala Arg Leu Ser Asp Ala Leu Ser Ile Pro Ile Met Ile Gln Asp
130 135 140

Ala Pro Ala Ser Gly Thr Val Leu Ser Ala Pro Phe Leu Ala Gln Leu
145 150 155 160

Ala Arg Glu Ile Glu His Val Ala Tyr Phe Lys Ile Glu Thr Pro Gly
165 170 175

Ala Ala Asn Lys Leu Arg Glu Leu Ile Arg Leu Gly Gly Asp Ala Ile

```
            180                 185                 190

Glu Gly Pro Trp Asp Gly Glu Glu Ala Ile Thr Leu Leu Ala Asp Leu
        195                 200                 205

His Ala Gly Ala Thr Gly Ala Met Thr Gly Gly Ala Tyr Pro Asp Gly
    210                 215                 220

Ile Arg Pro Ile Leu Glu Ala His Arg Glu Gly Arg His Asp Asp Ala
225                 230                 235                 240

Phe Ala Arg Tyr Gln Thr Trp Leu Pro Leu Ile Asn His Glu Asn Arg
                245                 250                 255

Gln Ser Gly Ile Leu Thr Ala Lys Ala Leu Met Arg Glu Gly Gly Val
            260                 265                 270

Ile Ala Cys Glu Ala Pro Arg His Pro Met Pro Ala Leu His Pro Asp
        275                 280                 285

Thr Arg Ala Glu Leu Ile Ala Ile Ala Arg Arg Leu Asp Pro Leu Val
    290                 295                 300

Leu Arg Trp Ala Arg
305


<210> SEQ ID NO 66
<211> LENGTH: 455
<212> TYPE: PRT
<213> ORGANISM: Bacillus subtilis

<400> SEQUENCE: 66

Met Ser Ser Pro Ile Gln Glu Gln Val Gln Lys Glu Lys Arg Ser Asn
1               5                   10                  15

Ile Pro Ser Ile Ser Glu Met Lys Val Ile Pro Val Ala Gly His Asp
            20                  25                  30

Ser Met Leu Leu Asn Leu Ser Gly Ala His Ser Pro Phe Phe Thr Arg
        35                  40                  45

Asn Ile Val Ile Leu Thr Asp Ser Ser Gly Asn Gln Gly Val Gly Glu
    50                  55                  60

Val Pro Gly Gly Glu His Ile Arg Arg Thr Leu Glu Leu Ser Glu Pro
65                  70                  75                  80

Leu Val Val Gly Lys Ser Ile Gly Ala Tyr Gln Ala Ile Leu Gln Thr
                85                  90                  95

Val Arg Lys Gln Phe Gly Asp Gln Asp Arg Gly Gly Arg Gly Asn Gln
            100                 105                 110

Thr Phe Asp Leu Arg Thr Thr Val His Ala Val Thr Ala Leu Glu Ala
        115                 120                 125

Ala Leu Leu Asp Leu Leu Gly Lys Phe Leu Gln Glu Pro Val Ala Ala
    130                 135                 140

Leu Leu Gly Glu Gly Lys Gln Arg Asp Glu Val Lys Met Leu Gly Tyr
145                 150                 155                 160

Leu Phe Tyr Ile Gly Asp Arg Asn Arg Thr Thr Leu Pro Tyr Gln Ser
                165                 170                 175

Asp Glu Gln Ser Asp Cys Ala Trp Phe Arg Leu Arg His Glu Glu Ala
            180                 185                 190

Leu Thr Pro Glu Ala Ile Val Arg Leu Ala Glu Ser Ala Gln Glu Arg
        195                 200                 205

Tyr Gly Phe Gln Asp Phe Lys Leu Lys Gly Gly Val Leu Arg Gly Glu
    210                 215                 220

Glu Glu Ile Glu Ala Val Thr Ala Leu Ser Lys Arg Phe Pro Glu Ala
225                 230                 235                 240
```

```
Arg Ile Thr Leu Asp Pro Asn Gly Ala Trp Ser Leu Glu Glu Ala Ile
                245                 250                 255

Ala Leu Cys Lys Gly Lys Gln Asp Val Leu Ala Tyr Ala Glu Asp Pro
            260                 265                 270

Cys Gly Asp Glu Asn Gly Tyr Ser Ala Arg Glu Val Met Ala Glu Phe
        275                 280                 285

Arg Arg Ala Thr Gly Leu Pro Thr Ala Thr Asn Met Ile Ala Thr Asp
    290                 295                 300

Trp Arg Glu Met Gly His Ala Ile Gln Leu His Ala Val Asp Ile Pro
305                 310                 315                 320

Leu Ala Asp Pro His Phe Trp Thr Met Gln Gly Ser Val Arg Val Ala
                325                 330                 335

Gln Met Cys His Asp Trp Gly Leu Thr Trp Gly Ser His Ser Asn Asn
            340                 345                 350

His Phe Asp Ile Ser Leu Ala Met Phe Thr His Val Ala Ala Ala Ala
        355                 360                 365

Pro Gly Arg Ile Thr Ala Ile Asp Thr His Trp Ile Trp Gln Asp Gly
    370                 375                 380

Gln Arg Leu Thr Lys Gln Pro Phe Glu Ile Ser Ser Gly Cys Val Lys
385                 390                 395                 400

Val Pro Asp Lys Pro Gly Leu Gly Val Asp Ile Asp Met Glu Gln Val
                405                 410                 415

Glu Lys Ala His Glu Ile Tyr Arg Lys Met Asn Leu Gly Ala Arg Asn
            420                 425                 430

Asp Ala Ile Pro Met Gln Phe Leu Ile Ser Asn Trp Glu Phe Asp Arg
        435                 440                 445

Lys Arg Pro Cys Leu Val Arg
    450                 455
```

<210> SEQ ID NO 67
<211> LENGTH: 455
<212> TYPE: PRT
<213> ORGANISM: Bacillus subtilis

<400> SEQUENCE: 67

```
Met Ser Ser Pro Ile Gln Glu Gln Val Gln Lys Glu Lys Arg Ser Asn
1               5                   10                  15

Ile Pro Ser Ile Ser Glu Met Lys Val Ile Pro Val Ala Gly His Asp
            20                  25                  30

Ser Met Leu Leu Asn Leu Ser Gly Ala His Ser Pro Phe Phe Thr Arg
        35                  40                  45

Asn Ile Val Ile Leu Thr Asp Ser Ser Gly Asn Gln Gly Val Gly Glu
    50                  55                  60

Val Pro Gly Gly Glu His Ile Arg Arg Thr Leu Glu Leu Ser Glu Pro
65                  70                  75                  80

Leu Val Val Gly Lys Ser Ile Gly Ala Tyr Gln Ala Ile Leu Gln Thr
                85                  90                  95

Val Arg Lys Gln Phe Gly Asp Gln Asp Arg Gly Gly Arg Gly Asn Gln
            100                 105                 110

Thr Phe Asp Leu Arg Thr Thr Val His Ala Val Thr Ala Leu Glu Ala
        115                 120                 125

Ala Leu Leu Asp Phe Leu Gly Lys Phe Leu Gln Glu Pro Val Ala Ala
    130                 135                 140

Leu Leu Gly Glu Gly Lys Gln Arg Asp Glu Val Lys Met Leu Gly Tyr
145                 150                 155                 160
```

Leu Phe Tyr Ile Gly Asp Arg Asn Arg Thr Thr Leu Pro Tyr Gln Ser
165 170 175

Asp Glu Gln Ser Asp Cys Ala Trp Phe Arg Leu Arg His Glu Glu Ala
180 185 190

Leu Thr Pro Glu Ala Ile Val Arg Leu Ala Glu Ser Ala Gln Glu Arg
195 200 205

Tyr Gly Phe Gln Asp Phe Lys Leu Lys Gly Gly Val Leu Arg Gly Glu
210 215 220

Glu Glu Ile Glu Ala Val Thr Ala Leu Ser Lys Arg Phe Pro Glu Ala
225 230 235 240

Arg Ile Thr Leu Asp Pro Asn Gly Ala Trp Ser Leu Glu Glu Ala Ile
245 250 255

Ala Leu Cys Lys Gly Lys Gln Asp Val Leu Ala Tyr Ala Glu Asp Pro
260 265 270

Cys Gly Asp Glu Asn Gly Tyr Ser Ala Arg Glu Val Met Ala Glu Phe
275 280 285

Arg Arg Ala Thr Gly Leu Pro Thr Ala Thr Asn Met Ile Ala Thr Asp
290 295 300

Trp Arg Glu Met Gly His Ala Ile Gln Leu His Ala Val Asp Ile Pro
305 310 315 320

Leu Ala Asp Pro His Phe Trp Thr Met Gln Gly Ser Val Arg Val Ala
325 330 335

Gln Met Cys His Asp Trp Gly Leu Thr Trp Gly Ser His Ser Asn Asn
340 345 350

His Phe Asp Ile Ser Leu Ala Met Phe Thr His Val Ala Ala Ala Ala
355 360 365

Pro Gly Arg Ile Thr Ala Ile Asp Thr His Trp Ile Trp Gln Asp Gly
370 375 380

Gln Arg Leu Thr Lys Gln Pro Phe Glu Ile Ser Ser Gly Cys Val Lys
385 390 395 400

Val Pro Asp Lys Pro Gly Leu Gly Val Asp Ile Asp Met Glu Gln Val
405 410 415

Glu Lys Ala His Glu Ile Tyr Arg Lys Met Asn Leu Gly Ala Arg Asn
420 425 430

Asp Ala Ile Pro Met Gln Phe Leu Ile Ser Asn Trp Glu Phe Asp Arg
435 440 445

Lys Arg Pro Cys Leu Val Arg
450 455

<210> SEQ ID NO 68
<211> LENGTH: 455
<212> TYPE: PRT
<213> ORGANISM: Bacillus subtilis

<400> SEQUENCE: 68

Met Ser Ser Pro Ile Gln Glu Gln Val Gln Lys Glu Lys Arg Ser Asn
1 5 10 15

Ile Pro Ser Ile Thr Glu Met Lys Val Ile Pro Val Ala Gly His Asp
20 25 30

Ser Met Leu Leu Asn Leu Ser Gly Ala His Ser Pro Phe Phe Thr Arg
35 40 45

Asn Ile Val Ile Leu Thr Asp Ser Ser Gly Asn Gln Gly Val Gly Glu
50 55 60

Val Pro Gly Gly Glu His Ile Arg Arg Thr Leu Glu Leu Ser Glu Pro

-continued

```
65                  70                  75                  80

Leu Val Val Gly Lys Ser Ile Gly Ala Tyr Gln Ala Ile Leu Gln Thr
                85                  90                  95

Val Arg Lys Gln Phe Gly Asp Gln Asp Arg Gly Gly Arg Gly Asn Gln
            100                 105                 110

Thr Phe Asp Leu Arg Thr Thr Val His Ala Val Thr Ala Leu Glu Ala
        115                 120                 125

Ala Leu Leu Asp Leu Leu Gly Lys Phe Leu Gln Glu Pro Val Ala Ala
    130                 135                 140

Leu Leu Gly Glu Gly Lys Gln Arg Asp Glu Val Lys Met Leu Gly Tyr
145                 150                 155                 160

Leu Phe Tyr Ile Gly Asp Arg Lys Arg Thr Thr Leu Pro Tyr Gln Ser
                165                 170                 175

Asp Glu Gln Ser Asp Cys Ala Trp Phe Arg Leu Arg His Glu Glu Ala
            180                 185                 190

Leu Thr Pro Glu Ala Ile Val Arg Leu Ala Glu Ser Ala Gln Glu Arg
        195                 200                 205

Tyr Gly Phe Gln Asp Phe Lys Leu Lys Gly Gly Val Leu Gln Gly Glu
    210                 215                 220

Glu Glu Ile Glu Ala Val Thr Ala Leu Ser Lys Arg Phe Pro Glu Ala
225                 230                 235                 240

Arg Ile Thr Leu Asp Pro Asn Gly Ala Trp Ser Leu Glu Glu Ala Ile
                245                 250                 255

Ala Leu Cys Lys Gly Lys Gln Asp Val Leu Ala Tyr Ala Glu Asp Pro
            260                 265                 270

Cys Gly Asp Glu Asn Gly Tyr Ser Ala Arg Glu Val Met Ala Glu Phe
        275                 280                 285

Arg Arg Ala Thr Gly Leu Pro Thr Ala Thr Asn Met Ile Ala Thr Asp
    290                 295                 300

Trp Arg Glu Met Gly His Ala Ile Gln Leu His Ala Val Asp Ile Pro
305                 310                 315                 320

Leu Ala Asp Pro His Phe Trp Thr Met Gln Gly Ser Val Arg Val Ala
                325                 330                 335

Gln Met Cys His Asp Trp Gly Leu Thr Trp Gly Ser His Ser Asn Asn
            340                 345                 350

His Phe Asp Ile Ser Leu Ala Met Phe Thr His Val Ala Ala Ala Ala
        355                 360                 365

Pro Gly Arg Ile Thr Ala Ile Asp Thr His Trp Ile Trp Gln Asp Gly
    370                 375                 380

Gln Arg Leu Thr Lys Gln Pro Phe Glu Ile Ser Ser Gly Cys Val Lys
385                 390                 395                 400

Val Pro Asp Lys Pro Gly Leu Gly Ile Asp Ile Asp Met Glu Gln Val
                405                 410                 415

Glu Lys Ala His Glu Ile Tyr Arg Lys Met Asn Leu Gly Ala Arg Asn
            420                 425                 430

Asp Ala Ile Pro Met Gln Phe Leu Ile Ser Asn Trp Glu Phe Asp Arg
        435                 440                 445

Lys Arg Pro Cys Leu Val Arg
    450                 455
```

<210> SEQ ID NO 69
<211> LENGTH: 455
<212> TYPE: PRT
<213> ORGANISM: Bacillus subtilis

<400> SEQUENCE: 69

Met Ser Ser Pro Ile Gln Glu Gln Val Gln Lys Glu Lys Arg Ser Asn
1 5 10 15

Ile Pro Ser Ile Cys Glu Met Lys Val Ile Pro Val Ala Gly His Asp
20 25 30

Ser Met Leu Leu Asn Leu Ser Gly Ala His Ser Pro Phe Phe Thr Arg
35 40 45

Asn Ile Val Ile Leu Thr Asp Ser Ser Gly Asn Gln Gly Val Gly Glu
50 55 60

Val Pro Gly Gly Glu Gln Ile Arg Arg Thr Leu Glu Leu Ala Glu Pro
65 70 75 80

Leu Val Val Gly Lys Ser Ile Gly Ala Tyr Gln Ser Ile Leu Gln Thr
85 90 95

Val Arg Lys Gln Phe Ala Asp Gln Asp Arg Gly Gly Arg Gly Ile Gln
100 105 110

Thr Phe Asp Leu Arg Thr Thr Val His Ala Val Thr Ala Leu Glu Ala
115 120 125

Ala Leu Leu Asp Leu Leu Gly Lys Phe Leu Gln Glu Pro Val Ala Ala
130 135 140

Leu Leu Gly Glu Gly Lys Gln Arg Asp Glu Val Lys Met Leu Gly Tyr
145 150 155 160

Leu Phe Tyr Ile Gly Asp Arg Lys Gln Thr Thr Leu Pro Tyr Gln Ser
165 170 175

Asp Glu Gln Ser Asp Cys Gly Trp Phe Arg Leu Arg His Glu Glu Ala
180 185 190

Leu Thr Pro Glu Ala Ile Val Arg Leu Ala Glu Ser Ala Gln Glu Arg
195 200 205

Tyr Gly Phe Gln Asp Phe Lys Leu Lys Gly Gly Val Leu Arg Gly Glu
210 215 220

Asp Glu Ile Glu Ala Val Thr Ala Leu Ala Lys Arg Phe Pro Glu Ala
225 230 235 240

Arg Ile Thr Leu Asp Pro Asn Gly Ala Trp Ser Leu Glu Glu Ala Ile
245 250 255

Ala Leu Cys Lys Gly Lys His Asp Val Leu Ala Tyr Ala Glu Asp Pro
260 265 270

Cys Gly Asp Glu Asn Gly Tyr Ser Ala Arg Glu Val Met Ala Glu Phe
275 280 285

Arg Arg Ala Thr Gly Leu Pro Thr Ala Thr Asn Met Ile Ala Thr Asp
290 295 300

Trp Arg Glu Met Gly His Ala Ile Gln Leu His Ala Val Asp Ile Pro
305 310 315 320

Leu Ala Asp Pro His Phe Trp Thr Met Gln Gly Ser Val Arg Val Ala
325 330 335

Gln Met Cys His Asp Trp Gly Leu Thr Trp Gly Ser His Ser Asn Asn
340 345 350

His Phe Asp Ile Ser Leu Ala Met Phe Thr His Val Ala Ala Ala Ala
355 360 365

Pro Gly Arg Ile Thr Ala Ile Asp Thr His Trp Ile Trp Gln Asp Gly
370 375 380

Gln Arg Leu Thr Lys Gln Pro Phe Glu Ile Ser Glu Gly Cys Val Lys
385 390 395 400

Val Pro Asn Lys Pro Gly Leu Gly Ile Asp Ile Asp Met Glu Gln Val

```
                405                 410                 415

Glu Lys Ala His Glu Leu Tyr Arg Lys Met Asn Leu Gly Ala Arg Asn
            420                 425                 430

Asp Ala Val Pro Met Gln Phe Leu Ile Ser Asn Trp Glu Phe Asp Arg
        435                 440                 445

Lys Arg Pro Cys Leu Val Arg
    450                 455


<210> SEQ ID NO 70
<211> LENGTH: 455
<212> TYPE: PRT
<213> ORGANISM: Bacillus subtilis

<400> SEQUENCE: 70

Met Ser Ser Pro Met Gln Glu Gln Ile Gln Lys Glu Lys Arg Ser Asn
1               5                   10                  15

Val Pro Ser Ile Ser Glu Met Lys Val Ile Pro Val Ala Gly His Asp
            20                  25                  30

Ser Met Leu Leu Asn Leu Ser Gly Ala His Ser Pro Phe Phe Thr Arg
        35                  40                  45

Asn Ile Val Ile Leu Thr Asp Ser Ser Gly Asn Gln Gly Val Gly Glu
    50                  55                  60

Val Pro Gly Gly Glu His Ile Arg Arg Thr Leu Glu Leu Ser Glu Pro
65                  70                  75                  80

Leu Val Val Gly Lys Ser Ile Gly Ala Tyr Gln Ala Ile Leu Gln Thr
                85                  90                  95

Val Arg Lys Gln Phe Gly Asp Gln Asp Arg Gly Gly Arg Gly Asn Gln
            100                 105                 110

Thr Phe Asp Leu Arg Thr Thr Val His Ala Val Thr Ala Leu Glu Ala
        115                 120                 125

Ala Leu Leu Asp Leu Leu Gly Lys Phe Leu Gln Glu Pro Val Ala Ala
    130                 135                 140

Leu Leu Gly Glu Gly Lys Gln Arg Asp Glu Val Lys Met Leu Gly Tyr
145                 150                 155                 160

Leu Phe Tyr Ile Gly Asp Arg Lys Arg Thr Thr Leu Pro Tyr Gln Ser
                165                 170                 175

Asp Glu Gln Ser Tyr Cys Ala Trp Phe Arg Leu Arg His Glu Glu Ala
            180                 185                 190

Leu Thr Pro Glu Ala Ile Val Arg Leu Ala Glu Ser Ala Gln Glu Arg
        195                 200                 205

Tyr Gly Phe Gln Asp Phe Lys Leu Lys Gly Gly Val Leu Arg Gly Glu
    210                 215                 220

Glu Glu Ile Glu Ala Val Thr Ala Leu Ser Lys Arg Phe Pro Glu Ala
225                 230                 235                 240

Arg Ile Thr Leu Asp Pro Asn Gly Ala Trp Ser Leu Glu Glu Ala Ile
                245                 250                 255

Ala Leu Cys Lys Gly Lys Gln Asp Val Leu Ala Tyr Ala Glu Asp Pro
            260                 265                 270

Cys Gly Asp Glu Asn Gly Tyr Ser Ala Arg Glu Val Met Ala Glu Phe
        275                 280                 285

Arg Arg Ala Thr Gly Leu Pro Thr Ala Thr Asn Met Ile Ala Thr Asp
    290                 295                 300

Trp Arg Glu Met Gly His Ala Ile Gln Leu His Ala Val Asp Ile Pro
305                 310                 315                 320
```

-continued

```
Leu Ala Asp Pro His Phe Trp Thr Met Gln Gly Ser Val Arg Val Ala
                325                 330                 335

Gln Met Cys Asn Asp Trp Gly Leu Thr Trp Gly Ser His Ser Asn Asn
            340                 345                 350

His Phe Asp Ile Ser Leu Ala Met Phe Thr His Val Ala Ala Ala Ala
        355                 360                 365

Pro Gly Arg Ile Thr Ala Ile Asp Thr His Trp Ile Trp Gln Asp Gly
    370                 375                 380

Gln Arg Leu Thr Lys Gln Pro Phe Glu Ile Ser Ser Gly Cys Val Lys
385                 390                 395                 400

Val Pro Asp Lys Pro Gly Leu Gly Val Asp Ile Asp Met Glu Gln Val
                405                 410                 415

Glu Lys Ala His Glu Ile Tyr Arg Lys Met Asn Leu Gly Ala Arg Asn
            420                 425                 430

Asp Ala Ile Pro Met Gln Ser Leu Ile Ser Asn Trp Glu Phe Asp Arg
        435                 440                 445

Lys Arg Pro Cys Leu Val Arg
    450                 455


<210> SEQ ID NO 71
<211> LENGTH: 510
<212> TYPE: PRT
<213> ORGANISM: Bacillus subtilis

<400> SEQUENCE: 71

Met Ala Met Asn Leu Arg Lys Asn Gln Ala Pro Leu Tyr Ile Lys Val
1               5                   10                  15

His Glu Ile Asp Asn Thr Ala Ile Ile Val Asn Asp Gly Gly Leu Pro
            20                  25                  30

Lys Gly Thr Val Phe Ser Cys Gly Leu Val Leu Glu Glu Asp Val Pro
        35                  40                  45

Gln Gly His Lys Val Ala Leu Thr Asp Leu Asn Gln Gly Asp Glu Ile
    50                  55                  60

Val Arg Tyr Gly Glu Val Ile Gly Phe Ala Asp Glu Thr Ile Lys Arg
65                  70                  75                  80

Gly Ser Trp Ile Arg Glu Ala Leu Val Arg Met Pro Ala Pro Pro Ala
                85                  90                  95

Leu Asp Asp Leu Pro Leu Ala Asn Arg Val Pro Gln Pro Arg Pro Pro
            100                 105                 110

Leu Glu Gly Tyr Thr Phe Glu Gly Tyr Arg Asn Ala Asp Gly Ser Ala
        115                 120                 125

Gly Thr Lys Asn Ile Leu Gly Ile Thr Thr Ser Val Gln Cys Val Val
    130                 135                 140

Gly Val Leu Asp Tyr Ala Val Lys Arg Ile Lys Glu Glu Leu Leu Pro
145                 150                 155                 160

Lys Tyr Pro Asn Val Asp Asp Val Val Pro Leu His His Gln Tyr Gly
                165                 170                 175

Cys Gly Val Ala Ile Asn Ala Pro Asp Ala Val Ile Pro Ile Arg Thr
            180                 185                 190

Ile Gln Asn Leu Ala Lys His Pro Asn Phe Gly Gly Glu Val Met Val
        195                 200                 205

Ile Gly Leu Gly Cys Glu Lys Leu Leu Pro Glu Arg Ile Ala Ser Glu
    210                 215                 220

Asn Asp Asp Asp Ile Leu Ser Leu Gln Asp His Arg Gly Phe Ala Ala
225                 230                 235                 240
```

```
Met Ile Gln Ser Ile Leu Glu Met Ala Glu Glu Arg Leu Ile Arg Leu
                245                 250                 255

Asn Ser Arg Thr Arg Val Ser Cys Pro Val Ser Asp Leu Val Ile Gly
            260                 265                 270

Leu Gln Cys Gly Gly Ser Asp Ala Phe Ser Gly Val Thr Ala Asn Pro
        275                 280                 285

Ala Val Gly Tyr Ala Ala Asp Leu Leu Val Arg Ala Gly Ala Thr Val
    290                 295                 300

Leu Phe Ser Glu Val Thr Glu Val Arg Asp Ala Ile His Leu Leu Thr
305                 310                 315                 320

Pro Arg Ala Val Ser Glu Glu Val Gly Gln Ser Leu Ile Lys Glu Met
                325                 330                 335

Lys Trp Tyr Asp Ser Tyr Leu Arg Arg Gly Asp Ala Asp Arg Ser Ala
            340                 345                 350

Asn Pro Ser Pro Gly Asn Lys Lys Gly Gly Leu Ser Asn Val Val Glu
        355                 360                 365

Lys Ala Leu Gly Ser Val Ala Lys Ser Gly Thr Ser Pro Ile Ser Gly
    370                 375                 380

Val Leu Gly Pro Gly Glu Arg Ala Lys Gln Lys Gly Leu Leu Phe Ala
385                 390                 395                 400

Ala Thr Pro Ala Ser Asp Phe Val Cys Gly Thr Leu Gln Leu Ala Ala
                405                 410                 415

Gly Met Asn Leu Gln Val Phe Thr Thr Gly Arg Gly Thr Pro Tyr Gly
            420                 425                 430

Leu Ala Ala Ala Pro Val Leu Lys Val Ser Thr Arg His Ser Leu Ser
        435                 440                 445

Glu His Trp Ala Asp Leu Ile Asp Ile Asn Ala Gly Arg Ile Ala Thr
    450                 455                 460

Gly Glu Ala Ser Ile Glu Asp Val Gly Trp Glu Ile Phe Arg Thr Ile
465                 470                 475                 480

Leu Asp Val Ala Ser Gly Arg Lys Gln Thr Trp Ala Asp Arg Trp Gly
                485                 490                 495

Leu His Asn Asp Leu Cys Leu Phe Asn Pro Ala Pro Val Thr
            500                 505                 510


<210> SEQ ID NO 72
<211> LENGTH: 510
<212> TYPE: PRT
<213> ORGANISM: Bacillus subtilis

<400> SEQUENCE: 72

Met Ala Met Asn Leu Arg Lys Asn Gln Ala Pro Leu Tyr Ile Lys Val
1               5                   10                  15

His Glu Ile Asp Asn Thr Ala Ile Ile Val Asn Asp Gly Gly Leu Pro
            20                  25                  30

Lys Gly Thr Val Phe Ser Cys Gly Leu Val Leu Glu Glu Asp Val Pro
        35                  40                  45

Gln Gly His Lys Val Ala Leu Thr Asp Leu Asn Gln Gly Asp Glu Ile
    50                  55                  60

Val Arg Tyr Gly Glu Val Ile Gly Phe Ala Asp Glu Thr Ile Lys Arg
65                  70                  75                  80

Gly Ser Trp Ile Arg Glu Ala Leu Val Arg Met Pro Ala Pro Pro Ala
                85                  90                  95

Leu Asp Asp Leu Pro Leu Ala Asn Arg Val Pro Gln Pro Arg Pro Pro
```

-continued

```
            100                 105                 110

Leu Glu Gly Tyr Thr Phe Glu Gly Tyr Arg Asn Ala Asp Gly Ser Ala
        115                 120                 125

Gly Thr Lys Asn Ile Leu Gly Ile Thr Thr Ser Val Gln Cys Val Val
    130                 135                 140

Gly Val Leu Asp Tyr Ala Val Lys Arg Ile Lys Glu Glu Leu Leu Pro
145                 150                 155                 160

Lys Tyr Pro Asn Val Asp Asp Val Val Pro Leu His His Gln Tyr Gly
                165                 170                 175

Cys Gly Val Ala Ile Asn Ala Pro Asp Ala Val Ile Pro Ile Arg Thr
            180                 185                 190

Ile Gln Asn Leu Ala Lys His Pro Asn Phe Gly Gly Glu Val Met Val
        195                 200                 205

Ile Gly Leu Gly Cys Glu Lys Leu Leu Pro Glu Arg Ile Ala Ser Glu
    210                 215                 220

Asn Asp Asp Asp Ile Leu Ser Leu Gln Asp His Arg Gly Phe Ala Ala
225                 230                 235                 240

Met Ile Gln Ser Ile Leu Glu Met Ala Glu Glu Arg Leu Ile Arg Leu
                245                 250                 255

Asn Ser Arg Thr Arg Val Ser Cys Pro Val Ser Asp Leu Val Ile Gly
            260                 265                 270

Leu Gln Cys Gly Gly Ser Asp Ala Phe Ser Gly Val Thr Ala Asn Pro
        275                 280                 285

Ala Val Gly Tyr Ala Ala Asp Leu Leu Val Arg Ala Gly Ala Thr Val
    290                 295                 300

Leu Phe Ser Glu Val Thr Glu Val Arg Asp Ala Ile His Leu Leu Thr
305                 310                 315                 320

Pro Arg Ala Val Ser Glu Glu Val Gly Gln Ser Leu Ile Lys Glu Met
                325                 330                 335

Lys Trp Tyr Asp Ser Tyr Leu Arg Arg Gly Asp Ala Asp Arg Ser Ala
            340                 345                 350

Asn Pro Ser Pro Gly Asn Lys Lys Gly Gly Leu Ser Asn Val Val Glu
        355                 360                 365

Lys Ala Leu Gly Ser Val Ala Lys Ser Gly Thr Ser Pro Ile Ser Gly
    370                 375                 380

Val Leu Gly Pro Gly Glu Arg Ala Glu Gln Lys Gly Leu Leu Phe Ala
385                 390                 395                 400

Ala Thr Pro Ala Ser Asp Phe Val Cys Gly Thr Leu Gln Leu Ala Ala
                405                 410                 415

Gly Met Asn Leu Gln Val Phe Thr Thr Gly Arg Gly Thr Pro Tyr Gly
            420                 425                 430

Leu Ala Ala Ala Pro Val Leu Lys Val Ser Thr Arg His Ser Leu Ser
        435                 440                 445

Glu His Trp Ala Asp Leu Ile Asp Ile Asn Ala Gly Arg Ile Ala Thr
    450                 455                 460

Gly Glu Ala Ser Ile Glu Asp Val Gly Trp Glu Ile Phe Arg Thr Ile
465                 470                 475                 480

Leu Asp Val Ala Ser Gly Arg Lys Gln Thr Trp Ala Asp Arg Trp Gly
                485                 490                 495

Leu His Asn Asp Leu Cys Leu Phe Asn Pro Ala Pro Val Thr
            500                 505                 510
```

<210> SEQ ID NO 73

<211> LENGTH: 510
<212> TYPE: PRT
<213> ORGANISM: Bacillus subtilis

<400> SEQUENCE: 73

```
Met Ala Met Asn Leu Arg Lys Asn Gln Ala Pro Leu Tyr Ile Lys Val
1               5                   10                  15

His Glu Ile Asp Asn Thr Ala Ile Ile Val Asn Asp Gly Gly Leu Pro
            20                  25                  30

Lys Gly Thr Val Phe Ser Cys Gly Leu Val Leu Glu Glu Asp Val Pro
        35                  40                  45

Gln Gly His Lys Val Ala Leu Thr Asp Leu Asn Gln Gly Asp Glu Ile
    50                  55                  60

Val Arg Tyr Gly Glu Val Ile Gly Phe Ala Asp Glu Thr Ile Lys Arg
65                  70                  75                  80

Gly Ser Trp Ile Arg Glu Ala Leu Val Arg Met Pro Ala Pro Pro Ala
                85                  90                  95

Leu Asp Asp Leu Pro Leu Ala Asn Arg Val Pro Gln Pro Arg Pro Pro
            100                 105                 110

Leu Glu Gly Tyr Thr Phe Glu Gly Tyr Arg Asn Ala Asp Gly Ser Ala
        115                 120                 125

Gly Thr Lys Asn Ile Leu Gly Ile Thr Thr Ser Val Gln Cys Val Val
    130                 135                 140

Gly Val Leu Asp Tyr Ala Val Lys Arg Ile Lys Glu Glu Leu Leu Pro
145                 150                 155                 160

Lys Tyr Pro Asn Val Asp Asp Val Val Pro Leu His His Gln Tyr Gly
                165                 170                 175

Cys Gly Val Ala Ile Asn Ala Pro Asp Ala Val Ile Pro Ile Arg Thr
            180                 185                 190

Ile Gln Asn Leu Ala Lys His Pro Asn Phe Gly Gly Glu Val Met Val
        195                 200                 205

Ile Gly Leu Gly Cys Glu Lys Leu Leu Pro Glu Arg Ile Ala Ser Glu
    210                 215                 220

Asn Asp Asp Asp Ile Leu Ser Leu Gln Asp His Arg Gly Phe Ala Ala
225                 230                 235                 240

Met Ile Gln Ser Ile Leu Glu Met Ala Glu Glu Arg Leu Ile Arg Leu
                245                 250                 255

Asn Ser Arg Thr Arg Val Ser Cys Pro Val Ser Asp Leu Val Ile Gly
            260                 265                 270

Leu Gln Cys Gly Gly Ser Asp Ala Phe Ser Gly Val Thr Ala Asn Pro
        275                 280                 285

Ala Val Gly Tyr Ala Ala Asp Leu Leu Val Arg Ala Gly Ala Thr Val
    290                 295                 300

Leu Phe Ser Glu Val Thr Glu Val Arg Asp Ala Ile His Leu Leu Thr
305                 310                 315                 320

Pro Arg Ala Val Ser Glu Glu Val Gly Gln Ser Leu Ile Glu Glu Met
                325                 330                 335

Lys Trp Tyr Asp Ser Tyr Leu Arg Arg Gly Asp Ala Asp Arg Ser Ala
            340                 345                 350

Asn Pro Ser Pro Gly Asn Lys Lys Gly Gly Leu Ser Asn Val Val Glu
        355                 360                 365

Lys Ala Leu Gly Ser Val Ala Lys Ser Gly Thr Ser Pro Ile Ser Gly
    370                 375                 380

Val Leu Gly Pro Gly Glu Arg Ala Glu Gln Lys Gly Leu Leu Phe Ala
```

385 390 395 400

Ala Thr Pro Ala Ser Asp Phe Val Cys Gly Thr Leu Gln Leu Ala Ala
405 410 415

Gly Met Asn Leu Gln Val Phe Thr Thr Gly Arg Gly Thr Pro Tyr Gly
420 425 430

Leu Ala Ala Ala Pro Val Leu Lys Val Ser Thr Arg His Ser Leu Ser
435 440 445

Glu His Trp Ala Asp Leu Ile Asp Ile Asn Ala Gly Arg Ile Ala Thr
450 455 460

Gly Glu Ala Ser Ile Glu Asp Val Gly Trp Glu Ile Phe Arg Thr Ile
465 470 475 480

Leu Asp Val Ala Ser Gly Arg Lys Gln Thr Trp Ala Asp Arg Trp Gly
485 490 495

Leu His Asn Asp Leu Cys Leu Phe Asn Pro Ala Pro Val Thr
500 505 510

<210> SEQ ID NO 74
<211> LENGTH: 510
<212> TYPE: PRT
<213> ORGANISM: Bacillus subtilis

<400> SEQUENCE: 74

Met Ala Met Asn Leu Arg Lys Asn Gln Ala Pro Leu Tyr Ile Lys Val
1 5 10 15

His Glu Ile Asp Asn Thr Ala Ile Ile Val Asn Glu Gly Gly Leu Pro
20 25 30

Lys Gly Thr Val Phe Ser Cys Gly Leu Val Leu Glu Glu Asp Val Pro
35 40 45

Gln Gly His Lys Val Ala Leu Thr Asp Leu Asn Gln Gly Asp Glu Ile
50 55 60

Val Arg Tyr Gly Glu Val Ile Gly Phe Ala Asp Glu Thr Ile Lys Arg
65 70 75 80

Gly Ser Trp Ile Arg Glu Ala Leu Val Arg Met Pro Ala Pro Pro Ala
85 90 95

Leu Asp Asp Leu Pro Leu Glu Asn Arg Val Pro Gln Pro Arg Pro Pro
100 105 110

Leu Glu Gly Tyr Thr Phe Glu Gly Tyr Arg Asn Ala Asp Gly Ser Ala
115 120 125

Gly Thr Lys Asn Ile Leu Gly Ile Thr Thr Ser Val Gln Cys Val Val
130 135 140

Gly Val Leu Asp Tyr Ala Val Lys Arg Ile Lys Glu Glu Leu Leu Pro
145 150 155 160

Lys Tyr Pro Asn Val Asp Asp Val Val Pro Leu His His Gln Tyr Gly
165 170 175

Cys Gly Val Ala Ile Asn Ala Pro Asp Ala Val Ile Pro Ile Arg Thr
180 185 190

Ile Gln Asn Leu Ala Lys His Pro Asn Phe Gly Gly Glu Val Met Val
195 200 205

Ile Gly Leu Gly Cys Glu Lys Leu Leu Pro Glu Arg Ile Ala Ser Glu
210 215 220

Asn Asp Asp Asp Ile Leu Ser Leu Gln Asp His Arg Gly Phe Ala Ala
225 230 235 240

Met Ile Gln Ser Ile Leu Glu Met Ala Glu Glu Arg Leu Ile Arg Leu
245 250 255

```
Asn Ser Arg Thr Arg Val Ser Cys Pro Val Ser Asp Leu Val Ile Gly
            260                 265                 270

Leu Gln Cys Gly Gly Ser Asp Ala Phe Ser Gly Val Thr Ala Asn Pro
        275                 280                 285

Ala Val Gly Tyr Ala Ala Asp Leu Leu Val Arg Ala Gly Ala Thr Val
    290                 295                 300

Leu Phe Ser Glu Val Thr Glu Val Arg Asp Ala Ile His Leu Leu Thr
305                 310                 315                 320

Pro Arg Ala Val Ser Glu Glu Val Gly Gln Ser Leu Ile Lys Glu Met
                325                 330                 335

Lys Trp Tyr Asp Ser Tyr Leu Arg Arg Gly Asp Ala Asp Arg Ser Ala
            340                 345                 350

Asn Pro Ser Pro Gly Asn Lys Lys Gly Gly Leu Ser Asn Val Val Glu
        355                 360                 365

Lys Ala Leu Gly Ser Val Ala Lys Ser Gly Thr Ser Pro Ile Ser Gly
    370                 375                 380

Val Leu Gly Pro Gly Glu Arg Ala Glu Gln Lys Gly Leu Leu Phe Ala
385                 390                 395                 400

Ala Thr Pro Ala Ser Asp Phe Val Cys Gly Thr Leu Gln Leu Ala Ala
                405                 410                 415

Gly Met Asn Leu Gln Val Phe Thr Thr Gly Arg Gly Thr Pro Tyr Gly
            420                 425                 430

Leu Ala Ala Ala Pro Val Leu Lys Val Ser Thr Arg His Ser Leu Ser
        435                 440                 445

Glu His Trp Ala Asp Leu Ile Asp Ile Asn Ala Gly Gln Ile Ala Thr
    450                 455                 460

Gly Glu Ala Ser Ile Glu Asp Val Gly Trp Glu Ile Phe Arg Thr Ile
465                 470                 475                 480

Leu Asp Val Ala Ser Gly Arg Lys Gln Thr Trp Ala Asp Arg Trp Gly
                485                 490                 495

Leu His Asn Asp Leu Cys Leu Phe Asn Pro Ala Pro Val Thr
            500                 505                 510


<210> SEQ ID NO 75
<211> LENGTH: 510
<212> TYPE: PRT
<213> ORGANISM: Bacillus subtilis

<400> SEQUENCE: 75

Met Ala Met Asn Leu Arg Lys Asn Gln Ala Pro Leu Tyr Ile Lys Val
1               5                   10                  15

His Glu Ile Asp Asn Thr Ala Ile Ile Val Asn Asp Gly Gly Leu Pro
            20                  25                  30

Lys Gly Thr Val Phe Ser Cys Gly Leu Val Leu Glu Glu Asp Val Pro
        35                  40                  45

Gln Gly His Lys Val Ala Leu Thr Asp Leu Asn Gln Gly Asp Glu Ile
    50                  55                  60

Val Arg Tyr Gly Glu Val Ile Gly Phe Ala Asp Glu Thr Ile Lys Arg
65                  70                  75                  80

Gly Ser Trp Ile Arg Glu Asp Leu Val Arg Met Pro Ala Pro Pro Ala
                85                  90                  95

Leu Asp Asp Leu Pro Leu Ala Asn Arg Val Pro Gln Pro Arg Pro Ser
            100                 105                 110

Leu Glu Gly Tyr Thr Phe Glu Gly Tyr Arg Asn Ala Asp Gly Ser Thr
        115                 120                 125
```

```
Gly Thr Lys Asn Ile Leu Gly Ile Thr Thr Ser Val Gln Cys Val Val
    130                 135                 140

Gly Val Leu Asp Tyr Ala Val Lys Arg Ile Lys Glu Glu Leu Leu Pro
145                 150                 155                 160

Lys Tyr Pro Asn Val Asp Asp Val Val Pro Leu His His Gln Tyr Gly
                165                 170                 175

Cys Gly Val Ala Ile Asn Ala Pro Asp Ala Val Ile Pro Ile Arg Thr
            180                 185                 190

Ile Gln Asn Leu Ala Lys His Pro Asn Phe Gly Gly Glu Val Met Val
        195                 200                 205

Ile Gly Leu Gly Cys Glu Lys Leu Leu Pro Glu Arg Ile Ala Ser Glu
    210                 215                 220

Asn Gly Asp Asp Ile Leu Ser Leu Gln Asp His Arg Gly Phe Ala Ala
225                 230                 235                 240

Met Ile Gln Ser Ile Leu Glu Met Ala Glu Glu Arg Leu Ile Arg Leu
                245                 250                 255

Asn Ser Arg Thr Arg Val Ser Cys Pro Val Ser Asp Leu Val Ile Gly
            260                 265                 270

Leu Gln Cys Gly Gly Ser Asp Ala Phe Ser Gly Val Thr Ala Asn Pro
        275                 280                 285

Ala Val Gly Tyr Ala Ala Asp Leu Leu Val Arg Ala Gly Ala Thr Val
    290                 295                 300

Leu Phe Ser Glu Val Thr Glu Val Arg Asp Ala Ile His Leu Leu Thr
305                 310                 315                 320

Pro Arg Ala Val Ser Glu Glu Val Gly Gln Ser Leu Ile Lys Glu Met
                325                 330                 335

Lys Trp Tyr Asp Ser Tyr Leu Arg Arg Gly Asp Ala Asp Arg Ser Ala
            340                 345                 350

Asn Pro Ser Pro Gly Asn Lys Lys Gly Gly Leu Ser Asn Val Val Glu
        355                 360                 365

Lys Ala Leu Gly Ser Val Ala Lys Ser Gly Thr Ser Pro Ile Ser Gly
    370                 375                 380

Val Leu Gly Pro Gly Glu Arg Ala Lys Gln Lys Gly Leu Leu Phe Ala
385                 390                 395                 400

Ala Thr Pro Ala Ser Asp Phe Val Cys Gly Thr Leu Gln Leu Ala Ala
                405                 410                 415

Gly Met Asn Leu Gln Val Phe Thr Thr Gly Arg Gly Thr Pro Tyr Gly
            420                 425                 430

Leu Ala Ala Ala Pro Val Leu Lys Val Ser Thr Arg His Ser Leu Ser
        435                 440                 445

Glu His Trp Ala Asp Leu Ile Asp Ile Asn Ala Gly Arg Ile Ala Thr
    450                 455                 460

Gly Glu Ala Ser Ile Glu Asp Val Gly Trp Glu Ile Phe Arg Thr Ile
465                 470                 475                 480

Leu Asp Val Ala Ser Gly Arg Lys Gln Thr Trp Ala Asp Arg Trp Gly
                485                 490                 495

Leu His Asn Asp Leu Cys Leu Phe Asn Pro Ala Pro Val Thr
            500                 505                 510


<210> SEQ ID NO 76
<211> LENGTH: 308
<212> TYPE: PRT
<213> ORGANISM: Bacillus subtilis
```

<400> SEQUENCE: 76

Met Ser Arg Ile Arg Lys Ala Pro Ala Gly Ile Leu Gly Phe Pro Val
1               5                   10                  15

Ala Pro Phe Asn Thr Gln Gly Lys Leu Glu Glu Glu Ala Leu Phe Gln
            20                  25                  30

Asn Ile Glu Phe Leu Leu Asn Glu Gly Leu Glu Ala Ile Phe Ile Ala
        35                  40                  45

Cys Gly Ser Gly Glu Phe Gln Ser Leu Ser Gln Lys Glu Tyr Glu Gln
    50                  55                  60

Met Val Glu Val Ala Val Ser Ala Ala Gly Gly Lys Val Pro Val Tyr
65                  70                  75                  80

Thr Gly Val Gly Gly Asn Leu Ser Thr Ala Leu Asp Trp Ala Gln Leu
                85                  90                  95

Ser Glu Lys Lys Gly Ala Asp Gly Tyr Leu Ile Leu Pro Pro Tyr Leu
            100                 105                 110

Val His Gly Glu Gln Glu Gly Leu Tyr Gln Tyr Ala Lys Thr Ile Ile
        115                 120                 125

Glu Ser Thr Asp Leu Asn Ala Ile Leu Tyr Gln Arg Asp Asn Ala Val
    130                 135                 140

Leu Ser Val Glu Gln Ile Lys Arg Leu Thr Glu Cys Glu Gln Leu Val
145                 150                 155                 160

Gly Val Lys Asp Gly Val Gly Asn Met Asp Leu Asn Ile Asn Leu Val
                165                 170                 175

Tyr Thr Ile Gly Asp Arg Leu Gly Trp Leu Asn Gly Met Pro Met Ala
            180                 185                 190

Glu Val Thr Met Pro Ala Tyr Leu Pro Ile Gly Phe His Ser Tyr Ser
        195                 200                 205

Ser Ala Ile Ser Asn Tyr Ile Pro His Ile Ser Arg Met Phe Tyr Asp
    210                 215                 220

Ala Leu Lys Asn Gly Asn Asp Glu Leu Val Lys Glu Leu Tyr Arg His
225                 230                 235                 240

Val Ile Leu Pro Ile Asn Asp Ile Arg Lys Gln Arg Lys Gly Tyr Ala
                245                 250                 255

Val Ser Leu Ile Lys Ala Gly Met Glu Ile Met Gly Leu Asn Val Arg
            260                 265                 270

Asn Thr Ala Arg Pro Pro Val Gly Pro Val Glu Lys Asp His Tyr Gln
        275                 280                 285

Gln Leu Glu Ala Ile Leu Lys Gln Ala Ala Asp Arg Phe Pro Lys Lys
    290                 295                 300

Ala Ala Thr Val
305

<210> SEQ ID NO 77
<211> LENGTH: 308
<212> TYPE: PRT
<213> ORGANISM: Bacillus subtilis

<400> SEQUENCE: 77

Met Ser Arg Ile Arg Lys Ala Pro Ala Gly Ile Leu Gly Phe Pro Val
1               5                   10                  15

Ala Pro Phe Asn Thr Gln Gly Lys Leu Glu Glu Glu Ala Leu Phe Gln
            20                  25                  30

Asn Ile Glu Phe Leu Leu Asn Glu Gly Leu Glu Ala Ile Phe Ile Ala
        35                  40                  45

```
Cys Gly Ser Gly Glu Phe Gln Ser Leu Ser Gln Lys Glu Tyr Glu Gln
    50                  55                  60

Met Val Glu Val Ala Val Ser Ala Ala Gly Gly Lys Val Pro Val Tyr
65                  70                  75                  80

Thr Gly Val Gly Gly Asn Leu Ser Thr Ala Leu Glu Trp Ala Gln Leu
                85                  90                  95

Ser Glu Lys Lys Gly Ala Asp Gly Tyr Leu Ile Leu Pro Pro Tyr Leu
            100                 105                 110

Val His Gly Glu Gln Glu Gly Leu Tyr Gln Tyr Ala Lys Thr Ile Ile
        115                 120                 125

Glu Ser Thr Asp Leu Asn Ala Ile Leu Tyr Gln Arg Asp Asn Ala Val
    130                 135                 140

Leu Ser Val Glu Gln Ile Lys Arg Leu Thr Glu Cys Glu Gln Leu Val
145                 150                 155                 160

Gly Val Lys Asp Gly Val Gly Asn Met Asp Leu Asn Ile Asn Leu Val
                165                 170                 175

Tyr Thr Ile Gly Asp Arg Leu Gly Trp Leu Asn Gly Met Pro Met Ala
            180                 185                 190

Glu Val Thr Met Pro Ala Tyr Leu Pro Ile Gly Phe His Ser Tyr Ser
        195                 200                 205

Ser Ala Ile Ser Asn Tyr Ile Pro His Ile Ser Arg Met Phe Tyr Asp
    210                 215                 220

Ala Leu Lys Asn Gly Asn Asp Glu Leu Val Lys Glu Leu Tyr Arg His
225                 230                 235                 240

Val Ile Leu Pro Ile Asn Asp Ile Arg Lys Gln Arg Lys Gly Tyr Ala
                245                 250                 255

Val Ser Leu Ile Lys Ala Gly Met Glu Ile Met Gly Leu Asn Val Arg
            260                 265                 270

Asn Thr Ala Arg Pro Pro Val Gly Pro Val Glu Lys Asp His Tyr Gln
        275                 280                 285

Gln Leu Glu Ala Ile Leu Lys Gln Ala Ala Asp Arg Phe Pro Lys Lys
    290                 295                 300

Ala Ala Thr Val
305


<210> SEQ ID NO 78
<211> LENGTH: 308
<212> TYPE: PRT
<213> ORGANISM: Bacillus vallismortis

<400> SEQUENCE: 78

Met Asn Arg Ile Arg Lys Ala Pro Thr Gly Ile Leu Gly Phe Pro Val
1               5                   10                  15

Ala Pro Phe Asn Thr Gln Gly Gln Leu Glu Glu Glu Ala Leu Phe Gln
            20                  25                  30

Asn Ile Glu Phe Leu Leu Glu Glu Gly Leu Glu Ala Ile Phe Ile Ala
        35                  40                  45

Cys Gly Ser Gly Glu Phe Gln Ser Leu Ser Gln Lys Glu Tyr Glu Gln
    50                  55                  60

Met Val Glu Val Ala Val Ser Ala Ala Glu Gly Lys Val Pro Val Tyr
65                  70                  75                  80

Thr Gly Val Gly Gly Asn Leu Ser Thr Ala Leu Glu Trp Ala Arg Leu
                85                  90                  95

Ser Glu Lys Lys Gly Ala Asp Gly Tyr Leu Ile Leu Pro Pro Tyr Leu
            100                 105                 110
```

```
Val His Gly Glu Gln Glu Gly Leu Tyr Gln Tyr Ala Lys Thr Ile Ile
        115                 120                 125

Glu Ser Thr Asp Leu Asn Ala Ile Leu Tyr Gln Arg Asp Asn Ala Val
    130                 135                 140

Leu Ser Leu Glu Gln Ile Lys Arg Leu Thr Glu Cys Glu Gln Leu Val
145                 150                 155                 160

Gly Val Lys Asp Gly Val Gly Asn Met Asp Leu Asn Ile Asn Leu Val
                165                 170                 175

Tyr Thr Leu Gly Asp Arg Leu Gly Trp Leu Asn Gly Met Pro Met Ala
            180                 185                 190

Glu Val Thr Met Pro Ala Tyr Leu Pro Ile Gly Phe His Ser Tyr Ser
        195                 200                 205

Ser Ala Ile Ser Asn Tyr Ile Pro His Ile Ser Arg Met Phe Tyr Asp
    210                 215                 220

Ala Leu Lys Asn Gly Asn Asp Glu Leu Val Lys Glu Leu Tyr Gln His
225                 230                 235                 240

Val Ile Leu Pro Ile Asn Asp Ile Arg Lys Gln Arg Lys Gly Tyr Ala
                245                 250                 255

Val Ser Leu Ile Lys Ala Gly Met Glu Ile Met Gly Leu Asn Val Arg
            260                 265                 270

Asn Thr Ala Arg Pro Pro Val Gly Pro Val Glu Lys Glu His Tyr Arg
        275                 280                 285

Gln Leu Glu Ala Ile Leu Lys Gln Ala Ala Asp Arg Phe Pro Lys Lys
    290                 295                 300

Ala Ala Thr Val
305


<210> SEQ ID NO 79
<211> LENGTH: 308
<212> TYPE: PRT
<213> ORGANISM: Bacillus subtilis

<400> SEQUENCE: 79

Met Ser Arg Ile Arg Lys Ala Pro Ala Gly Ile Leu Gly Phe Pro Val
1               5                   10                  15

Ala Pro Phe Asn Thr Gln Gly Lys Leu Glu Glu Glu Ala Leu Phe Gln
            20                  25                  30

Asn Ile Glu Phe Leu Leu Glu Glu Gly Leu Glu Ala Ile Phe Ile Ala
        35                  40                  45

Cys Gly Ser Gly Glu Phe Gln Ser Leu Ser Gln Lys Glu Tyr Glu Gln
    50                  55                  60

Met Val Glu Val Ala Ile Ser Ala Ala Gly Gly Lys Val Pro Val Tyr
65                  70                  75                  80

Thr Gly Val Gly Gly Asn Leu Ser Thr Ala Leu Glu Trp Ala Gln Leu
                85                  90                  95

Ser Glu Lys Lys Gly Ala Asp Gly Tyr Leu Ile Leu Pro Pro Tyr Leu
            100                 105                 110

Val His Gly Glu Gln Glu Gly Leu Tyr Gln Tyr Ala Lys Thr Ile Ile
        115                 120                 125

Glu Ser Thr Asp Leu Asn Ala Ile Leu Tyr Gln Arg Asp Asn Ala Val
    130                 135                 140

Leu Ser Val Glu Gln Ile Lys Arg Leu Thr Glu Phe Glu Gln Leu Val
145                 150                 155                 160

Gly Val Lys Asp Gly Val Gly Asn Met Asp Leu Asn Ile Asn Leu Val
```

```
                165                 170                 175

Tyr Thr Leu Gly Asp Arg Leu Gly Trp Leu Asn Gly Met Pro Met Ala
            180                 185                 190

Glu Val Thr Met Pro Ala Tyr Leu Pro Ile Gly Phe His Ser Tyr Ser
        195                 200                 205

Ser Ala Ile Ser Asn Tyr Ile Pro His Ile Ser Arg Met Phe Tyr Asp
    210                 215                 220

Ala Leu Lys Asn Gly Asp Asp Glu Leu Val Lys Glu Leu Tyr Gln His
225                 230                 235                 240

Val Ile Leu Pro Ile Asn Asp Ile Arg Lys Gln Arg Lys Gly Tyr Ala
                245                 250                 255

Val Ser Leu Ile Lys Ala Gly Met Glu Ile Met Gly Leu Asn Val Arg
            260                 265                 270

Asn Thr Ala Arg Pro Pro Val Gly Pro Val Glu Lys Asp His Tyr Gln
        275                 280                 285

Gln Leu Glu Ala Ile Leu Lys Gln Ala Ala Asp Arg Phe Pro Lys Lys
    290                 295                 300

Ala Ala Thr Val
305


<210> SEQ ID NO 80
<211> LENGTH: 308
<212> TYPE: PRT
<213> ORGANISM: Bacillus subtilis

<400> SEQUENCE: 80

Met Ser Arg Ile Arg Lys Ala Pro Ala Gly Ile Leu Gly Phe Pro Val
1               5                   10                  15

Ala Pro Phe Asn Thr Gln Gly Thr Leu Glu Glu Glu Ala Leu Phe Gln
            20                  25                  30

Asn Ile Glu Phe Leu Leu Asn Glu Gly Leu Glu Ala Ile Phe Ile Ala
        35                  40                  45

Cys Gly Ser Gly Glu Phe Gln Ser Leu Ser Gln Lys Glu Tyr Glu Gln
    50                  55                  60

Met Val Glu Val Ala Val Ser Ala Ala Gly Gly Lys Val Pro Val Tyr
65                  70                  75                  80

Thr Gly Val Gly Gly Asn Leu Ser Thr Ala Leu Asp Trp Ala Gln Leu
                85                  90                  95

Ser Glu Lys Lys Gly Ala Asp Gly Tyr Leu Ile Leu Pro Pro Tyr Leu
            100                 105                 110

Val His Gly Glu Gln Glu Gly Leu Tyr Gln Tyr Ala Lys Thr Ile Ile
        115                 120                 125

Glu Ser Thr Asp Leu Asn Ala Ile Leu Tyr Gln Arg Asp Asn Ala Val
    130                 135                 140

Leu Ser Val Glu Gln Ile Lys Arg Leu Thr Glu Cys Glu Gln Leu Val
145                 150                 155                 160

Gly Val Lys Asp Gly Val Gly Asn Met Asp Leu Asn Ile Asn Leu Val
                165                 170                 175

Tyr Thr Ile Gly Asp Arg Leu Gly Trp Leu Asn Gly Met Pro Met Ala
            180                 185                 190

Glu Val Thr Met Pro Ala Tyr Leu Pro Ile Gly Phe His Ser Tyr Ser
        195                 200                 205

Ser Ala Ile Ser Asn Tyr Ile Pro His Ile Ser Arg Met Phe Tyr Asp
    210                 215                 220
```

```
Ala Leu Lys Asn Gly Asn Asp Glu Leu Val Lys Glu Leu Tyr Arg His
225                 230                 235                 240

Val Ile Leu Pro Ile Asn Asp Ile Arg Lys Gln Arg Lys Gly Tyr Ala
                245                 250                 255

Val Ser Leu Ile Lys Ala Gly Met Glu Ile Met Gly Leu Asn Val Arg
            260                 265                 270

Asn Thr Ala Arg Pro Pro Val Gly Pro Val Glu Lys Asp His Tyr Gln
        275                 280                 285

Gln Leu Glu Ala Ile Leu Lys Gln Pro Ala Asp Arg Phe Pro Lys Lys
    290                 295                 300

Ala Ala Thr Val
305


<210> SEQ ID NO 81
<211> LENGTH: 255
<212> TYPE: PRT
<213> ORGANISM: Pseudomonas putida

<400> SEQUENCE: 81

Met Ala Ala Glu Ser Tyr Arg Leu Gln Ala Leu Asp Pro Ser Arg Ala
1               5                   10                  15

Trp His Arg Phe Phe Ala Thr Val Gln Gln Gln Val Glu Lys Arg Ala
            20                  25                  30

Phe Gly Asp Asp Ser Ser Glu His Cys Leu Arg Asn Ala Gln Gln Glu
        35                  40                  45

Leu Thr Met Leu Gly Val Thr Asp Tyr Gly Ala Phe Val Ile Ala Phe
    50                  55                  60

Leu Ile Leu Leu Ala Ile Pro Gly Pro Gly Asn Phe Ala Leu Ile Thr
65                  70                  75                  80

Ala Thr Gly Lys Gly Gly Ile Lys Ala Gly Leu Ala Ala Thr Cys Gly
                85                  90                  95

Val Ile Val Gly Asp Gln Val Leu Leu Trp Leu Ala Val Ala Gly Val
            100                 105                 110

Ala Thr Leu Leu Ala Thr Tyr Pro Ala Ala Phe His Met Val Gln Trp
        115                 120                 125

Ala Gly Ala Ala Tyr Leu Ala Tyr Leu Gly Leu Arg Met Leu Leu Ser
    130                 135                 140

Lys Pro Gly Gly Ala Ala His Thr Cys Arg Met Asp Asn Gly Gln Tyr
145                 150                 155                 160

Leu Arg Gln Thr Met Met Ile Thr Leu Leu Asn Pro Lys Ala Ile Met
                165                 170                 175

Phe Tyr Met Ala Phe Phe Pro Leu Phe Val Asp Pro Val Lys His Gln
            180                 185                 190

Gly Leu Val Thr Phe Gly Phe Met Ala Ala Thr Val Ala Val Val Thr
        195                 200                 205

Phe Leu Tyr Gly Leu Ile Ala Val Val Leu Thr His Gln Leu Ala Glu
    210                 215                 220

Arg Met Arg Ala Ser Pro Arg Ile Ala Asn Met Phe Glu Arg Leu Ala
225                 230                 235                 240

Gly Ala Cys Leu Val Gly Phe Gly Ile Lys Leu Ala Ala Met Arg
                245                 250                 255


<210> SEQ ID NO 82
<211> LENGTH: 232
<212> TYPE: PRT
<213> ORGANISM: Pseudomonas putida
```

<400> SEQUENCE: 82

Met Gln Gln Gln Val Glu Lys Arg Ala Phe Gly Asp Asp Ser Ser Ala
1               5                   10                  15

His Cys Leu Arg Asn Ala Gln Gln Glu Leu Thr Met Leu Gly Val Thr
            20                  25                  30

Asp Tyr Gly Ala Phe Val Ile Ala Phe Leu Ile Leu Leu Ala Ile Pro
        35                  40                  45

Gly Pro Gly Asn Phe Ala Leu Ile Thr Ala Thr Gly Lys Gly Gly Ile
    50                  55                  60

Lys Ala Gly Leu Ala Ala Thr Cys Gly Val Ile Val Gly Asp Gln Val
65                  70                  75                  80

Leu Leu Trp Leu Ala Val Ala Gly Val Ala Thr Leu Leu Ala Thr Tyr
                85                  90                  95

Pro Ala Ala Phe His Val Val Gln Trp Ala Gly Ala Ala Tyr Leu Ala
            100                 105                 110

Tyr Leu Gly Leu Arg Met Leu Leu Ser Lys Pro Gly Gly Ala Ala His
        115                 120                 125

Thr Cys Arg Met Asp Asn Gly Gln Tyr Leu Arg Gln Thr Met Met Ile
    130                 135                 140

Thr Leu Leu Asn Pro Lys Ala Ile Met Phe Tyr Met Ala Phe Phe Pro
145                 150                 155                 160

Leu Phe Val Asp Pro Val Lys His Gln Gly Leu Val Thr Phe Gly Phe
                165                 170                 175

Met Ala Ala Thr Val Ala Val Val Thr Phe Leu Tyr Gly Leu Ile Ala
            180                 185                 190

Val Val Leu Thr His Gln Leu Ala Glu Arg Met Arg Ala Ser Pro Arg
        195                 200                 205

Ile Ala Asn Met Phe Glu Arg Leu Ala Gly Ala Cys Leu Val Gly Phe
    210                 215                 220

Gly Ile Lys Leu Ala Ala Met Arg
225                 230

<210> SEQ ID NO 83
<211> LENGTH: 232
<212> TYPE: PRT
<213> ORGANISM: Pseudomonas putida

<400> SEQUENCE: 83

Met Gln Gln Gln Val Glu Lys Arg Ala Val Gly Asp Asp Ser Ser Ala
1               5                   10                  15

His Cys Leu Arg Asn Ala Gln Gln Glu Leu Thr Met Leu Gly Val Thr
            20                  25                  30

Asp Tyr Gly Ala Phe Val Ile Ala Phe Leu Ile Leu Leu Ala Ile Pro
        35                  40                  45

Gly Pro Gly Asn Phe Ala Leu Ile Thr Ala Thr Gly Lys Gly Gly Ile
    50                  55                  60

Lys Ala Gly Leu Ala Ala Thr Cys Gly Val Ile Val Gly Asp Gln Val
65                  70                  75                  80

Leu Leu Trp Leu Ala Val Ala Gly Val Ala Thr Leu Leu Ala Thr Tyr
                85                  90                  95

Pro Ala Ala Phe His Met Val Gln Trp Ala Gly Ala Ala Tyr Leu Ala
            100                 105                 110

Tyr Leu Gly Leu Arg Met Leu Leu Ser Lys Pro Gly Gly Ala Ala His
        115                 120                 125

```
Thr Cys Arg Met Asp Asn Gly Gln Tyr Leu Arg Gln Thr Met Met Ile
    130                 135                 140

Thr Leu Leu Asn Pro Lys Ala Ile Met Phe Tyr Met Ala Phe Phe Pro
145                 150                 155                 160

Leu Phe Val Asp Pro Val Lys His Gln Gly Leu Val Thr Phe Gly Phe
                165                 170                 175

Met Ala Ala Thr Val Ala Val Val Thr Phe Leu Tyr Gly Leu Ile Ala
            180                 185                 190

Val Val Leu Thr His Gln Leu Ala Glu Arg Met Arg Ala Asn Pro Arg
        195                 200                 205

Ile Ala Asn Met Phe Glu Arg Leu Ala Gly Ala Cys Leu Val Gly Phe
    210                 215                 220

Gly Ile Lys Leu Ala Ala Met Arg
225                 230


<210> SEQ ID NO 84
<211> LENGTH: 205
<212> TYPE: PRT
<213> ORGANISM: Pseudomonas putida

<400> SEQUENCE: 84

Met Leu Gly Val Thr Asp Tyr Gly Ala Phe Val Ile Ala Phe Leu Ile
1               5                   10                  15

Leu Leu Ala Ile Pro Gly Pro Gly Asn Phe Ala Leu Ile Thr Ala Thr
            20                  25                  30

Gly Lys Gly Gly Ile Lys Ala Gly Leu Ala Ala Thr Cys Gly Val Ile
        35                  40                  45

Val Gly Asp Gln Val Leu Leu Trp Leu Ala Val Ala Gly Val Ala Thr
    50                  55                  60

Leu Leu Ala Thr Tyr Pro Ala Ala Phe His Met Val Gln Trp Ala Gly
65                  70                  75                  80

Ala Ala Tyr Leu Ala Tyr Leu Gly Leu Arg Met Leu Leu Ser Lys Pro
                85                  90                  95

Gly Gly Ala Ala His Thr Cys Arg Met Asp Asn Gly Gln Tyr Leu Arg
            100                 105                 110

Gln Thr Met Met Ile Thr Leu Leu Asn Pro Lys Ala Ile Met Phe Tyr
        115                 120                 125

Met Ala Phe Phe Pro Leu Phe Val Asp Pro Val Lys His Gln Gly Leu
    130                 135                 140

Val Thr Phe Gly Phe Met Ala Ala Thr Val Ala Val Val Thr Phe Leu
145                 150                 155                 160

Tyr Gly Leu Ile Ala Val Val Leu Thr His Gln Leu Ala Glu Arg Met
                165                 170                 175

Arg Ala Asn Pro Arg Ile Ala Asn Met Phe Glu Arg Leu Ala Gly Ala
            180                 185                 190

Cys Leu Val Gly Phe Gly Ile Lys Leu Ala Ala Met Arg
        195                 200                 205


<210> SEQ ID NO 85
<211> LENGTH: 205
<212> TYPE: PRT
<213> ORGANISM: Pseudomonas putida

<400> SEQUENCE: 85

Met Leu Gly Val Thr Asp Tyr Gly Ala Phe Val Ile Ala Phe Ile Ile
1               5                   10                  15
```

```
Leu Leu Ala Ile Pro Gly Pro Gly Asn Phe Ala Leu Ile Thr Ala Thr
            20                  25                  30

Gly Lys Gly Gly Ile Lys Ala Gly Leu Ala Ala Thr Cys Gly Val Ile
        35                  40                  45

Val Gly Asp Gln Val Leu Leu Trp Leu Ala Val Ala Gly Val Ala Thr
    50                  55                  60

Leu Leu Ala Thr Tyr Pro Ala Ala Phe His Ile Val Gln Trp Ala Gly
65                  70                  75                  80

Ala Ala Tyr Leu Ala Tyr Leu Gly Leu Arg Met Leu Leu Ser Lys Pro
                85                  90                  95

Gly Asp Ala Pro Arg Thr Ser Arg Met Asp Asn Gly Gln Tyr Leu Arg
            100                 105                 110

Gln Thr Met Leu Ile Thr Leu Leu Asn Pro Lys Ala Ile Met Phe Tyr
        115                 120                 125

Met Ala Phe Phe Pro Leu Phe Ile Asp Pro Val Lys His Gln Gly Leu
    130                 135                 140

Val Thr Phe Gly Phe Met Ala Ala Thr Val Ala Val Ile Thr Phe Leu
145                 150                 155                 160

Tyr Gly Leu Ile Ala Val Val Leu Thr His Arg Leu Ala Glu Arg Met
                165                 170                 175

Arg Ala Asn Pro Arg Ile Thr Asn Met Phe Glu Arg Leu Ala Gly Ala
            180                 185                 190

Cys Leu Val Gly Phe Gly Ile Lys Leu Ala Ala Met Arg
        195                 200                 205


<210> SEQ ID NO 86
<211> LENGTH: 296
<212> TYPE: PRT
<213> ORGANISM: Pseudomonas putida

<400> SEQUENCE: 86

Met Arg Pro Thr Glu Asn Gly Val Leu His Leu Arg Lys Lys Phe Val
1               5                   10                  15

Ala Ser Leu Leu Ala Val Ala Ile Ala Ser Thr Thr Ala Cys Ala Gln
            20                  25                  30

Leu Gly Ile Ser Lys Glu Gln Ala Gly Thr Val Ile Gly Gly Leu Ala
        35                  40                  45

Gly Val Ala Ile Gly Ser Thr Met Gly Ser Gly Asn Gly Lys Ile Ala
    50                  55                  60

Ala Ala Leu Ile Ala Gly Gly Ile Gly Ala Tyr Val Gly Asn Arg Ile
65                  70                  75                  80

Gly His Met Leu Asp Glu Lys Asp Gln Gln Ala Leu Ala Leu Arg Thr
                85                  90                  95

Gln Glu Val Leu Ser Gln Gln Gln Thr Thr Ala Ser Ala Gln Pro Val
            100                 105                 110

Thr Trp Lys Ser Asp His Ser Gly Ala Thr Ala Gln Ile Val Pro Gly
        115                 120                 125

Lys Glu Tyr Thr Lys Thr Lys Gln Val Glu Val Lys Arg Ala Pro Lys
    130                 135                 140

Ile Gln Ala Val Pro Ser Met Lys Leu Ile Asn Glu Pro Tyr Val Thr
145                 150                 155                 160

Ile Ser Asp Asn Leu Asn Val Arg Ala Ala Pro Asn Gln Ala Gly Glu
                165                 170                 175

Lys Val Gly Ser Leu Lys Asn His Thr Glu Phe Thr Ala Val Gly Ser
```

```
            180                 185                 190

Thr Gly Asp Trp Ile Leu Val Gly Arg Lys Gly Val Thr Val Gly Tyr
        195                 200                 205

Val His Lys Asn Tyr Val Glu Pro Lys Ala Gln Ala Val Ala Lys Arg
    210                 215                 220

Val Thr Pro Ala Val Asn Leu Asp Glu Leu Asp Val Ala Ala Ser Lys
225                 230                 235                 240

Glu Thr Gln Gly Phe Asp Leu Asp Ser Val Gln Ser Leu Pro Thr Gln
                245                 250                 255

Thr Val Ala Ala Glu Ala Ala Cys Arg Pro Val Thr Val Ser Leu Lys
            260                 265                 270

Ser Gln Ser Gly Gln Thr Glu Gln Glu Gln Asn Thr Phe Cys Lys Gln
        275                 280                 285

Ala Asn Gly Thr Trp Glu Leu Ile
    290                 295


<210> SEQ ID NO 87
<211> LENGTH: 285
<212> TYPE: PRT
<213> ORGANISM: Pseudomonas putida

<400> SEQUENCE: 87

Met Arg Lys Lys Phe Val Ala Ser Leu Leu Ala Val Ala Ile Ala Thr
1               5                   10                  15

Thr Thr Ala Cys Ala Gln Leu Gly Ile Ser Lys Glu Gln Ala Gly Thr
            20                  25                  30

Val Ile Gly Gly Leu Ala Gly Val Ala Ile Gly Ser Thr Met Gly Ser
        35                  40                  45

Gly Asn Gly Lys Ile Ala Ala Ala Leu Ile Ala Gly Gly Ile Gly Ala
    50                  55                  60

Tyr Val Gly Asn Arg Ile Gly His Met Leu Asp Glu Lys Asp Gln Gln
65                  70                  75                  80

Ala Leu Ala Leu Arg Thr Gln Glu Val Leu Ser Gln Ser Ala Thr Ala
                85                  90                  95

Ser Ala Gln Pro Val Thr Trp Lys Ser Asp His Ser Gly Ala Thr Ala
            100                 105                 110

Gln Ile Thr Pro Gly Lys Glu Tyr Thr Gln Thr Lys Lys Val Glu Val
        115                 120                 125

Lys Arg Ala Pro Lys Ile Gln Ala Val Pro Ser Met Lys Leu Ile Asn
    130                 135                 140

Glu Pro Tyr Val Thr Ile Ser Asp Asn Leu Asn Val Arg Ala Ala Pro
145                 150                 155                 160

Asn Thr Thr Gly Glu Lys Val Gly Ser Leu Lys Ser His Thr Glu Phe
                165                 170                 175

Thr Ala Val Gly Ser Thr Gly Asp Trp Ile Leu Val Gly Arg Lys Gly
            180                 185                 190

Val Thr Val Gly Tyr Val His Lys Asn Tyr Val Glu Pro Lys Ala Gln
        195                 200                 205

Ala Ile Ala Lys Arg Ala Ala Pro Ala Val Asn Leu Asp Asp Leu Asp
    210                 215                 220

Val Ala Ala Asn Lys Glu Thr Gln Gly Phe Asp Leu Asp Ser Ile Gln
225                 230                 235                 240

Ser Leu Pro Thr Glu Thr Val Ala Ala Glu Ala Ala Cys Arg Pro Val
                245                 250                 255
```

Thr Val Ser Leu Lys Ser Gln Ser Gly Gln Thr Glu Gln Glu Gln Asn
260 265 270

Thr Phe Cys Lys Gln Ala Asn Gly Thr Trp Glu Leu Ile
275 280 285

<210> SEQ ID NO 88
<211> LENGTH: 286
<212> TYPE: PRT
<213> ORGANISM: Pseudomonas sp. TJI-51

<400> SEQUENCE: 88

Met Arg Lys Lys Phe Val Ala Ser Leu Leu Ala Val Ala Ile Ala Ser
1 5 10 15

Thr Thr Ala Cys Ala Gln Leu Gly Ile Ser Lys Glu Gln Ala Gly Thr
20 25 30

Val Ile Gly Gly Leu Ala Gly Val Ala Ile Gly Ser Thr Leu Gly Ser
35 40 45

Gly Asn Gly Lys Ile Ala Ala Ala Leu Ile Ala Gly Gly Ile Gly Ala
50 55 60

Tyr Val Gly Asn Arg Ile Gly Asn Met Leu Asp Glu Lys Asp Gln Gln
65 70 75 80

Ala Leu Ala Leu Arg Thr Gln Glu Val Leu Ser Gln Gln Gln Ala Thr
85 90 95

Ala Ser Ala Gln Pro Val Thr Trp Lys Ser Asp His Ser Gly Ala Ser
100 105 110

Ala Gln Ile Val Pro Gly Lys Glu Tyr Thr Lys Thr Lys Gln Val Glu
115 120 125

Val Lys Arg Ala Pro Lys Ile Gln Ala Val Pro Ser Met Lys Leu Ile
130 135 140

Asn Glu Pro Tyr Val Thr Thr Ser Asp Asn Leu Asn Val Arg Ala Ala
145 150 155 160

Pro Asn Ala Ser Gly Glu Lys Val Gly Ser Leu Lys Asn His Thr Glu
165 170 175

Phe Thr Ala Val Gly Ala Thr Gly Asp Trp Ile Leu Val Gly Arg Lys
180 185 190

Gly Val Thr Val Gly Tyr Val His Lys Asp Tyr Val Glu Pro Lys Ala
195 200 205

Gln Ala Val Ala Lys Arg Val Thr Pro Ala Val Asn Leu Asp Glu Leu
210 215 220

Asp Val Ala Ala Ser Lys Glu Thr Gln Ala Phe Asp Leu Asp Ser Leu
225 230 235 240

Gln Ser Leu Pro Thr Gln Thr Val Ala Ala Glu Ala Ala Cys Arg Pro
245 250 255

Val Thr Val Ser Leu Lys Ala Gln Asn Gly Lys Thr Glu Gln Glu Gln
260 265 270

Asn Thr Phe Cys Lys Gln Ala Asn Gly Thr Trp Glu Leu Ile
275 280 285

<210> SEQ ID NO 89
<211> LENGTH: 286
<212> TYPE: PRT
<213> ORGANISM: Pseudomonas putida

<400> SEQUENCE: 89

Met Arg Lys Lys Phe Val Ala Ser Leu Leu Ala Val Ala Ile Ala Ser
1 5 10 15

```
Thr Thr Ala Cys Ala Gln Leu Gly Ile Ser Lys Glu Gln Ala Gly Thr
            20                  25                  30

Val Ile Gly Gly Leu Ala Gly Val Ala Ile Gly Ser Thr Met Gly Ser
        35                  40                  45

Gly Asn Gly Lys Ile Ala Ala Ala Leu Ile Ala Gly Gly Ile Gly Ala
    50                  55                  60

Tyr Val Gly Asn Arg Ile Gly His Met Leu Asp Glu Lys Asp Gln Gln
65                  70                  75                  80

Ala Leu Ala Leu Arg Thr Gln Glu Val Leu Ser Gln Gln Gln Ala Thr
                85                  90                  95

Ala Ser Ala Gln Pro Val Thr Trp Lys Ser Asp His Ser Gly Ala Thr
            100                 105                 110

Ala Gln Ile Val Pro Gly Lys Glu Tyr Thr Gln Thr Lys Lys Val Glu
        115                 120                 125

Val Lys Arg Ala Pro Lys Ile Gln Ala Val Pro Ser Met Lys Leu Ile
    130                 135                 140

Asn Glu Pro Tyr Val Thr Val Ser Asp Asn Leu Asn Val Arg Ala Ala
145                 150                 155                 160

Pro Asn Gln Ser Gly Glu Lys Val Gly Ser Leu Lys Asn His Thr Glu
                165                 170                 175

Phe Thr Ala Val Gly Ser Thr Gly Asp Trp Ile Leu Val Gly Arg Lys
            180                 185                 190

Gly Val Thr Val Gly Tyr Val His Lys Asn Tyr Val Glu Pro Lys Ala
        195                 200                 205

Gln Ala Val Ala Lys Arg Val Thr Pro Ala Val Asn Leu Asp Glu Leu
    210                 215                 220

Asp Val Ala Ala Ser Lys Glu Thr Gln Gly Phe Asp Leu Asp Ser Val
225                 230                 235                 240

Gln Ser Leu Pro Thr Glu Thr Val Ala Ala Glu Ala Ala Cys Arg Pro
                245                 250                 255

Val Thr Val Ser Leu Lys Ser Gln Ser Gly Gln Thr Glu Gln Glu Gln
            260                 265                 270

Asn Thr Phe Cys Lys Gln Ala Asn Gly Thr Trp Glu Leu Ile
        275                 280                 285


<210> SEQ ID NO 90
<211> LENGTH: 286
<212> TYPE: PRT
<213> ORGANISM: Pseudomonas putida

<400> SEQUENCE: 90

Met Arg Lys Lys Phe Val Ala Ser Leu Leu Ala Val Ala Ile Ala Ser
1               5                   10                  15

Thr Thr Ala Cys Ala Gln Leu Gly Ile Ser Lys Glu Gln Ala Gly Thr
            20                  25                  30

Val Ile Gly Gly Leu Ala Gly Val Ala Ile Gly Ser Thr Met Gly Ser
        35                  40                  45

Gly Asn Gly Lys Ile Ala Ala Ala Leu Ile Ala Gly Gly Ile Gly Ala
    50                  55                  60

Tyr Val Gly Asn Arg Ile Gly His Met Leu Asp Glu Lys Asp Gln Gln
65                  70                  75                  80

Ala Leu Ala Leu Arg Thr Gln Glu Val Leu Ser Gln Gln Gln Thr Thr
                85                  90                  95

Ala Ser Ala Gln Pro Val Thr Trp Lys Ser Asp His Ser Gly Ala Thr
            100                 105                 110
```

```
Ala Gln Ile Val Pro Gly Lys Glu Tyr Thr Lys Thr Lys Gln Val Glu
        115                 120                 125

Val Lys Arg Ala Pro Lys Ile Gln Ala Val Pro Ser Met Lys Leu Ile
    130                 135                 140

Asn Glu Pro Tyr Val Thr Ile Ser Asp Asn Leu Asn Val Arg Ala Ala
145                 150                 155                 160

Pro Asn Gln Ala Gly Glu Lys Val Gly Ser Leu Lys Asn His Thr Glu
                165                 170                 175

Phe Thr Ala Val Gly Ser Thr Gly Asp Trp Ile Leu Val Gly Arg Lys
            180                 185                 190

Gly Val Thr Val Gly Tyr Val His Lys Asn Tyr Val Glu Pro Lys Ala
        195                 200                 205

Gln Ala Val Ala Lys Arg Val Thr Pro Ala Val Asn Leu Asp Glu Leu
    210                 215                 220

Asp Val Ala Ala Ser Lys Glu Thr Gln Gly Phe Asp Leu Asp Ser Val
225                 230                 235                 240

Gln Ser Leu Pro Thr Gln Thr Val Ala Ala Glu Ala Ala Cys Arg Pro
                245                 250                 255

Val Thr Val Ser Leu Lys Ser Gln Ser Gly Gln Thr Glu Gln Glu Gln
            260                 265                 270

Asn Thr Phe Cys Lys Gln Ala Asn Gly Thr Trp Glu Leu Ile
        275                 280                 285


<210> SEQ ID NO 91
<211> LENGTH: 487
<212> TYPE: PRT
<213> ORGANISM: Pseudomonas putida

<400> SEQUENCE: 91

Met Pro Ile Cys Ser Ser Gly Trp Arg Gly Leu Ala Trp Trp Asp Ser
1               5                   10                  15

Ala Ser Asn Trp Arg Arg Cys Ala Asp Pro Lys Pro Asp Ser Val Arg
            20                  25                  30

Ala Arg Leu Thr Ala Thr Leu Lys Lys Pro Pro Ala Thr His Gly Ser
        35                  40                  45

Arg Gly Leu Val His Ser Ala Ile Thr Gln Ser Ile Gly Phe Gln Leu
    50                  55                  60

Ile Gly Leu Ala His Glu Gln Arg Arg Lys Gln Ala Leu Ala Phe Leu
65                  70                  75                  80

Glu Gly Val Leu Leu Phe Glu Arg Ala Val Phe Asp Gln Leu Leu Pro
                85                  90                  95

Asp Gly Ala Phe Arg Val Ala Val Val Leu Gly Leu Gly Ala Lys Val
            100                 105                 110

Thr Ala Pro Arg Arg Gln Pro Asn Leu Leu Ala Glu Gly Cys Glu Leu
        115                 120                 125

Cys Leu Gly Asp Leu Leu Leu Val Phe Ala Glu Ser Leu Phe Gln Arg
    130                 135                 140

Phe Glu Ala Ala Val Ala His Arg Val Val Leu Asp Leu Gly Leu Ala
145                 150                 155                 160

Gly Lys Ala Ala His Arg Phe Ser Gln His Arg Leu Ala Gly Val Arg
                165                 170                 175

Ala Val Arg Ala Asn Gln His Arg Ala Gln Gly Thr Leu Glu Leu Gly
            180                 185                 190

Phe Asp Ile Val Gln Phe Arg Gln Arg Leu Glu Val Gly Leu Ala His
```

```
        195                 200                 205

Asp Phe Pro His Leu Gly Ala Val Val Ala Val Gly Asp His Glu Arg
    210                 215                 220

His Arg Ala Phe Ala Ile Ala Gly Ala Leu Asp Gly Glu Val Gln Val
225                 230                 235                 240

Asp Arg Gly Thr Lys Val Thr Gly Ala Ala Asp Gln Lys Arg Ala Gly
                245                 250                 255

Tyr Trp Leu Ala His Arg His Val Gly Ala Pro Gly Glu Val Arg Arg
            260                 265                 270

Gly Gly Pro Thr Ile Gly Gly Gln Leu Gly Thr Trp Leu Asp Phe Val
        275                 280                 285

Ala Asp Ile Arg His Gln His Asp Phe Gly Pro Leu Gly Gly Asn Val
    290                 295                 300

Arg Val Ala His Leu His Ala Gln Gln Leu Asp Met Asn Ala Ala Ile
305                 310                 315                 320

Leu Ala Val Ser Val Met Gly Gln Leu Gln Arg Ile Ser Leu Gln Val
                325                 330                 335

His Pro Gly His Ile Ala Ala Asp Ile Glu Leu Val Leu Gly Pro Ala
            340                 345                 350

Arg Gln Ala Phe Phe Ser Arg Thr Thr Leu Tyr Gly Leu His Gln Ala
        355                 360                 365

Arg Gln Ala Ala His Glu Leu Leu Gly Ala Ile Gly Leu Arg Arg Arg
    370                 375                 380

His Ala Asp Leu Arg Val Gly Tyr Arg Gln Val Ala Gly Lys Arg Arg
385                 390                 395                 400

Val Gly Asn Val Pro Leu Arg Gln His Ile Leu Lys Glu Ile Ala Leu
                405                 410                 415

Leu Glu Val Val Val Val Gly Gln Arg Ser Leu Leu Ala Arg Ala Gly
            420                 425                 430

Asp His Arg Ile Ala Thr Thr Glu His Gln His Arg Cys Gly His Thr
        435                 440                 445

Ala Asn Gln Gln Leu Leu Leu Val His Leu Phe Asp His Gly Val Cys
    450                 455                 460

Leu Thr Gly Pro Trp Arg Lys Arg Cys Ser Ser Arg Ser Arg Thr Val
465                 470                 475                 480

Gly Arg Pro Arg Gly Ser Ser
                485


<210> SEQ ID NO 92
<211> LENGTH: 577
<212> TYPE: PRT
<213> ORGANISM: Glycine max

<400> SEQUENCE: 92

Met Ser Asn Ile Ala Phe Arg Ser Thr Ile Val Phe Leu Leu Phe Ser
1               5                   10                  15

Ala Val Leu Ser Thr Pro Pro Glu Asp Pro Ile Lys Cys Ala Thr Ser
            20                  25                  30

Glu Asn Thr Thr Cys Thr Ile Thr Asn Ser Tyr Gly Ala Phe Pro Asp
        35                  40                  45

Arg Ser Ile Cys Lys Ala Ala Gln Val Leu Tyr Pro Thr Thr Glu Gln
    50                  55                  60

Glu Leu Val Ser Val Val Ala Ser Ala Thr Arg Asn Lys Thr Lys Met
65                  70                  75                  80
```

-continued

```
Lys Val Ala Thr Arg Phe Ser His Ser Ile Pro Lys Leu Val Cys Pro
                85                  90                  95

Glu Gly Glu Asn Gly Leu Leu Ile Ser Thr Lys Tyr Leu Asn Lys Ile
            100                 105                 110

Leu Lys Val Asp Val Glu Thr Arg Thr Met Thr Val Glu Ser Gly Val
        115                 120                 125

Thr Leu Gln Gln Leu Ile Asn Glu Ala Ala Lys Val Gly Leu Ala Leu
    130                 135                 140

Pro Tyr Ala Pro Tyr Trp Trp Gly Leu Thr Ile Gly Gly Leu Met Gly
145                 150                 155                 160

Thr Gly Ala His Gly Ser Thr Leu Arg Gly Lys Gly Ser Ala Val His
                165                 170                 175

Asp Tyr Val Val Glu Leu Arg Ile Val Arg Pro Ala Gly Pro Glu Asp
            180                 185                 190

Gly Tyr Ala Met Val Glu Asn Leu Asn Glu Gln His Glu Asp Leu Asn
        195                 200                 205

Ala Ala Lys Val Ser Leu Gly Val Leu Gly Val Ile Ser Gln Ile Thr
    210                 215                 220

Leu Lys Leu Glu Pro Leu Phe Lys Arg Ser Ile Thr Tyr Val Ala Lys
225                 230                 235                 240

Asp Asp Ser Asp Leu Gly Gly Gln Val Val Ala Phe Gly Asp Ala His
                245                 250                 255

Glu Phe Ala Asp Ile Thr Trp Tyr Pro Ser Gln His Lys Ala Ile Tyr
            260                 265                 270

Arg Val Asp Asp Arg Val Pro Ile Asn Thr Ser Gly Asn Gly Leu Tyr
        275                 280                 285

Asp Phe Ile Pro Phe Arg Pro Thr Pro Ser Leu Ala Ser Val Phe Ile
    290                 295                 300

Arg Thr Thr Glu Glu Ile Gln Glu Ser Thr Asn Asp Ala Asn Gly Lys
305                 310                 315                 320

Cys Ile Val Ala Ser Thr Ala Ser Asn Thr Leu Ile Thr Ala Ala Tyr
                325                 330                 335

Gly Leu Thr Asn Asn Gly Ile Ile Phe Ala Gly Tyr Pro Ile Ile Gly
            340                 345                 350

Phe Gln Asn Arg Leu Gln Ser Ser Gly Ser Cys Leu Asp Ser Leu Gln
        355                 360                 365

Asp Ala Leu Ile Thr Thr Cys Ala Trp Asp Pro Arg Met Lys Gly Leu
    370                 375                 380

Phe Phe His Gln Thr Thr Phe Ser Ile Arg Leu Ser Phe Val Lys Ser
385                 390                 395                 400

Phe Ile Glu Asp Val Gln Lys Leu Val Glu Leu Glu Pro Lys Gly Leu
                405                 410                 415

Cys Val Leu Gly Leu Tyr Asn Gly Met Leu Met Arg Tyr Val Thr Ala
            420                 425                 430

Ser Ser Ala Tyr Leu Gly His Gln Glu Asn Ala Leu Asp Ile Asp Ile
        435                 440                 445

Thr Tyr Tyr Arg Ser Lys Asp Pro Met Thr Pro Arg Leu Tyr Glu Asp
    450                 455                 460

Ile Leu Glu Glu Val Glu Gln Leu Gly Ile Phe Lys Tyr Gly Gly Leu
465                 470                 475                 480

Pro His Trp Gly Lys Asn Arg Asn Leu Ala Phe Glu Gly Ala Ile Lys
                485                 490                 495

Lys Tyr Lys Ser Ala Glu Tyr Phe Leu Lys Val Lys Glu Lys Tyr Asp
```

```
            500                 505                 510

Leu Asp Gly Leu Phe Ser Ser Thr Trp Thr Asp Gln Val Leu Gly Leu
        515                 520                 525

Lys Asp Gly Val Thr Ile Leu Lys Asp Gly Cys Ala Leu Glu Gly Leu
    530                 535                 540

Cys Ile Cys Leu Gln Asp Ser His Cys Asn Pro Ser Lys Gly Tyr Tyr
545                 550                 555                 560

Cys Arg Pro Gly Lys Val Tyr Lys Glu Ala Arg Val Cys Thr Asn Leu
                565                 570                 575

Lys


<210> SEQ ID NO 93
<211> LENGTH: 619
<212> TYPE: PRT
<213> ORGANISM: Pseudomonas putida

<400> SEQUENCE: 93

Met Lys Lys His Ala Leu Ala Leu Ala Val Ile Gly Ala Cys Gly Leu
1               5                   10                  15

Val Pro Gln Ala Phe Ala His Glu Leu Ala Phe Ser Lys Lys Asp Asn
            20                  25                  30

Ile Lys Val Glu Val Pro Gly Asp Ala Thr Ser Trp Cys Lys Pro Gln
        35                  40                  45

Val Asp Leu Thr Ile Thr Arg Pro Ala Trp Asp Asn Gln Glu Leu Leu
    50                  55                  60

Ala Gly Leu Leu Thr Lys Leu Pro Phe Val Phe Ala Lys Asp Cys Ser
65                  70                  75                  80

Thr Ala Lys Val Ser Trp Lys Ala Val Asp Ala Lys Gly Asn Leu Tyr
                85                  90                  95

Ala Ser Gly Ser Gly Asn Ala Ser Asn Leu Gly Leu Val Thr Leu Ala
            100                 105                 110

Ala Ala Pro Ala Thr Ala Ala Pro Ala Pro Ala Ala Ala Pro Thr Pro
        115                 120                 125

Thr Pro Ala Pro Ala Pro Ala Pro Ala Pro Ala Pro Ala Ala Ala Ala
    130                 135                 140

Ala Pro Ala Val Val Glu Ala Ala Pro Ala Gln Ala Lys Pro Ala Pro
145                 150                 155                 160

Ala Pro Ala Pro Ala Pro Ala Pro Ala Val Ala Ala Glu Pro Ala Pro
                165                 170                 175

Ala Pro Glu Ala Pro Ala Ala Ala Pro Val Val Pro Pro Ala Pro Ala
            180                 185                 190

Pro Ala Thr Ala Val Ala Ala Ala Pro Thr Ser Asp Phe Gly Arg Ser
        195                 200                 205

Val Val Leu Glu Asn Arg Asn Leu Met Gln Val Thr Asp Gly Thr Gly
    210                 215                 220

Cys Lys Trp Val Leu Ser Thr Ser Ile Ile Gly Asp Gly Asp Thr Leu
225                 230                 235                 240

Ser Phe Gly Thr Thr Pro Ala Met Pro Cys Pro Ala Ser Gly Phe Gly
                245                 250                 255

Glu Gly Ser Phe Asp Lys Ile Ser Trp Lys Ala Val Gly Thr Tyr Arg
            260                 265                 270

Gly Asp Asn Trp Thr Arg Val Tyr Ala His Pro Ser Gly Leu Ile Phe
        275                 280                 285

Asn Lys Asn Leu Glu Pro Ala Val Lys Asp Lys Ala Val Ser Tyr Leu
```

290 295 300

Thr Pro Gln Ala Asp Gln Ala Ala Phe Leu Val Gly Glu Ile Pro Gly
305 310 315 320

Arg Gln Met Lys Val Tyr Leu Thr Phe Thr Arg Ser Ser Tyr Gly Val
325 330 335

Leu Arg Pro Phe Ser Ser Asp Pro Tyr Tyr Val Ala Val Thr Pro Asp
340 345 350

Glu Ser Phe Ala Leu Asp Ala Thr Lys Tyr Lys Glu Ala Ala Leu Glu
355 360 365

Ile Phe Asp Leu Ile Lys Thr Thr Ser Pro Thr Thr Thr Asp Val Ala
370 375 380

Asn Leu Phe Ile Val Lys Asp Leu Ser Ala Ile Ser Asn Asn Ile Trp
385 390 395 400

Gly Asn Asp Ala Gln Lys Ile Thr Arg Asn Arg Ile Gly Ile Asn Arg
405 410 415

Gln Gly Leu Phe Phe Asp Val Arg Asp Gly Ala Asn Trp Ala Val Gln
420 425 430

Arg Glu Gln Gln Arg Val Arg Glu Gln Arg Gln Arg Gln Gln Glu Leu
435 440 445

Ala Arg Val His Thr Arg Val Leu Glu Arg Tyr Gln Gln Leu Gln Asp
450 455 460

Gly Met Ser Asp Phe Lys Gly Arg Glu Thr Glu Ala Leu Ala Gln Met
465 470 475 480

Ala Gly Ile Lys Val Arg Phe Ala Ser Pro Leu Glu Gln Gln Asn Pro
485 490 495

Ala Thr Ser Ala Ser Val Val Pro Met Met Val His Val Thr Gly Lys
500 505 510

Lys Gly Asp Phe Tyr Ser Ile Asp Phe Pro Ser Asn Gly Arg Leu Val
515 520 525

Ala Asp Glu Glu Tyr Ser Glu Gly Trp Tyr Val Thr Gln Val Ala Asn
530 535 540

Ala Thr Pro Tyr Tyr Pro Leu Asp Asp Gly Arg Ala Val Pro Thr Tyr
545 550 555 560

Arg Ala Tyr Ser Ala Gly Glu Pro Glu Ala Cys Lys Gln Asp His Cys
565 570 575

Ala Asp Arg Val Ser Phe Gly Ala Val Leu Ala Lys Glu Phe Pro Asn
580 585 590

Ala Gly Ile Asp Phe Ser Trp Thr Pro Glu Val Ser Gln Gln Tyr Val
595 600 605

Asn Asp Trp Asn Asn Ala Ser Ala Met Val Gln
610 615

<210> SEQ ID NO 94
<211> LENGTH: 411
<212> TYPE: PRT
<213> ORGANISM: Pseudomonas putida

<400> SEQUENCE: 94

Met Val Leu Glu Asn Arg Asn Leu Met Gln Val Thr Asp Gly Thr Gly
1 5 10 15

Cys Lys Trp Val Leu Ser Thr Ser Ile Ile Gly Asp Gly Asp Thr Leu
20 25 30

Ser Phe Gly Thr Thr Pro Ala Met Pro Cys Pro Ala Ser Gly Phe Gly
35 40 45

```
Glu Gly Ser Phe Asp Lys Ile Ser Trp Lys Ala Val Gly Thr Tyr Arg
    50                  55                  60

Gly Asp Asn Trp Thr Arg Val Tyr Ala His Pro Ser Gly Leu Ile Phe
65                  70                  75                  80

Asn Lys His Leu Glu Pro Ala Val Lys Asp Lys Ala Val Ser Tyr Leu
                85                  90                  95

Thr Pro Gln Ala Asp Gln Ala Ala Phe Leu Val Gly Glu Ile Pro Gly
            100                 105                 110

Arg Gln Met Lys Val Tyr Leu Thr Phe Thr Arg Ser Ser Tyr Gly Val
        115                 120                 125

Leu Arg Pro Phe Gly Ser Asp Pro Tyr Tyr Val Ala Val Thr Pro Asp
    130                 135                 140

Glu Ser Phe Ala Leu Asp Ala Thr Lys Tyr Lys Glu Ala Ala Leu Glu
145                 150                 155                 160

Ile Phe Asp Leu Ile Lys Thr Thr Ser Pro Thr Thr Thr Asp Val Ala
                165                 170                 175

Asn Leu Phe Ile Val Lys Asp Leu Ser Ala Ile Ser Asn Asn Ile Trp
            180                 185                 190

Gly Asn Asp Ala Gln Lys Ile Thr Arg Asn Arg Ile Gly Ile Asn Arg
        195                 200                 205

Gln Gly Leu Phe Phe Asp Val Arg Asp Gly Ala Asn Trp Ala Val Gln
    210                 215                 220

Arg Glu Gln Gln Arg Val Arg Glu Gln Arg Gln Arg Gln Gln Glu Leu
225                 230                 235                 240

Ala Arg Val His Thr Arg Val Leu Glu Arg Tyr Gln Gln Leu Gln Asp
                245                 250                 255

Gly Met Ser Asp Phe Lys Gly Arg Glu Thr Glu Ala Leu Ala Gln Met
            260                 265                 270

Ala Gly Ile Lys Val Arg Phe Ala Ser Pro Leu Glu Gln Gln Asn Pro
        275                 280                 285

Ala Thr Ser Ala Ser Val Val Pro Met Met Val His Val Thr Gly Lys
    290                 295                 300

Lys Gly Asp Phe Tyr Ser Ile Asp Phe Pro Ser Asn Gly Arg Leu Val
305                 310                 315                 320

Ala Asp Glu Glu Tyr Ser Glu Gly Trp Tyr Val Thr Gln Val Ala Asn
                325                 330                 335

Ala Thr Pro Tyr Tyr Pro Leu Asp Asp Gly Arg Ala Val Pro Thr Tyr
            340                 345                 350

Arg Ala Tyr Ser Ala Gly Glu Pro Glu Ala Cys Lys Gln Asp His Cys
        355                 360                 365

Ala Asp Arg Val Ser Phe Gly Ala Val Leu Ala Lys Glu Phe Pro Asn
    370                 375                 380

Ala Gly Ile Asp Phe Ser Trp Thr Pro Glu Val Ser Gln Gln Tyr Val
385                 390                 395                 400

Asn Asp Trp Asn Asn Ala Ser Ala Met Val Gln
                405                 410
```

```
<210> SEQ ID NO 95
<211> LENGTH: 632
<212> TYPE: PRT
<213> ORGANISM: Pseudomonas putida

<400> SEQUENCE: 95

Met Lys Lys His Ala Leu Ala Leu Ala Val Ile Gly Ala Cys Gly Leu
1               5                   10                  15
```

-continued

```
Val Pro Gln Ala Phe Ala His Glu Leu Ala Phe Ser Lys Lys Asp Asn
            20                  25                  30

Ile Lys Val Glu Val Pro Gly Asp Ala Thr Thr Trp Cys Lys Pro Gln
        35                  40                  45

Val Asp Leu Thr Ile Thr Arg Pro Ala Trp Asp Asn Gln Glu Leu Leu
    50                  55                  60

Ser Gly Leu Leu Thr Lys Leu Pro Phe Val Phe Ala Lys Asp Cys Ser
65                  70                  75                  80

Thr Ala Lys Val Ser Trp Lys Ala Val Asp Ala Lys Gly Asn Leu Tyr
                85                  90                  95

Ala Ser Gly Ser Gly Asn Ala Ser Asn Leu Gly Leu Val Thr Leu Ala
            100                 105                 110

Ala Ala Pro Ala Thr Ala Ala Pro Ala Pro Ala Ala Ala Val Ala Pro
        115                 120                 125

Ala Pro Ala Pro Ala Gln Pro Glu Ala Pro Ala Ala Ala Ala Pro Thr
    130                 135                 140

Pro Ala Pro Ala Pro Ala Pro Ala Pro Ala Pro Ala Ala Ala Ala Ala
145                 150                 155                 160

Pro Ala Val Val Glu Ala Ala Pro Ala Gln Ala Lys Pro Ala Pro Ala
                165                 170                 175

Pro Ala Pro Ala Pro Ala Val Ala Ala Glu Pro Ala Pro Thr Pro Glu
            180                 185                 190

Ala Pro Ala Ala Ala Pro Val Val Pro Pro Ala Pro Ala Pro Ala Thr
        195                 200                 205

Ala Val Ala Ala Ala Pro Thr Ser Asp Phe Gly Arg Ser Val Val Leu
    210                 215                 220

Glu Asn Arg Asn Leu Met Gln Val Thr Asp Gly Thr Gly Cys Lys Trp
225                 230                 235                 240

Val Leu Ser Thr Ser Ile Ile Gly Asp Gly Asp Thr Leu Ser Phe Gly
                245                 250                 255

Thr Thr Pro Ala Met Pro Cys Pro Ala Ser Gly Phe Gly Glu Gly Ser
            260                 265                 270

Phe Asp Lys Ile Ser Trp Lys Ala Val Gly Thr Tyr Arg Gly Asp Asn
        275                 280                 285

Trp Thr Arg Val Tyr Ala His Pro Ser Gly Leu Ile Phe Asn Lys His
    290                 295                 300

Leu Glu Pro Ala Val Lys Asp Lys Ala Val Ser Tyr Leu Thr Pro Gln
305                 310                 315                 320

Ala Asp Gln Ala Ala Phe Leu Val Gly Glu Ile Pro Gly Arg Gln Met
                325                 330                 335

Lys Val Tyr Leu Thr Phe Thr Arg Ser Ser Tyr Gly Val Leu Arg Pro
            340                 345                 350

Phe Gly Ser Asp Pro Tyr Tyr Val Ala Val Thr Pro Asp Glu Ser Phe
        355                 360                 365

Ala Leu Asp Ala Thr Lys Tyr Lys Glu Ala Ala Leu Glu Ile Phe Asp
    370                 375                 380

Leu Ile Lys Thr Thr Ser Pro Thr Thr Thr Asp Val Ala Asn Leu Phe
385                 390                 395                 400

Ile Val Lys Asp Leu Ser Ala Ile Ser Asn Asn Ile Trp Gly Asn Asp
                405                 410                 415

Ala Gln Lys Ile Thr Arg Asn Arg Ile Gly Ile Asn Arg Gln Gly Leu
            420                 425                 430

Phe Phe Asp Val Arg Asp Gly Ala Asn Trp Ala Val Gln Arg Glu Gln
```

```
        435                 440                 445

Gln Arg Val Arg Glu Gln Arg Gln Arg Gln Gln Glu Leu Ala Arg Val
    450                 455                 460

His Thr Arg Val Leu Glu Arg Tyr Gln Gln Leu Gln Asp Gly Met Ser
465                 470                 475                 480

Asp Phe Lys Gly Arg Glu Thr Glu Ala Leu Ala Gln Met Ala Gly Ile
                485                 490                 495

Lys Val Arg Phe Ala Ser Pro Leu Glu Gln Gln Asn Pro Ala Thr Ser
            500                 505                 510

Ala Ser Val Val Pro Met Met Val His Val Thr Gly Lys Lys Gly Asp
        515                 520                 525

Phe Tyr Ser Ile Asp Phe Pro Ser Asn Gly Arg Leu Val Ala Asp Glu
    530                 535                 540

Glu Tyr Ser Glu Gly Trp Tyr Val Thr Gln Val Ala Asn Ala Thr Pro
545                 550                 555                 560

Tyr Tyr Pro Leu Asp Asp Gly Arg Ala Val Pro Thr Tyr Arg Ala Tyr
                565                 570                 575

Ser Ala Gly Glu Pro Glu Ala Cys Lys Gln Asp His Cys Ala Asp Arg
            580                 585                 590

Val Ser Phe Gly Ala Val Leu Ala Lys Glu Phe Pro Asn Ala Gly Ile
        595                 600                 605

Asp Phe Ser Trp Thr Pro Glu Val Ser Gln Gln Tyr Val Asn Asp Trp
    610                 615                 620

Asn Asn Ala Ser Ala Met Val Gln
625                 630


<210> SEQ ID NO 96
<211> LENGTH: 642
<212> TYPE: PRT
<213> ORGANISM: Pseudomonas putida

<400> SEQUENCE: 96

Met Lys Lys His Ala Leu Ala Leu Ala Val Ile Gly Ala Cys Gly Leu
1               5                   10                  15

Val Pro Gln Ala Phe Ala His Glu Leu Ala Phe Ser Lys Lys Asp Asn
            20                  25                  30

Ile Lys Val Glu Val Pro Gly Asp Ala Thr Thr Trp Cys Lys Pro Gln
        35                  40                  45

Val Asp Leu Thr Ile Thr Arg Pro Ala Trp Asp Asn Gln Glu Leu Leu
    50                  55                  60

Ser Gly Leu Leu Thr Lys Leu Pro Phe Val Phe Ala Lys Asp Cys Ser
65                  70                  75                  80

Thr Ala Lys Val Ser Trp Lys Ala Val Asp Ala Lys Gly Asn Leu Tyr
                85                  90                  95

Ala Ser Gly Ser Gly Asn Ala Ser Asn Leu Gly Leu Val Thr Leu Ala
            100                 105                 110

Ala Ala Pro Ala Pro Ala Pro Ala Pro Ala Pro Ala Pro Ala Pro Ala
        115                 120                 125

Ala Ala Ala Pro Ala Pro Ala Ala Ala Val Ala Pro Ala Pro Ala Pro
    130                 135                 140

Ala Gln Pro Glu Ala Pro Ala Ala Ala Ala Pro Thr Pro Ala Pro Ala
145                 150                 155                 160

Pro Ala Pro Ala Pro Ala Ala Ala Ala Ala Pro Ala Val Val Glu Ala
                165                 170                 175
```

```
Ala Ala Ala Gln Ala Lys Pro Ala Pro Ala Pro Ala Pro Ala Pro Ala
            180                 185                 190

Val Ala Ala Glu Pro Ala Pro Thr Pro Glu Ala Pro Ala Ala Ala Pro
        195                 200                 205

Val Val Pro Pro Ala Pro Ala Pro Ala Thr Ala Val Ala Ala Ala Pro
    210                 215                 220

Thr Ser Asp Phe Gly Arg Ser Val Val Leu Glu Asn Arg Asn Leu Met
225                 230                 235                 240

Gln Val Thr Asp Gly Thr Gly Cys Lys Trp Val Leu Ser Thr Ser Ile
                245                 250                 255

Ile Gly Asp Gly Asp Thr Leu Ser Phe Gly Thr Thr Pro Ala Met Pro
            260                 265                 270

Cys Pro Ala Ser Gly Phe Gly Glu Gly Ser Phe Asp Lys Ile Ser Trp
        275                 280                 285

Lys Ala Val Gly Thr Tyr Arg Gly Asp Asn Trp Thr Arg Val Tyr Ala
    290                 295                 300

His Pro Ser Gly Leu Ile Phe Asn Lys Asn Leu Glu Pro Ala Val Lys
305                 310                 315                 320

Asp Lys Ala Val Ser Tyr Leu Thr Pro Gln Ala Asp Gln Ala Ala Phe
                325                 330                 335

Leu Val Gly Glu Ile Pro Gly Arg Gln Met Lys Val Tyr Leu Thr Phe
            340                 345                 350

Thr Arg Ser Ser Tyr Gly Val Leu Arg Pro Phe Gly Ser Asp Pro Tyr
        355                 360                 365

Tyr Val Ala Val Thr Pro Asp Glu Ser Phe Ala Leu Asp Ala Thr Lys
    370                 375                 380

Tyr Lys Glu Ala Ala Leu Glu Ile Phe Asp Leu Ile Lys Thr Thr Ser
385                 390                 395                 400

Pro Thr Thr Thr Asp Val Ala Asn Leu Phe Ile Val Lys Asp Leu Ser
                405                 410                 415

Ala Ile Ser Asn Asn Ile Trp Gly Asn Asp Ala Gln Lys Ile Thr Arg
            420                 425                 430

Asn Arg Ile Gly Ile Asn Arg Gln Gly Leu Phe Phe Asp Val Arg Asp
        435                 440                 445

Gly Ala Asn Trp Ala Val Gln Arg Glu Gln Gln Arg Val Arg Glu Gln
    450                 455                 460

Arg Gln Arg Gln Gln Glu Leu Ala Arg Val His Thr Arg Val Leu Glu
465                 470                 475                 480

Arg Tyr Gln Gln Leu Gln Asp Gly Met Ser Asp Phe Lys Gly Arg Glu
                485                 490                 495

Thr Glu Ala Leu Ala Gln Met Ala Gly Ile Lys Val Arg Phe Ala Ser
            500                 505                 510

Pro Leu Glu Gln Gln Asn Pro Ala Thr Ser Ala Ser Val Val Pro Met
        515                 520                 525

Met Val His Val Thr Gly Lys Lys Gly Asp Phe Tyr Ser Ile Asp Phe
    530                 535                 540

Pro Ser Asn Gly Arg Leu Val Ala Asp Glu Glu Tyr Ser Glu Gly Trp
545                 550                 555                 560

Tyr Val Thr Gln Val Ala Asn Ala Thr Pro Tyr Tyr Pro Leu Asp Asp
                565                 570                 575

Gly Arg Ala Val Pro Thr Tyr Arg Ala Tyr Ser Ala Gly Glu Pro Glu
            580                 585                 590

Ala Cys Lys Gln Asp His Cys Ala Asp Arg Val Ser Phe Gly Ala Val
```

```
        595                 600                 605

Leu Ala Lys Glu Phe Pro Asn Ala Gly Ile Asp Phe Ser Trp Thr Pro
    610                 615                 620

Glu Val Ser Gln Gln Tyr Val Asn Asp Trp Asn Asn Ala Ser Ala Met
625                 630                 635                 640

Val Gln


<210> SEQ ID NO 97
<211> LENGTH: 637
<212> TYPE: PRT
<213> ORGANISM: Pseudomonas putida

<400> SEQUENCE: 97

Met Lys Lys His Ala Leu Ala Leu Ala Val Val Gly Ala Cys Gly Leu
1               5                   10                  15

Val Pro Gln Ala Phe Ala His Glu Leu Ala Phe Ser Lys Lys Glu Asn
            20                  25                  30

Ile Lys Val Glu Val Pro Gly Asp Ala Ala Thr Trp Cys Lys Pro Glu
        35                  40                  45

Val Glu Leu Thr Ile Thr Arg Pro Ala Trp Asp Lys Gln Glu Leu Leu
    50                  55                  60

Ser Gly Leu Leu Thr Lys Leu Pro Phe Val Phe Ala Lys Asp Cys Ala
65                  70                  75                  80

Thr Ala Lys Val Ser Trp Lys Ala Val Asp Ala Lys Gly Asn Leu Tyr
                85                  90                  95

Ala Ser Gly Ser Gly Asn Ala Thr Asn Leu Gly Leu Val Thr Leu Ala
            100                 105                 110

Val Ala Pro Ala Ala Ala Ser Ala Ala Pro Ala Pro Ala Pro Ala Pro
        115                 120                 125

Ala Pro Ala Pro Ala Pro Ala Pro Ala Pro Ala Pro Ala Val Ala Ala
    130                 135                 140

Leu Ala Pro Ala Ala Pro Ala Val Pro Ala Pro Ala Glu Ala Pro Ala
145                 150                 155                 160

Ala Val Ala Ala Ala Pro Ala Pro Ala Val Val Glu Pro Ala Pro Ala
                165                 170                 175

Lys Ala Glu Val Ala Pro Ala Pro Val Val Ala Ala Glu Pro Ala Pro
            180                 185                 190

Ala Pro Val Ala Glu Thr Pro Val Ala Ala Pro Val Ala Pro Pro Val
        195                 200                 205

Pro Ala Pro Ala Asp Ala Val Ala Ala Ala Pro Thr Ser Asp Phe Gly
    210                 215                 220

Arg Ala Val Val Leu Gln Asn Arg Asn Leu Met Gln Val Thr Asp Gly
225                 230                 235                 240

Thr Gly Cys Lys Trp Val Leu Ser Thr Ser Ile Ile Ser Asp Gly Asp
                245                 250                 255

Thr Leu Ser Phe Gly Thr Thr Pro Val Met Pro Cys Pro Ala Ser Gly
            260                 265                 270

Phe Gly Glu Gly Ser Phe Glu Lys Ile Ser Trp Lys Ala Val Gly Thr
        275                 280                 285

Tyr Arg Gly Asp Asn Trp Thr Arg Val Tyr Ala His Pro Ser Gly Leu
    290                 295                 300

Ile Phe Asn Lys Asn Leu Glu Ser Ala Val Lys Asp Lys Ala Val Ser
305                 310                 315                 320

Tyr Leu Thr Ala Asp Ala Asp Gln Ala Ala Phe Leu Val Gly Glu Ile
```

-continued

```
                325                 330                 335

Pro Ser Arg Gln Met Lys Val Tyr Leu Thr Phe Thr Arg Ser Ser Tyr
            340                 345                 350

Gly Val Leu Arg Pro Phe Ser Ser Asp Pro Tyr Tyr Val Ala Val Thr
        355                 360                 365

Pro Asp Glu Ser Phe Ala Leu Asp Ala Ala Lys Tyr Lys Glu Ala Ala
    370                 375                 380

Leu Glu Ile Phe Asp Leu Ile Lys Ala Thr Ser Pro Thr Thr Thr Asp
385                 390                 395                 400

Val Ala Asn Leu Phe Ile Val Lys Asp Ile Ser Ala Ile Thr Asn Ser
                405                 410                 415

Met Trp Gly Asn Asp Ala Gln Lys Ile Thr Arg Asn Arg Ile Gly Ile
            420                 425                 430

Thr Arg Gln Gly Leu Phe Phe Asp Val Arg Glu Gly Ala Asn Trp Ala
        435                 440                 445

Val Gln Arg Glu Gln Gln Arg Val Arg Glu Glu Arg Gln Arg Gln Gln
    450                 455                 460

Glu Leu Ala Arg Val His Thr Arg Val Leu Glu Arg Tyr Gln Gln Leu
465                 470                 475                 480

Gln Asp Gly Met Ser Asp Phe Lys Gly Arg Glu Thr Glu Ala Leu Ala
                485                 490                 495

Gln Met Ala Gly Ile Lys Val Arg Phe Ala Ser Pro Leu Ala Gln Gln
            500                 505                 510

Asp Pro Ala Thr Ser Ala Arg Val Ala Pro Met Met Val His Val Thr
        515                 520                 525

Gly Lys Lys Gly Asp Phe Tyr Thr Leu Asp Phe Pro Ser Lys Gly Arg
    530                 535                 540

Leu Val Ala Asp Glu Glu Tyr Ser Glu Gly Trp Tyr Val Thr Gln Val
545                 550                 555                 560

Ala Asn Ala Thr Pro Tyr Tyr Pro Leu Asp Asp Gly Arg Ala Val Pro
                565                 570                 575

Thr Tyr Arg Ala Tyr Ser Ala Gly Glu Pro Glu Ala Cys Gln Gln Asp
            580                 585                 590

His Cys Ala Asp Arg Val Ser Phe Gly Ala Val Leu Ala Lys Glu Phe
        595                 600                 605

Pro Asn Ala Gly Ile Asp Phe Ser Trp Thr Pro Glu Val Ser Gln Lys
    610                 615                 620

Tyr Val Asn Asp Trp Asn Asn Ala Ser Ala Met Val Gln
625                 630                 635


<210> SEQ ID NO 98
<211> LENGTH: 548
<212> TYPE: PRT
<213> ORGANISM: Lactococcus lactis

<400> SEQUENCE: 98

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60
```

-continued

```
Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Pro Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Asn Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Gly Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
```

```
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Val Leu Ala Lys
        515                 520                 525

Glu Asp Ala Pro Lys Val Leu Lys Lys Met Gly Lys Leu Phe Ala Glu
    530                 535                 540

Gln Asn Lys Ser
545


<210> SEQ ID NO 99
<211> LENGTH: 548
<212> TYPE: PRT
<213> ORGANISM: Lactococcus lactis

<400> SEQUENCE: 99

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Val Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Val Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Pro Asn Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300
```

```
Ile Asn Glu Gly Lys Ile Phe Ser Glu Ser Ile Gln Asn Phe Asp Phe
305                 310                 315                 320

Glu Ser Leu Ile Ser Ser Leu Leu Asp Leu Ser Gly Ile Glu Tyr Lys
                325                 330                 335

Gly Lys Tyr Ile Asp Lys Lys Gln Glu Asn Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Phe Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Val Leu Ala Lys
        515                 520                 525

Glu Asp Ala Pro Lys Val Leu Lys Lys Met Gly Lys Leu Phe Ala Glu
    530                 535                 540

Gln Asn Lys Ser
545


<210> SEQ ID NO 100
<211> LENGTH: 547
<212> TYPE: PRT
<213> ORGANISM: Lactococcus lactis

<400> SEQUENCE: 100

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125
```

```
Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
    370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
    530                 535                 540
```

Gln Asn Lys
545

<210> SEQ ID NO 101
<211> LENGTH: 570
<212> TYPE: PRT
<213> ORGANISM: Lactococcus lactis

<400> SEQUENCE: 101

Met Gly Ser Ser His His His His His His Ser Ser Gly Leu Val Pro
1               5                   10                  15

Arg Gly Ser His Met Ala Ser Met Tyr Thr Val Gly Asp Tyr Leu Leu
            20                  25                  30

Asp Arg Leu His Glu Leu Gly Ile Glu Glu Ile Phe Gly Val Pro Gly
        35                  40                  45

Asp Tyr Asn Leu Gln Phe Leu Asp Gln Ile Ile Ser Arg Glu Asp Met
    50                  55                  60

Lys Trp Ile Gly Asn Ala Asn Glu Leu Asn Ala Ser Tyr Met Ala Asp
65                  70                  75                  80

Gly Tyr Ala Arg Thr Lys Lys Ala Ala Ala Phe Leu Thr Thr Phe Gly
                85                  90                  95

Val Gly Glu Leu Ser Ala Ile Asn Gly Leu Ala Gly Ser Tyr Ala Glu
            100                 105                 110

Asn Leu Pro Val Val Glu Ile Val Gly Ser Pro Thr Ser Lys Val Gln
        115                 120                 125

Asn Asp Gly Lys Phe Val His His Thr Leu Ala Asp Gly Asp Phe Lys
    130                 135                 140

His Phe Met Lys Met His Glu Pro Val Thr Ala Ala Arg Thr Leu Leu
145                 150                 155                 160

Thr Ala Glu Asn Ala Thr Tyr Glu Ile Asp Arg Val Leu Ser Gln Leu
                165                 170                 175

Leu Lys Glu Arg Lys Pro Val Tyr Ile Asn Leu Pro Val Asp Val Ala
            180                 185                 190

Ala Ala Lys Ala Glu Lys Pro Ala Leu Ser Leu Glu Lys Glu Ser Ser
        195                 200                 205

Thr Thr Asn Thr Thr Glu Gln Val Ile Leu Ser Lys Ile Glu Glu Ser
    210                 215                 220

Leu Lys Asn Ala Gln Lys Pro Val Val Ile Ala Gly His Glu Val Ile
225                 230                 235                 240

Ser Phe Gly Leu Glu Lys Thr Val Thr Gln Phe Val Ser Glu Thr Lys
                245                 250                 255

Leu Pro Ile Thr Thr Leu Asn Phe Gly Lys Ser Ala Val Asp Glu Ser
            260                 265                 270

Leu Pro Ser Phe Leu Gly Ile Tyr Asn Gly Lys Leu Ser Glu Ile Ser
        275                 280                 285

Leu Lys Asn Phe Val Glu Ser Ala Asp Phe Ile Leu Met Leu Gly Val
    290                 295                 300

Lys Leu Thr Asp Ser Ser Thr Gly Ala Phe Thr His His Leu Asp Glu
305                 310                 315                 320

Asn Lys Met Ile Ser Leu Asn Ile Asp Glu Gly Ile Ile Phe Asn Lys
                325                 330                 335

Val Val Glu Asp Phe Asp Phe Arg Ala Val Val Ser Ser Leu Ser Glu
            340                 345                 350

Leu Lys Gly Ile Glu Tyr Glu Gly Gln Tyr Ile Asp Lys Gln Tyr Glu
        355                 360                 365

```
Glu Phe Ile Pro Ser Ser Ala Pro Leu Ser Gln Asp Arg Leu Trp Gln
    370                 375                 380

Ala Val Glu Ser Leu Thr Gln Ser Asn Glu Thr Ile Val Ala Glu Gln
385                 390                 395                 400

Gly Thr Ser Phe Phe Gly Ala Ser Thr Ile Phe Leu Lys Ser Asn Ser
                405                 410                 415

Arg Phe Ile Gly Gln Pro Leu Trp Gly Ser Ile Gly Tyr Thr Phe Pro
            420                 425                 430

Ala Ala Leu Gly Ser Gln Ile Ala Asp Lys Glu Ser Arg His Leu Leu
        435                 440                 445

Phe Ile Gly Asp Gly Ser Leu Gln Leu Thr Val Gln Glu Leu Gly Leu
    450                 455                 460

Ser Ile Arg Glu Lys Leu Asn Pro Ile Cys Phe Ile Ile Asn Asn Asp
465                 470                 475                 480

Gly Tyr Thr Val Glu Arg Glu Ile His Gly Pro Thr Gln Ser Tyr Asn
                485                 490                 495

Asp Ile Pro Met Trp Asn Tyr Ser Lys Leu Pro Glu Thr Phe Gly Ala
            500                 505                 510

Thr Glu Asp Arg Val Val Ser Lys Ile Val Arg Thr Glu Asn Glu Phe
        515                 520                 525

Val Ser Val Met Lys Glu Ala Gln Ala Asp Val Asn Arg Met Tyr Trp
    530                 535                 540

Ile Glu Leu Val Leu Glu Lys Glu Asp Ala Pro Lys Leu Leu Lys Lys
545                 550                 555                 560

Met Gly Lys Leu Phe Ala Glu Gln Asn Lys
                565                 570


<210> SEQ ID NO 102
<211> LENGTH: 457
<212> TYPE: PRT
<213> ORGANISM: Lactococcus lactis

<400> SEQUENCE: 102

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
```

```
                165                 170                 175

Ser Leu Pro Leu Lys Lys Glu Asn Pro Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asn Glu Gly Lys Ile Phe Asn Glu Arg Ile Gln Asn Phe Asp Phe
305                 310                 315                 320

Glu Ser Leu Ile Ser Ser Leu Leu Asp Leu Ser Gly Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Arg Lys Leu Gln Val Gln Val Ser Gln Pro
        435                 440                 445

Ser Ser Ser His Met Asn Ser Tyr Ser
    450                 455


<210> SEQ ID NO 103
<211> LENGTH: 387
<212> TYPE: PRT
<213> ORGANISM: Escherichia coli

<400> SEQUENCE: 103

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80
```

```
Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385


<210> SEQ ID NO 104
<211> LENGTH: 387
<212> TYPE: PRT
<213> ORGANISM: Escherichia coli

<400> SEQUENCE: 104

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60
```

Ile Glu Pro Asn Pro Ala Tyr Glu Thr Leu Met Asn Ala Val Lys Leu
65 70 75 80

Val Arg Glu Gln Lys Val Thr Phe Leu Leu Ala Val Gly Gly Gly Ser
85 90 95

Val Leu Asp Gly Thr Lys Phe Ile Ala Ala Ala Asn Tyr Pro Glu
100 105 110

Asn Ile Asp Pro Trp His Ile Leu Gln Thr Gly Gly Lys Glu Ile Lys
115 120 125

Ser Ala Ile Pro Met Gly Cys Val Leu Thr Leu Pro Ala Thr Gly Ser
130 135 140

Glu Ser Asn Ala Gly Ala Val Ile Ser Arg Lys Thr Thr Gly Asp Lys
145 150 155 160

Gln Ala Phe His Ser Ala His Val Gln Pro Val Phe Ala Val Leu Asp
165 170 175

Pro Val Tyr Thr Tyr Thr Leu Pro Pro Arg Gln Val Ala Asn Gly Val
180 185 190

Val Asp Ala Phe Val His Thr Val Glu Gln Tyr Val Thr Lys Pro Val
195 200 205

Asp Ala Lys Ile Gln Asp Arg Phe Ala Glu Gly Ile Leu Leu Thr Leu
210 215 220

Ile Glu Asp Gly Pro Lys Ala Leu Lys Glu Pro Glu Asn Tyr Asp Val
225 230 235 240

Arg Ala Asn Val Met Trp Ala Ala Thr Gln Ala Leu Asn Gly Leu Ile
245 250 255

Gly Ala Gly Val Pro Gln Asp Trp Ala Thr His Met Leu Gly His Glu
260 265 270

Leu Thr Ala Met His Gly Leu Asp His Ala Gln Thr Leu Ala Ile Val
275 280 285

Leu Pro Ala Leu Trp Asn Glu Lys Arg Asp Thr Lys Arg Ala Lys Leu
290 295 300

Leu Gln Tyr Ala Glu Arg Ile Trp Asn Ile Thr Glu Gly Ser Asp Asp
305 310 315 320

Glu Arg Ile Asp Ala Ala Ile Ala Ala Thr Arg Asn Phe Phe Glu Gln
325 330 335

Leu Gly Val Pro Thr His Leu Ser Asp Tyr Gly Leu Asp Gly Ser Ser
340 345 350

Ile Pro Ala Leu Leu Lys Lys Leu Glu Glu His Gly Met Thr Gln Leu
355 360 365

Gly Glu Asn His Asp Ile Thr Leu Asp Val Ser Arg Arg Ile Tyr Glu
370 375 380

Ala Ala Arg
385

<210> SEQ ID NO 105
<211> LENGTH: 387
<212> TYPE: PRT
<213> ORGANISM: Escherichia coli

<400> SEQUENCE: 105

Met Asn Asn Phe Asn Leu His Thr Pro Thr Arg Ile Leu Phe Gly Lys
1 5 10 15

Gly Ala Ile Ala Gly Leu Arg Glu Gln Ile Pro His Asp Ala Arg Val
20 25 30

Leu Ile Thr Tyr Gly Gly Gly Ser Val Lys Lys Thr Gly Val Leu Asp

```
        35                  40                  45

Gln Val Leu Asn Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385


<210> SEQ ID NO 106
<211> LENGTH: 387
<212> TYPE: PRT
<213> ORGANISM: Escherichia coli

<400> SEQUENCE: 106

Met Asn Asn Phe Asn Leu His Thr Pro Thr Arg Ile Leu Phe Gly Lys
1               5                   10                  15
```

```
Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Glu Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385
```

<210> SEQ ID NO 107
<211> LENGTH: 387
<212> TYPE: PRT
<213> ORGANISM: Escherichia coli

<400> SEQUENCE: 107

-continued

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Lys
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385
```

<210> SEQ ID NO 108
<211> LENGTH: 38

<212> TYPE: DNA
<213> ORGANISM: artificial
<220> FEATURE:
<223> OTHER INFORMATION: synthetic oligonucleotide primer

<400> SEQUENCE: 108
gggcccggta ccatgtcctc agccatctat cccagcct 38

<210> SEQ ID NO 109
<211> LENGTH: 57
<212> TYPE: DNA
<213> ORGANISM: artificial
<220> FEATURE:
<223> OTHER INFORMATION: synthetic oligonucleotide primer

<400> SEQUENCE: 109
gggcccgctc agcaagcttg ctagcggatc cttaacgcca gccggcgtcg atccagt 57

<210> SEQ ID NO 110
<211> LENGTH: 52
<212> TYPE: DNA
<213> ORGANISM: artificial
<220> FEATURE:
<223> OTHER INFORMATION: synthetic oligonucleotide primer

<400> SEQUENCE: 110
gggcccggat ccaggagaaa ttaactatga ccgctcaagt cacttgcgta tg 52

<210> SEQ ID NO 111
<211> LENGTH: 44
<212> TYPE: DNA
<213> ORGANISM: artificial
<220> FEATURE:
<223> OTHER INFORMATION: synthetic oligonucleotide primer

<400> SEQUENCE: 111
gggcccaagc ttgctagctt agacaaggcg gacctcatgc tggg 44

<210> SEQ ID NO 112
<211> LENGTH: 52
<212> TYPE: DNA
<213> ORGANISM: artificial
<220> FEATURE:
<223> OTHER INFORMATION: synthetic oligonucleotide primer

<400> SEQUENCE: 112
gggcccgcta gcaggagaaa ttaactatga ggtccgcctt gtctaaccgc ac 52

<210> SEQ ID NO 113
<211> LENGTH: 38
<212> TYPE: DNA
<213> ORGANISM: artificial
<220> FEATURE:
<223> OTHER INFORMATION: synthetic oligonucleotide primer

<400> SEQUENCE: 113
gggcccaagc ttttagtggt tgtggcgggg cagcttgg 38

<210> SEQ ID NO 114
<211> LENGTH: 52
<212> TYPE: DNA
<213> ORGANISM: artificial
<220> FEATURE:
<223> OTHER INFORMATION: synthetic oligonucleotide primer

<400> SEQUENCE: 114
gggcccaagc ttaggagaaa ttaactatgg tttgtcggcg gcttctagca tg 52

<210> SEQ ID NO 115
<211> LENGTH: 59
<212> TYPE: DNA
<213> ORGANISM: artificial
<220> FEATURE:
<223> OTHER INFORMATION: synthetic oligonucleotide primer

<400> SEQUENCE: 115
gcgcagctgg cgttgttgtc cttggccttt ctgagcagca gggccgaacg accttcgaa 59

<210> SEQ ID NO 116
<211> LENGTH: 39
<212> TYPE: DNA
<213> ORGANISM: artificial
<220> FEATURE:
<223> OTHER INFORMATION: synthetic oligonucleotide primer

<400> SEQUENCE: 116
gggcccgctc agcttagagg aggccgcggc cggccaggt 39

<210> SEQ ID NO 117
<211> LENGTH: 60
<212> TYPE: DNA
<213> ORGANISM: artificial
<220> FEATURE:
<223> OTHER INFORMATION: synthetic oligonucleotide primer

<400> SEQUENCE: 117
actgaccgaa ttcattaaag aggagaaagg taccatgtat acagtaggag attacctatt 60

<210> SEQ ID NO 118
<211> LENGTH: 26
<212> TYPE: DNA
<213> ORGANISM: artificial
<220> FEATURE:
<223> OTHER INFORMATION: synthetic oligonucleotide primer

<400> SEQUENCE: 118
ttatgattta ttttgttcag caaata 26

<210> SEQ ID NO 119
<211> LENGTH: 60
<212> TYPE: DNA
<213> ORGANISM: artificial
<220> FEATURE:
<223> OTHER INFORMATION: synthetic oligonucleotide primer

<400> SEQUENCE: 119
ctgaacaaaa taaatcataa aggagaaatt aactatgaac aactttaatc tgcacacccc 60

<210> SEQ ID NO 120
<211> LENGTH: 60
<212> TYPE: DNA
<213> ORGANISM: artificial
<220> FEATURE:
<223> OTHER INFORMATION: synthetic oligonucleotide primer

<400> SEQUENCE: 120
actgaccgaa ttcattaaag aggagaaagg taccatggct tcggtacacg gcaccacata 60

<210> SEQ ID NO 121
<211> LENGTH: 26
<212> TYPE: DNA
<213> ORGANISM: artificial

<220> FEATURE:
<223> OTHER INFORMATION: synthetic oligonucleotide primer

<400> SEQUENCE: 121
ttacttcacc gggcttacgg tgctta 26

<210> SEQ ID NO 122
<211> LENGTH: 38
<212> TYPE: DNA
<213> ORGANISM: artificial
<220> FEATURE:
<223> OTHER INFORMATION: synthetic oligonucleotide primer

<400> SEQUENCE: 122
gggcccggta ccatgaccga caccctgcgc cattacat 38

<210> SEQ ID NO 123
<211> LENGTH: 38
<212> TYPE: DNA
<213> ORGANISM: artificial
<220> FEATURE:
<223> OTHER INFORMATION: synthetic oligonucleotide primer

<400> SEQUENCE: 123
gggccctcta gattacgacc acgagtagga ggttttgg 38

<210> SEQ ID NO 124
<211> LENGTH: 60
<212> TYPE: DNA
<213> ORGANISM: artificial
<220> FEATURE:
<223> OTHER INFORMATION: synthetic oligonucleotide primer

<400> SEQUENCE: 124
attgtgagcg gataacaatt tcacacagga aacagctatg accatgatta cgccaagctt 60

<210> SEQ ID NO 125
<211> LENGTH: 60
<212> TYPE: DNA
<213> ORGANISM: artificial
<220> FEATURE:
<223> OTHER INFORMATION: synthetic oligonucleotide primer

<400> SEQUENCE: 125
cagctatgac catgattacg ccaagcttgg tacctcgtag gaacaatttc gggcccctgc 60

<210> SEQ ID NO 126
<211> LENGTH: 60
<212> TYPE: DNA
<213> ORGANISM: artificial
<220> FEATURE:
<223> OTHER INFORMATION: synthetic oligonucleotide primer

<400> SEQUENCE: 126
cttcaggctg ggatagatgg ctgaggacat tttttgatta aaattaaaaa aactttttgt 60

<210> SEQ ID NO 127
<211> LENGTH: 60
<212> TYPE: DNA
<213> ORGANISM: artificial
<220> FEATURE:
<223> OTHER INFORMATION: synthetic oligonucleotide primer

<400> SEQUENCE: 127
acaaaaagtt tttttaattt taatcaaaaa atgtcctcag ccatctatcc cagcctgaag 60

<210> SEQ ID NO 128
<211> LENGTH: 60
<212> TYPE: DNA
<213> ORGANISM: artificial
<220> FEATURE:
<223> OTHER INFORMATION: synthetic oligonucleotide primer

<400> SEQUENCE: 128
tgatcatgaa ttaataaaag tgttcgcaaa ttaacgccag ccggcgtcga tccagtattc 60

<210> SEQ ID NO 129
<211> LENGTH: 60
<212> TYPE: DNA
<213> ORGANISM: artificial
<220> FEATURE:
<223> OTHER INFORMATION: synthetic oligonucleotide primer

<400> SEQUENCE: 129
gaatactgga tcgacgccgg ctggcgttaa tttgcgaaca cttttattaa ttcatgatca 60

<210> SEQ ID NO 130
<211> LENGTH: 60
<212> TYPE: DNA
<213> ORGANISM: artificial
<220> FEATURE:
<223> OTHER INFORMATION: synthetic oligonucleotide primer

<400> SEQUENCE: 130
actcacgagt aattcttgca aatgcctcct aggagacact ttttgaagcg ggatacagaa 60

<210> SEQ ID NO 131
<211> LENGTH: 60
<212> TYPE: DNA
<213> ORGANISM: artificial
<220> FEATURE:
<223> OTHER INFORMATION: synthetic oligonucleotide primer

<400> SEQUENCE: 131
ttctgtatcc cgcttcaaaa agtgtctcct aggaggcatt tgcaagaatt actcgtgagt 60

<210> SEQ ID NO 132
<211> LENGTH: 60
<212> TYPE: DNA
<213> ORGANISM: artificial
<220> FEATURE:
<223> OTHER INFORMATION: synthetic oligonucleotide primer

<400> SEQUENCE: 132
atcccatacg caagtgactt gagcggtcat tgttttatat ttgttgtaaa aagtagataa 60

<210> SEQ ID NO 133
<211> LENGTH: 60
<212> TYPE: DNA
<213> ORGANISM: artificial
<220> FEATURE:
<223> OTHER INFORMATION: synthetic oligonucleotide primer

<400> SEQUENCE: 133
ttatctactt tttacaacaa atataaaaca atgaccgctc aagtcacttg cgtatgggat 60

<210> SEQ ID NO 134
<211> LENGTH: 60
<212> TYPE: DNA
<213> ORGANISM: artificial
<220> FEATURE:
<223> OTHER INFORMATION: synthetic oligonucleotide primer

<400> SEQUENCE: 134
attgatctat cgatttcaat tcaattcaat ttagacaagg cggacctcat gctggggttg 60

<210> SEQ ID NO 135
<211> LENGTH: 60
<212> TYPE: DNA
<213> ORGANISM: artificial
<220> FEATURE:
<223> OTHER INFORMATION: synthetic oligonucleotide primer

<400> SEQUENCE: 135
caaccccagc atgaggtccg ccttgtctaa attgaattga attgaaatcg atagatcaat 60

<210> SEQ ID NO 136
<211> LENGTH: 60
<212> TYPE: DNA
<213> ORGANISM: artificial
<220> FEATURE:
<223> OTHER INFORMATION: synthetic oligonucleotide primer

<400> SEQUENCE: 136
ccgatgtatg ggtttggttg ccagaagctg agcttggagc aggaagaata cactatactg 60

<210> SEQ ID NO 137
<211> LENGTH: 60
<212> TYPE: DNA
<213> ORGANISM: artificial
<220> FEATURE:
<223> OTHER INFORMATION: synthetic oligonucleotide primer

<400> SEQUENCE: 137
cagtatagtg tattcttcct gctccaagct cagcttctgg caaccaaacc catacatcgg 60

<210> SEQ ID NO 138
<211> LENGTH: 60
<212> TYPE: DNA
<213> ORGANISM: artificial
<220> FEATURE:
<223> OTHER INFORMATION: synthetic oligonucleotide primer

<400> SEQUENCE: 138
gggcgtgcgg ttagacaagg cggacctcat tgtatatgag atagttgatt gtatgcttgg 60

<210> SEQ ID NO 139
<211> LENGTH: 60
<212> TYPE: DNA
<213> ORGANISM: artificial
<220> FEATURE:
<223> OTHER INFORMATION: synthetic oligonucleotide primer

<400> SEQUENCE: 139
ccaagcatac aatcaactat ctcatataca atgaggtccg ccttgtctaa ccgcacgccc 60

<210> SEQ ID NO 140
<211> LENGTH: 60
<212> TYPE: DNA
<213> ORGANISM: artificial
<220> FEATURE:
<223> OTHER INFORMATION: synthetic oligonucleotide primer

<400> SEQUENCE: 140
aataaaaatc ataaatcata agaaattcgc ttagtggttg tggcggggca gcttggccgc 60

<210> SEQ ID NO 141

<211> LENGTH: 60
<212> TYPE: DNA
<213> ORGANISM: artificial
<220> FEATURE:
<223> OTHER INFORMATION: synthetic oligonucleotide primer

<400> SEQUENCE: 141
gcggccaagc tgccccgcca caaccactaa gcgaatttct tatgatttat gatttttatt 60

<210> SEQ ID NO 142
<211> LENGTH: 60
<212> TYPE: DNA
<213> ORGANISM: artificial
<220> FEATURE:
<223> OTHER INFORMATION: synthetic oligonucleotide primer

<400> SEQUENCE: 142
gaaggtatgg gtgcagtgtg cttatctact agttgtggaa gaacgattac aacaggtgtt 60

<210> SEQ ID NO 143
<211> LENGTH: 60
<212> TYPE: DNA
<213> ORGANISM: artificial
<220> FEATURE:
<223> OTHER INFORMATION: synthetic oligonucleotide primer

<400> SEQUENCE: 143
aacacctgtt gtaatcgttc ttccacaact agtagataag cacactgcac ccataccttc 60

<210> SEQ ID NO 144
<211> LENGTH: 60
<212> TYPE: DNA
<213> ORGANISM: artificial
<220> FEATURE:
<223> OTHER INFORMATION: synthetic oligonucleotide primer

<400> SEQUENCE: 144
ggtccatgct agaagccgcc gacaaaccat tttgattgat ttgactgtgt tattttgcgt 60

<210> SEQ ID NO 145
<211> LENGTH: 60
<212> TYPE: DNA
<213> ORGANISM: artificial
<220> FEATURE:
<223> OTHER INFORMATION: synthetic oligonucleotide primer

<400> SEQUENCE: 145
acgcaaaata acacagtcaa atcaatcaaa atggtttgtc ggcggcttct agcatggacc 60

<210> SEQ ID NO 146
<211> LENGTH: 60
<212> TYPE: DNA
<213> ORGANISM: artificial
<220> FEATURE:
<223> OTHER INFORMATION: synthetic oligonucleotide primer

<400> SEQUENCE: 146
actttaacta ataattagag attaaatcgc ttagaggagg ccgcggccgg ccaggttgcg 60

<210> SEQ ID NO 147
<211> LENGTH: 60
<212> TYPE: DNA
<213> ORGANISM: artificial
<220> FEATURE:
<223> OTHER INFORMATION: synthetic oligonucleotide primer

<400> SEQUENCE: 147
cgcaacctgg ccggccgcgg cctcctctaa gcgatttaat ctctaattat tagttaaagt 60

<210> SEQ ID NO 148
<211> LENGTH: 60
<212> TYPE: DNA
<213> ORGANISM: artificial
<220> FEATURE:
<223> OTHER INFORMATION: synthetic oligonucleotide primer

<400> SEQUENCE: 148
acgttgtaaa acgacggcca gtgaattctc tagagcttgt cttgagcaat tgcagagtcg 60

<210> SEQ ID NO 149
<211> LENGTH: 60
<212> TYPE: DNA
<213> ORGANISM: artificial
<220> FEATURE:
<223> OTHER INFORMATION: synthetic oligonucleotide primer

<400> SEQUENCE: 149
agttgggtaa cgccagggtt ttcccagtca cgacgttgta aaacgacggc cagtgaattc 60

<210> SEQ ID NO 150
<211> LENGTH: 60
<212> TYPE: DNA
<213> ORGANISM: artificial
<220> FEATURE:
<223> OTHER INFORMATION: synthetic oligonucleotide primer

<400> SEQUENCE: 150
ctaataggta atctcctact gtatacatgg atcctttttg attaaaatta aaaaaacttt 60

<210> SEQ ID NO 151
<211> LENGTH: 60
<212> TYPE: DNA
<213> ORGANISM: artificial
<220> FEATURE:
<223> OTHER INFORMATION: synthetic oligonucleotide primer

<400> SEQUENCE: 151
aaagtttttt taattttaat caaaaaggat ccatgtatac agtaggagat tacctattag 60

<210> SEQ ID NO 152
<211> LENGTH: 60
<212> TYPE: DNA
<213> ORGANISM: artificial
<220> FEATURE:
<223> OTHER INFORMATION: synthetic oligonucleotide primer

<400> SEQUENCE: 152
tcatgaatta ataaaagtgt tcgcaaaggt accttatgat ttattttgtt cagcaaatag 60

<210> SEQ ID NO 153
<211> LENGTH: 60
<212> TYPE: DNA
<213> ORGANISM: artificial
<220> FEATURE:
<223> OTHER INFORMATION: synthetic oligonucleotide primer

<400> SEQUENCE: 153
ctatttgctg aacaaaataa atcataaggt acctttgcga acacttttat taattcatga 60

<210> SEQ ID NO 154
<211> LENGTH: 60
<212> TYPE: DNA
<213> ORGANISM: artificial

<220> FEATURE:
<223> OTHER INFORMATION: synthetic oligonucleotide primer

<400> SEQUENCE: 154
cttactcacg agtaattctt gcaaatgcct agacactttt tgaagcggga tacagaaaaa 60

<210> SEQ ID NO 155
<211> LENGTH: 60
<212> TYPE: DNA
<213> ORGANISM: artificial
<220> FEATURE:
<223> OTHER INFORMATION: synthetic oligonucleotide primer

<400> SEQUENCE: 155
tttttctgta tcccgcttca aaaagtgtct aggcatttgc aagaattact cgtgagtaag 60

<210> SEQ ID NO 156
<211> LENGTH: 60
<212> TYPE: DNA
<213> ORGANISM: artificial
<220> FEATURE:
<223> OTHER INFORMATION: synthetic oligonucleotide primer

<400> SEQUENCE: 156
tggggtgtgc agattaaagt tgttcattct agatgtttta tatttgttgt aaaaagtaga 60

<210> SEQ ID NO 157
<211> LENGTH: 60
<212> TYPE: DNA
<213> ORGANISM: artificial
<220> FEATURE:
<223> OTHER INFORMATION: synthetic oligonucleotide primer

<400> SEQUENCE: 157
tctacttttt acaacaaata taaaacatct agaatgaaca actttaatct gcacacccca 60

<210> SEQ ID NO 158
<211> LENGTH: 60
<212> TYPE: DNA
<213> ORGANISM: artificial
<220> FEATURE:
<223> OTHER INFORMATION: synthetic oligonucleotide primer

<400> SEQUENCE: 158
gatctatcga tttcaattca attcaatctc gagttagcgg gcggcttcgt atatacggcg 60

<210> SEQ ID NO 159
<211> LENGTH: 60
<212> TYPE: DNA
<213> ORGANISM: artificial
<220> FEATURE:
<223> OTHER INFORMATION: synthetic oligonucleotide primer

<400> SEQUENCE: 159
cgccgtatat acgaagccgc ccgctaactc gagattgaat tgaattgaaa tcgatagatc 60

<210> SEQ ID NO 160
<211> LENGTH: 60
<212> TYPE: DNA
<213> ORGANISM: artificial
<220> FEATURE:
<223> OTHER INFORMATION: synthetic oligonucleotide primer

<400> SEQUENCE: 160
gtcacgacgt tgtaaaacga cggccagtga attctgagct tggagcagga agaatacact 60